US010273546B2

(12) United States Patent
Abate-Shen et al.

(10) Patent No.: US 10,273,546 B2
(45) Date of Patent: Apr. 30, 2019

(54) METHOD AND COMPOSITION FOR DIAGNOSIS OR TREATMENT OF AGGRESSIVE PROSTATE CANCER

(71) Applicant: The Trustees of Columbia University in the City of New York, New York, NY (US)

(72) Inventors: Corinne Abate-Shen, New York, NY (US); Andrea Califano, New York, NY (US); Michael Shen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/119,608

(22) PCT Filed: Feb. 19, 2015

(86) PCT No.: PCT/US2015/016653
§ 371 (c)(1),
(2) Date: Aug. 17, 2016

(87) PCT Pub. No.: WO2015/127104
PCT Pub. Date: Aug. 27, 2015

(65) Prior Publication Data
US 2017/0051281 A1 Feb. 23, 2017

Related U.S. Application Data

(60) Provisional application No. 61/966,271, filed on Feb. 19, 2014.

(51) Int. Cl.
A61K 48/00 (2006.01)
C12N 15/11 (2006.01)
(Continued)

(52) U.S. Cl.
CPC .......... *C12Q 1/6886* (2013.01); *C12N 15/113* (2013.01); *G01N 33/57434* (2013.01);
(Continued)

(58) Field of Classification Search
CPC ...... C12N 15/11; C12N 15/113; A61K 38/00; C12Q 1/6886; C12Q 2600/118; G01N 33/57434
See application file for complete search history.

(56) References Cited

U.S. PATENT DOCUMENTS

2008/0113351 A1    5/2008  Naito et al.
2011/0172929 A1    7/2011  Califano
2013/0142784 A1    6/2013  Raychaudhuri et al.

OTHER PUBLICATIONS

Ye et al. (Molecular and Cellular Biology, 1997 vol. 17:1626-1641).*

(Continued)

Primary Examiner — Terra C Gibbs
(74) Attorney, Agent, or Firm — Leason Ellis LLP

(57) ABSTRACT

Methods, pharmaceutical formulations and medicaments for treating prostate cancer or preventing the progression of a nonaggressive form of prostate cancer to an aggressive form, in a mammal, include a therapeutically effective amount of one or more active agents that reduce the expression or biological activity of both Forkhead box protein M1 (FOXM1) and Centromere protein F (CENPF) or biologically active fragments thereof or biologically active fragments thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding either FOXM1 or CENPF proteins. A method is also presented for discovering synergistic master (Continued)

regulators of other phenotype transitions, wherein the master regulators are conserved among different species.

5 Claims, 32 Drawing Sheets

Specification includes a Sequence Listing.

(51) Int. Cl.
| | | |
|---|---|---|
| C07H 21/02 | (2006.01) | |
| C07H 21/04 | (2006.01) | |
| C12Q 1/6886 | (2018.01) | |
| G01N 33/574 | (2006.01) | |
| C12N 15/113 | (2010.01) | |
| G06F 19/18 | (2011.01) | |
| G06F 19/22 | (2011.01) | |

(52) U.S. Cl.
CPC ............. *G06F 19/18* (2013.01); *G06F 19/22* (2013.01); *C12N 2310/14* (2013.01); *C12N 2320/32* (2013.01); *C12Q 2600/112* (2013.01); *C12Q 2600/118* (2013.01); *C12Q 2600/158* (2013.01); *G01N 2333/47* (2013.01)

(56) References Cited

OTHER PUBLICATIONS

SIDNET Transcription factor Human pGIPZ shRNA Collection (Nov. 2009).*
International Search Report dated May 27, 2015 corresponding to International Application No. PCT/US2015/016553; 3 pages.
Written Opinion dated May 27, 2015 corresponding to International Application No. PCT/US2015/016550; 8 pages.
Kalin et al. Increased levels of the FoxM1 transcription factor accelerate development and progression of prostate carcinomas in both TRAMP and LADY transgenic mice, Cancer Res. Feb. 1, 2006 (Feb. 1, 2006), vol. 66, pp. 1712-1720.
Lefebvre et al. "A human B-cell interactome identifies MYB and FOXM1 as master regulators of proliferation in germinal centers," Mol Syst Biol. Jun. 8, 2010 (Jun. 8, 2010), vol. 5:377, pp. 1-10.
Aytes et al. "Cross-species regulatory network analysis indentifies a synergistic interaction between FOXM1 and CENPF that drives prostate cancer malignancy," Cancer Cell. May 12, 2014 (May 12, 2014), vol. 25, pp. 638-651.
Akavia, U. D., Litvin, O., Kim, J., Sanchez-Garcia, F., Kotliar, D., Causton, H. C., Pochanard, P., Mozes, E., Garraway, L.A., and Pe'er, D. (2010). An integrated approach to uncover drivers of cancer Cell 143, 1005-1017.
Alvarez-Fernandez, M., and Medema, R.H. (2013). Novel functions of FoxMl: from molecular mechanisms to cancer therapy. Frontiers in oncology 3, 30.
Aytes, A., Mitrofanova, A., Kinkade, C. W., Lefebvre, C., Lei, M., Phelan, V., LeKaye, H.C., Koutcher, J. A., Cardiff, R. D., Califano, A., et al. (2013). ETV4 promotes metastasis in response to activation of PB-kinase and Ras signaling in a mouse model of advanced prostate cancer. Proc Natl Acad Sci USA 110, E3506-3515.
Baca, S. C., Prandi, D., Lawrence, M. S., Mosquera, J.M., Romanel, A., Drier, Y., Park, K., Kitabayashi, N., MacDonald, T. Y., Ghandi, M., et al. (2013). Punctuated evolution of prostate cancer genomes. Cell 153, 666-677.
Barringer, K., Orgel, L., Wahl, G., Gingeras, T. R. (1990). Blunt-end and single-strand ligations by *Escherichia coli* ligase: influence on an in vitro amplification scheme. Gene 89:117-122.
Basso, K., Margolin, A. A., Stolovitzky, G., Klein, U., Dalla-Favera, R., and Califano, A. (2005). Reverse engineering of regulatory networks in human B cells. Nat Genet 37, 382-390.
Berger, S., Kimmel, A., Abelson, J., Simon, M. (1987). Methods in Enzymology 152:307-316.

Bomont, P., Maddox, P., Shah, J. V., Desai, A. B., and Cleveland, D. W. (2005). Unstable microtubule capture at kinetochores depleted of the centromere-associated protein CENPF. EMBO J 24, 3927-3939.
Burg, L. J., Juffras, A. M., Wu, Y., Blomquist, C. L., Du, Y. (1996). Single molecule detection of RNA reporter probes by amplification with Q~ replicase. Mol. Cell. Probes 10:257-271.
Cai, Y., Balli, D., Ustiyan, V., Fulford, L.A., Hiller, A., Misetic, V., Zhang, Y., Paluch, A. M., Waltz, S. E., Kasper, S., and Kalin, T. V. (2013). Foxm1 Expression in Prostate Epithelial Cells is Essential for Prostate Carcinogenesis. J Biol Chem 288, 22527-22541.
Carro, M. S., Lim, W. K., Alvarez, M. J., Bollo, R. J., Zhao, X., Snyder, E. Y., Sulman, E. P., Anne, S. L., Doetsch, F., Colman, H., et al. (2010). The transcriptional network for mesenchymal transformation of brain tumours. Nature 463, 318-325.
Donovan, M. J., Hamann, S., Clayton, M., Khan, F. M., Sapir, M., Bayer-Zubek, V., Fernandez, G., Mesa-Tejada, R., Teverovskiy, M., Reuter, V. E., et al. (2008). Systems pathology approach for the prediction of prostate cancer progression after radical prostatectomy. J Clin Oncol 26, 3923-3929.
Faith, J. J., Hayete, B., Thaden, J. T., Mogno, I., Wierzbowski, J., Cottarel, G., Kasif, S.,Collins, J. J., and Gardner, T. S. (2007). Large-scale mapping and validation of *Escherichia coli* transcriptional regulation from a compendium of expression profiles. PLoS Biol 5, e8.
Feng, J., Huang, H., and Yen, T. J. (2006). CENP-F is a novel microtubule-binding protein that is essential for kinetochore attachments and affects the duration of the mitotic checkpoint delay. Chromosoma 115, 320-329.
Frediksson, S., Gullberg, M., Jarvius, J., Olsson, C., Pietras, K., Gustafsdottir, S. M., Ostman, A., Landegren, U. (2002). Protein detection using proximity-dependent DNA ligation assays. Nat. Biotechnol. 20, 473-477.
Glinsky, G. V., Glinskii, A. B., Stephenson, A. J., Hoffman, R. M., and Gerald, W. L. (2004). Gene expression profiling predicts clinical outcome of prostate cancer. J Clin Invest 113, 913-923.
Guatelli, J.C., Whitfield, K. M., Kwoh, D. Y., Barringer, K. J., Richman, D. D., Gingeras, T. R. (1990). Isothermal, in vitro amplification of nucleic acids by a multienzyme reaction modeled after retroviral replication. Proc. Natl. Acad. Sci. USA 87:1874-78.
Halasi, M., and Gartel, A. L. (2013a). FOX(MI) news—it is cancer. Mol Cancer Tuer 12, 245-254.
Halasi, M., and Gartel, A. L. (2013b). Targeting FOXM1 in cancer Biochemical pharmacology 85, 644-652.
Hanahan, D., and Weinberg, R. A. (2011). Hallmarks of cancer: the next generation. Cell 144, 646-67.
Hasegawa, S., Furukawa, Y., Li, M., Satoh, S., Kato, T., Watanabe, T., Katagiri, T., Tsunoda, T., Yamaoka, Y., Nakamura, Y. (2002). Genome-Wide Analysis of Gene Expression in Intestinal-Type Gastric Cancers Using a Complementary DNA Microarray Representing 23,040 Genes. Cancer Res 62:7012-7.
Holt, S. V., Vergnolle, M.A., Hussein, D., Wozniak, M. J., Allan, V. J., and Taylor, S.S. (2005). Silencing Cenp-F weakens centromeric cohesion, prevents chromosome alignment and activates the spindle checkpoint. J Cell Sci 118, 4889-4900.
Innis, M. ed. (1990). PCR Protocols: A Guide to Methods and Applications. Academic Press, N.Y.
Innis, M. ed. (1995). PCR Strategies. Academic Press, N.Y.
Irshad, S., and Abate-Shen, C. (2013). Modeling prostate cancer in mice: something old, something new, something premalignant, something metastatic. Cancer metastasis reviews 32, 109-122.
Ittmann, M., Huang, J., Radaelli, E., Martin, P., Signoretti, S., Sullivan, R., Simons, B. W., Ward, J.M., Robinson, B. D., Chu, G. C., et al. (2013). Animal models of human prostate cancer: the consensus report of the New York meeting of the Mouse Models of Human Cancers Consortium Prostate Pathology Committee. Cancer Res 73, 2718-2736.
Jones, A. C., Sampson, J. R., Hoogendoorn, B., Cohen, D., Cheadle, J.P. (2000). Application and evaluation of denaturing HPLC for molecular genetic analysis in tuberous sclerosis. Hum Genet. 106(6):663-8.
Kalin, T. V., Ustiyan, V., and Kalinichenko, V. V. (2011). Multiple faces of FoxM1 transcription factor: lessons from transgenic mouse models. Cell Cycle 10, 396-405.

(56) References Cited

OTHER PUBLICATIONS

Kalin, T. V., Wang, I. C., Ackerson, T. J., Major, M. L., Detrisac, C. J., Kalinichenko, V. V., Lyubimov, A., and Costa, R. H. (2006). Increased levels of the FoxMl transcription factor accelerate development and progression of prostate carcinomas in both TRAMP and LADY transgenic mice. Cancer Res 66, 1712-1720.

Kitahara, 0., Furukawa, Y., Tanaka, T., Kihara, C., Ono, K., Yanagawa, R., Nita, M., Takagi, T., Nakamura, Y., Tsunoda, T. (2001). Alterations of Gene Expression during Colorectal Carcinogenesis Revealed by cDNA Microarrays after Laser-Capture Microdissection of Tumor Tissues and Normal Epithelia. Cancer Res 61: 3544-9.

Koo, C. Y., Muir, K. W., and Lam, E.W. (2012). FOXMI: From cancer initiation to progression and treatment. Biochim Biophys Acta 1819, 28-37.

Kwoh, D. Y., Davis, G. R., Whitfield, K. M., Chappelle, H. L., DiMichele, L J., Gingeras, T. R. (1989). Proc. Natl. Acad. Sci. USA 86:1173-77.

Landegren, U., Kaiser, R., Sanders, J., Hood, L. (1988). A ligase-mediated gene detection technique. Science 241:1077-80.

Lefebvre, C., Rajbhandari, P., Alvarez, M. J., Bandaru, P., Lim, W. K., Sato, M., Wang, K., Sumazin, P., Kustagi, M., Bisikirska, B. C., et al. (2010). A human B-cell interactome identifies MYB and FOXMI as master regulators of proliferation in germinal centers. Mol Syst Biol 6, 377.

Lefebvre, C., Rieckhof, G., and Califano, A. (2012). Reverse-engineering human regulatory networks. Wiley interdisciplinary reviews Systems biology and medicine 4, 311-325.

Lin, Y-M., Furukawa, Y., Tsunoda, T., Yue, C.-T., Yang, K.-C., Nakamura, Y. (2002). Molecular diagnosis of colorectal tumors by expression profiles of 50 genes expressed differentially in adenomas and carcinomas. Oncogene 21:4120-8.

Ma, L., Zhao, X., and Zhu, X. (2006). Mitosin/CENP-F in mitosis, transcriptional control, and differentiation. Journal of biomedical science 13, 205-213.

Margolin, A. A., Nemenman, I., Basso, K., Wiggins, C., Stolovitzky, G., Dalla Favera, R., and Califano, A. (2006a). ARACNE: an algolithm for the reconstruction of gene regulatory networks in a mammalian cellular context. BMC Bioinformatics 7 Suppl 1, S7.

Margolin, A. A., Wang, K., Lim, W. K., Kustagi, M., Nemenman, I., and Califano, A. (2006b). Reverse engineering cellular networks. Nat Protoc 1, 662-671.

McCaffrey, A. P., Meuse, L., Pham, T. T., Conklin, D.S., Hannon, G. J., Kay M.A. (2002). RNA interference in adult mice. Nature, 418:38-9.

McManus, M. T., Petersen, C. P., Haines, B. B., Chen, J., Sharp P.A. (2002). Gene silencing using micro-RNA designed hairpins. RNA, 8:842-50.

Okabe, H., Satoh, S., Kato, T., Kitahara, 0., Yanagawa, R., Yamaoka, Y., Tsunoda, T., Furukawa, Y., Nakamura, Y. (2001). Genome-wide Analysis of Gene Expression in Human Hepatocellular Carcinomas Using cDNA Microarray: Identification of Genes Involved in Viral Carcinogenesis and Tumor Progression. Cancer Res 61:2129-37.

Paddison, P. J., Caudy, A. A., Bernstein, E., Hannon, G. J., Conklin, D.S. (2002). Short hairpin RNAs (shRNAs) induce sequence-specific silencing in mammalian cells. Genes Dev, 16:948-58.

Pan, J., and Yeung, S. C. (2005). Recent advances in understanding the antineoplastic mechanisms of farnesyltransferase inhibitors. Cancer Res 65, 9109-9112.

Radhak:rishnan, S. K., Bhat, U. G., Hughes, D. E., Wang, I. C., Costa, R.H., and Gartel, A. L. (2006). Identification of a chemical inhibitor of the oncogenic transcliption factor forkhead box MI. Cancer Res 66, 9731-9735.

Ryan, C. J., and Tindall, D. J. (2011). Androgen receptor rediscovered: the new biology and targeting the androgen receptor therapeutically. J Clin Oncol 29, 3651-3658.

Sano, T., Smith, C. L., Cantor, C.R. (1992). Immuno-PCR: Very sensitive antigen detection by means of specific antibody-DNA conjugates. Science 258, 120-122.

Sboner, A., Demichelis, F., Calza, S., Pawitan, Y., Setlur, S. R., Hoshida, Y., Pemer, S., Adami, H. 0., Fall, K., Mucci, L.A., et al. (2010). Molecular sampling of prostate cancer: a dilemma for predicting disease progression. BMC Med Genomics 3, 8.

Scher, H. I., and Sawyers, C. L. (2005). Biology of progressive, castration-resistant prostate cancer: directed therapies targeting the androgen-receptor signaling axis. J Clin Oncol 23, 8253-8261.

Schoenborn, J. R., Nelson, P., and Fang, M. (2013). Genomic profiling defines subtypes of prostate cancer with the potential for therapeutic stratification. Clin Cancer Res 19, 4058-4066.

Shah, R. B., Mehra, R., Chinnaiyan, A. M., Shen, R., Ghosh, D., Zhou, M., Macvicar, G. R., Varambally, S., Harwood, J., Bismar, T. A., et al. (2004). Androgen-independent prostate cancer is a heterogeneous group of diseases: lessons from a rapid autopsy program. Cancer Res 64, 9209-9216.

Shen, M. M., and Abate-Shen, C. (2010). Molecular genetics of prostate cancer: new prospects for old challenges. Genes Dev 24, 1967-2000.

Smith, J. H., Radcliffe, D., Rigmy, S., Mahan, D., Lane, D. J., Klinger, J. D. (1997). Performance of an automated Q-beta replicase amplification assay for *Mycobacterium tuberculosis* in a clinical trial. Clin. Microbiol. 35:1477-1491.

Sooknanan, R., Malek, L. T. (1995). A detection and amplification system uniquely suited for RNA. Nature Biotechnology 13:563-564.

Taylor, B. S., Schultz, N., Hieronymus, H., Gopalan, A., Xiao, Y., Carver, B. S., Arora, V. K., Kaushik, P., Cerami, E., Reva, B. (2010). Integrative genomic profiling of human prostate cancer. Cancer Cell 18, 11-22.

Uddin, M. N., Patel N. J., Bhowmik T., D'Souza B., Akalkotkar A., Etzlar F., Oettinger C. W., D'Souza, M. (2013). Enhanced bioavailability of orally administered antisense oligonucleotide to nuclear factor kappa B mRNA after microencapsulation with albumin,. J Drug Target 21(5), 450-457 (doi:10.3109/1061186X.2013.765440).

Varis, A., Salmela, A. L., and Kallio, M. J. (2006). Cenp-F (mitosin) is more than a mitotic marker. Chromosoma 115, 288-295.

Wu, D. Y., Wallace, R. B. (1989). The ligation amplification reaction (LAR)-amplification of specific DNA sequences using sequential rounds of template-dependent ligation. Genomics 4:560-569.

Yu, J.-Y., DeRuiter, S. L., Turner, D. L. (2002). RNA interference by expression of shortinterfering RN As and hairpin Rn As in mammalian cells. Proc Natl Acad Sci USA, 99:6047-52.

Zhang, H. T., Kacharmina, J.E., Miyashiro, K., Greene, M. I., Eberwine, J. (2001). Protein quantification from complex protein mixtures using a proteomics methodology with single-cell resolution. J. Proc. Natl. Acad. Sci. USA 98, 5497-5502.

Zhang, N., Wei, P., Gong, A., Chiu, W. T., Lee, H. T., Colman, H., Huang, H., Xue, J., Liu, M., Wang, Y., et al. (2011). FoxMl promotes beta-catenin nuclear localization and controls Wnt target-gene expression and glioma tumorigenesis. Cancer Cell 20, 427-442.

Zhang, Q. C., Petrey, D., Deng, L., Qiang, L., Shi, Y., Thu, C. A., Bisikirska, B., Lefebvre, C., Accili, D., Hunter, T., et al. (2012). Structure-based prediction of protein-protein interactions on a genome-wide scale. Nature 490, 556-560.

Ding et al., "SMAD4-dependent barrier constrains prostate cancer growth and metastatic progression", Nature vol. 470, pp. 269-273 (2011).

* cited by examiner

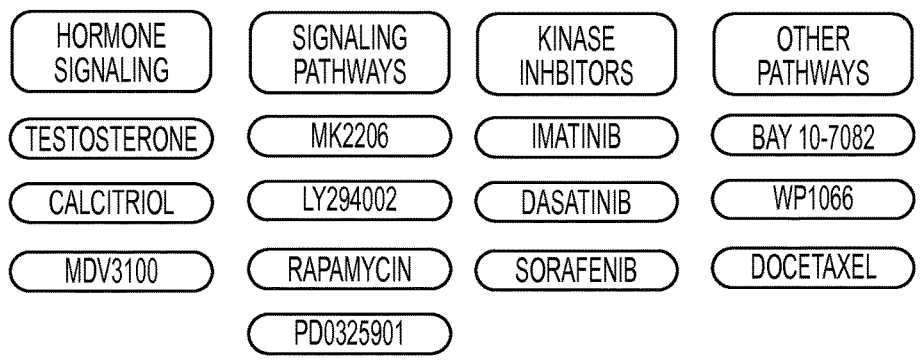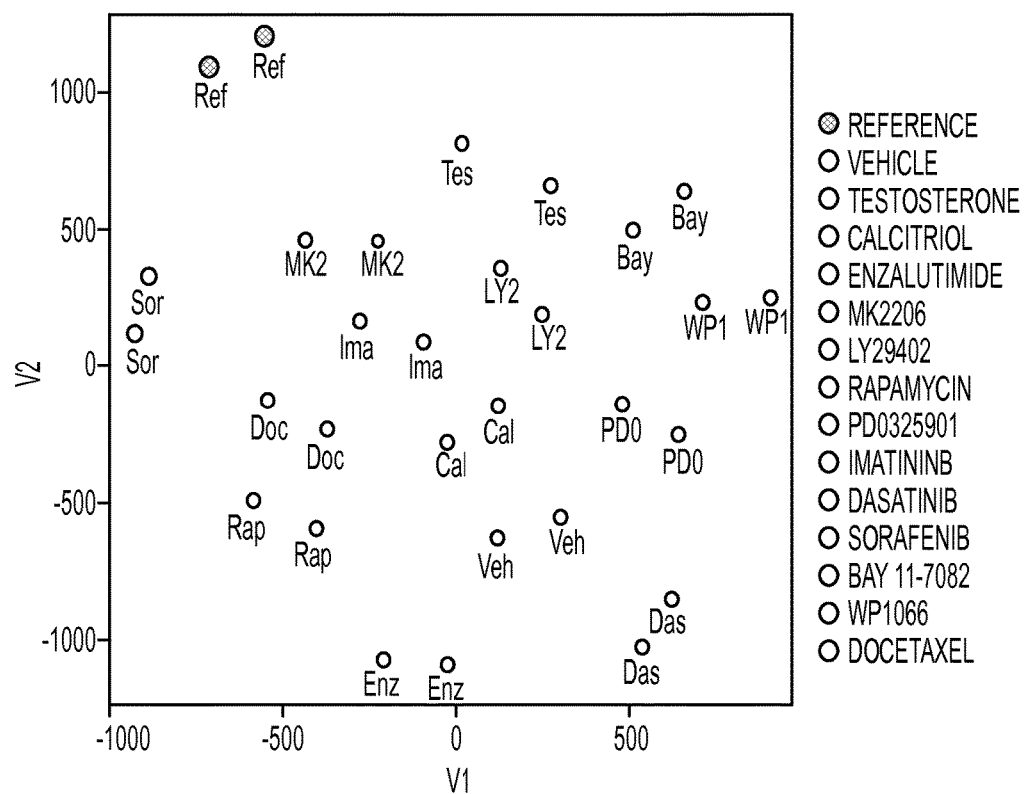
FIG. 1C

FIG. 3C

| Conserved MR | MARINa Joint p value | COX Expression p value | COX Activity p value | Oncomine expression p value |
|---|---|---|---|---|
| CHAF1A | $2.3 \times 10^{-5}$ | 0.9190 | 0.2662 | 0.0030 |
| TRIB3 | $1.8 \times 10^{-4}$ | 0.1174 | 0.1893 | 0.00004 |
| FOXM1 | $3.0 \times 10^{-4}$ | 0.0100 | 0.0094 | 0.0045 |
| CENPF | $8.3 \times 10^{-4}$ | 0.0010 | 0.0019 | 0.0015 |
| PSRC1 | $8.4 \times 10^{-4}$ | 0.2249 | 0.1394 | 0.021 |
| TSFM | $1.0 \times 10^{-3}$ | 0.0650 | 0.5167 | 0.251 |
| ASF1B | $7.0 \times 10^{-3}$ | 0.1725 | 0.0408 | 0.044 |

FIG. 3D

Predicted Synergy (p value)

|  | CENPF | FOXM1 | TRIB3 | CHAF1A | PSRC1 | ASF1B |
|---|---|---|---|---|---|---|
| CENPF | — | <0.001 | 1 | 1 | 1 | 1 |
| FOXM1 |  | — | 1 | 1 | 1 | 0.110 |
| TRIB3 |  |  | — | 1 | 1 | 1 |
| CHAF1A |  |  |  | — | 1 | 1 |
| PSRC1 |  |  |  |  | — | 1 |
| ASF1B |  |  |  |  |  | — |
| TSFM |  |  |  |  |  |  |

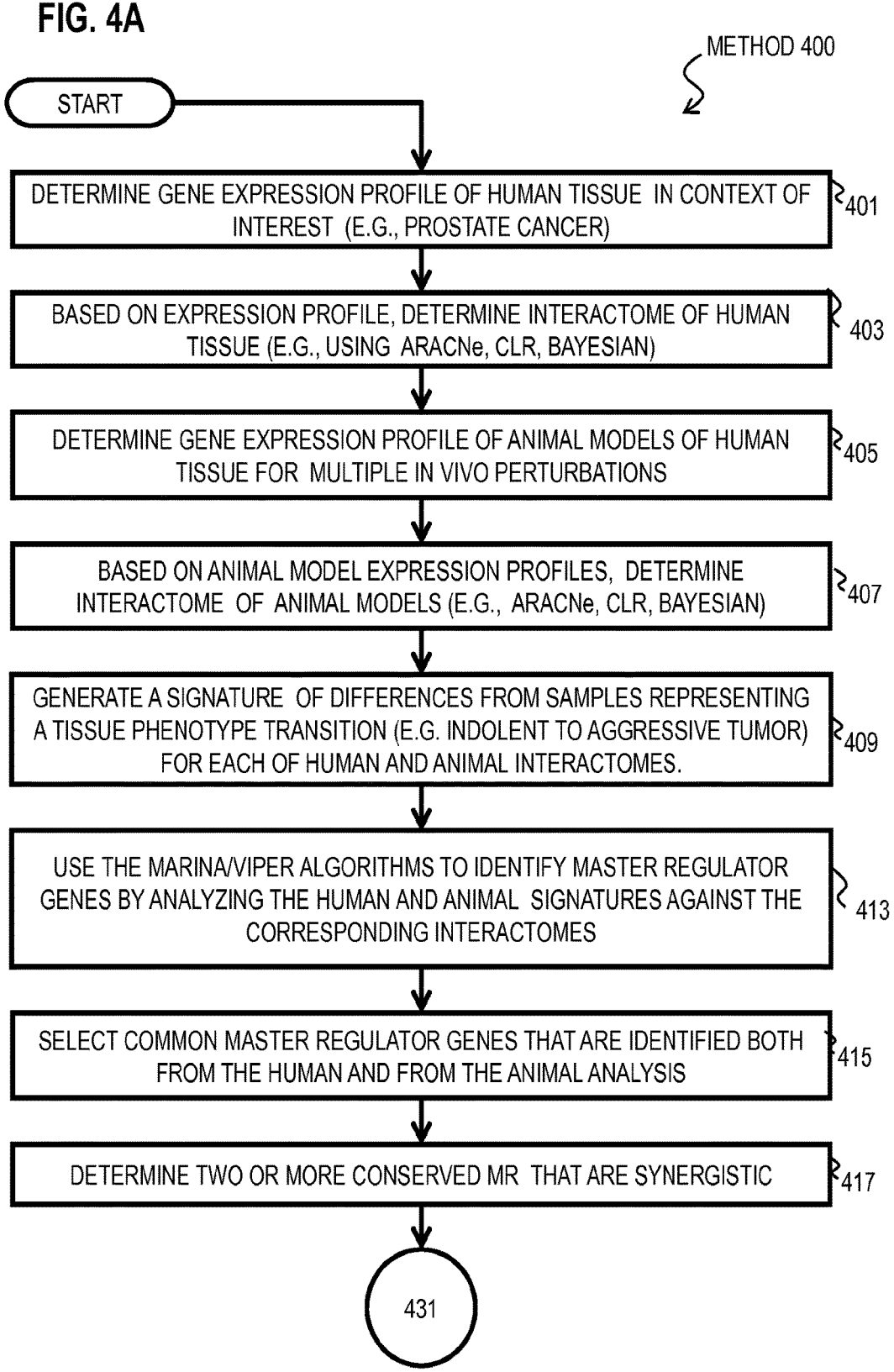

| DESCRIPTION | | PRIMARY DATASET | SECONDARY DATASETS | |
|---|---|---|---|---|
| | | TAYLOR | Yu | WANG (a) |
| GEO ACCESSION # | | GSE21034 | GSE6919 | GSE17951 |
| PATIENTS/SAMPLES | | 131 PRIMARY<br>29 AD. NORMAL<br>19 METASTASES<br>6 CELL LINES | 63 PRIMARY<br>17 NORMAL<br>58 AD. NORMAL | 109 PRIMARY<br>32 BIOPSIES<br>13 NORMAL |
| MEDIAN AGE (YEARS ± MAD) | | 58±4.4 | NA | NA |
| PATHOLOGY STAGE T | T2<br>T3<br>T4 | 85<br>39<br>7 | 25<br>36<br>2 | NA |
| CLINICAL T-STAGE | T1<br>T2<br>T3 | 75<br>51<br>5 | NA | NA |
| PATHOLOGY STAGE N | N0<br>N1<br>Nx | 102<br>6<br>23 | NA | NA |
| PATHOLOGY GLEASON SCORE | ≤5<br>6<br>7<br><br>≥8 | 0<br>41<br>54 (3+4)<br>20 (4+3)<br>15 | 3<br>15<br><br>27<br>18 | NA |
| BIOPSY GLEASON SCORE | ≤5<br>6<br>7<br><br>≥8 | 1<br>77<br>29 (3+4)<br>13 (4+3)<br>11 | NA | NA |
| SVI% | NEGATIVE<br>POSITIVE | 89.3%<br>10.8% | NA | NA |
| EXTRACAPSULAR EXTENSION % | PRESENT<br>ABSENT | 67.7%<br>32.3% | NA | NA |
| BCR MEDIAN (MONTHS ± MAD) | | 17.8±10.6 (N=27) | NA | NA |
| MEDIAN OVERALL SURVIVAL (MONTHS ± MAD) | | NA | NA | NA |
| MEDIAN TIME TO METASTASIS (MONTHS ± MAD) | | NA | NA | NA |

FIG. 5

| SECONDARY DATASETS | | RNA (GENE EXPRESSION) | | PROTEIN (IMMUNOHISTOCHEMISTRY) | |
|---|---|---|---|---|---|
| WANG (b) | BALK | SBONER | GLINSKY | OUTCOME TMA (MSKCC) | METASTASIS TMA (MICH) |
| GSE8218 | GSE32269 | GSE16560 | NA | | |
| 144 PRIMARY 4 NORMAL | 22 PRIMARY 29 BONE METASTASES 4 NORMAL BONE | 281 TURP | 79 PRIMARY | 916 PRIMARY (821 INFORMATIVE CASES) | 60 METASTASES (53 INFORMATIVE) |
| NA | NA | 74±5 | 60±6 | 61.6±7.5 | NA |
| NA | NA | NA | NA | 555<br>240<br>26 | NA |
| NA | NA | NA | NA | 404<br>398<br>18<br>1 (NA) | NA |
| NA | NA | NA | 79<br>3 (N1 OR Nx) | NA | NA |
| NA | NA | NA | 2<br>15<br>30 (3+4)<br>14 (4+3)<br>18 | 27<br>240<br>347 (3+4)<br>103 (4+3)<br>82 | NA |
| NA | NA | 0<br>83<br>79 (3+4)<br>38 (4+3)<br>81 | 13<br>24<br>20 (3+4)<br>12 (4+3)<br>10 | 82<br>423<br>156 (3+4)<br>72 (4+3)<br>56<br>32 (NA) | NA |
| NA | NA | NA | 87.3%<br>12.7% | 95.9%<br>4.1% | NA |
| NA | NA | NA | 78.4%<br>21.6 | 80.5%<br>19.5% | NA |
| NA | NA | NA | 51.5±30.4 (N=37) | 21.4±25.5 (N=266) | NA |
| NA | NA | 75±40 | NA | 87.4±39.3 (N=247) | NA |
| NA | NA | NA | NA | 54.2±44.1 (N=79) | NA |

C-Statistics Model - MSKCC TMA

Prostate Cancer-Specific Survival

|  | C index | Confidence interval | p value |
|---|---|---|---|
| Gleason | 0.65 | 0.48 - 0.81 | 0.038 |
| FOXM1 & CENPF | 0.71 | 0.59 - 0.84 | $2.4 \times 10^{-4}$ |
| Gleason + FOXM1 & CENPF | 0.86 | 0.80 - 0.93 | $1.0 \times 10^{-30}$ | p value for improvement $2.7 \times 10^{-4}$

Time to Metastases

|  | C index | Confidence interval | p value |
|---|---|---|---|
| Gleason | 0.61 | 0.54 - 0.70 | 0.002 |
| FOXM1 & CENPF | 0.77 | 0.71 - 0.83 | $3.1 \times 10^{-19}$ |
| n + FOXM1 & CENPF | 0.86 | 0.81 - 0.89 | $6.5 \times 10^{-58}$ | p value for improvement $5.3 \times 10^{-13}$

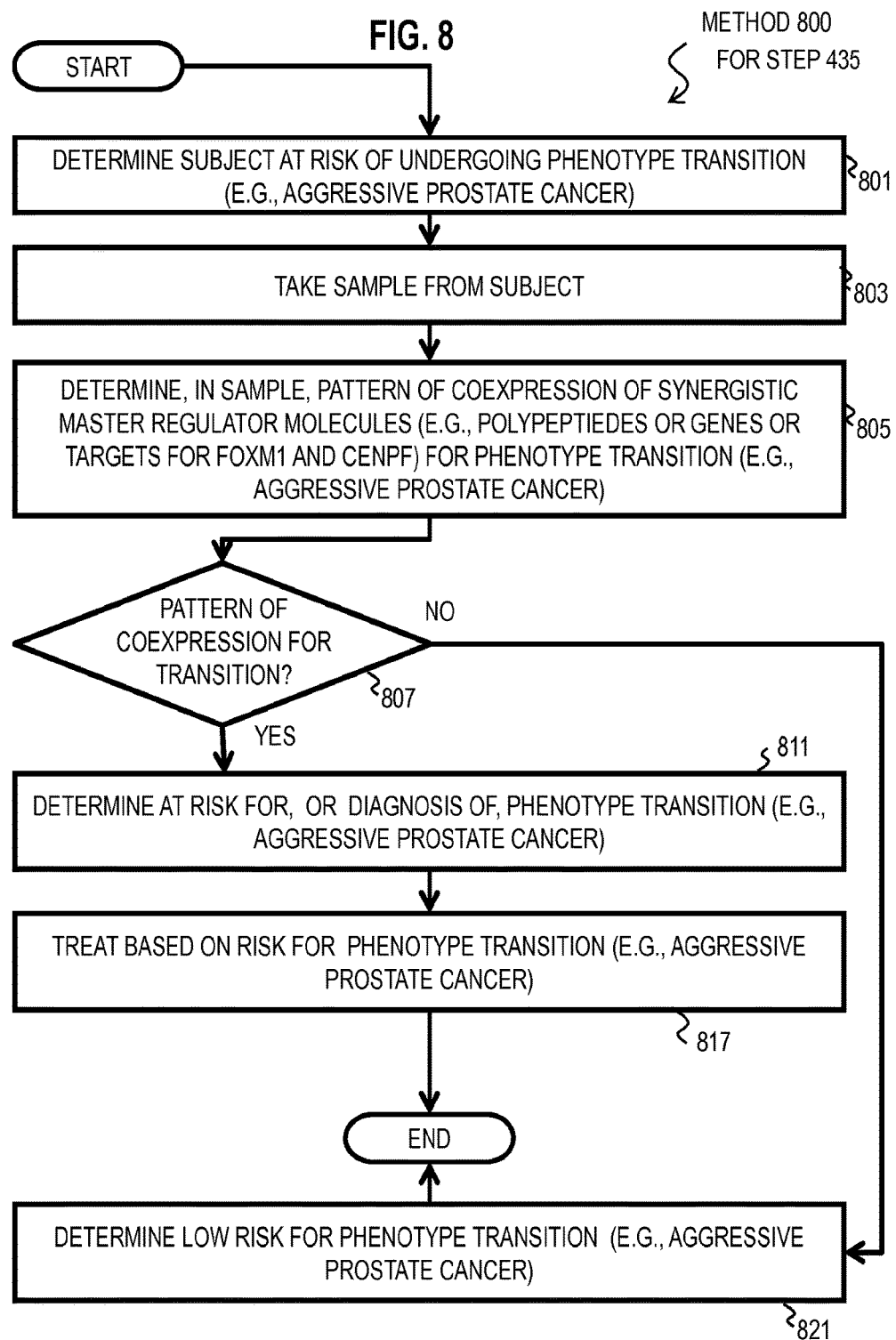

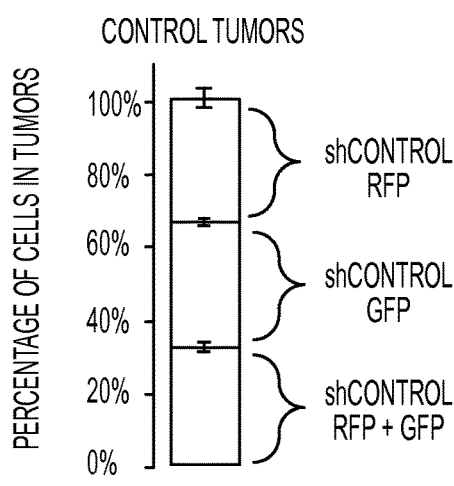
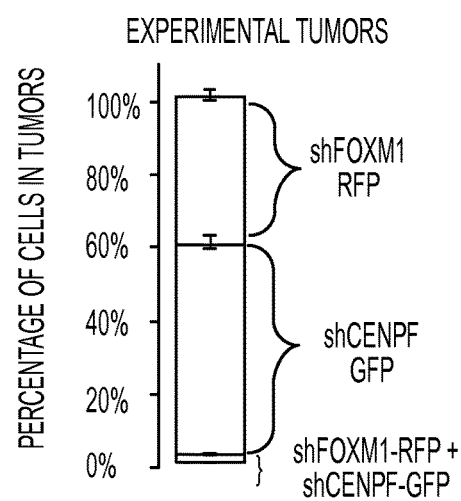
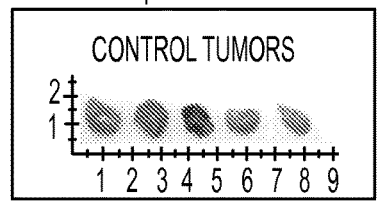
FIG. 11L
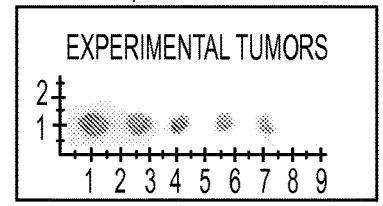
FIG. 11M

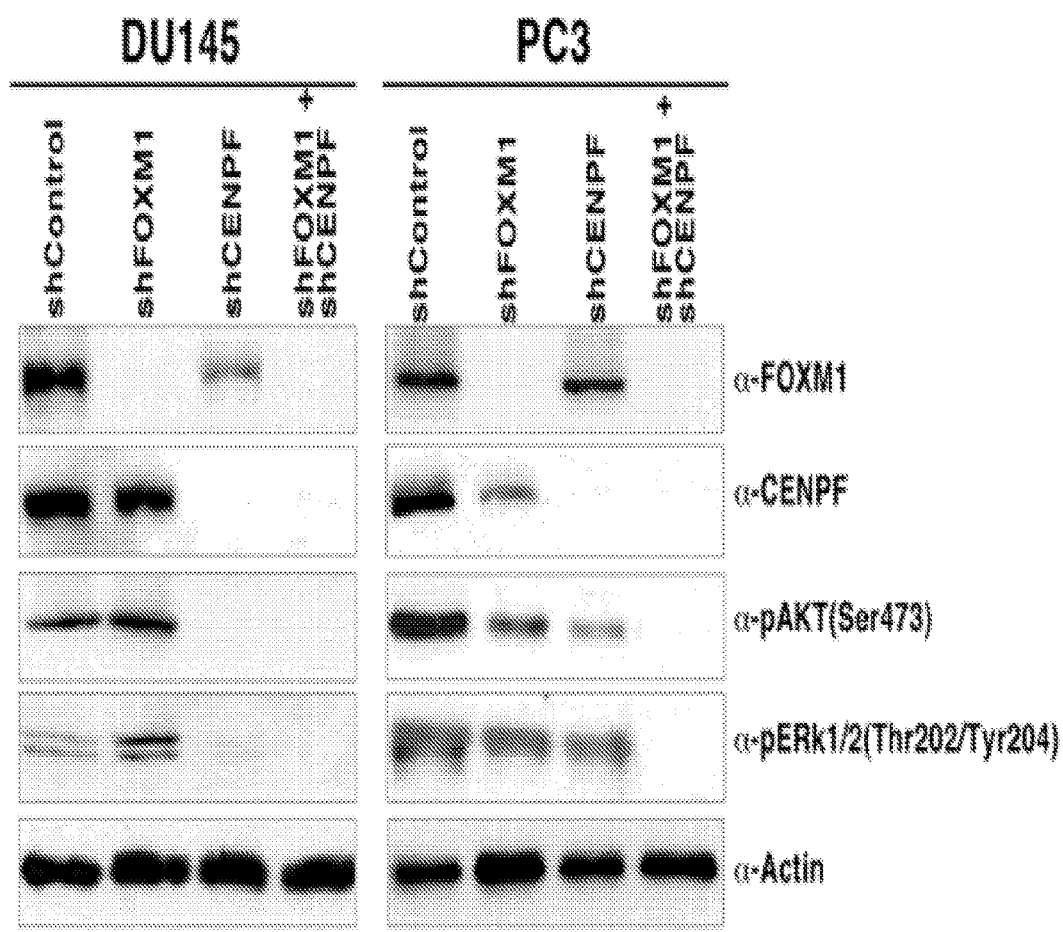

SEQUENCE LISTING

```
<160> NUMBER OF SEQ ID NOS: 56

<210> SEQ ID NO 1
<211> LENGTH: 19
<212> TYPE: DNA
<213> ORGANISM: Artificial Sequence
<220> FEATURE:
<223> OTHER INFORMATION: Synthetic: FOXM1 shRNA#1

<400> SEQUENCE: 1
ataattagag gataatttg                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic: FOXM1 shRNA#2

<400> SEQUENCE: 2
tgatggtcat gttccggcg                                                  19

<210> SEQ ID NO 3
<211> LENGTH: 19
<212> TYPE: DNA
<213> ORGANISM: Artificial Sequence
<220> FEATURE:
```

<223> OTHER INFORMATION: Synthetic: CENPFshRNA#1

<400> SEQUENCE: 3
atctgattca ctcagtctg                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic: CENPF shRNA#2

<400> SEQUENCE: 4
tttcttccaa cagtaactg                                                    19

<210> SEQ ID NO 5
<211> LENGTH: 21
<212> TYPE: DNA
<213> ORGANISM: Artificial Sequence
<220> FEATURE:
<223> OTHER INFORMATION: Synthetic: FOXM1 forward primer

<400> SEQUENCE: 5
cgtcggccac tgattctcaa a                                                 21

<210> SEQ ID NO 6
<211> LENGTH: 20
<212> TYPE: DNA
<213> ORGANISM: Artificial Sequence
<220> FEATURE:
<223> OTHER INFORMATION: Synthetic: CENPF forward primer

<400> SEQUENCE: 6
ctctcccgtc aacagcgttc                                                   20

<210> SEQ ID NO 7
<211> LENGTH: 21
<212> TYPE: DNA
<213> ORGANISM: Artificial Sequence
<220> FEATURE:
<223> OTHER INFORMATION: Synthetic: BRCA1 forward primer

<400> SEQUENCE: 7
gctcgtggaa gatttcggtg t                                                 21

<210> SEQ ID NO 8
<211> LENGTH: 22
<212> TYPE: DNA
<213> ORGANISM: Artificial Sequence
<220> FEATURE:
<223> OTHER INFORMATION: Synthetic: BUB1 forward primer

<400> SEQUENCE: 8
aaatgaccct ctggatgttt gg                                                22

<210> SEQ ID NO 9
<211> LENGTH: 21
<212> TYPE: DNA
<213> ORGANISM: Artificial Sequence
<220> FEATURE:
<223> OTHER INFORMATION: Synthetic: KI67 forward primer

<400> SEQUENCE: 9
gggccaatcc tgtcgcttaa t                                                 21

```
<210> SEQ ID NO 10
<211> LENGTH: 19
<212> TYPE: DNA
<213> ORGANISM: Artificial Sequence
<220> FEATURE:
<223> OTHER INFORMATION: Synthetic: CYCLIN A2 forward primer

<400> SEQUENCE: 10
cgctggcggt actgaagtc                                              19

<210> SEQ ID NO 11
<211> LENGTH: 21
<212> TYPE: DNA
<213> ORGANISM: Artificial Sequence
<220> FEATURE:
<223> OTHER INFORMATION: Synthetic: TIMELESS forward primer

<400> SEQUENCE: 11
tctgatccgc tatttgaggc a                                           21

<210> SEQ ID NO 12
<211> LENGTH: 19
<212> TYPE: DNA
<213> ORGANISM: Artificial Sequence
<220> FEATURE:
<223> OTHER INFORMATION: Synthetic: CDC25 forward primer

<400> SEQUENCE: 12
acgcacctat ccctgtctc                                              19

<210> SEQ ID NO 13
<211> LENGTH: 22
<212> TYPE: DNA
<213> ORGANISM: Artificial Sequence
<220> FEATURE:
<223> OTHER INFORMATION: Synthetic: TRIP13 forward primer

<400> SEQUENCE: 13
actgttgcac ttcacatttt cc                                          22

<210> SEQ ID NO 14
<211> LENGTH: 21
<212> TYPE: DNA
<213> ORGANISM: Artificial Sequence
<220> FEATURE:
<223> OTHER INFORMATION: Synthetic: PLK1 forward primer

<400> SEQUENCE: 14
aaagagatcc cggaggtcct a                                           21

<210> SEQ ID NO 15
<211> LENGTH: 21
<212> TYPE: DNA
<213> ORGANISM: Artificial Sequence
<220> FEATURE:
<223> OTHER INFORMATION: Synthetic: HMMR forward primer

<400> SEQUENCE: 15
atgatggcta agcaagaagg c                                           21

<210> SEQ ID NO 16
<211> LENGTH: 19
<212> TYPE: DNA
<213> ORGANISM: Artificial Sequence
<220> FEATURE:
<223> OTHER INFORMATION: Synthetic: MYBL2 forward primer
```

<400> SEQUENCE: 16
ccggagcaga gggatagca                                                      19

<210> SEQ ID NO 17
<211> LENGTH: 23
<212> TYPE: DNA
<213> ORGANISM: Artificial Sequence
<220> FEATURE:
<223> OTHER INFORMATION: Synthetic: ACTIN forward primer

<400> SEQUENCE: 17
gtctgccttg gtagtggata atg                                                 23

<210> SEQ ID NO 18
<211> LENGTH: 21
<212> TYPE: DNA
<213> ORGANISM: Artificial Sequence
<220> FEATURE:
<223> OTHER INFORMATION: Synthetic: GAPDH forward primer

<400> SEQUENCE: 18
tgtgggcatc aatggatttg g                                                   21

<210> SEQ ID NO 19
<211> LENGTH: 21
<212> TYPE: DNA
<213> ORGANISM: Artificial Sequence
<220> FEATURE:
<223> OTHER INFORMATION: Synthetic: FOXM1 reverse primer

<400> SEQUENCE: 19
ggcaggggat ctcttaggtt c                                                   21

<210> SEQ ID NO 20
<211> LENGTH: 22
<212> TYPE: DNA
<213> ORGANISM: Artificial Sequence
<220> FEATURE:
<223> OTHER INFORMATION: Synthetic: CENPF reverse primer

<400> SEQUENCE: 20
gttgtgcata ttcttggctt gc                                                  22

<210> SEQ ID NO 21
<211> LENGTH: 23
<212> TYPE: DNA
<213> ORGANISM: Artificial Sequence
<220> FEATURE:
<223> OTHER INFORMATION: Synthetic: BRCA1 reverse primer

<400> SEQUENCE: 21
tcatcaatca cggacgtatc atc                                                 23

<210> SEQ ID NO 22
<211> LENGTH: 23
<212> TYPE: DNA
<213> ORGANISM: Artificial Sequence
<220> FEATURE:
<223> OTHER INFORMATION: Synthetic: BUB1 reverse primer

<400> SEQUENCE: 22
gcataaacgc cctaatttaa gcc                                                 23

<210> SEQ ID NO 23
<211> LENGTH: 19

```
<212> TYPE: DNA
<213> ORGANISM: Artificial Sequence
<220> FEATURE:
<223> OTHER INFORMATION: Synthetic: KI67 reverse primer

<400> SEQUENCE: 23
gttatgcgct tgcgaacct                                                19

<210> SEQ ID NO 24
<211> LENGTH: 21
<212> TYPE: DNA
<213> ORGANISM: Artificial Sequence
<220> FEATURE:
<223> OTHER INFORMATION: Synthetic: CYCLIN A2 reverse primer

<400> SEQUENCE: 24
gaggaacggt gacatgctca t                                             21

<210> SEQ ID NO 25
<211> LENGTH: 20
<212> TYPE: DNA
<213> ORGANISM: Artificial Sequence
<220> FEATURE:
<223> OTHER INFORMATION: Synthetic: TIMELESS reverse primer

<400> SEQUENCE: 25
ggcagaaggt cgctctgtag                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic: CDC25 reverse primer

<400> SEQUENCE: 26
ctggaagcgt ctgatggcaa                                               20

<210> SEQ ID NO 27
<211> LENGTH: 21
<212> TYPE: DNA
<213> ORGANISM: Artificial Sequence
<220> FEATURE:
<223> OTHER INFORMATION: Synthetic: TRIP13 reverse primer

<400> SEQUENCE: 27
tcgaggagat gggatttgac t                                             21

<210> SEQ ID NO 28
<211> LENGTH: 22
<212> TYPE: DNA
<213> ORGANISM: Artificial Sequence
<220> FEATURE:
<223> OTHER INFORMATION: Synthetic: PLK1 reverse primer

<400> SEQUENCE: 28
ggctgcggtg aatggatatt tc                                            22

<210> SEQ ID NO 29
<211> LENGTH: 22
<212> TYPE: DNA
<213> ORGANISM: Artificial Sequence
<220> FEATURE:
<223> OTHER INFORMATION: Synthetic: HMMR reverse primer

<400> SEQUENCE: 29
```
tttcccttga gactcttcga ga                                        22

<210> SEQ ID NO 30
<211> LENGTH: 20
<212> TYPE: DNA
<213> ORGANISM: Artificial Sequence
<220> FEATURE:
<223> OTHER INFORMATION: Synthetic: MYBL2 reverse primer

<400> SEQUENCE: 30
cagtgcggtt agggaagtgg                                           20

<210> SEQ ID NO 31
<211> LENGTH: 20
<212> TYPE: DNA
<213> ORGANISM: Artificial Sequence
<220> FEATURE:
<223> OTHER INFORMATION: Synthetic: ACTIN reverse primer

<400> SEQUENCE: 31
tcgaggacgc cctatcatgg                                           20

<210> SEQ ID NO 32
<211> LENGTH: 22
<212> TYPE: DNA
<213> ORGANISM: Artificial Sequence
<220> FEATURE:
<223> OTHER INFORMATION: Synthetic: GAPDH reverse primer

<400> SEQUENCE: 32
acaccatgta ttccgggtca at                                        22

<210> SEQ ID NO 33
<211> LENGTH: 20
<212> TYPE: DNA
<213> ORGANISM: Artificial Sequence
<220> FEATURE:
<223> OTHER INFORMATION: Synthetic: FOXM1 forward primer

<400> SEQUENCE: 33
ccggagcttt cagtttgttc                                           20

<210> SEQ ID NO 34
<211> LENGTH: 21
<212> TYPE: DNA
<213> ORGANISM: Artificial Sequence
<220> FEATURE:
<223> OTHER INFORMATION: Synthetic: CENPF forward primer

<400> SEQUENCE: 34
cacctccagt agagggctt g                                          21

<210> SEQ ID NO 35
<211> LENGTH: 20
<212> TYPE: DNA
<213> ORGANISM: Artificial Sequence
<220> FEATURE:
<223> OTHER INFORMATION: Synthetic: AURKA forward primer

<400> SEQUENCE: 35
aggacaaggg ccttcttagg                                           20

<210> SEQ ID NO 36
<211> LENGTH: 20
<212> TYPE: DNA
<213> ORGANISM: Artificial Sequence

```
<220> FEATURE:
<223> OTHER INFORMATION: Synthetic: AURKB forward primer

<400> SEQUENCE: 36
ggggtccaag gcactgctac                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic: BIRC5 forward primer

<400> SEQUENCE: 37
ccattaaccg ccagatttga                                              20

<210> SEQ ID NO 38
<211> LENGTH: 22
<212> TYPE: DNA
<213> ORGANISM: Artificial Sequence
<220> FEATURE:
<223> OTHER INFORMATION: Synthetic: CDC25 forward primer

<400> SEQUENCE: 38
aagagcccat cagttccgct tg                                           22

<210> SEQ ID NO 39
<211> LENGTH: 20
<212> TYPE: DNA
<213> ORGANISM: Artificial Sequence
<220> FEATURE:
<223> OTHER INFORMATION: Synthetic: PLK1 forward primer

<400> SEQUENCE: 39
ccagagggag aagatgtcca                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic: CYCLIN B2 forward primer

<400> SEQUENCE: 40
tcctttgccg aaagctagag                                              20

<210> SEQ ID NO 41
<211> LENGTH: 18
<212> TYPE: DNA
<213> ORGANISM: Artificial Sequence
<220> FEATURE:
<223> OTHER INFORMATION: Synthetic: FOXM1 reverse primer

<400> SEQUENCE: 41
cggaatgccg agacaagg                                                18

<210> SEQ ID NO 42
<211> LENGTH: 20
<212> TYPE: DNA
<213> ORGANISM: Artificial Sequence
<220> FEATURE:
<223> OTHER INFORMATION: Synthetic: CENPF reverse primer

<400> SEQUENCE: 42
tacctccacg cctattggtc                                              20
```

<210> SEQ ID NO 43
<211> LENGTH: 20
<212> TYPE: DNA
<213> ORGANISM: Artificial Sequence
<220> FEATURE:
<223> OTHER INFORMATION: Synthetic: AURKA reverse primer

<400> SEQUENCE: 43
tagtgggtgg ggagacagac                                                    20

<210> SEQ ID NO 44
<211> LENGTH: 20
<212> TYPE: DNA
<213> ORGANISM: Artificial Sequence
<220> FEATURE:
<223> OTHER INFORMATION: Synthetic: AURKB reverse primer

<400> SEQUENCE: 44
ggggcgggag atttgaaaag                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic: BIRC5 reverse primer

<400> SEQUENCE: 45
tgtagagatg cggtggtcct                                                    20

<210> SEQ ID NO 46
<211> LENGTH: 22
<212> TYPE: DNA
<213> ORGANISM: Artificial Sequence
<220> FEATURE:
<223> OTHER INFORMATION: Synthetic: CDC25 reverse primer

<400> SEQUENCE: 46
cccattttac agacctggac gc                                                 22

<210> SEQ ID NO 47
<211> LENGTH: 20
<212> TYPE: DNA
<213> ORGANISM: Artificial Sequence
<220> FEATURE:
<223> OTHER INFORMATION: Synthetic: PLK1 reverse primer

<400> SEQUENCE: 47
gtcgttgtcc tcgaaaaagc                                                    20

<210> SEQ ID NO 48
<211> LENGTH: 21
<212> TYPE: DNA
<213> ORGANISM: Artificial Sequence
<220> FEATURE:
<223> OTHER INFORMATION: Synthetic: CYCLIN B2 reverse primer

<400> SEQUENCE: 48
gcaactgcca atctgaaaaa g                                                  21

<210> SEQ ID NO 49
<211> LENGTH: 3506
<212> TYPE: DNA
<213> ORGANISM: Homo sapiens
<220> FEATURE:
<221> NAME/KEY: misc_feature
<223> OTHER INFORMATION: Human nucleic acid sequence of forkhead box M1
      (FOXM1)

<400> SEQUENCE: 49

| | | | | | |
|---|---|---|---|---|---|
| tttcaaacag | cggaacaaac | tgaaagctcc | ggtgccagac | cccaccccg | gccccggccc | 60 |
| gggacccct | cccctcccgg | gatccccgg | ggttcccacc | ccgcccgcac | cgccggggac | 120 |
| ccggccggtc | cggcgcgagc | ccccgtccgg | ggccctggct | cggccccag | gttggaggag | 180 |
| cccggagccc | gccttcggag | ctacggccta | acggcggcgg | cgactgcagt | ctggagggtc | 240 |
| cacacttgtg | attctcaatg | gagagtgaaa | acgcagattc | ataatgaaaa | ctagccccg | 300 |
| tcggccactg | attctcaaaa | gacggaggct | gccccttcct | gttcaaaatg | ccccaagtga | 360 |
| aacatcagag | gaggaaccta | agagatcccc | tgcccaacag | gagtctaatc | aagcagaggc | 420 |
| ctccaaggaa | gtggcagagt | ccaactcttg | caagtttcca | gctgggatca | agattattaa | 480 |
| ccacccacc | atgcccaaca | cgcaagtagt | ggccatcccc | aacaatgcta | atattcacag | 540 |
| catcatcaca | gcactgactg | ccaagggaaa | agagagtggc | agtagtgggc | caacaaatt | 600 |
| catcctcatc | agctgtgggg | gagccccaac | tcagcctcca | ggactccggc | tcaaaccca | 660 |
| aaccagctat | gatgccaaaa | ggacagaagt | gaccctggag | accttgggac | caaaacctgc | 720 |
| agctagggat | gtgaatcttc | ctagaccacc | tggagccctt | tgcgagcaga | acgggagac | 780 |
| ctgtgatggt | gaggcagcag | gctgcactat | caacaatagc | ctatccaaca | tccagtggct | 840 |
| tcgaaagatg | agttctgatg | gactgggctc | ccgcagcatc | aagcaagaga | tggaggaaaa | 900 |
| ggagaattgt | cacctggagc | agcgacaggt | taaggttgag | gagccttcga | gaccatcagc | 960 |
| gtcctggcag | aactctgtgt | ctgagcggcc | accctactct | tacatggcca | tgatacaatt | 1020 |
| cgccatcaac | agcactgaga | ggaagcgcat | gactttgaaa | gacatctata | cgtggattga | 1080 |
| ggaccacttt | ccctactta | agcacattgc | caagccaggc | tggaagaact | ccatccgcca | 1140 |
| caacctttcc | ctgcacgaca | tgtttgtccg | ggagacgtct | gccaatgcca | aggtctcctt | 1200 |
| ctggaccatt | cacccagtg | ccaaccgcta | cttgacattg | gaccaggtgt | ttaagcagca | 1260 |
| gcagaaacga | ccgaatccag | agctccgccg | gaacatgacc | atcaaaaccg | aactccccct | 1320 |
| gggcgcacgg | cggaagatga | agccactgct | accacgggtc | agctcatacc | tggtacctat | 1380 |
| ccagttcccg | gtgaaccagt | cactggtgtt | gcagccctcg | gtgaaggtgc | cattgcccct | 1440 |
| ggcggcttcc | ctcatgagct | cagagcttgc | ccgccatagc | aagcgagtcc | gcattgcccc | 1500 |
| caaggtgctg | ctagctgagg | aggggatagc | tcctctttct | tctgcaggac | agggaaaga | 1560 |
| ggagaaactc | ctgtttggag | aagggttttc | tcctttgctt | ccagttcaga | ctatcaagga | 1620 |
| ggaagaaatc | cagcctgggg | aggaaatgcc | acacttagcg | agacccatca | aagtggagag | 1680 |
| cccctccttg | gaagagtggc | cctccccggc | cccatctttc | aaagaggaat | catctcactc | 1740 |
| ctgggaggat | tcgtcccaat | ctcccacccc | aagacccaag | aagtcctaca | gtgggcttag | 1800 |
| gtccccaacc | cggtgtgtct | cggaaatgct | tgtgattcaa | cacagggaga | ggagggagag | 1860 |
| gagccggtct | cggaggaaac | agcatctact | gcctccctgt | gtggatgagc | cggagctgct | 1920 |
| cttctcagag | gggcccagta | cttcccgctg | ggccgcagag | ctcccgttcc | cagcagactc | 1980 |
| ctctgaccct | gcctcccagc | tcagctactc | ccaggaagtg | ggaggacctt | ttaagacacc | 2040 |
| cattaaggaa | acgctgccca | tctcctccac | cccgagcaaa | tctgtcctcc | ccagaacccc | 2100 |
| tgaatcctgg | aggctcacgc | ccccagccaa | agtaggggga | ctggatttca | gcccagtaca | 2160 |
| aacctcccag | ggtgcctctg | accccttgcc | tgaccccctg | gggctgatgg | atctcagcac | 2220 |

```
cactcccttg caaagtgctc ccccccttga atcaccgcaa aggctcctca gttcagaacc   2280
cttagacctc atctccgtcc cctttggcaa ctcttctccc tcagatatag acgtccccaa   2340
gccaggctcc ccggagccac aggtttctgg ccttgcagcc aatcgttctc tgacagaagg   2400
cctggtcctg gacacaatga atgacagcct cagcaagatc ctgctggaca tcagcttttcc  2460
tggcctggac gaggacccac tgggccctga caacatcaac tggtcccagt ttattcctga   2520
gctacagtag agccctgccc ttgccccgtt gctcaagctg tccaccatcc cgggcactcc   2580
aaggctcagt gcaccccaag cctctgagtg aggacagcag gcagggactg ttctgctcct   2640
catagctccc tgctgcctga ttatgcaaaa gtagcagtca caccctagcc actgctggga   2700
ccttgtgttc cccaagagta tctgattcct ctgctgtccc tgccaggagc tgaagggtgg   2760
gaacaacaaa ggcaatggtg aaaagagatt aggaaccccc cagcctgttt ccattctctg   2820
cccagcagtc tcttaccttc cctgatcttt gcagggtggt ccgtgtaaat agtataaatt   2880
ctccaaatta tcctctaatt ataaatgtaa gcttatttcc ttagatcatt atccagagac   2940
tgccagaagg tgggtaggat gacctggggt ttcaattgac ttctgttcct tgcttttagt   3000
tttgatagaa gggaagacct gcagtgcacg gtttcttcca ggctgaggta cctggatctt   3060
gggttcttca ctgcagggac ccagacaagt ggatctgctt gccagagtcc ttttttgcccc  3120
tccctgccac ctccccgtgt ttccaagtca gctttcctgc aagaagaaat cctggttaaa   3180
aaagtctttt gtattgggtc aggagttgaa tttggggtgg gaggatggat gcaactgaag   3240
cagagtgtgg gtgcccagat gtgcgctatt agatgtttct ctgataatgt ccccaatcat   3300
accagggaga ctggcattga cgagaactca ggtggaggct tgagaaggcc gaagggccc    3360
ctgacctgcc tggcttcctt agcttgcccc tcagctttgc aaagagccac cctaggcccc   3420
agctgaccgc atgggtgtga gccagcttga gaacactaac tactcaataa aagcgaaggt   3480
ggacatgaaa aaaaaaaaa aaaaaa                                         3506
```

<210> SEQ ID NO 50
<211> LENGTH: 748
<212> TYPE: PRT
<213> ORGANISM: Homo sapiens
<220> FEATURE:
<221> NAME/KEY: misc_feature
<223> OTHER INFORMATION: Human forkhead box protein M1 isoform 4

<400> SEQUENCE: 50

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125
```

```
Tyr Asp Ala Lys Arg Thr Glu Val Thr Leu Glu Thr Leu Gly Pro Lys
    130                 135                 140

Pro Ala Arg Asp Val Asn Leu Pro Arg Pro Pro Gly Ala Leu Cys
145                 150                 155                 160

Glu Gln Lys Arg Glu Thr Cys Asp Gly Glu Ala Ala Gly Cys Thr Ile
                165                 170                 175

Asn Asn Ser Leu Ser Asn Ile Gln Trp Leu Arg Lys Met Ser Ser Asp
            180                 185                 190

Gly Leu Gly Ser Arg Ser Ile Lys Gln Glu Met Glu Glu Lys Glu Asn
        195                 200                 205

Cys His Leu Glu Gln Arg Gln Val Lys Val Glu Glu Pro Ser Arg Pro
    210                 215                 220

Ser Ala Ser Trp Gln Asn Ser Val Ser Glu Arg Pro Pro Tyr Ser Tyr
225                 230                 235                 240

Met Ala Met Ile Gln Phe Ala Ile Asn Ser Thr Glu Arg Lys Arg Met
                245                 250                 255

Thr Leu Lys Asp Ile Tyr Thr Trp Ile Glu Asp His Phe Pro Tyr Phe
            260                 265                 270

Lys His Ile Ala Lys Pro Gly Trp Lys Asn Ser Ile Arg His Asn Leu
        275                 280                 285

Ser Leu His Asp Met Phe Val Arg Glu Thr Ser Ala Asn Gly Lys Val
    290                 295                 300

Ser Phe Trp Thr Ile His Pro Ser Ala Asn Arg Tyr Leu Thr Leu Asp
305                 310                 315                 320

Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
        355                 360                 365

Pro Val Asn Gln Ser Leu Val Leu Gln Pro Ser Val Lys Val Pro Leu
    370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
        435                 440                 445

Ile Gln Pro Gly Glu Glu Met Pro His Leu Ala Arg Pro Ile Lys Val
    450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
    530                 535                 540

Leu Leu Phe Ser Glu Gly Pro Ser Thr Ser Arg Trp Ala Ala Glu Leu
```

```
545                 550                 555                 560
Pro Phe Pro Ala Asp Ser Ser Asp Pro Ala Ser Gln Leu Ser Tyr Ser
                565                 570                 575
Gln Glu Val Gly Gly Pro Phe Lys Thr Pro Ile Lys Glu Thr Leu Pro
                580                 585                 590
Ile Ser Ser Thr Pro Ser Lys Ser Val Leu Pro Arg Thr Pro Glu Ser
                595                 600                 605
Trp Arg Leu Thr Pro Pro Ala Lys Val Gly Gly Leu Asp Phe Ser Pro
            610                 615                 620
Val Gln Thr Ser Gln Gly Ala Ser Asp Pro Leu Pro Asp Pro Leu Gly
625                 630                 635                 640
Leu Met Asp Leu Ser Thr Thr Pro Leu Gln Ser Ala Pro Pro Leu Glu
                645                 650                 655
Ser Pro Gln Arg Leu Leu Ser Ser Glu Pro Leu Asp Leu Ile Ser Val
                660                 665                 670
Pro Phe Gly Asn Ser Ser Pro Ser Asp Ile Asp Val Pro Lys Pro Gly
                675                 680                 685
Ser Pro Glu Pro Gln Val Ser Gly Leu Ala Ala Asn Arg Ser Leu Thr
            690                 695                 700
Glu Gly Leu Val Leu Asp Thr Met Asn Asp Ser Leu Ser Lys Ile Leu
705                 710                 715                 720
Leu Asp Ile Ser Phe Pro Gly Leu Asp Glu Asp Pro Leu Gly Pro Asp
                725                 730                 735
Asn Ile Asn Trp Ser Gln Phe Ile Pro Glu Leu Gln
                740                 745

<210> SEQ ID NO 51
<211> LENGTH: 4391
<212> TYPE: DNA
<213> ORGANISM: Mus musculus
<220> FEATURE:
<221> NAME/KEY: misc_feature
<223> OTHER INFORMATION: Mus musculus forkhead box M1 (Foxm1), mRNA

<400> SEQUENCE: 51
gcgggaccca cccccggccc gggctccccc gtcacccgc cccgggctcc caccccggcc       60
gtcccgccgg acccgccgc ccgggcccgg ctcggccccg cgtggagcag acgcggcctg      120
tgagggtcaa agcttgcgat tctcgatgga gagcgaaagc acagcctcac gatgagaacc      180 agccccgcc ggccactgat tctcaaaaga cggaggctgc ccttcctgt ccagaatgcc      240 ccgagtgaaa catcagagga agaagcaaag aggtccctg cccagccgga gcctgctcca      300
gcacaggcct cccaagaggt ggcagagtcc agctcttgca aatttccagc cggaatcaag      360
attatcaacc accccaccac gcccaacaca caagtggtgg ccatcccag caacgctgat      420 atccagagca tcatcacagc gctaactgcc aaagggaagg agagcggcag cagcgggccc      480
aaccggttca tcctcatcag ctctgggggg ccctcctctc acccttccca gcctcaagcc      540
cacagcagcc gggattccaa gagagcagag gtgatcacgg agacgttggg accgaagcca      600
gcagctaagg gtgtgcctgt tcccaagcct cctggagccc ctccaaggca agacaggag      660 agctatgctg gtggtgaggc ggcaggctgc acgctggaca cagcttaac caatatccag      720 tggcttggaa agatgagttc tgacgggctg ggccctgca gcgttaagca ggaactggaa      780
gagaaggaga attgtcacct ggagcagaat cgggttaagg ttgaggagcc ctcaggagtg      840
tcaacatctt ggcaggactc tgtgtctgag aggccaccct actcttatat ggccatgata      900
```

```
cagtttgcca tcaacagcac tgagagaaag cgcatgacct tgaaggacat ctacacttgg    960
attgaggacc acttccctta ctttaagcac attgccaagc caggctggaa gaactctatt   1020
cgtcacaacc tttctctcca tgacatgttt gttcgagaga catctgccaa tggcaaggtc   1080
tccttctgga ccattcaccc aagtgccaat cgctacttga cattggacca agtgtttaag   1140
ccactggaac cagggtctcc acaatcgccc gagcacttgg aatcacagca gaaacgaccc   1200
aatcctgagc tccatagaaa tgtgaccatc aaaactgaaa tcccactggg cgcacggcga   1260
aagatgaagc ctctgctccc tcgggttagc tcatacctgg tgcccatcca gttcccagtg   1320
aaccagtccc tggtgttaca gccctcagtg aaggttccct gcctctggc agcatcgctt    1380 atgagctcag agctcgcccg tcatagcaag cgagtccgca ttgcacccaa ggtgttgcta   1440
tccagtgaag aatagccccc gcttcctgcc acagaaccac cgaaggagga gaaaccctg    1500 cttggagggg aagggctgtt gccttactt cctattcagt ccattaagga agaagaaatg    1560
cagcctgagg aggacatagc acacttagag aggcctatca agtggagag ccctcccttg    1620 gaagagtggc cctctccgtg tgcatcgctc aaagaggagc tatccaactc ctgggaagat   1680
tcttcctgct ctcctacccc aaagcccaag aagtcctact gtgggctcaa gtccccaacg   1740
cgctgtgtct cagaaatgct ggtgactaag cgaagagaga aaagggaggt gagccgatcc   1800
cggaggaaac agcaccttca gccccctgt ctggatgagc ctgacctgtt cttctcagag    1860
gactccagca catttcggcc agccgtggag ctcctggcgg agtcttccga gcctgcaccc   1920
cacctcagct gccctcagga gagggagga ccttt caaga ccccccatcaa ggagacattg   1980 cctgtctcct ccactcctag caagtctgtg ctctctagag accctgagtc ctggaggctc   2040
acacctccag ccaaagttgg ggggttagat tcagcccag tacgaacccc ccagggtgcc    2100
tttggccttc tgcctgactc actggggttg atggagctga ataccacccc tttgaaaagt   2160
ggtcctctct ttgactcgcc ccgggagctc ctcaactcag agcctttga cctggcctct    2220 gaccccttcg gcagccctcc accaccacat gtggaaggcc caagcctgg ctcccccgag    2280 ctgcagattc ccagccttc agccaaccgt tctctcacag aaggccttgt cctggacaca    2340
atgaatgata gcctcagcaa gatccttcta gacatcagtt tccctggcct ggaggaggac   2400
cctctgggcc ctgacaacat caactggtct cagttcatcc cttagctgcg atagaggcaa   2460
ggccttgccc ctgccactca agccgcctgc tatcctggca cttgtgtggc tcagggtacc   2520
ccaagccgtc tgagggaagc tagcaggcaa gggctgagct gtgccctttg acctaattat   2580
gtcaagatga tagccgcatc taagccacac caggacctat gcaagcagta ggatccccca   2640
gagtccgagt cctccactcc ctgctggcaa gtgaagtggg tgtgacgagc catgaggacc   2700
aggaagtgcc cattagtcac tcggtgctcc tggcagggta acccttataa atggtgtcag   2760
ctccccaagt tgtcctgtaa ctataaatgt aagcgtattt ccttagctca ttatccagag   2820
atggccagga tggggagagg gacgggttg cactttgctt ctgcttgtgg cctctggggg    2880
aaggacctgc agtgcagtct ctccacactg tgggttctgc tataggcttc tagagataca   2940
ggttgccgtg ccaggatcct gcttactgcc cttctcgc agctccccaa gtctccaagt    3000
cagtggtact gcatgaagaa atcctgctgt gaaagcctat tggattcggg tgtagggaga   3060
tgggtgtgcc tgaagcaaaa gcatgggtac tcacaggagt cctattaggt gtttctctga   3120
tagtgttccc aatcatgcca gggagtctac cactgagatc tcaggctgag gcctgagaag   3180
gagaaagtga cccctcactt gcctggcttc cttagcttgc tcctgagctt tgcaaaaaac   3240
caccctagac cccactctac aagctacaga acaacactac tgtaactacc tactaaataa   3300
```

```
agcccgtggc actggtcttg gaattgagcg agaggtggag cctggggtg atgggcaagg    3360
cctgccctg ctgcatgggc cttccacaga tgctctctcc cgcacccttc ttggactctg    3420
aggttgccag ctttgtctgt tgcgatgatt catatctata atctcagcct ttgagaggta    3480
gaggctggag gatcagccct ctatgctaca tgagatcctg ccaacagagt ccagttccca    3540
ctgttccctg ccctgcccac ctcttccttg ccaccccaga ccttgttcca tgggaccaga    3600
ctctgactta ggtccttgtt gatcccttgg taacaacagc agttatagtc ctccaattcc    3660
ctcccattcc attcagtatt caggcctgaa agccgaaact gttgtaggtg tctcattacc    3720
acctctatcc cagctccaag cccaggagcc agccccttc ctgctcctga gccttcccag    3780
gcaaggctct cgctcagcag ctcctgttac caagtttgta accagaactg acagcgaaaa    3840
gcatcaggga ctgaggagcc tcccaggaca ggcaagggcc tcctcccagc agcaccagtc    3900
aggaagcatc accatagcaa ccctagcagc aaacaatggt accagaaagg ctttcctcc    3960
aaagccgcct ctcctggctc tgtggctcag aggaagaatg ccaacatcc cgaagaaaac    4020
atccctccaa aagtcaagcc tgagccaagt atctcgtacc agggagcctt tcctgaaggt    4080
agagtggggc ccaacaacgc agccagcctt tcaggttgtc ctgagcagta gtctctggta    4140
cataagccag tttctgcttt catcctgtgg taccctaagt tggagctcag aacagaaagg    4200
agaagcctgg gcaacaggtt gaagaggcct tatctaaagg acttgggatc agaaatgtgc    4260
ttagctttgg gatttacttt tggatttttgg agtatgtgta tgtatgtcaa actatgttgg    4320
gcaaggaccc caaacttaat ataaaattcc tttgtttcat atgtaaaaaa aaaaaaaaaa    4380
aaaaaaaaaa a                                                        4391
```

<210> SEQ ID NO 52
<211> LENGTH: 757
<212> TYPE: PRT
<213> ORGANISM: Mus musculus
<220> FEATURE:
<221> NAME/KEY: misc_feature
<223> OTHER INFORMATION: Mus musculus forkhead box protein M1

<400> SEQUENCE: 52

```
Met Arg Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Ala
            20                  25                  30

Lys Arg Ser Pro Ala Gln Pro Glu Pro Ala Pro Ala Gln Ala Ser Gln
        35                  40                  45

Glu Val Ala Glu Ser Ser Ser Cys Lys Phe Pro Ala Gly Ile Lys Ile
    50                  55                  60

Ile Asn His Pro Thr Thr Pro Asn Thr Gln Val Ala Ile Pro Ser
65                  70                  75                  80

Asn Ala Asp Ile Gln Ser Ile Ile Thr Ala Leu Thr Ala Lys Gly Lys
                85                  90                  95

Glu Ser Gly Ser Ser Gly Pro Asn Arg Phe Ile Leu Ile Ser Ser Gly
            100                 105                 110

Gly Pro Ser Ser His Pro Ser Gln Pro Gln Ala His Ser Ser Arg Asp
        115                 120                 125

Ser Lys Arg Ala Glu Val Ile Thr Glu Thr Leu Gly Pro Lys Pro Ala
    130                 135                 140

Ala Lys Gly Val Pro Val Pro Lys Pro Pro Gly Ala Pro Pro Arg Gln
145                 150                 155                 160
```

```
Arg Gln Glu Ser Tyr Ala Gly Gly Glu Ala Ala Gly Cys Thr Leu Asp
            165                 170                 175

Asn Ser Leu Thr Asn Ile Gln Trp Leu Gly Lys Met Ser Ser Asp Gly
        180                 185                 190

Leu Gly Pro Cys Ser Val Lys Gln Glu Leu Glu Glu Lys Glu Asn Cys
            195                 200                 205

His Leu Glu Gln Asn Arg Val Lys Val Glu Glu Pro Ser Gly Val Ser
        210                 215                 220

Thr Ser Trp Gln Asp Ser Val Ser Glu Arg Pro Pro Tyr Ser Tyr Met
225                 230                 235                 240

Ala Met Ile Gln Phe Ala Ile Asn Ser Thr Glu Arg Lys Arg Met Thr
                245                 250                 255

Leu Lys Asp Ile Tyr Thr Trp Ile Glu Asp His Phe Pro Tyr Phe Lys
            260                 265                 270

His Ile Ala Lys Pro Gly Trp Lys Asn Ser Ile Arg His Asn Leu Ser
        275                 280                 285

Leu His Asp Met Phe Val Arg Glu Thr Ser Ala Asn Gly Lys Val Ser
    290                 295                 300

Phe Trp Thr Ile His Pro Ser Ala Asn Arg Tyr Leu Thr Leu Asp Gln
305                 310                 315                 320

Val Phe Lys Pro Leu Glu Pro Gly Ser Pro Gln Ser Pro Glu His Leu
                325                 330                 335

Glu Ser Gln Gln Lys Arg Pro Asn Pro Glu Leu His Arg Asn Val Thr
            340                 345                 350

Ile Lys Thr Glu Ile Pro Leu Gly Ala Arg Arg Lys Met Lys Pro Leu
        355                 360                 365

Leu Pro Arg Val Ser Ser Tyr Leu Val Pro Ile Gln Phe Pro Val Asn
    370                 375                 380

Gln Ser Leu Val Leu Gln Pro Ser Val Lys Val Pro Leu Pro Leu Ala
385                 390                 395                 400

Ala Ser Leu Met Ser Ser Glu Leu Ala Arg His Ser Lys Arg Val Arg
                405                 410                 415

Ile Ala Pro Lys Val Leu Leu Ser Glu Gly Ile Ala Pro Leu Pro
            420                 425                 430

Ala Thr Glu Pro Pro Lys Glu Glu Lys Pro Leu Leu Gly Gly Glu Gly
        435                 440                 445

Leu Leu Pro Leu Leu Pro Ile Gln Ser Ile Lys Glu Glu Met Gln
    450                 455                 460

Pro Glu Glu Asp Ile Ala His Leu Glu Arg Pro Ile Lys Val Glu Ser
465                 470                 475                 480

Pro Pro Leu Glu Glu Trp Pro Ser Pro Cys Ala Ser Leu Lys Glu Glu
                485                 490                 495

Leu Ser Asn Ser Trp Glu Asp Ser Ser Cys Ser Pro Thr Pro Lys Pro
            500                 505                 510

Lys Lys Ser Tyr Cys Gly Leu Lys Ser Pro Thr Arg Cys Val Ser Glu
        515                 520                 525

Met Leu Val Thr Lys Arg Arg Glu Lys Arg Glu Val Ser Arg Ser Arg
    530                 535                 540

Arg Lys Gln His Leu Gln Pro Pro Cys Leu Asp Glu Pro Asp Leu Phe
545                 550                 555                 560

Phe Ser Glu Asp Ser Ser Thr Phe Arg Pro Ala Val Glu Leu Leu Ala
                565                 570                 575
```

```
Glu Ser Ser Glu Pro Ala Pro His Leu Ser Cys Pro Gln Glu Gly
            580                 585                 590

Gly Pro Phe Lys Thr Pro Ile Lys Glu Thr Leu Pro Val Ser Thr
        595                 600                 605

Pro Ser Lys Ser Val Leu Ser Arg Asp Pro Glu Ser Trp Arg Leu Thr
    610                 615                 620

Pro Pro Ala Lys Val Gly Gly Leu Asp Phe Ser Pro Val Arg Thr Pro
625                 630                 635                 640

Gln Gly Ala Phe Gly Leu Leu Pro Asp Ser Leu Gly Leu Met Glu Leu
                645                 650                 655

Asn Thr Thr Pro Leu Lys Ser Gly Pro Leu Phe Asp Ser Pro Arg Glu
            660                 665                 670

Leu Leu Asn Ser Glu Pro Phe Asp Leu Ala Ser Asp Pro Phe Gly Ser
            675                 680                 685

Pro Pro Pro His Val Glu Gly Pro Lys Pro Gly Ser Pro Glu Leu
        690                 695                 700

Gln Ile Pro Ser Leu Ser Ala Asn Arg Ser Leu Thr Glu Gly Leu Val
705                 710                 715                 720

Leu Asp Thr Met Asn Asp Ser Leu Ser Lys Ile Leu Leu Asp Ile Ser
                725                 730                 735

Phe Pro Gly Leu Glu Glu Asp Pro Leu Gly Pro Asp Asn Ile Asn Trp
            740                 745                 750

Ser Gln Phe Ile Pro
        755
```

```
<210> SEQ ID NO 53
<211> LENGTH: 10316
<212> TYPE: DNA
<213> ORGANISM: Homo sapiens
<220> FEATURE:
<221> NAME/KEY: misc_feature
<223> OTHER INFORMATION: Human centromere protein F (CENPF), mRNA

<400> SEQUENCE: 53
gagaccagaa gcgggcgaat tgggcaccgg tggcggctgc gggcagtttg aattagactc    60
tgggctccag ccccgccgaag ccgcgccaga actgtactct ccgagaggtc gttttcccgt   120
ccccgagagc aagtttattt acaaatgttg gagtaataaa gaaggcagaa caaaatgagc   180
tgggctttgg aagaatggaa agaagggctg cctacaagag ctcttcagaa aattcaagag   240
cttgaaggac agcttgacaa actgaagaag gaaaagcagc aaaggcagtt tcagcttgac   300
agtctcgagg ctgcgctgca gaagcaaaaa cagaaggttg aaaatgaaaa accgagggt    360 acaaacctga aagggagaa tcaaagattg atggaaatat gtgaaagtct ggagaaaact   420
aagcagaaga tttctcatga acttcaagtc aaggagtcac aagtgaattt ccaggaagga   480
caactgaatt caggcaaaaa acaaatagaa aaactggaac aggaacttaa aaggtgtaaa   540
tctgagcttg aaagaagcca acaagctgcg cagtctgcag atgtctctct gaatccatgc   600
aatacaccac aaaaaatttt tacaactcca ctaacaccaa gtcaatatta tagtggttcc   660
aagtatgaag atctaaaaga aaatataat aaagaggttg aagaacgaaa aagattagag   720
gcagaggtta aagccttgca ggctaaaaaa gcaagccaga ctcttccaca agccaccatg   780
aatcaccgcg acattgcccg gcatcaggct tcatcatctg tgttctcatg gcagcaagag   840
aagaccccaa gtcatctttc atctaattct caaagaactc aattaggag agatttctct   900 gcatcttact tttctgggga acaagaggtg actccaagtc gatcaacttt gcaaataggg   960
```

```
aaaagagatg ctaatagcag tttctttgac aattctagca gtcctcatct tttggatcaa   1020
ttaaaagcgc agaatcaaga gctaagaaac aagattaatg agttggaact acgcctgcaa   1080
ggacatgaaa aagaaatgaa aggccaagtg aataagtttc aagaactcca actccaactg   1140
gagaaagcaa aagtggaatt aattgaaaaa gagaaagttt tgaacaaatg tagggatgaa   1200
ctagtgagaa caacagcaca atacgaccag gcgtcaacca agtatactgc attggaacaa   1260
aaactgaaaa aattgacgga agatttgagt tgtcagcgac aaaatgcaga aagtgccaga   1320
tgttctctgg aacagaaaat taaggaaaaa gaaaaggagt ttcaagagga gctctcccgt   1380
caacagcgtt ctttccaaac actgaccagg agtgcatcc agatgaaggc cagactcacc    1440
caggagttac agcaagccaa gaatatgcac aacgtcctgc aggctgaact ggataaactc   1500
acatcagtaa agcaacagct agaaaacaat ttggaagagt ttaagcaaaa gttgtgcaga   1560
gctgaacagg cgttccaggc gagtcagatc aaggagaatg agctgaggag aagcatggag   1620
gaaatgaaga aggaaaacaa cctccttaag agtcactctg agcaaaaggc cagagaagtc   1680
tgccacctgg aggcagaact caagaacatc aaacagtgtt taaatcagag ccagaatttt   1740
gcagaagaaa tgaaagcgaa gaatacctct caggaaacca tgttaagaga tcttcaagaa   1800
aaaataaatc agcaagaaaa ctccttgact ttagaaaaac tgaagcttgc tgtggctgat   1860
ctggaaaagc agcgagattg ttctcaagac cttttgaaga aaagagaaca tcacattgaa   1920
caacttaatg ataagttaag caagacagag aaagagtcca aagccttgct gagtgcttta   1980
gagttaaaaa agaaagaata tgaagaattg aaagaagaga aaactctgtt ttcttgttgg   2040
aaaagtgaaa acgaaaaact tttaactcag atggaatcag aaaaggaaaa cttgcagagt   2100
aaaattaatc acttggaaac ttgtctgaag acacagcaaa taaaagtca tgaatacaac    2160 gagagagtaa gaacgctgga gatggacaga gaaaacctaa gtgtcgagat cagaaaacctt  2220 cacaacgtgt tagacagtaa gtcagtggag gtagagaccc agaaactagc ttatatggag   2280
ctacagcaga aagctgagtt ctcagatcag aaacatcaga aggaaataga aaatatgtgt   2340
ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caaagatgct tctctggtga caaatgaaga tcatcagaga   2520 agtctttttgg cttttgatca gcagcctgcc atgcatcatt cctttgcaaa tataattgga   2580
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
cagcgcatta gtaagttaca ggaagacact tctgctcacc agaatgttgt tgctgaaacc   2880
ttaagtgccc ttgagaacaa ggaaaaagag ctgcaacttt taaatgataa ggtagaaact   2940
gagcaggcag agattcaaga attaaaaaag agcaaccatc tacttgaaga ctctctaaag   3000
gagctacaac ttttatccga aaccctaagc ttggagaaga agaaatgag ttccatcatt    3060 tctctaaata aagggaaat tgaagagctg acccaagaga tgggactct aaggaaatt      3120 aatgcatcct taaatcaaga gaagatgaac ttaatccaga aaagtgagag ttttgcaaac   3180
tatatagatg aaagggagaa aagcatttca gagttatctg atcagtacaa gcaagaaaaa   3240
cttattttac tacaaagatg tgaagaaacc ggaaatgcat atgaggatct tagtcaaaaa   3300
tacaaagcag cacaggaaaa gaattctaaa ttagaatgct tgctaaatga atgcactagt   3360
```

```
ctttgtgaaa ataggaaaaa tgagttggaa cagctaaagg aagcatttgc aaaggaacac    3420
caagaattct taacaaaatt agcatttgct gaagaaagaa atcagaatct gatgctagag    3480
ttggagacag tgcagcaagc tctgagatct gagatgacag ataaccaaaa caattctaag    3540
agcgaggctg gtggtttaaa gcaagaaatc atgactttaa aggaagaaca aaacaaaatg    3600
caaaaggaag ttaatgactt attacaagag aatgaacagc tgatgaaggt aatgaagact    3660
aaacatgaat gtcaaaatct agaatcagaa ccaattagga actctgtgaa agaaagagag    3720
agtgagagaa atcaatgtaa ttttaaacct cagatggatc ttgaagttaa agaaatttct    3780
ctagatagtt ataatgcgca gttggtgcaa ttagaagcta tgctaagaaa taaggaatta    3840
aaacttcagg aaagtgagaa ggagaaggag tgcctgcagc atgaattaca gacaattaga    3900
ggagatcttg aaaccagcaa tttgcaagac atgcagtcac aagaaattag tggccttaaa    3960
gactgtgaaa tagatgcgga agaaaagtat atttcagggc ctcatgagtt gtcaacaagt    4020
caaaacgaca atgcacacct tcagtgctct ctgcaaacaa caatgaacaa gctgaatgag    4080
ctagagaaaa tatgtgaaat actgcaggct gaaaagtatg aactcgtaac tgagctgaat    4140
gattcaaggt cagaatgtat cacagcaact aggaaaatgg cagaagaggt agggaaacta    4200
ctaaatgaag ttaaaatatt aaatgatgac agtggtcttc tccatggtga gttagtggaa    4260
gacataccag gaggtgaatt tggtgaacaa ccaaatgaac agcaccctgt gtctttggct    4320
ccattggacg agagtaattc ctacgagcac ttgacattgt cagacaaaga agttcaaatg    4380
cactttgccg aattgcaaga gaaattctta tctttacaaa gtgaacacaa aattttacat    4440
gatcagcact gtcagatgag ctctaaaatg tcagagctgc agacctatgt tgactcatta    4500
aaggccgaaa atttggtctt gtcaacgaat ctgagaaact ttcaaggtga cttggtgaag    4560
gagatgcagc tgggcttgga ggaggggctc gttccatccc tgtcatcctc ttgtgtgcct    4620
gacagctcta gtcttagcag tttgggagac tcctcctttt acagagctct tttagaacag    4680
acaggagata tgtctctttt gagtaattta gaaggggctg tttcagcaaa ccagtgcagt    4740
gtagatgaag tattttgcag cagtctgcag gaggagaatc tgaccaggaa agaaacccct    4800
tcggccccag cgaagggtgt tgaagagctt gagtccctct gtgaggtgta ccggcagtcc    4860
ctcgagaagc tagaagagaa aatgaaaagt caagggatta tgaaaaataa ggaaattcaa    4920
gagctcgagc agttattaag ttctgaaagg caagagcttg actgccttag gaagcagtat    4980
ttgtcagaaa atgaacagtg gcaacagaag ctgacaagcg tgactctgga gatggagtcc    5040
aagttggcgg cagaaaagaa acagacggaa caactgtcac ttgagctgga agtagcacga    5100
ctccagctac aaggtctgga cttaagttct cggtctttgc ttggcatcga cacagaagat    5160
gctattcaag gccgaaatga gagctgtgac atatcaaaag aacatacttc agaaactaca    5220
gaaagaacac caaagcatga tgttcatcag atttgtgata agatgctcca gcaggacctc    5280
aatctagaca ttgagaaaat aactgagact ggtgcagtga acccacagg agagtgctct    5340 ggggaacagt ccccagatac caattatgag cctccagggg aagataaaac ccagggctct    5400
tcagaatgca tttctgaatt gtcattttct ggtcctaatg ctttggtacc tatggatttc    5460
ctggggaatc aggaagatat ccataatctt caactgcggg taaaagagac atcaaatgag    5520
aatttgagat tacttcatgt gatagaggac cgtgacagaa aagttgaaag tttgctaaat    5580
gaaatgaaag aattagactc aaaactccat ttacaggagg tacaactaat gaccaaaatt    5640
gaagcatgca tagaattgga aaaaatagtt ggggaactta agaagaaaa ctcagattta    5700
```

```
agtgaaaaat tggaatattt ttcttgtgat caccaggagt tactccagag agtagaaact   5760
tctgaaggcc tcaattctga tttagaaatg catgcagata aatcatcacg tgaagatatt   5820
ggagataatg tggccaaggt gaatgacagc tggaaggaga gatttcttga tgtggaaaat   5880
gagctgagta ggatcagatc ggagaaagct agcattgagc atgaagccct ctacctggag   5940
gctgacttag aggtagttca aacagagaag ctatgtttag aaaaagacaa tgaaaataag   6000
cagaaggtta ttgtctgcct tgaagaagaa ctctcagtgg tcacaagtga gagaaaccag   6060
cttcgtggag aattagatac tatgtcaaaa aaaaccacgg cactggatca gttgtctgaa   6120
aaaatgaagg agaaaacaca agagcttgag tctcatcaaa gtgagtgtct ccattgcatt   6180
caggtggcag aggcagaggt gaaggaaaag acggaactcc ttcagacttt gtcctctgat   6240
gtgagtgagc tgttaaaaga caaaactcat ctccaggaaa agctgcagag tttggaaaag   6300
gactcacagg cactgtcttt gacaaaatgt gagctggaaa accaaattgc acaactgaat   6360
aaagagaaag aattgcttgt caaggaatct gaaagcctgc aggccagact gagtgaatca   6420
gattatgaaa agctgaatgt ctccaaggcc ttggaggccg cactggtgga gaaaggtgag   6480
ttcgcattga ggctgagctc aacacaggag gaagtgcatc agctgagaag aggcatcgag   6540
aaactgagag ttcgcattga ggccgatgaa aagaagcagc tgcacatcgc agagaaactg   6600
aaagaacgcg agcgggagaa tgattcactt aaggataaag ttgagaacct gaaagggaa   6660 ttgcagatgt cagaagaaaa ccaggagcta gtgattcttg atgccgagaa ttccaaagca   6720
gaagtagaga ctctaaaaac acaaatagaa gagatggcca aagcctgaa agtttttgaa   6780 ttagaccttg tcacgttaag gtctgaaaaa gaaaatctga caaaacaaat acaagaaaaa   6840
caaggtcagt tgtcagaact agacaagtta ctctcttcat ttaaaagtct gttagaagaa   6900
aaggagcaag cagagataca gatcaaagaa gaatctaaaa ctgcagtgga gatgcttcag   6960
aatcagttaa aggagctaaa tgaggcagta gcagccttgt gtggtgacca agaaattatg   7020
aaggccacag aacagagtct agacccacca atagaggaag agcatcagct gagaaatagc   7080
attgaaaagc tgagagcccg cctagaagct gatgaaaaga agcagctctg tgtcttacaa   7140
caactgaagg aaagtgagca tcatgcagat ttacttaagg gtagagtgga gaaccttgaa   7200
agagagctag agatagccag gacaaaccaa gagcatgcag ctcttgaggc agagaattcc   7260
aaaggagagg tagagaccct aaaagcaaaa atagaaggga tgacccaaag tctgagaggt   7320
ctggaattag atgttgttac tataaggtca gaaaaagaaa atctgacaaa tgaattacaa   7380
aaagagcaag agcgaatatc tgaattagaa ataataaatt catcatttga aaatattttg   7440
caagaaaaag agcaagagaa agtacagatg aaagaaaaat caagcactgc catggagatg   7500
cttcaaacac aattaaaaga gctcaatgag agagtggcag ccctgcataa tgaccaagaa   7560
gcctgtaagg ccaaagagca gaatcttagt agtcaagtag agtgtcttga acttgagaag   7620
gctcagttgc tacaaggcct tgatgaggcc aaaaataatt atattgtttt gcaatcttca   7680
gtgaatggcc tcattcaaga agtagaagat ggcaagcaga aactggagaa gaaggatgaa   7740
gaaatcagta gactgaaaaa tcaaattcaa gaccaagagc agcttgtctc taaactgtcc   7800
caggtggaag agagcacca actttggaag gagcaaaact agaactgag aaatctgaca   7860 gtggaattgg agcagaagat ccaagtgcta caatccaaaa atgcctcttt gcaggacaca   7920
ttagaagtgc tgcagagttc ttacaagaat ctagagaatg agcttgaatt gacaaaaatg   7980 gacaaaaatgt cctttgttga aaagtaaac aaaatgactg caaggaaac tgagctgcag   8040 agggaaatgc atgagatggc acagaaaaca gcagagctgc aagaagaact cagtggagag   8100
```

```
aaaaataggc tagctggaga gttgcagtta ctgttggaag aaataaagag cagcaaagat    8160
caattgaagg agctcacact agaaaatagt gaattgaaga agagcctaga ttgcatgcac    8220
aaagaccagg tggaaaagga agggaaagtg agagaggaaa tagctgaata tcagctacgg    8280
cttcatgaag ctgaaaagaa acaccaggct ttgcttttgg acacaaacaa acagtatgaa    8340
gtagaaatcc agacataccg agagaaattg acttctaaag aagaatgtct cagttcacag    8400
aagctggaga tagacctttt aaagtctagt aagaagagc tcaataattc attgaaagct    8460
actactcaga ttttggaaga attgaagaaa accaagatgg acaatctaaa atatgtaaat    8520
cagttgaaga aggaaaatga acgtgcccag gggaaaatga agttgttgat caaatcctgt    8580
aaacagctgg aagaggaaaa ggagatactg cagaaagaac tctctcaact tcaagctgca    8640
caggagaagc agaaaacagg tactgttatg gataccaagg tcgatgaatt aacaactgag    8700
atcaaagaac tgaaagaaac tcttgaagaa aaaaccaagg aggcagatga atacttggat    8760
aagtactgtt ccttgcttat aagccatgaa agttagaga aagctaaaga gatgttagag    8820
acacaagtgg cccatctgtg ttcacagcaa tctaaacaag attcccgagg gtctcctttg    8880
ctaggtccag ttgttccagg accatctcca atcccttctg ttactgaaaa gaggttatca    8940
tctggccaaa ataaagcttc aggcaagagg caaagatcca gtggaatatg ggagaatggt    9000
agaggaccaa cacctgctac cccagagagc ttttctaaaa aaagcaagaa agcagtcatg    9060
agtggtattc accctgcaga agacacggaa ggtactgagt ttgagccaga gggacttcca    9120
gaagttgtaa agaaagggtt tgctgacatc ccgacaggaa agactagccc atatatcctg    9180
cgaagaacaa ccatggcaac tcggaccagc ccccgcctgg ctgcacagaa gttagcgcta    9240
tccccactga gtctcggcaa agaaaatctt gcagagtcct ccaaaccaac agctggtggc    9300
agcagatcac aaaaggtcaa agttgctcag cggagcccag tagattcagg caccatcctc    9360
cgagaaccca ccacgaaatc cgtcccagtc aataatcttc ctgagagaag tccgactgac    9420
agccccagag agggcctgag ggtcaagcga ggccgacttg tccccagccc caaagctgga    9480
ctggagtcca acggcagtga gaactgtaag gtccagtgaa ggcactttgt gtgtcagtac    9540
ccctgggagg tgccagtcat tgaatagata aggctgtgcc tacaggactt ctctttagtc    9600
agggcatgct ttattagtga ggagaaaaca attccttaga agtcttaaat atattgtact    9660
ctttagatct cccatgtgta ggtattgaaa aagtttggaa gcactgatca cctgttagca    9720
ttgccattcc tctactgcaa tgtaaatagt ataaagctat gtatataaag cttttttggta   9780
atatgttaca attaaaatga caagcactat atcacaatct ctgtttgtat gtgggtttta    9840
cactaaaaaa atgcaaaaca cattttattc ttctaattaa cagctcctag gaaaatgtag    9900
acttttgctt tatgatattc tatctgtagt atgaggcatg gaatagtttt gtatcggaa     9960
tttctcagag ctgagtaaaa tgaaggaaaa gcatgttatg tgttttttaag gaaaatgtgc   10020
acacatatac atgtaggagt gtttatcttt tccttacaat ctgttttaga catctttgct   10080
tatgaaacct gtacatatgt gtgtgtgggt atgtgtttat ttccagtgag ggctgcaggc   10140
ttcctagagg tgtgctatac catgcgtctg tcgttgtgct ttttttctgtt tttagaccaa   10200
ttttttacag ttctttggta agcattgtcg tatctggtga tggattaaca tatagccttt   10260
gttttctaat aaaatagtcg ccttcgtttt ctgtaaaaaa aaaaaaaaaa aaaaaa        10316
```

<210> SEQ ID NO 54
<211> LENGTH: 3114
<212> TYPE: PRT

<213> ORGANISM: Homo sapiens
<220> FEATURE:
<221> NAME/KEY: misc_feature
<223> OTHER INFORMATION: Human centromere protein F

<400> SEQUENCE: 54

```
Met Ser Trp Ala Leu Glu Glu Trp Lys Glu Gly Leu Pro Thr Arg Ala
1               5                   10                  15

Leu Gln Lys Ile Gln Glu Leu Glu Gly Gln Leu Asp Lys Leu Lys Lys
            20                  25                  30

Glu Lys Gln Gln Arg Gln Phe Gln Leu Asp Ser Leu Glu Ala Ala Leu
        35                  40                  45

Gln Lys Gln Lys Gln Lys Val Glu Asn Glu Lys Thr Glu Gly Thr Asn
    50                  55                  60

Leu Lys Arg Glu Asn Gln Arg Leu Met Glu Ile Cys Glu Ser Leu Glu
65                  70                  75                  80

Lys Thr Lys Gln Lys Ile Ser His Glu Leu Gln Val Lys Glu Ser Gln
                85                  90                  95

Val Asn Phe Gln Glu Gly Gln Leu Asn Ser Gly Lys Lys Gln Ile Glu
            100                 105                 110

Lys Leu Glu Gln Glu Leu Lys Arg Cys Lys Ser Glu Leu Glu Arg Ser
        115                 120                 125

Gln Gln Ala Ala Gln Ser Ala Asp Val Ser Leu Asn Pro Cys Asn Thr
    130                 135                 140

Pro Gln Lys Ile Phe Thr Thr Pro Leu Thr Pro Ser Gln Tyr Tyr Ser
145                 150                 155                 160

Gly Ser Lys Tyr Glu Asp Leu Lys Glu Lys Tyr Asn Lys Glu Val Glu
                165                 170                 175

Glu Arg Lys Arg Leu Glu Ala Glu Val Lys Ala Leu Gln Ala Lys Lys
            180                 185                 190

Ala Ser Gln Thr Leu Pro Gln Ala Thr Met Asn His Arg Asp Ile Ala
        195                 200                 205

Arg His Gln Ala Ser Ser Ser Val Phe Ser Trp Gln Gln Glu Lys Thr
    210                 215                 220

Pro Ser His Leu Ser Ser Asn Ser Gln Arg Thr Pro Ile Arg Arg Asp
225                 230                 235                 240

Phe Ser Ala Ser Tyr Phe Ser Gly Glu Gln Glu Val Thr Pro Ser Arg
                245                 250                 255

Ser Thr Leu Gln Ile Gly Lys Arg Asp Ala Asn Ser Ser Phe Phe Asp
            260                 265                 270

Asn Ser Ser Pro His Leu Leu Asp Gln Leu Lys Ala Gln Asn Gln
        275                 280                 285

Glu Leu Arg Asn Lys Ile Asn Glu Leu Glu Leu Arg Leu Gln Gly His
    290                 295                 300

Glu Lys Glu Met Lys Gly Gln Val Asn Lys Phe Gln Glu Leu Gln Leu
305                 310                 315                 320

Gln Leu Glu Lys Ala Lys Val Glu Leu Ile Glu Lys Glu Lys Val Leu
                325                 330                 335

Asn Lys Cys Arg Asp Glu Leu Val Arg Thr Thr Ala Gln Tyr Asp Gln
            340                 345                 350

Ala Ser Thr Lys Tyr Thr Ala Leu Glu Gln Lys Leu Lys Lys Leu Thr
        355                 360                 365

Glu Asp Leu Ser Cys Gln Arg Gln Asn Ala Glu Ser Ala Arg Cys Ser
    370                 375                 380
```

```
Leu Glu Gln Lys Ile Lys Glu Lys Glu Phe Gln Glu Glu Leu
385                 390                 395                 400

Ser Arg Gln Gln Arg Ser Phe Gln Thr Leu Asp Gln Glu Cys Ile Gln
            405                 410                 415

Met Lys Ala Arg Leu Thr Gln Glu Leu Gln Gln Ala Lys Asn Met His
            420                 425                 430

Asn Val Leu Gln Ala Glu Leu Asp Lys Leu Thr Ser Val Lys Gln Gln
            435                 440                 445

Leu Glu Asn Asn Leu Glu Glu Phe Lys Gln Lys Leu Cys Arg Ala Glu
            450                 455                 460

Gln Ala Phe Gln Ala Ser Gln Ile Lys Glu Asn Glu Leu Arg Arg Ser
465                 470                 475                 480

Met Glu Glu Met Lys Lys Glu Asn Asn Leu Leu Lys Ser His Ser Glu
            485                 490                 495

Gln Lys Ala Arg Glu Val Cys His Leu Glu Ala Glu Leu Lys Asn Ile
            500                 505                 510

Lys Gln Cys Leu Asn Gln Ser Gln Asn Phe Ala Glu Glu Met Lys Ala
            515                 520                 525

Lys Asn Thr Ser Gln Glu Thr Met Leu Arg Asp Leu Gln Glu Lys Ile
            530                 535                 540

Asn Gln Gln Glu Asn Ser Leu Thr Leu Glu Lys Leu Lys Leu Ala Val
545                 550                 555                 560

Ala Asp Leu Glu Lys Gln Arg Asp Cys Ser Gln Asp Leu Leu Lys Lys
            565                 570                 575

Arg Glu His His Ile Glu Gln Leu Asn Asp Lys Leu Ser Lys Thr Glu
            580                 585                 590

Lys Glu Ser Lys Ala Leu Leu Ser Ala Leu Glu Leu Lys Lys Lys Glu
            595                 600                 605

Tyr Glu Glu Leu Lys Glu Glu Lys Thr Leu Phe Ser Cys Trp Lys Ser
            610                 615                 620

Glu Asn Glu Lys Leu Leu Thr Gln Met Glu Ser Glu Lys Glu Asn Leu
625                 630                 635                 640

Gln Ser Lys Ile Asn His Leu Glu Thr Cys Leu Lys Thr Gln Gln Ile
            645                 650                 655

Lys Ser His Glu Tyr Asn Glu Arg Val Arg Thr Leu Glu Met Asp Arg
            660                 665                 670

Glu Asn Leu Ser Val Glu Ile Arg Asn Leu His Asn Val Leu Asp Ser
            675                 680                 685

Lys Ser Val Glu Val Glu Thr Gln Lys Leu Ala Tyr Met Glu Leu Gln
            690                 695                 700

Gln Lys Ala Glu Phe Ser Asp Gln Lys His Gln Lys Glu Ile Glu Asn
705                 710                 715                 720

Met Cys Leu Lys Thr Ser Gln Leu Thr Gly Gln Val Glu Asp Leu Glu
            725                 730                 735

His Lys Leu Gln Leu Leu Ser Asn Glu Ile Met Asp Lys Asp Arg Cys
            740                 745                 750

Tyr Gln Asp Leu His Ala Glu Tyr Glu Ser Leu Arg Asp Leu Leu Lys
            755                 760                 765

Ser Lys Asp Ala Ser Leu Val Thr Asn Glu Asp His Gln Arg Ser Leu
            770                 775                 780

Leu Ala Phe Asp Gln Gln Pro Ala Met His His Ser Phe Ala Asn Ile
785                 790                 795                 800

Ile Gly Glu Gln Gly Ser Met Pro Ser Glu Arg Ser Glu Cys Arg Leu
```

```
            805                 810                 815

Glu Ala Asp Gln Ser Pro Lys Asn Ser Ala Ile Leu Gln Asn Arg Val
            820                 825                 830

Asp Ser Leu Glu Phe Ser Leu Glu Ser Gln Lys Gln Met Asn Ser Asp
            835                 840                 845

Leu Gln Lys Gln Cys Glu Glu Leu Val Gln Ile Lys Gly Glu Ile Glu
        850                 855                 860

Glu Asn Leu Met Lys Ala Glu Gln Met His Gln Ser Phe Val Ala Glu
865                 870                 875                 880

Thr Ser Gln Arg Ile Ser Lys Leu Gln Glu Asp Thr Ser Ala His Gln
                885                 890                 895

Asn Val Val Ala Glu Thr Leu Ser Ala Leu Glu Asn Lys Glu Lys Glu
            900                 905                 910

Leu Gln Leu Leu Asn Asp Lys Val Glu Thr Gln Ala Glu Ile Gln
        915                 920                 925

Glu Leu Lys Lys Ser Asn His Leu Leu Glu Asp Ser Leu Lys Glu Leu
    930                 935                 940

Gln Leu Leu Ser Glu Thr Leu Ser Leu Glu Lys Lys Glu Met Ser Ser
945                 950                 955                 960

Ile Ile Ser Leu Asn Lys Arg Glu Ile Glu Glu Leu Thr Gln Glu Asn
                965                 970                 975

Gly Thr Leu Lys Glu Ile Asn Ala Ser Leu Asn Gln Gly Lys Met Asn
            980                 985                 990

Leu Ile Gln Lys Ser Glu Ser Phe Ala Asn Tyr Ile Asp Glu Arg Glu
            995                 1000                1005

Lys Ser Ile Ser Glu Leu Ser Asp Gln Tyr Lys Gln Glu Lys Leu
    1010                1015                1020

Ile Leu Leu Gln Arg Cys Glu Thr Gly Asn Ala Tyr Glu Asp
    1025                1030                1035

Leu Ser Gln Lys Tyr Lys Ala Ala Gln Glu Lys Asn Ser Lys Leu
    1040                1045                1050

Glu Cys Leu Leu Asn Glu Cys Thr Ser Leu Cys Glu Asn Arg Lys
    1055                1060                1065

Asn Glu Leu Glu Gln Leu Lys Glu Ala Phe Ala Lys Glu His Gln
    1070                1075                1080

Glu Phe Leu Thr Lys Leu Ala Phe Ala Glu Glu Arg Asn Gln Asn
    1085                1090                1095

Leu Met Leu Glu Leu Glu Thr Val Gln Gln Ala Leu Arg Ser Glu
    1100                1105                1110

Met Thr Asp Asn Gln Asn Asn Ser Lys Ser Glu Ala Gly Gly Leu
    1115                1120                1125

Lys Gln Glu Ile Met Thr Leu Lys Glu Glu Gln Asn Lys Met Gln
    1130                1135                1140

Lys Glu Val Asn Asp Leu Leu Gln Glu Asn Glu Gln Leu Met Lys
    1145                1150                1155

Val Met Lys Thr Lys His Glu Cys Gln Asn Leu Glu Ser Glu Pro
    1160                1165                1170

Ile Arg Asn Ser Val Lys Glu Arg Glu Ser Glu Arg Asn Gln Cys
    1175                1180                1185

Asn Phe Lys Pro Gln Met Asp Leu Glu Val Lys Glu Ile Ser Leu
    1190                1195                1200

Asp Ser Tyr Asn Ala Gln Leu Val Gln Leu Glu Ala Met Leu Arg
    1205                1210                1215
```

```
Asn Lys Glu Leu Lys Leu Gln Glu Ser Glu Lys Glu Lys Glu Cys
    1220              1225             1230
Leu Gln His Glu Leu Gln Thr Ile Arg Gly Asp Leu Glu Thr Ser
    1235              1240             1245
Asn Leu Gln Asp Met Gln Ser Gln Glu Ile Ser Gly Leu Lys Asp
    1250              1255             1260
Cys Glu Ile Asp Ala Glu Glu Lys Tyr Ile Ser Gly Pro His Glu
    1265              1270             1275
Leu Ser Thr Ser Gln Asn Asp Asn Ala His Leu Gln Cys Ser Leu
    1280              1285             1290
Gln Thr Thr Met Asn Lys Leu Asn Glu Leu Glu Lys Ile Cys Glu
    1295              1300             1305
Ile Leu Gln Ala Glu Lys Tyr Glu Leu Val Thr Glu Leu Asn Asp
    1310              1315             1320
Ser Arg Ser Glu Cys Ile Thr Ala Thr Arg Lys Met Ala Glu Glu
    1325              1330             1335
Val Gly Lys Leu Leu Asn Glu Val Lys Ile Leu Asn Asp Asp Ser
    1340              1345             1350
Gly Leu Leu His Gly Glu Leu Val Glu Asp Ile Pro Gly Gly Glu
    1355              1360             1365
Phe Gly Glu Gln Pro Asn Glu Gln His Pro Val Ser Leu Ala Pro
    1370              1375             1380
Leu Asp Glu Ser Asn Ser Tyr Glu His Leu Thr Leu Ser Asp Lys
    1385              1390             1395
Glu Val Gln Met His Phe Ala Glu Leu Gln Glu Lys Phe Leu Ser
    1400              1405             1410
Leu Gln Ser Glu His Lys Ile Leu His Asp Gln His Cys Gln Met
    1415              1420             1425
Ser Ser Lys Met Ser Glu Leu Gln Thr Tyr Val Asp Ser Leu Lys
    1430              1435             1440
Ala Glu Asn Leu Val Leu Ser Thr Asn Leu Arg Asn Phe Gln Gly
    1445              1450             1455
Asp Leu Val Lys Glu Met Gln Leu Gly Leu Glu Glu Gly Leu Val
    1460              1465             1470
Pro Ser Leu Ser Ser Ser Cys Val Pro Asp Ser Ser Ser Leu Ser
    1475              1480             1485
Ser Leu Gly Asp Ser Ser Phe Tyr Arg Ala Leu Leu Glu Gln Thr
    1490              1495             1500
Gly Asp Met Ser Leu Leu Ser Asn Leu Glu Gly Ala Val Ser Ala
    1505              1510             1515
Asn Gln Cys Ser Val Asp Glu Val Phe Cys Ser Ser Leu Gln Glu
    1520              1525             1530
Glu Asn Leu Thr Arg Lys Glu Thr Pro Ser Ala Pro Ala Lys Gly
    1535              1540             1545
Val Glu Glu Leu Glu Ser Leu Cys Glu Val Tyr Arg Gln Ser Leu
    1550              1555             1560
Glu Lys Leu Glu Glu Lys Met Glu Ser Gln Gly Ile Met Lys Asn
    1565              1570             1575
Lys Glu Ile Gln Glu Leu Glu Gln Leu Leu Ser Ser Glu Arg Gln
    1580              1585             1590
Glu Leu Asp Cys Leu Arg Lys Gln Tyr Leu Ser Glu Asn Glu Gln
    1595              1600             1605
```

-continued

Trp Gln Gln Lys Leu Thr Ser Val Thr Leu Glu Met Glu Ser Lys
1610                1615                1620

Leu Ala Ala Glu Lys Lys Gln Thr Glu Gln Leu Ser Leu Glu Leu
1625                1630                1635

Glu Val Ala Arg Leu Gln Leu Gln Gly Leu Asp Leu Ser Ser Arg
1640                1645                1650

Ser Leu Leu Gly Ile Asp Thr Glu Asp Ala Ile Gln Gly Arg Asn
1655                1660                1665

Glu Ser Cys Asp Ile Ser Lys Glu His Thr Ser Glu Thr Thr Glu
1670                1675                1680

Arg Thr Pro Lys His Asp Val His Gln Ile Cys Asp Lys Asp Ala
1685                1690                1695

Gln Gln Asp Leu Asn Leu Asp Ile Glu Lys Ile Thr Glu Thr Gly
1700                1705                1710

Ala Val Lys Pro Thr Gly Glu Cys Ser Gly Glu Gln Ser Pro Asp
1715                1720                1725

Thr Asn Tyr Glu Pro Pro Gly Glu Asp Lys Thr Gln Gly Ser Ser
1730                1735                1740

Glu Cys Ile Ser Glu Leu Ser Phe Ser Gly Pro Asn Ala Leu Val
1745                1750                1755

Pro Met Asp Phe Leu Gly Asn Gln Glu Asp Ile His Asn Leu Gln
1760                1765                1770

Leu Arg Val Lys Glu Thr Ser Asn Glu Asn Leu Arg Leu Leu His
1775                1780                1785

Val Ile Glu Asp Arg Asp Arg Lys Val Glu Ser Leu Leu Asn Glu
1790                1795                1800

Met Lys Glu Leu Asp Ser Lys Leu His Leu Gln Glu Val Gln Leu
1805                1810                1815

Met Thr Lys Ile Glu Ala Cys Ile Glu Leu Glu Lys Ile Val Gly
1820                1825                1830

Glu Leu Lys Lys Glu Asn Ser Asp Leu Ser Glu Lys Leu Glu Tyr
1835                1840                1845

Phe Ser Cys Asp His Gln Glu Leu Leu Gln Arg Val Glu Thr Ser
1850                1855                1860

Glu Gly Leu Asn Ser Asp Leu Glu Met His Ala Asp Lys Ser Ser
1865                1870                1875

Arg Glu Asp Ile Gly Asp Asn Val Ala Lys Val Asn Asp Ser Trp
1880                1885                1890

Lys Glu Arg Phe Leu Asp Val Glu Asn Glu Leu Ser Arg Ile Arg
1895                1900                1905

Ser Glu Lys Ala Ser Ile Glu His Glu Ala Leu Tyr Leu Glu Ala
1910                1915                1920

Asp Leu Glu Val Val Gln Thr Glu Lys Leu Cys Leu Glu Lys Asp
1925                1930                1935

Asn Glu Asn Lys Gln Lys Val Ile Val Cys Leu Glu Glu Leu
1940                1945                1950

Ser Val Val Thr Ser Glu Arg Asn Gln Leu Arg Gly Glu Leu Asp
1955                1960                1965

Thr Met Ser Lys Lys Thr Thr Ala Leu Asp Gln Leu Ser Glu Lys
1970                1975                1980

Met Lys Glu Lys Thr Gln Glu Leu Glu Ser His Gln Ser Glu Cys
1985                1990                1995

Leu His Cys Ile Gln Val Ala Glu Ala Glu Val Lys Glu Lys Thr

```
            2000                2005                2010
Glu Leu Leu Gln Thr Leu Ser  Ser Asp Val Ser Glu  Leu Leu Lys
            2015                2020                2025

Asp Lys Thr His Leu Gln Glu  Lys Leu Gln Ser Leu  Glu Lys Asp
            2030                2035                2040

Ser Gln Ala Leu Ser Leu Thr  Lys Cys Glu Leu Glu  Asn Gln Ile
            2045                2050                2055

Ala Gln Leu Asn Lys Glu Lys  Glu Leu Leu Val Lys  Glu Ser Glu
            2060                2065                2070

Ser Leu Gln Ala Arg Leu Ser  Glu Ser Asp Tyr Glu  Lys Leu Asn
            2075                2080                2085

Val Ser Lys Ala Leu Glu Ala  Ala Leu Val Glu Lys  Gly Glu Phe
            2090                2095                2100

Ala Leu Arg Leu Ser Ser Thr  Gln Glu Glu Val His  Gln Leu Arg
            2105                2110                2115

Arg Gly Ile Glu Lys Leu Arg  Val Arg Ile Glu Ala  Asp Glu Lys
            2120                2125                2130

Lys Gln Leu His Ile Ala Glu  Lys Leu Lys Glu Arg  Glu Arg Glu
            2135                2140                2145

Asn Asp Ser Leu Lys Asp Lys  Val Glu Asn Leu Glu  Arg Glu Leu
            2150                2155                2160

Gln Met Ser Glu Glu Asn Gln  Glu Leu Val Ile Leu  Asp Ala Glu
            2165                2170                2175

Asn Ser Lys Ala Glu Val Glu  Thr Leu Lys Thr Gln  Ile Glu Glu
            2180                2185                2190

Met Ala Arg Ser Leu Lys Val  Phe Glu Leu Asp Leu  Val Thr Leu
            2195                2200                2205

Arg Ser Glu Lys Glu Asn Leu  Thr Lys Gln Ile Gln  Glu Lys Gln
            2210                2215                2220

Gly Gln Leu Ser Glu Leu Asp  Lys Leu Leu Ser Ser  Phe Lys Ser
            2225                2230                2235

Leu Leu Glu Glu Lys Glu Gln  Ala Glu Ile Gln Ile  Lys Glu Glu
            2240                2245                2250

Ser Lys Thr Ala Val Glu Met  Leu Gln Asn Gln Leu  Lys Glu Leu
            2255                2260                2265

Asn Glu Ala Val Ala Ala Leu  Cys Gly Asp Gln Glu  Ile Met Lys
            2270                2275                2280

Ala Thr Glu Gln Ser Leu Asp  Pro Pro Ile Glu Glu  Glu His Gln
            2285                2290                2295

Leu Arg Asn Ser Ile Glu Lys  Leu Arg Ala Arg Leu  Glu Ala Asp
            2300                2305                2310

Glu Lys Lys Gln Leu Cys Val  Leu Gln Gln Leu Lys  Glu Ser Glu
            2315                2320                2325

His His Ala Asp Leu Leu Lys  Gly Arg Val Glu Asn  Leu Glu Arg
            2330                2335                2340

Glu Leu Glu Ile Ala Arg Thr  Asn Gln Glu His Ala  Ala Leu Glu
            2345                2350                2355

Ala Glu Asn Ser Lys Gly Glu  Val Glu Thr Leu Lys  Ala Lys Ile
            2360                2365                2370

Glu Gly Met Thr Gln Ser Leu  Arg Gly Leu Glu Leu  Asp Val Val
            2375                2380                2385

Thr Ile Arg Ser Glu Lys Glu  Asn Leu Thr Asn Glu  Leu Gln Lys
            2390                2395                2400
```

```
Glu Gln Glu Arg Ile Ser Glu Leu Glu Ile Ile Asn Ser Ser Phe
    2405            2410                2415

Glu Asn Ile Leu Gln Glu Lys Glu Gln Glu Lys Val Gln Met Lys
    2420            2425                2430

Glu Lys Ser Ser Thr Ala Met Glu Met Leu Gln Thr Gln Leu Lys
    2435            2440                2445

Glu Leu Asn Glu Arg Val Ala Ala Leu His Asn Asp Gln Glu Ala
    2450            2455                2460

Cys Lys Ala Lys Glu Gln Asn Leu Ser Ser Gln Val Glu Cys Leu
    2465            2470                2475

Glu Leu Glu Lys Ala Gln Leu Leu Gln Gly Leu Asp Glu Ala Lys
    2480            2485                2490

Asn Asn Tyr Ile Val Leu Gln Ser Ser Val Asn Gly Leu Ile Gln
    2495            2500                2505

Glu Val Glu Asp Gly Lys Gln Lys Leu Glu Lys Lys Asp Glu Glu
    2510            2515                2520

Ile Ser Arg Leu Lys Asn Gln Ile Gln Asp Gln Glu Gln Leu Val
    2525            2530                2535

Ser Lys Leu Ser Gln Val Glu Gly Glu His Gln Leu Trp Lys Glu
    2540            2545                2550

Gln Asn Leu Glu Leu Arg Asn Leu Thr Val Glu Leu Glu Gln Lys
    2555            2560                2565

Ile Gln Val Leu Gln Ser Lys Asn Ala Ser Leu Gln Asp Thr Leu
    2570            2575                2580

Glu Val Leu Gln Ser Ser Tyr Lys Asn Leu Glu Asn Glu Leu Glu
    2585            2590                2595

Leu Thr Lys Met Asp Lys Met Ser Phe Val Glu Lys Val Asn Lys
    2600            2605                2610

Met Thr Ala Lys Glu Thr Glu Leu Gln Arg Glu Met His Glu Met
    2615            2620                2625

Ala Gln Lys Thr Ala Glu Leu Gln Glu Glu Leu Ser Gly Glu Lys
    2630            2635                2640

Asn Arg Leu Ala Gly Glu Leu Gln Leu Leu Leu Glu Glu Ile Lys
    2645            2650                2655

Ser Ser Lys Asp Gln Leu Lys Glu Leu Thr Leu Glu Asn Ser Glu
    2660            2665                2670

Leu Lys Lys Ser Leu Asp Cys Met His Lys Asp Gln Val Glu Lys
    2675            2680                2685

Glu Gly Lys Val Arg Glu Glu Ile Ala Glu Tyr Gln Leu Arg Leu
    2690            2695                2700

His Glu Ala Glu Lys Lys His Gln Ala Leu Leu Leu Asp Thr Asn
    2705            2710                2715

Lys Gln Tyr Glu Val Glu Ile Gln Thr Tyr Arg Glu Lys Leu Thr
    2720            2725                2730

Ser Lys Glu Glu Cys Leu Ser Ser Gln Lys Leu Glu Ile Asp Leu
    2735            2740                2745

Leu Lys Ser Ser Lys Glu Glu Leu Asn Asn Ser Leu Lys Ala Thr
    2750            2755                2760

Thr Gln Ile Leu Glu Glu Leu Lys Lys Thr Lys Met Asp Asn Leu
    2765            2770                2775

Lys Tyr Val Asn Gln Leu Lys Lys Glu Asn Glu Arg Ala Gln Gly
    2780            2785                2790
```

| | | | | | | | | | | | |
|---|---|---|---|---|---|---|---|---|---|---|---|
|Lys|Met|Lys|Leu|Leu|Ile|Lys|Ser|Cys|Lys|Gln|Leu|Glu|Glu|Glu|
|2795| | | | |2800| | | | |2805| | | | |

Lys Met Lys Leu Leu Ile Lys Ser Cys Lys Gln Leu Glu Glu Glu
        2795                    2800                    2805

Lys Glu Ile Leu Gln Lys Glu Leu Ser Gln Leu Gln Ala Ala Gln
        2810                    2815                    2820

Glu Lys Gln Lys Thr Gly Thr Val Met Asp Thr Lys Val Asp Glu
        2825                    2830                    2835

Leu Thr Thr Glu Ile Lys Glu Leu Lys Glu Thr Leu Glu Glu Lys
        2840                    2845                    2850

Thr Lys Glu Ala Asp Glu Tyr Leu Asp Lys Tyr Cys Ser Leu Leu
        2855                    2860                    2865

Ile Ser His Glu Lys Leu Glu Lys Ala Lys Glu Met Leu Glu Thr
        2870                    2875                    2880

Gln Val Ala His Leu Cys Ser Gln Gln Ser Lys Gln Asp Ser Arg
        2885                    2890                    2895

Gly Ser Pro Leu Leu Gly Pro Val Val Pro Gly Pro Ser Pro Ile
        2900                    2905                    2910

Pro Ser Val Thr Glu Lys Arg Leu Ser Ser Gly Gln Asn Lys Ala
        2915                    2920                    2925

Ser Gly Lys Arg Gln Arg Ser Ser Gly Ile Trp Glu Asn Gly Arg
        2930                    2935                    2940

Gly Pro Thr Pro Ala Thr Pro Glu Ser Phe Ser Lys Lys Ser Lys
        2945                    2950                    2955

Lys Ala Val Met Ser Gly Ile His Pro Ala Glu Asp Thr Glu Gly
        2960                    2965                    2970

Thr Glu Phe Glu Pro Glu Gly Leu Pro Glu Val Val Lys Lys Gly
        2975                    2980                    2985

Phe Ala Asp Ile Pro Thr Gly Lys Thr Ser Pro Tyr Ile Leu Arg
        2990                    2995                    3000

Arg Thr Thr Met Ala Thr Arg Thr Ser Pro Arg Leu Ala Ala Gln
        3005                    3010                    3015

Lys Leu Ala Leu Ser Pro Leu Ser Leu Gly Lys Glu Asn Leu Ala
        3020                    3025                    3030

Glu Ser Ser Lys Pro Thr Ala Gly Gly Ser Arg Ser Gln Lys Val
        3035                    3040                    3045

Lys Val Ala Gln Arg Ser Pro Val Asp Ser Gly Thr Ile Leu Arg
        3050                    3055                    3060

Glu Pro Thr Thr Lys Ser Val Pro Val Asn Asn Leu Pro Glu Arg
        3065                    3070                    3075

Ser Pro Thr Asp Ser Pro Arg Glu Gly Leu Arg Val Lys Arg Gly
        3080                    3085                    3090

Arg Leu Val Pro Ser Pro Lys Ala Gly Leu Glu Ser Asn Gly Ser
        3095                    3100                    3105

Glu Asn Cys Lys Val Gln
        3110

<210> SEQ ID NO 55
<211> LENGTH: 11130
<212> TYPE: DNA
<213> ORGANISM: Mus musculus
<220> FEATURE:
<221> NAME/KEY: misc_feature
<223> OTHER INFORMATION: Mouse centromere protein F (Cenpf), mRNA

<400> SEQUENCE: 55
agtttgaatc gctcgtgctg gtcggggagg aacggtgcgc tgtgtgagga gctcggcggt    60

-continued

| | |
|---|---|
| gaggaactcg gggctcgcag agcccggagc caggttctgt gaggagctca gtttacttct | 120 |
| aaatgcttta aaataaaac aagatgagct gggccctgga agaatggaag gaaggtctcc | 180 |
| cctccagagc tcttcagaag atccaagagc ttgaaggaca gctggagaag ctgaagaagg | 240 |
| agaaacaaca gaggcagttc cagctggact ctctcgaagc tgcgctgcag aagcagaagc | 300 |
| agaaggttga agacggaaag actgagggtg cagacctgaa aagggaaaat caaaggttga | 360 |
| tggagatatg cgaacatttg gagaagtcaa ggcagaagct gtctcatgaa cttcaagtta | 420 |
| aggagtcaca agtgaatctc caagagagcc aactgagctc atgcaaaaag caaatagaaa | 480 |
| aactggaaca ggaacttaag cggtgtaaat ctgaatttga aagaagccaa caagttgcac | 540 |
| aatcggcaga tgtttctctg aatccatgca gtacaccaca gaaactcttt gcaactccac | 600 |
| tcacaccgag ttccacatac gaagatctga agaaaaata taataaagaa gttgaagaac | 660 |
| ggaagaggtt agaggaagag gttaaagctt tgcatgcaaa aaagtgagc ctgcctgttt | 720 |
| cccaagccac catgaaccac cgggacattg cgagacatca ggcttcctca tcagtgtttc | 780 |
| cttggcaaca ggaaaatacc ccaagtcgcc tttcatcgga tgctctgaaa accccactga | 840 |
| ggagagacgg ctctgctgct cacttttttgg gggaagaagt gagtcctaac aaatcaagta | 900 |
| tgaagacagg gagaggagac tgcagcagcc tccctggtga gcctcacagc gctcagcttt | 960 |
| tgcaccaggc caaagcccag aatcaagacc taaaaagcaa gatgactgag ttagaactac | 1020 |
| gcctgcaagg gcaagaaaag gaaatgagaa gccaagtgaa taaatgtcaa gacttacagc | 1080 |
| tacagctgga gaagacgaaa gtggaattga ttgaaaagga gagattttg aataaaacca | 1140 |
| gagatgaagt agtgagaagc acagcacagt atgaccaggc cgcagccaag tgtactacct | 1200 |
| tggaacaaaa gctgaaaact ttgactgagg agttgagttg tcaccgacag aacgcagaga | 1260 |
| gtgctaaacg ttctctggaa cagaggatta aggagaaaga aaaggagctt caagaggagc | 1320 |
| tgtcccgaca gcatcaatct ttccaagctc tggacagtga gtacactcag atgaaaacca | 1380 |
| gacttaccca ggagttacag caagtcaagc atttgcacag caccctccag ctggaactgg | 1440 |
| agaaggtcac atcagtgaag cagcagttag aaaggaattt ggaagaaatt aggcttaagt | 1500 |
| tgagcagagc agaacaagct cttcaggcaa gtcaggtcgc agaaaacgag ctgaggagaa | 1560 |
| gcagtgagga aatgaagaag gagaacagtc tcattaggag tcagtctgag cagaggacca | 1620 |
| gagaagtctg ccacctggag gaagaacttg gtaaagtcaa agtgtctttg agtaagagcc | 1680 |
| agaattttgc agaagaaatg aaggctaaga atacctctca ggaaatcatg ttacgagatc | 1740 |
| ttcaggaaaa actaaatcag caagaaaact cactaacttt agagaagctg aaacttgccc | 1800 |
| tagctgatct ggaaagacag cgaaactgtt ctcaagatct cttgaagaaa agggaacatc | 1860 |
| acattgatca actgaataat aagttaaata agatagagaa agagtttgaa actttgctga | 1920 |
| gtgcttttgga attaaaaaag aaagaatgtg aagaattgaa agagagaaa atcagatttt | 1980 |
| cttttttggaa aattgatagt gaaaaactca taaatcagat agaatcagaa aaagaaatct | 2040 |
| tattgggtaa aattaaccac ttagagacca gcctcaagac acaacaagta agtcctgact | 2100 |
| ctaatgagag aataagaaca ctggagatgg aaagagaaaa ctttactgtg gagattaaaa | 2160 |
| accttcaaag tatgttagac agcaagatgg tagagatcaa gacacagaaa caagcttact | 2220 |
| tggaactgca gcagaaatcc gaatcctcgg accaaaagca tcagaaggag atagagaata | 2280 |
| tgtgcttgaa agcaaataag ctcactgggc aagttgaaag tttggaatgt aagcttcagt | 2340 |
| tattgtcaag tgaagtagtg accaaagacc agcagtacca agacttgcgt atggaatatg | 2400 |
| agacactgag ggatttgctc aagtccagag gatcttctct ggtgacaaat gaggataatc | 2460 |

```
agcgaagttc tgaggataat cagagaagtt ctgaggataa tcagagaggc tctttggctt    2520
ttgaacagca gcctgcagtg agtgattcct ttgcaaatgt aatggggaga aaaggaagca    2580
taaattcaga aaggagtgac tgctctgtag atgggggccg aagtccagaa catatagcca    2640
tcttacaaaa tagagtcact tcacttgaaa gttccttgga gtctcaaaac cagatgaatt    2700
cagatttgca aatgcggtgt gaagagttgc tacaaatcaa aggggaagta aagaaaaacc    2760
tcagtaaagc agagcagatt catcagaatt ttgtggctga aacaaatcaa tgtattagta    2820
aattgcagga agatgctgca gttcatcaga atattgttgc tgagacttta gcaacccttg    2880
agagtaagga aaaagagtta cagcttttga agaaaaatt agaagctcag caaacagagg     2940
ttcaaaagtt aaataagaat aactgtcttc ttgaaggtac tctgaaggag ctacagcttt    3000
tatctgacac tctgagctca gagaagaagg aaatgaattc tatcatctca ttaagtaaaa    3060
aaaacattga agagttaacc caagcaaacg aggctctcaa ggaagttaat gaggccttag    3120
agcaggagaa aatgaattta ctccaaaagc atgagaagat tacaagctgt atagcagaac    3180
aagagagaag cattgcagag ctgtctgatc agtacaagca agaaagactt caattattac    3240
aacggtgtga agaaacagaa gctgtgttgg aagatctcag gggaaactac aaaacagcac    3300
aagaaaacaa tgctaagtta gaatgcatgc tcagcgagtg cactgctctt tgtgaaaata    3360
gaaaaatgaa actggagcag ttaaaggaaa catttgcaaa ggaacagcaa gaattcttaa    3420
caaaattagc tttcgctgaa gagcaaaaca ggaaactaat gctagagttg gagatagagc    3480
aacaaactgt gagatccgag attacaaaca ccaacaagca ttccatgagt gcgactgatg    3540
gcttaaggca agaatgcttg actttaaacg aagagcaaaa tgagcagcaa acgaagtta    3600 gcaacttaac acatgagaat gagcaactga tggagttaac acagaccaaa catgattctt    3660
atctcgcagt agagccagtt gagaactctg taaaagcaac cgaagatgag ataggtaaga    3720
gtagttccca gtaccagatg gatatcgaca ctaaagacat ttctctagat agttataagg    3780
cacagctggt acatctagaa gctttggtaa gaattctgga agtacagctt gaccaaagtg    3840
aggaggagaa caagaagctg catctggaat tacagacgat tagagaggag ctagaaacca    3900
agagttcaca ggaccccag tcacaggcaa ggactgggct taaagactgt gacacagcag     3960
aagaaaagta tgtgtccatg ctacaggagt tgtcagcaag tcaaaacgag aatgcacact    4020
tacagtgctc tctacagaca gcagtgaaca aactgaatga gctagggaaa atgtgtgacg    4080
tattgagagt tgaaaagtta cagctagagt ctgagctgaa tgactcacgg acagagtgta    4140
tcacggcaac tagtcagatg acggcagagg tcgagaagct agtgagtgaa atgaaaatgc    4200
taaaccacga gagtgctctg tcccagaatg agctgatgaa ggacacctca ggtggtgaat    4260
ttcatgataa agcaaaccac agttctgtgt tcttgactcc tttggacagt agcaatttct    4320
gtgaacagat gaccttgtca agcaaagagg tccgagtgca cttttgctgaa ttacaggaga    4380 aattctcctg tttacaaagt gaacacaaaa ttttacatga tcagcactgt gaggtgagct    4440
ctaagatgtc agcactgcgt tcctacgtgg acacattaaa agctgaaaat tctgccttgt    4500
caatgagtct gagaaccttg cagggtgact tggtaaagga gggggagcct gcagctgagg    4560
gtgggcatgg tctgccactg tcgttctgtg ggcagacag cccgtctctg acaaattttg     4620
gagaaacgtc cttttacaaa gacgttttag aacaaactgg agacacatgt catctaagtt    4680
tagaagggaa cgcttcagca aattcttgtg acttggatga gagttctcc agcagtctgg     4740 aggaggagac tctgactgag aaggaaagcc cacctgcccc tgggaggact gttgagggac    4800
```

```
ttgaagtcct atgccaggtg tacttgcagt ccctcaagaa tctagaggag aaaactgaga    4860
gccaaaggat tatgaaaaat aaagaaattg aaaagcttga gcagttactg agttctgaga    4920
ggaaagagct aagctgcctt aggaagcagt atttgtcaga aaaggagcaa tggcagcaga    4980
agctaacaag tgtcactttg gaaatggagt ccaagttagc agaggagaag cagcagacca    5040
agactctgtc ccttgaactt gaggtagcac gacttcagtt acaggagctg gacctgagct    5100
ccaggtcttt gcttggcact gacttggaaa gtgttgttcg gtgccaaaac gataattatg    5160
atataaaaga atcagaagta tatatttcag agactacaga gaaaacacca aagcaggaca    5220
ctgaccaaac ttgtgataaa gatattcagc aggaccttgg tctggaaact tcagtcactg    5280
agagtgagac taccaggctc acaggagagg ggtgtgaaga gcagcctccg aagaccaatt    5340
gtgaggcacc agcggaggac aaaacccagg actgctcaga atgcatttct gaattgtgtt    5400
ctagttccaa tgttttggtg cccatggatg ttctggaaga tcaggggtct atccagaatc    5460
tccagttgca gaaagacacc ttaaatgaga atttgagatt acttcctgaa gtagaggact    5520
gggacaaaaa agttgaaagt ttgctaaatg aaattatgga ggcagattca aaactgagtt    5580
tacaggaagt acagctcaag atgaagattg caacatgcat acaattggaa aaaatagtca    5640
aggacctcag aaaggaaaaa gctgacttaa gtgaaaagtt ggaatccctt ccatgtaacc    5700
aggaggtatg tctgagagta gaaaggtcag aagaagatct tggtttttaat ttagatatgg    5760
gagcaaatga gttgttaagt aaatctacta agataatgc aaccaacaca gaagacaatt    5820
ataaggagaa gtttcttgat atggaaagag aactgaccag aattaagtct gagaaagcta    5880
atattgcagca tcacatccta tctgtggaaa ctaacttaga ggtggttcaa gcagagaagc    5940
tctgtttgga aagagacact gaaagtaagc aaaaggttat tattgacctt aagaagaac    6000
tatttacagt tataagtgag agaaacagac ttcgggaaga attagataat gtgtcaaaag    6060
aaagcaaagc actggatcag atgtctaaaa agatgaaaga gaaatagaa gagctggagt    6120
ctcaccaaag ggagagcctc cgtcacattg ggcagtagaa gtctgaggtc aaggacaaag    6180
cagatcttat tcagactctg tcctttaatg tgggtgagct aacaaaagac aaagctcatc    6240
tccaggagca gctgcagaat ttgcagaatg actcacaaga attatctttg gcgattggtg    6300
agctggaaat acaaattgga caactgaata agagaaaga tcactggtc aaggagtctc    6360
agaacttcca gatcaagctg actgagtcag agtgtgaaaa gcagacgatc tctaaggcct    6420
tggaggtggc actcaaggag aaaggtgagt ttgcagtgca gctgagctca gcccaggagg    6480
aggtgcatca gctgagacga ggcattgaga aactgagcgt ccgcattgag gccgatgaga    6540
agaagcacct cagtgctgtg gcgaagctga agaaagcca gcgtgaaagc gactcattga    6600
aggatacagt ggagactctg gagcgggaac tggagaggtc agaagaaaac caagagctgg    6660
caattcttga ttctgagaat ttgaaagcag aggtggagac ccttaaggca caaaaggatg    6720
aaaatgaccaa aagcctgaga attttcgaat tagaccttgt tacagttagg actgaaagag    6780
aaaatctagc aaagcagcta caagagaaac aaagtcgagt gtcagaatta gatgaacggt    6840
gctcttcctt gagaagactg ttggaagaga aggagcaagc aagagtacag atggaagaag    6900
actctaagtc tgcaatgctg atgcttcaga tgcagttaaa agaactcagg gaggaagtgg    6960
cagccttgtg taatgaccaa gaaaccttga aggcccaaga acagagtcta gaccaaccag    7020
gggaggaagt gcatcatttg aaaagtagca ttcgaaagct caaagttcac atagatgctg    7080
atgaaaagaa gcatcaaaac atcctagaac aactgaagga aagtaagcac catgcagact    7140
tgcttaagga ccgagttgag aaccttgaac aagaattgat actatcagag aaaaacatga    7200
```

-continued

```
tttt ccaagc tgaaaagtcc aaagcagaga tacagacttt aaaatcagaa attcaaagaa    7260
tggcccaaaa cctccaagac ttgcagttag aacttattag tacaaggtca gaaaatgaaa    7320
atctcatgaa agaattaaaa aaagagcaag agcgagtatc tgacttagaa acaataaatt    7380
cttctattga aaacttactg aaagataaag agcaagaaaa agtacagatg aaagaggaag    7440
ccaaaataac agtggagatg cttcaaactc aattaaagga gctaaacgag acagtggttt    7500
ccttgtgcaa tgaccaagag gtctctaaga ccaaagaaca gaatctgggt agtcaagtac    7560
aaactcttga acttgagaag gctcagctgc tacaggacct tggtgaggcc aagaataaat    7620
atattatttt tcagtcatct gtaaatgccc tcactcaaga agtagaagct ggcaaacaga    7680
aactagagaa gggggagaaa gagatcagga cactgaaaga gcaacttaaa agtcaggagc    7740
agcttgtgtg taaacttgcc caagtggaag gagagcagca actctggcag aagcagaaac    7800
tagagctgag aaatgtgact atggcactgg agcagaaggt ccaagtgctg caatctgaaa    7860
acaacacgtt gcagagcacc tatgaagcac tgcagaattc ccacaagagt ttagagagtg    7920
aacttggatt gataaagttg gagaaagtag cgcttgttga aagagttagc acaatatctg    7980
ggaaggaagc agagctgcag agggagctgc gagatatgct acagaaaaca acacagctga    8040
gcgaagacta caataaagag aaaaacaggc taacagaaga agtggaagtg ctgcgtgaag    8100
aactgcagaa caccaaagca gcgcacctga aatctgtgaa tcaacttgag aaggaacttc    8160
agcgtgctca ggggaaaata aagttgatgc tcaaatcctg tagacagctg gaaggagaaa    8220
aggagatgct gcagaaggag ctctcccagc ttgaagctgc acagcagcag agagcaggtt    8280
ctcttgtaga cagtaacgta gatgaagtaa tgactgagaa caaagcgctg aaagagactc    8340
tggaagaaaa agtcaaggaa gcagataagt acttggataa gtactgttcc ctgctgataa    8400
gccacgagga gctcgagaaa gccaaggaga tattagaaat agaagttgct cggctgaagt    8460
cacggcagtc cagacaggat ctccagagtt ctcctttgct taattcttcc attccaggac    8520
cgtctccaaa tacttctgtt agtgagatga agtcagcatc tggccaaaat aaagcttcag    8580
gcaagaggca aaggtccagt gggatttggg agcatggtaa acgggcagca ccttctacag    8640
cagagacatt ttctaagaaa agcaggaagt cggacagtaa gagcactcgc cctgctgagc    8700
acgagcagga aaccgagttt gagccagaag gcctcccaga agtcgttaaa aaagggtttg    8760
ctgacatccc aactggaaag acaagcccat atatccttcg gagaacaacc atggcaacca    8820
ggaccagccc ccgctttgct acacagaagt tagtgggatc ttccccatct ctgggcaaag    8880
aaaatgttgt agagtcctcc aaaccaacag ctggtggcag cagatcacaa aaggtcaagg    8940
ttgttcagga gagctcagcg gattcacaca ctgccttcca agaactccca gcaaaatctc    9000
tcacagccag taatattcct gggagaaact ctacagagag ccccagggag ggcctgaggg    9060
ccaagcgggc ctaccctgcc tccagcccag ctgctgggcc tgatcccacg aacaacgaaa    9120
actgccgggt ccagtgaagt gtccactcag ggttctggaa ggtggcatta ctcaaaggag    9180
cctgcctgtg gggacttgtc ttgagccaag gacacattat gtatcactag agaatacctg    9240
agtctttatg ctgtgtgtgt ggtgctcagg tctcccatat gtaagactgc aaacgttgaa    9300
agcacccatt acctagtagt cctaatcctt aaccctaagt gtaaatagca gtggatagag    9360
cgagagcatt tgctgcagtt aaatgggaag cgccatgatt tgtatgtgca ttttacactt    9420
gctactgcag tgatttgatt aggatcttcc tgtgtagatt gttaggcatc aaatcgttgt    9480
agatcaagag ttggagctga gttaagtgag gacagcctgt gtgcacagtg tgtggtatgg    9540
```

```
tcctcctttc tgtgtgtttc ataacttcct gcttctctga cctgtccata gcgtgtgggg    9600
agtttgcagt gtgcacttac tactagttag tctgattgtt tcatacactt ttgtggtggt    9660
gtagatcatg tttactgtca ctgttttcct gtcatcatag ttcttttggt atatatttct    9720
gtgtctggtg atatattaaa gtatgtcctt gtaaacttt  ttgtaaaagt tatttcctaa    9780
atataaaaac attatgacta gcaccactat gtcttcttaa ctaaaccac  ctcccataaa    9840 agtaaaaatg tttgaacaaa tgatacatgt ctttgaatgt gtgatactag tatacttact    9900
gaacgtgaga catactgtag aatgttggtc atacagatgg tttgagaata tggatatatt    9960
aaactagtat cttgtgctca ttaaatacta ttagcaaagg tacaagaatg ttcccatctg   10020
tctgttgata atagggcttg aaaagatgaa ggcattttga ctcaataaca aatgaaaaca   10080
cttgactaag cctctgtgcc gttgaataaa ggtgaaaggt tttccggctt taagttagta   10140
gtagatgatc tgttcttggc tttcatttca gattggtatc aaatgttcac aaacacagtc   10200
attttagatt tgaaaactgt ctcctgctgg tggtttcact gttggaatat aaaccactcc   10260
atcccctgag agcgatgctc tactctctca ggttgctcct gtcccaaggc caccatgtgc   10320
tccagcgctg aggtcaggcc agcagcttta agggatgcca caagagatgg aaagatccca   10380
tgccagggtg tcaccaagta cttttccagcg tccttaggaa tggcgtcctc ttcttgtagg   10440
ccatagctcc tctgtgacat gggatacttg cattcccaga agcaatggac tcatcttttg   10500
gttgcgtgcc aagctgaggg taaagaatgg cttgtttgtt gctgcaaatg aggaatatgt   10560
agacgatggt ccttggagag cagtatctga atagaaagca aaaggctttc attggtgaaa   10620
taccaggcat catgtgtgga cacatttctg aacatgttct gtgtggggtg agaaggtaat   10680
gacaggttca ttgtgtagcc tggctgccac aggtctcatc tgcctgcatc tgtctcccag   10740
gtcctgggat taaatgcgta taccaccaag cttgcaggtc agtgtttgaa ctttaatatt   10800
tataatccct tttcacatga gactctgtac ctggtatata atacaaatca gatgtgtact   10860
gataaattga agtttatt  tagactgaga atgtgactca gtgttcaagt attgtgtagt   10920
atgctcaaga acaggctttg aggggctggt gagatggctc agtgggtaag agcacctgac   10980
tgctcttctg aaggtccgga gttcaaatcc cagcaaccac atggtggctc acaaccatct   11040
gtaacgaaat ctggcaccct cttctggagt gactgaagac agctacagtg tacttacata   11100
taataaataa ataaatcttt aaaaaaaaaa                                    11130
```

<210> SEQ ID NO 56
<211> LENGTH: 2997
<212> TYPE: PRT
<213> ORGANISM: Mus musculus
<220> FEATURE:
<221> NAME/KEY: misc_feature
<223> OTHER INFORMATION: Mouse centromere protein F

<400> SEQUENCE: 56

```
Met Ser Trp Ala Leu Glu Glu Trp Lys Glu Gly Leu Pro Ser Arg Ala
1               5                   10                  15

Leu Gln Lys Ile Gln Glu Leu Glu Gly Gln Leu Glu Lys Leu Lys Lys
                20                  25                  30

Glu Lys Gln Gln Arg Gln Phe Gln Leu Asp Ser Leu Glu Ala Ala Leu
            35                  40                  45

Gln Lys Gln Lys Gln Lys Val Glu Asp Gly Lys Thr Glu Gly Ala Asp
        50                  55                  60

Leu Lys Arg Glu Asn Gln Arg Leu Met Glu Ile Cys Glu His Leu Glu
65                  70                  75                  80
```

```
Lys Ser Arg Gln Lys Leu Ser His Glu Leu Gln Val Lys Glu Ser Gln
                85                  90                  95
Val Asn Leu Gln Glu Ser Gln Leu Ser Ser Cys Lys Lys Gln Ile Glu
            100                 105                 110
Lys Leu Glu Gln Glu Leu Lys Arg Cys Lys Ser Glu Phe Glu Arg Ser
        115                 120                 125
Gln Gln Val Ala Gln Ser Ala Asp Val Ser Leu Asn Pro Cys Ser Thr
    130                 135                 140
Pro Gln Lys Leu Phe Ala Thr Pro Leu Thr Pro Ser Ser Thr Tyr Glu
145                 150                 155                 160
Asp Leu Lys Glu Lys Tyr Asn Lys Glu Val Glu Arg Lys Arg Leu
                165                 170                 175
Glu Glu Glu Val Lys Ala Leu His Ala Lys Lys Val Ser Leu Pro Val
            180                 185                 190
Ser Gln Ala Thr Met Asn His Arg Asp Ile Ala Arg His Gln Ala Ser
        195                 200                 205
Ser Ser Val Phe Pro Trp Gln Gln Glu Asn Thr Pro Ser Arg Leu Ser
    210                 215                 220
Ser Asp Ala Leu Lys Thr Pro Leu Arg Arg Asp Gly Ser Ala Ala His
225                 230                 235                 240
Phe Leu Gly Glu Glu Val Ser Pro Asn Lys Ser Ser Met Lys Thr Gly
                245                 250                 255
Arg Gly Asp Cys Ser Ser Leu Pro Gly Glu Pro His Ser Ala Gln Leu
            260                 265                 270
Leu His Gln Ala Lys Ala Gln Asn Gln Asp Leu Lys Ser Lys Met Thr
        275                 280                 285
Glu Leu Glu Leu Arg Leu Gln Gly Gln Glu Lys Glu Met Arg Ser Gln
    290                 295                 300
Val Asn Lys Cys Gln Asp Leu Gln Leu Gln Leu Glu Lys Thr Lys Val
305                 310                 315                 320
Glu Leu Ile Glu Lys Glu Arg Ile Leu Asn Lys Thr Arg Asp Glu Val
                325                 330                 335
Val Arg Ser Thr Ala Gln Tyr Asp Gln Ala Ala Ala Lys Cys Thr Thr
            340                 345                 350
Leu Glu Gln Lys Leu Lys Thr Leu Thr Glu Glu Leu Ser Cys His Arg
        355                 360                 365
Gln Asn Ala Glu Ser Ala Lys Arg Ser Leu Gly Gln Arg Ile Lys Glu
    370                 375                 380
Lys Glu Lys Glu Leu Gln Glu Leu Ser Arg Gln His Gln Ser Phe
385                 390                 395                 400
Gln Ala Leu Asp Ser Glu Tyr Thr Gln Met Lys Thr Arg Leu Thr Gln
                405                 410                 415
Glu Leu Gln Gln Val Lys His Leu His Ser Thr Leu Gln Leu Glu Leu
            420                 425                 430
Glu Lys Val Thr Ser Val Lys Gln Gln Leu Glu Arg Asn Leu Glu Glu
        435                 440                 445
Ile Arg Leu Lys Leu Ser Arg Ala Glu Gln Ala Leu Gln Ala Ser Gln
    450                 455                 460
Val Ala Glu Asn Glu Leu Arg Arg Ser Ser Glu Glu Met Lys Lys Glu
465                 470                 475                 480
Asn Ser Leu Ile Arg Ser Gln Ser Glu Gln Arg Thr Arg Glu Val Cys
                485                 490                 495
```

```
His Leu Glu Glu Glu Leu Gly Lys Val Lys Val Ser Leu Ser Lys Ser
            500                 505                 510

Gln Asn Phe Ala Glu Glu Met Lys Ala Lys Asn Thr Ser Gln Glu Ile
            515                 520                 525

Met Leu Arg Asp Leu Gln Glu Lys Leu Asn Gln Gln Glu Asn Ser Leu
            530                 535                 540

Thr Leu Glu Lys Leu Lys Leu Ala Leu Ala Asp Leu Glu Arg Gln Arg
545                 550                 555                 560

Asn Cys Ser Gln Asp Leu Leu Lys Lys Arg Glu His His Ile Asp Gln
            565                 570                 575

Leu Asn Asn Lys Leu Asn Lys Ile Glu Lys Glu Phe Glu Thr Leu Leu
            580                 585                 590

Ser Ala Leu Glu Leu Lys Lys Lys Glu Cys Glu Glu Leu Lys Glu Glu
            595                 600                 605

Lys Asn Gln Ile Ser Phe Trp Lys Ile Asp Ser Glu Lys Leu Ile Asn
            610                 615                 620

Gln Ile Glu Ser Glu Lys Glu Ile Leu Leu Gly Lys Ile Asn His Leu
625                 630                 635                 640

Glu Thr Ser Leu Lys Thr Gln Gln Val Ser Pro Asp Ser Asn Glu Arg
            645                 650                 655

Ile Arg Thr Leu Glu Met Glu Arg Glu Asn Phe Thr Val Glu Ile Lys
            660                 665                 670

Asn Leu Gln Ser Met Leu Asp Ser Lys Met Val Glu Ile Lys Thr Gln
            675                 680                 685

Lys Gln Ala Tyr Leu Glu Leu Gln Gln Lys Ser Glu Ser Ser Asp Gln
            690                 695                 700

Lys His Gln Lys Glu Ile Glu Asn Met Cys Leu Lys Ala Asn Lys Leu
705                 710                 715                 720

Thr Gly Gln Val Glu Ser Leu Glu Cys Lys Leu Gln Leu Leu Ser Ser
            725                 730                 735

Glu Val Val Thr Lys Asp Gln Gln Tyr Gln Asp Leu Arg Met Glu Tyr
            740                 745                 750

Glu Thr Leu Arg Asp Leu Leu Lys Ser Arg Gly Ser Ser Leu Val Thr
            755                 760                 765

Asn Glu Asp Asn Gln Arg Ser Ser Glu Asp Asn Gln Arg Ser Ser Glu
            770                 775                 780

Asp Asn Gln Arg Gly Ser Leu Ala Phe Glu Gln Gln Pro Ala Val Ser
785                 790                 795                 800

Asp Ser Phe Ala Asn Val Met Gly Arg Lys Gly Ser Ile Asn Ser Glu
            805                 810                 815

Arg Ser Asp Cys Ser Val Asp Gly Gly Arg Ser Pro Glu His Ile Ala
            820                 825                 830

Ile Leu Gln Asn Arg Val Thr Ser Leu Glu Ser Ser Leu Glu Ser Gln
            835                 840                 845

Asn Gln Met Asn Ser Asp Leu Gln Met Arg Cys Glu Glu Leu Leu Gln
            850                 855                 860

Ile Lys Gly Glu Val Glu Glu Asn Leu Ser Lys Ala Glu Gln Ile His
865                 870                 875                 880

Gln Asn Phe Val Ala Glu Thr Asn Gln Cys Ile Ser Lys Leu Gln Glu
            885                 890                 895

Asp Ala Ala Val His Gln Asn Ile Val Ala Glu Thr Leu Ala Thr Leu
            900                 905                 910

Glu Ser Lys Glu Lys Glu Leu Gln Leu Leu Lys Glu Lys Leu Glu Ala
```

-continued

```
            915                 920                 925
Gln Gln Thr Glu Val Gln Lys Leu Asn Lys Asn Asn Cys Leu Leu Glu
        930                 935                 940

Gly Thr Leu Lys Glu Leu Gln Leu Leu Ser Asp Thr Leu Ser Ser Glu
945                 950                 955                 960

Lys Lys Glu Met Asn Ser Ile Ile Ser Leu Ser Lys Lys Asn Ile Glu
                965                 970                 975

Glu Leu Thr Gln Ala Asn Glu Ala Leu Lys Glu Val Asn Glu Ala Leu
                980                 985                 990

Glu Gln Glu Lys Met Asn Leu Leu Gln Lys His Glu Lys Ile Thr Ser
                995                1000                1005

Cys Ile Ala Glu Gln Glu Arg Ser Ile Ala Glu Leu Ser Asp Gln
    1010                1015                1020

Tyr Lys Gln Glu Arg Leu Gln Leu Leu Gln Arg Cys Glu Glu Thr
    1025                1030                1035

Glu Ala Val Leu Glu Asp Leu Arg Gly Asn Tyr Lys Thr Ala Gln
    1040                1045                1050

Glu Asn Asn Ala Lys Leu Glu Cys Met Leu Ser Glu Cys Thr Ala
    1055                1060                1065

Leu Cys Glu Asn Arg Lys Asn Glu Leu Glu Gln Leu Lys Glu Thr
    1070                1075                1080

Phe Ala Lys Glu Gln Gln Glu Phe Leu Thr Lys Leu Ala Phe Ala
    1085                1090                1095

Glu Glu Gln Asn Arg Lys Leu Met Leu Glu Leu Glu Ile Glu Gln
    1100                1105                1110

Gln Thr Val Arg Ser Glu Ile Thr Asn Thr Asn Lys His Ser Met
    1115                1120                1125

Ser Ala Thr Asp Gly Leu Arg Gln Glu Cys Leu Thr Leu Asn Glu
    1130                1135                1140

Glu Gln Asn Glu Gln Gln Asn Glu Val Ser Asn Leu Thr His Glu
    1145                1150                1155

Asn Glu Gln Leu Met Glu Leu Thr Gln Thr Lys His Asp Ser Tyr
    1160                1165                1170

Leu Ala Val Glu Pro Val Glu Asn Ser Val Lys Ala Thr Glu Asp
    1175                1180                1185

Glu Ile Gly Lys Ser Ser Ser Gln Tyr Gln Met Asp Ile Asp Thr
    1190                1195                1200

Lys Asp Ile Ser Leu Asp Ser Tyr Lys Ala Gln Leu Val His Leu
    1205                1210                1215

Glu Ala Leu Val Arg Ile Leu Glu Val Gln Leu Asp Gln Ser Glu
    1220                1225                1230

Glu Glu Asn Lys Lys Leu His Leu Glu Leu Gln Thr Ile Arg Glu
    1235                1240                1245

Glu Leu Glu Thr Lys Ser Ser Gln Asp Pro Gln Ser Gln Ala Arg
    1250                1255                1260

Thr Gly Leu Lys Asp Cys Asp Thr Ala Glu Glu Lys Tyr Val Ser
    1265                1270                1275

Met Leu Gln Glu Leu Ser Ala Ser Gln Asn Glu Asn Ala His Leu
    1280                1285                1290

Gln Cys Ser Leu Gln Thr Ala Val Asn Lys Leu Asn Glu Leu Gly
    1295                1300                1305

Lys Met Cys Asp Val Leu Arg Val Glu Lys Leu Gln Leu Glu Ser
    1310                1315                1320
```

```
Glu Leu Asn Asp Ser Arg Thr Glu Cys Ile Thr Ala Thr Ser Gln
1325                1330                1335

Met Thr Ala Glu Val Glu Lys Leu Val Ser Glu Met Lys Met Leu
1340                1345                1350

Asn His Glu Ser Ala Leu Ser Gln Asn Glu Leu Met Lys Asp Thr
1355                1360                1365

Ser Gly Gly Glu Phe His Asp Lys Ala Asn His Ser Ser Val Phe
1370                1375                1380

Leu Thr Pro Leu Asp Ser Ser Asn Phe Cys Glu Gln Met Thr Leu
1385                1390                1395

Ser Ser Lys Glu Val Arg Val His Phe Ala Glu Leu Gln Glu Lys
1400                1405                1410

Phe Ser Cys Leu Gln Ser Glu His Lys Ile Leu His Asp Gln His
1415                1420                1425

Cys Glu Val Ser Ser Lys Met Ser Ala Leu Arg Ser Tyr Val Asp
1430                1435                1440

Thr Leu Lys Ala Glu Asn Ser Ala Leu Ser Met Ser Leu Arg Thr
1445                1450                1455

Leu Gln Gly Asp Leu Val Lys Glu Gly Glu Pro Ala Ala Glu Gly
1460                1465                1470

Gly His Gly Leu Pro Leu Ser Phe Cys Gly Ala Asp Ser Pro Ser
1475                1480                1485

Leu Thr Asn Phe Gly Glu Thr Ser Phe Tyr Lys Asp Val Leu Glu
1490                1495                1500

Gln Thr Gly Asp Thr Cys His Leu Ser Leu Glu Gly Asn Ala Ser
1505                1510                1515

Ala Asn Ser Cys Asp Leu Asp Glu Glu Phe Ser Ser Ser Leu Glu
1520                1525                1530

Glu Glu Thr Leu Thr Glu Lys Glu Ser Pro Pro Ala Pro Gly Arg
1535                1540                1545

Thr Val Glu Gly Leu Glu Val Leu Cys Gln Val Tyr Leu Gln Ser
1550                1555                1560

Leu Lys Asn Leu Glu Glu Lys Thr Glu Ser Gln Arg Ile Met Lys
1565                1570                1575

Asn Lys Glu Ile Glu Lys Leu Glu Gln Leu Leu Ser Ser Glu Arg
1580                1585                1590

Lys Glu Leu Ser Cys Leu Arg Lys Gln Tyr Leu Ser Glu Lys Glu
1595                1600                1605

Gln Trp Gln Gln Lys Leu Thr Ser Val Thr Leu Glu Met Glu Ser
1610                1615                1620

Lys Leu Ala Glu Glu Lys Gln Gln Thr Lys Thr Leu Ser Leu Glu
1625                1630                1635

Leu Glu Val Ala Arg Leu Gln Leu Gln Glu Leu Asp Leu Ser Ser
1640                1645                1650

Arg Ser Leu Leu Gly Thr Asp Leu Glu Ser Val Val Arg Cys Gln
1655                1660                1665

Asn Asp Asn Tyr Asp Ile Lys Glu Ser Glu Val Tyr Ile Ser Glu
1670                1675                1680

Thr Thr Glu Lys Thr Pro Lys Gln Asp Thr Asp Gln Thr Cys Asp
1685                1690                1695

Lys Asp Ile Gln Gln Asp Leu Gly Leu Glu Thr Ser Val Thr Glu
1700                1705                1710
```

```
Ser Glu Thr Thr Arg Leu Thr Gly Glu Gly Cys Glu Glu Gln Pro
    1715                1720                1725

Pro Lys Thr Asn Cys Glu Ala Pro Ala Glu Asp Lys Thr Gln Asp
    1730                1735                1740

Cys Ser Glu Cys Ile Ser Glu Leu Cys Ser Ser Asn Val Leu
    1745                1750                1755

Val Pro Met Asp Val Leu Glu Asp Gln Gly Ser Ile Gln Asn Leu
    1760                1765                1770

Gln Leu Gln Lys Asp Thr Leu Asn Glu Asn Leu Arg Leu Leu Pro
    1775                1780                1785

Glu Val Glu Asp Trp Asp Lys Lys Val Glu Ser Leu Leu Asn Glu
    1790                1795                1800

Ile Met Glu Ala Asp Ser Lys Leu Ser Leu Gln Glu Val Gln Leu
    1805                1810                1815

Lys Met Lys Ile Ala Thr Cys Ile Gln Leu Glu Lys Ile Val Lys
    1820                1825                1830

Asp Leu Arg Lys Glu Lys Ala Asp Leu Ser Glu Lys Leu Glu Ser
    1835                1840                1845

Leu Pro Cys Asn Gln Glu Val Cys Leu Arg Val Glu Arg Ser Glu
    1850                1855                1860

Glu Asp Leu Gly Phe Asn Leu Asp Met Gly Ala Asn Glu Leu Leu
    1865                1870                1875

Ser Lys Ser Thr Lys Asp Asn Ala Thr Asn Thr Glu Asp Asn Tyr
    1880                1885                1890

Lys Glu Lys Phe Leu Asp Met Glu Arg Glu Leu Thr Arg Ile Lys
    1895                1900                1905

Ser Glu Lys Ala Asn Ile Glu His His Ile Leu Ser Val Glu Thr
    1910                1915                1920

Asn Leu Glu Val Val Gln Ala Glu Lys Leu Cys Leu Glu Arg Asp
    1925                1930                1935

Thr Glu Ser Lys Gln Lys Val Ile Ile Asp Leu Lys Glu Glu Leu
    1940                1945                1950

Phe Thr Val Ile Ser Glu Arg Asn Arg Leu Arg Glu Glu Leu Asp
    1955                1960                1965

Asn Val Ser Lys Glu Ser Lys Ala Leu Asp Gln Met Ser Lys Lys
    1970                1975                1980

Met Lys Glu Lys Ile Glu Glu Leu Glu Ser His Gln Arg Glu Ser
    1985                1990                1995

Leu Arg His Ile Gly Ala Val Glu Ser Glu Val Lys Asp Lys Ala
    2000                2005                2010

Asp Leu Ile Gln Thr Leu Ser Phe Asn Val Gly Glu Leu Thr Lys
    2015                2020                2025

Asp Lys Ala His Leu Gln Glu Gln Leu Gln Asn Leu Gln Asn Asp
    2030                2035                2040

Ser Gln Glu Leu Ser Leu Ala Ile Gly Glu Leu Glu Ile Gln Ile
    2045                2050                2055

Gly Gln Leu Asn Lys Glu Lys Glu Ser Leu Val Lys Glu Ser Gln
    2060                2065                2070

Asn Phe Gln Ile Lys Leu Thr Glu Ser Glu Cys Glu Lys Gln Thr
    2075                2080                2085

Ile Ser Lys Ala Leu Glu Val Ala Leu Lys Glu Lys Gly Glu Phe
    2090                2095                2100

Ala Val Gln Leu Ser Ser Ala Gln Glu Glu Val His Gln Leu Arg
```

-continued

```
            2105                2110                2115
Arg Gly Ile Glu Lys Leu Ser Val Arg Ile Glu Ala Asp Glu Lys
        2120                2125                2130
Lys His Leu Ser Ala Val Ala Lys Leu Lys Glu Ser Gln Arg Glu
        2135                2140                2145
Ser Asp Ser Leu Lys Asp Thr Val Glu Thr Leu Glu Arg Glu Leu
        2150                2155                2160
Glu Arg Ser Glu Glu Asn Gln Glu Leu Ala Ile Leu Asp Ser Glu
        2165                2170                2175
Asn Leu Lys Ala Glu Val Glu Thr Leu Lys Ala Gln Lys Asp Glu
        2180                2185                2190
Met Thr Lys Ser Leu Arg Ile Phe Glu Leu Asp Leu Val Thr Val
        2195                2200                2205
Arg Thr Glu Arg Glu Asn Leu Ala Lys Gln Leu Gln Glu Lys Gln
        2210                2215                2220
Ser Arg Val Ser Glu Leu Asp Glu Arg Cys Ser Ser Leu Arg Arg
        2225                2230                2235
Leu Leu Glu Glu Lys Glu Gln Ala Arg Val Gln Met Glu Glu Asp
        2240                2245                2250
Ser Lys Ser Ala Met Leu Met Leu Gln Met Gln Leu Lys Glu Leu
        2255                2260                2265
Arg Glu Glu Val Ala Ala Leu Cys Asn Asp Gln Glu Thr Leu Lys
        2270                2275                2280
Ala Gln Glu Gln Ser Leu Asp Gln Pro Gly Glu Glu Val His His
        2285                2290                2295
Leu Lys Ser Ser Ile Arg Lys Leu Lys Val His Ile Asp Ala Asp
        2300                2305                2310
Glu Lys Lys His Gln Asn Ile Leu Glu Gln Leu Lys Glu Ser Lys
        2315                2320                2325
His His Ala Asp Leu Leu Lys Asp Arg Val Glu Asn Leu Glu Gln
        2330                2335                2340
Glu Leu Ile Leu Ser Glu Lys Asn Met Ile Phe Gln Ala Glu Lys
        2345                2350                2355
Ser Lys Ala Glu Ile Gln Thr Leu Lys Ser Glu Ile Gln Arg Met
        2360                2365                2370
Ala Gln Asn Leu Gln Asp Leu Gln Leu Glu Leu Ile Ser Thr Arg
        2375                2380                2385
Ser Glu Asn Glu Asn Leu Met Lys Glu Leu Lys Lys Glu Gln Glu
        2390                2395                2400
Arg Val Ser Asp Leu Glu Thr Ile Asn Ser Ser Ile Glu Asn Leu
        2405                2410                2415
Leu Lys Asp Lys Glu Gln Glu Lys Val Gln Met Lys Glu Glu Ala
        2420                2425                2430
Lys Ile Thr Val Glu Met Leu Gln Thr Gln Leu Lys Glu Leu Asn
        2435                2440                2445
Glu Thr Val Val Ser Leu Cys Asn Asp Gln Glu Val Ser Lys Thr
        2450                2455                2460
Lys Glu Gln Asn Leu Gly Ser Gln Val Thr Leu Glu Leu Glu
        2465                2470                2475
Lys Ala Gln Leu Leu Gln Asp Leu Gly Glu Ala Lys Asn Lys Tyr
        2480                2485                2490
Ile Ile Phe Gln Ser Ser Val Asn Ala Leu Thr Gln Glu Val Glu
        2495                2500                2505
```

-continued

Ala Gly Lys Gln Lys Leu Glu Lys Gly Lys Glu Ile Arg Thr
    2510            2515            2520

Leu Lys Glu Gln Leu Lys Ser Gln Glu Gln Leu Val Cys Lys Leu
    2525            2530            2535

Ala Gln Val Glu Gly Glu Gln Gln Leu Trp Gln Lys Gln Lys Leu
    2540            2545            2550

Glu Leu Arg Asn Val Thr Met Ala Leu Glu Gln Lys Val Gln Val
    2555            2560            2565

Leu Gln Ser Glu Asn Asn Thr Leu Gln Ser Thr Tyr Glu Ala Leu
    2570            2575            2580

Gln Asn Ser His Lys Ser Leu Glu Ser Glu Leu Gly Leu Ile Lys
    2585            2590            2595

Leu Glu Lys Val Ala Leu Val Glu Arg Val Ser Thr Ile Ser Gly
    2600            2605            2610

Lys Glu Ala Glu Leu Gln Arg Glu Leu Arg Asp Met Leu Gln Lys
    2615            2620            2625

Thr Thr Gln Leu Ser Glu Asp Tyr Asn Lys Glu Lys Asn Arg Leu
    2630            2635            2640

Thr Glu Glu Val Glu Val Leu Arg Glu Glu Leu Gln Asn Thr Lys
    2645            2650            2655

Ala Ala His Leu Lys Ser Val Asn Gln Leu Glu Lys Glu Leu Gln
    2660            2665            2670

Arg Ala Gln Gly Lys Ile Lys Leu Met Leu Lys Ser Cys Arg Gln
    2675            2680            2685

Leu Glu Gly Glu Lys Glu Met Leu Gln Lys Glu Leu Ser Gln Leu
    2690            2695            2700

Glu Ala Ala Gln Gln Gln Arg Ala Gly Ser Leu Val Asp Ser Asn
    2705            2710            2715

Val Asp Glu Val Met Thr Glu Asn Lys Ala Leu Lys Glu Thr Leu
    2720            2725            2730

Glu Glu Lys Val Lys Glu Ala Asp Lys Tyr Leu Asp Lys Tyr Cys
    2735            2740            2745

Ser Leu Leu Ile Ser His Glu Glu Leu Glu Lys Ala Lys Glu Ile
    2750            2755            2760

Leu Glu Ile Glu Val Ala Arg Leu Lys Ser Arg Gln Ser Arg Gln
    2765            2770            2775

Asp Leu Gln Ser Ser Pro Leu Leu Asn Ser Ser Ile Pro Gly Pro
    2780            2785            2790

Ser Pro Asn Thr Ser Val Ser Glu Met Lys Ser Ala Ser Gly Gln
    2795            2800            2805

Asn Lys Ala Ser Gly Lys Arg Gln Arg Ser Ser Gly Ile Trp Glu
    2810            2815            2820

His Gly Lys Arg Ala Ala Pro Ser Thr Ala Glu Thr Phe Ser Lys
    2825            2830            2835

Lys Ser Arg Lys Ser Asp Ser Lys Ser Thr Arg Pro Ala Glu His
    2840            2845            2850

Glu Gln Glu Thr Glu Phe Glu Pro Glu Gly Leu Pro Glu Val Val
    2855            2860            2865

Lys Lys Gly Phe Ala Asp Ile Pro Thr Gly Lys Thr Ser Pro Tyr
    2870            2875            2880

Ile Leu Arg Arg Thr Thr Met Ala Thr Arg Thr Ser Pro Arg Phe
    2885            2890            2895

-continued

| | | | | | | | | | | | |
|---|---|---|---|---|---|---|---|---|---|---|---|
| Ala | Thr 2900 | Gln | Lys | Leu | Val | Gly 2905 | Ser | Ser | Pro | Ser | Leu 2910 | Gly | Lys | Glu |
| Asn | Val 2915 | Val | Glu | Ser | Ser | Lys 2920 | Pro | Thr | Ala | Gly | Gly 2925 | Ser | Arg | Ser |
| Gln | Lys 2930 | Val | Lys | Val | Val | Gln 2935 | Glu | Ser | Ser | Ala | Asp 2940 | Ser | His | Thr |
| Ala | Phe 2945 | Gln | Glu | Leu | Pro | Ala 2950 | Lys | Ser | Leu | Thr | Ala 2955 | Ser | Asn | Ile |
| Pro | Gly 2960 | Arg | Asn | Ser | Thr | Glu 2965 | Ser | Pro | Arg | Glu | Gly 2970 | Leu | Arg | Ala |
| Lys | Arg 2975 | Ala | Tyr | Pro | Ala | Ser 2980 | Ser | Pro | Ala | Ala | Gly 2985 | Pro | Asp | Pro |
| Thr | Asn 2990 | Asn | Glu | Asn | Cys | Arg 2995 | Val | Gln | | | | | | |

METHOD AND COMPOSITION FOR DIAGNOSIS OR TREATMENT OF AGGRESSIVE PROSTATE CANCER

CROSS-REFERENCE TO RELATED APPLICATIONS

This application claims benefit of Provisional Appln. 61/966,271, filed Feb. 19, 2014, the entire contents of which are hereby incorporated by reference as if fully set forth herein, under 35 U.S.C. § 119(e).

STATEMENT OF GOVERNMENTAL INTEREST

This invention was made with Government support under CA084294, U54 CA121852 and CA154293 awarded by the National Institutes of Health. The Government has certain rights in the invention.

BACKGROUND

Cancer is not a single entity but rather a highly individualized spectrum of diseases characterized by a number of genetic and genomic alterations (Hanahan and Weinberg, 2011). Distinguishing molecular alterations that constitute true drivers of cancer phenotypes from the multitude that are simply de-regulated has proven to be a daunting task, which is further exacerbated by the complexity of elucidating how such drivers interact synergistically to elicit cancer phenotypes. Prostate cancer is particularly challenging because its notorious heterogeneity, combined with a relative paucity of recurrent gene mutations, has made prostate cancer especially difficult to identify molecularly distinct subtypes with known clinical outcomes (Baca et al., 2013; Schoenborn et al., 2013; Shen and Abate-Shen, 2010). Additionally, while early-stage prostate tumors are readily treatable (Cooperberg et al., 2007), advanced prostate cancer frequently progresses to castration-resistant disease, which is often metastatic and nearly always fatal (Ryan and Tindall, 2011; Scher and Sawyers, 2005).

It should be noted that several factors, including an increase in the aging population and widespread screening for prostate specific antigen (PSA), have contributed to a substantial rise in diagnoses of prostate cancer. The primary means of determining the appropriate treatment course for men diagnosed with prostate cancer still relies on Gleason grading, a histopathological evaluation that lacks a precise molecular correlate. While patients with high Gleason score (Gleason ≥8) tumors are recommended to undergo immediate treatment, the appropriate treatment for those with low (Gleason 6) or intermediate (Gleason 7) Gleason score tumors remains more ambiguous. Indeed, although the majority of Gleason grade 6 tumors, as well as many Gleason grade 7 tumors, are likely to remain indolent (i.e., low-risk, non-aggressive or non-invasive), a minority (~10%) will progress to aggressive disease.

Indeed, the current lack of reliable and reproducible assays to identify tumors destined to remain indolent versus those that are aggressive, has resulted in substantial overtreatment of patients that would not die of the disease if left untreated. Consequently, "active surveillance" has emerged as an alternative for monitoring men with indolent prostate cancer, with the goal of avoiding treatment unless there is evidence of disease progression. The obvious advantage of active surveillance is that it avoids overtreatment; however, the potential concern is that it may miss the opportunity for early intervention for patients with aggressive tumors. Therefore, better methods with a molecular correlate for diagnosing aggressive prostate cancer have great value.

SUMMARY

Applicants have determined that there is a need to identify molecular determinants of cancers, including but not limited to, aggressive prostate cancer subtypes, a need to identify other prognostic biomarkers of disease outcome, and a need to treat such cancers. The subject matter disclosed herein addresses this need.

In a first set of embodiments, a method for treating prostate cancer or preventing the progression of a nonaggressive form of prostate cancer to an aggressive form, in a mammal, includes administering to the mammal a therapeutically effective amount of one or more active agents that reduce the expression or biological activity of both Forkhead box protein M1 (FOXM1) and Centromere protein F (CENPF) or biologically active fragments thereof or biologically active fragments thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding either FOXM1 or CENPF proteins.

In a second set of embodiments, a pharmaceutical formulation for treating prostate cancer or reducing or preventing the progression of a nonaggressive form of prostate cancer to an aggressive form, includes a therapeutically effective amount of one or more active agents that reduce the expression or biological activity of both Forkhead box protein M1 (FOXM1) and Centromere protein F (CENPF) selected from the group consisting of an isolated shRNA, siRNA, antisense RNA, antisense DNA, Chimeric Antisense DNA/RNA, microRNA, and ribozymes that are sufficiently complementary to either a gene or an mRNA encoding the FOXM1 or CENPF protein.

In a third set of embodiments, a medicament treating prostate cancer or reducing or preventing the progression of a nonaggressive form of prostate cancer to an aggressive form, includes one or more active agents in a therapeutically effective amount that reduce the expression or biological activity of both Forkhead box protein M1 (FOXM1) and Centromere protein F (CENPF) or biologically active fragments thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding either FOXM1 or CENPF proteins.

In another set of embodiments, a method includes receiving, automatically on a processor, data that indicates human gene expression profiles for human tissue in a context of interest comprising a plurality of cell phenotypes including at least one gene expression profile representing a first cell phenotype and at least one other gene expression profile representing a second cell phenotype. The method also includes determining, automatically on a processor based on the human gene expression profiles, data that indicates an interactome of human tissue in the context of interest and data that indicates a human signature that represents a ranking of genes differentially expressed in the second cell phenotype compared to the first cell phenotype. The method also includes determining, automatically on a processor based on the interactome of human tissue and the human signature, data that indicates human master regulator molecules most likely to have produced the human signature. The method further includes receiving, automatically on a processor, data that indicates animal model gene expression profiles for animal tissue in the context of interest based on multiple in vivo perturbations of one or more genetically distinct animals including at least one gene expression profile representing the first cell phenotype and at least one other gene expression profile representing the second cell phenotype. The method still further includes determining, automatically on a processor based on the animal model gene expression profile, data that indicates an interactome of animal tissue in the context of interest and data that indicates an animal signature that represents a ranking of genes differentially expressed in the second cell phenotype compared to the first cell phenotype. Even further, the method includes determining, automatically on a processor based on the interactome of animal tissue and the animal signature, data that indicates animal master regulator molecules most likely to have produced the animal signature. The method next includes determining, automatically on a processor based on the human master regulator molecule and the animal master regulator molecules, data that indicates conserved master regulator molecules that are most likely to have produced both the human signature and the animal signature. In some embodiments of this set, the method yet further includes determining, automatically on a processor based on the conserved master regulator molecules, data that indicates two or more synergistic conserved master regulator molecules that have a net combined effect greater than a sum of individual effects.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1C is a block diagram and graph that illustrate example effects on gene profiling data for mouse models in response to various perturbagens, according to an embodiment;

FIG. 3C is a table that illustrates example ranking of master regulators for their impacts on prostate cancer by various available algorithms, according to an embodiment;

FIG. 3D is a table that illustrates example predicted synergy of FOXM1 and CENPF among the subset of master regulators using available algorithms, according to an embodiment;

FIG. 4A and FIG. 4B are flow charts that illustrate an example method for determining various synergistic master regulators for other phenotype transitions, according to an embodiment;

FIG. 5 is a table that illustrates example clinical datasets used to determine whether synergistic master regulators FOXM1 and CENPF are prognostic biomarkers of prostate cancer outcomes, according to an embodiment;

FIG. 7 is a table that illustrates example prognostic power of coexpression of protein levels of FOXM1 and CENPF, with death due to prostate cancer and time to metastasis as evaluation endpoints, according to an embodiment;

FIG. 8 is a flow chart that illustrates an example diagnostic method for determining whether a subjects is at risk based on coexpression of the synergistic master regulators FOXM1 and CENPF, according to an embodiment;

FIG. 11L and FIG. 11M are graphs that illustrate example percentages of red, green or yellow cells relative to the total number of fluorescent cells for control tumors and experimental tumors, respectively, indicating profound selection against cells silenced for both FOXM1 and CENPF according to an embodiment;

FIG. 11N is an image of Western blots that illustrate example changes in expression of the indicated representative markers of the PI3-kinase and MAP kinase signaling pathways associated with tumor growth in DU145 and PC3 prostate cancer cells after silencing either FOXM1 or CENPF or both, according to an embodiment.

DEFINITIONS

Figure 1A:
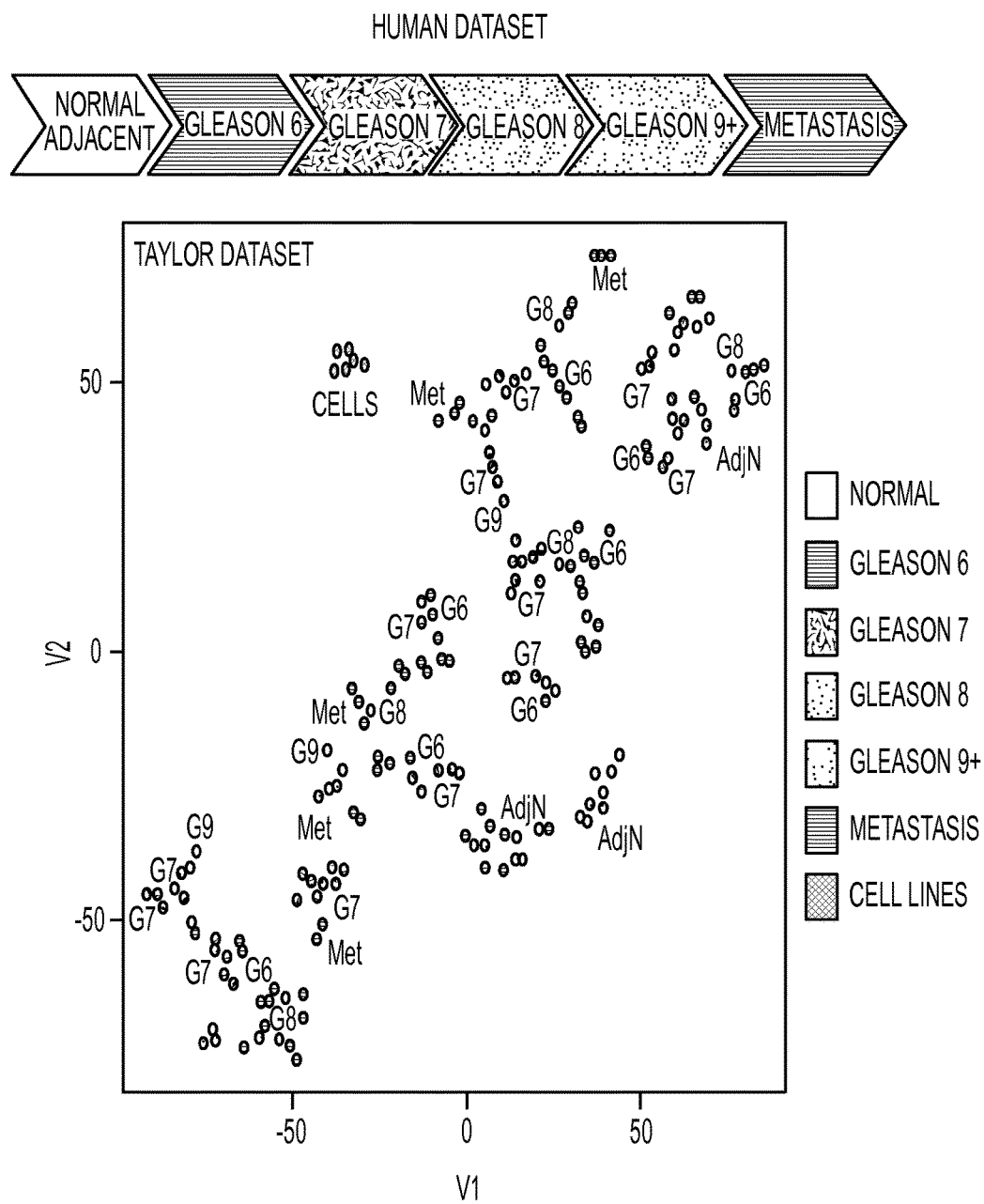
FIG. 1A is a block diagram and graph that illustrate example gene profiling data for multiple human subjects with various stages of prostate cancer, according to an embodiment.

Unless defined otherwise, technical and scientific terms used herein have the same meaning as commonly understood by one of ordinary skill in the art to which this invention belongs. The practice of the present invention will employ, unless indicated specifically to the contrary, conventional methods of molecular biology and recombinant DNA techniques within the skill of the art, many of which are described below for the purpose of illustration. Such techniques are fully explained in the literature. See, e.g., Singleton et al., Dictionary of Microbiology and Molecular Biology 3rd.sup.ed., J. Wiley & Sons (2001); March, Advanced Organic Chemistry Reactions, Mechanisms and Structure 5th.sup.ed., J. Wiley & Sons (2001); Sambrook & Russell, eds., Molecular Cloning: A Laboratory Manual 3rd ed., Cold Spring Harbor Laboratory Press (2001); Glover, ed., DNA Cloning: A Practical Approach, vol. I & II (2002); Gait, ed., Oligonucleotide Synthesis: A practical approach, Oxford University Press (1984); Herdewijn, ed., Oligonucleotide Synthesis: Methods and Applications, Humana Press (2005); Hames & Higgins, eds., Nucleic Acid Hybridisation: A Practical Approach, IRL Press (1985); Buzdin & Lukyanov, eds., Nucleic Acid Hybridization: Modern Applications, Springer (2007); Hames & Higgins, eds., Transcription and Translation: A Practical Approach, IRL Press (1984); Freshney, ed., Animal Cell Culture, Oxford UP (1986); Freshney, Culture of Animal Cells: A Manual of Basic Technique and Specialized Applications, 6th ed., John Wiley & Sons (2010); Perbal, A Practical Guide to Molecular Cloning, 3rd ed., Wiley-Liss (2014); Farrell, RNA Methodologies: A Laboratory Guide for Isolation and Characterization, 3rd ed., Elsevier/Focal Press (2005); Lilley & Dahlberg, eds., Methods in Enzymology: DNA Structures, Part A: Synthesis and Physical Analysis of DNA, Academic Press (1992); Harlow & Lane, Using Antibodies: A Laboratory Manual: Portable Protocol no. 1, Cold Spring Harbor Laboratory Press (1999); Harlow & Lane, eds., Antibodies: A Laboratory Manual, Cold Spring Harbor Laboratory Press (1988); Seethala & Fernandes, eds., Handbook of Drug Screening, Marcel Dekker (2001); and Roskams & Rodgers, eds., Lab Ref: A Handbook of Recipes, Reagents, and Other Reference Tools for Use at the Bench, Cold Spring Harbor Laboratory (2002) provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "nucleic acid" as used herein refers to any natural and synthetic linear and sequential arrays of nucleotides and nucleosides, cDNA, genomic DNA, mRNA, oligonucleotides and derivatives thereof. The term "nucleic acid" further includes modified or derivatized nucleotides.

An "isolated" nucleic acid molecule is one which is separated from other nucleic acid molecules which are present in the natural source of the nucleic acid molecule, namely cancerous or noncancerous biological samples. An "isolated" nucleic acid molecule, such as a cDNA molecule, can be substantially free of other cellular material or culture medium when produced by recombinant techniques, or substantially free of chemical precursors or other chemicals when chemically synthesized.

As used herein, "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

As used herein, an "inhibitory oligonucleotide" includes antisense, siRNA, shRNA, ribozymes and MIRs or other oligonucleotide that reduces the expression of a targeted FOXM1 or CENPF gene or protein.

"Biological sample" refers to a sample of prostate cells. The sample can be prostate cancer cells, for example, those taken from a prostate biopsy from a subject having prostate cancer, or of normal prostate cells either taken from a normal control subject or in some embodiments from a noncancerous area of the prostate of the subject having prostate cancer.

In other embodiments, the biological sample comprises circulating prostate cancer cells isolated from the blood, cerebrospinal fluid (CSF) or serum of a subject having prostate cancer or exosomes derived from prostate cancer cells.

"Indolent prostate cancer" means low-risk, non-aggressive or non-invasive prostate cancers which would not lead to subject death if left untreated.

"Aggressive prostate cancer" means prostate cancer that leads to a shortened life expectancy of the subject or an increased occurrence of metastasis to other tissue cancers.

"At high risk of progressing to aggressive prostate cancer" means that the subject has prostate cancer that, more likely than not, is or will become aggressive prostate cancer.

"Administering" or "administration of" a drug or therapeutic pharmaceutical composition to a subject as used herein means any method known in the art including both direct administration, including self-administration (including oral administration or intravenous, subcutaneous, intramuscular or intraperitoneal injections, local administration directly into or onto a target tissue (prostate tumor or prostate gland) or administration by any route or method that delivers a therapeutically effective amount of the drug or composition to the prostate cancer cells or tumor or tissue to which it is targeted.

Administration of an agent "in combination with" includes parallel administration of two agents to the patient over a period of time, co-administration (in which the agents are administered at approximately the same time, e.g., within about a few minutes to a few hours of one another), and co-formulation (in which the agents are combined or compounded into a single dosage form suitable for oral, subcutaneous or parenteral administration).

A "subject" is a mammal, typically a human, but optionally a mammalian animal of veterinary importance, including but not limited to horses, cattle, sheep, dogs, and cats. In some embodiments a "subject" refers to either one who has been previously diagnosed with or identified as suffering from prostate cancer or to one who does not have prostate cancer, i.e., a normal or control subject.

As used herein, the term "diagnosis" includes the detection, typing, monitoring, dosing, and comparison at various stages of prostate cancer in a subject. Diagnosis includes the assessment of a predisposition or risk of developing an aggressive form of prostate cancer.

A "therapeutically effective amount" of an active agent or pharmaceutical composition is an amount that achieves the intended therapeutic effect, e.g., alleviation, amelioration, palliation or elimination of one or more manifestations of prostate cancer, including aggressive prostate cancer in the subject. The full therapeutic effect does not necessarily occur by administration of one dose and may occur only after administration of a series of doses. Thus, a therapeutically effective amount may be administered in one or more administrations.

As used herein, "active agent" includes any small molecules, polypeptides, antibodies, nucleic acids (including antisense RNA, siRNA, microRNAs, and ribozymes that reduce the expression (including by reducing transcription or translation of the gene or mRNA, respectively) and/or biological activity of FOXM1 or CEPF.

As used herein, the terms "treat," "treatment," "treating," or "amelioration" when used in reference to prostate cancer refer to therapeutic treatments for the prostate cancer, wherein the object is to reverse, alleviate, ameliorate, inhibit, slow down or stop the progression of the prostate cancer to an aggressive form, or reduce the severity of a symptom or condition. The term "treating" includes reducing or alleviating at least one adverse effect or symptom of a condition. Treatment is generally "effective" if one or more symptoms or clinical markers such as prostate-specific antigen (PSA) are reduced.

A "prophylactically effective amount" of a drug is an amount of a drug that, when administered to a subject, will have the intended prophylactic effect, e.g., preventing or delaying the conversion/transition of a non-aggressive prostate cancer to an aggressive prostate cancer. The full prophylactic effect does not necessarily occur by administration of one dose and may occur only after administration of a series of doses. Thus, a prophylactically effective amount may be administered in one or more administrations.

"FOXM1" as used herein refers to Forkhead box protein M1 is a protein that in humans is encoded by the FOXM1 gene. The protein encoded by this gene is a member of the FOX family of transcription factors. FOXM1 is also referred to as FKHL16; FOXM1B; HFH-11; HFH11; HNF-3; INS-1; MPHOSPH2; MPP-2; MPP2; PIG29; TGT3; TRIDENT. The human and mouse reference mRNA sequences are NM_001243088 (SEQ ID NO: 49) and NM_008021 (SEQ ID NO: 51), respectively. The human and mouse protein sequences are NP_001230017 (SEQ ID NO: 50) and NP_032047 (SEQ ID NO: 52), respectively. For the purpose of the methods and compositions of the invention, "FOXM1 protein" includes orthologs (analogs in different species).

"CENPF" as used herein refers to centromere protein F, a protein that in humans is encoded by the CENPF gene. The CENPF protein associates with the centromere-kinetochore complex. The protein is a component of the nuclear matrix during the G2 phase of interphase. CENPF is also referred to as CENF; PRO 1779; hcp-1. The human and mouse reference mRNA sequences are NM_016343 (SEQ ID NO: 53) and NM_001081363 (SEQ ID NO: 55) respectively; and the human and mouse protein sequences are NP_057427 (SEQ ID NO: 54) and NP_001074832 (SEQ ID NO: 56), respectively. For the purpose of the methods and compositions of the invention, "CENPF protein" includes orthologs (analogs in different species).

"Protein expression" refers to expression of protein as measured quantitatively by methods including without limitation Western blot, 2-dimensional SDS-PAGE and mass spectrometry.

"mRNA expression" refers to the expression of mRNA that can be measured quantitatively by methods including but not limited to nuclease protection assays, northern blots, real time quantitative PCR, and in-situ hybridization.

"Control level" and "normal level of expression" as used herein refer to a level or range of levels of FOXM1 or CENPF expressed in normal prostate tissue or indolent prostate cancer tumors.

"Threshold" or "threshold level" as used herein refers to a level or range of levels that separate normal level of expression of FOXM1 and CENPF from a pattern, level or ranges of levels of expression of FOXM1 and CENPF that indicate a high risk of aggressive prostate cancer. When the levels of expression of FOXM1 and CENPF are equal to or greater than the threshold level then it is determined that the subject is at high risk of developing aggressive prostate cancer or has aggressive prostate cancer, and vice versa.

"Protein" as used herein is a generic term referring to and used interchangeably with biologically active native protein, fragments, peptides, or analogs thereof.

"Therapeutic agent" and "active agent" as used herein refer to any inhibitory oligonucleotide, small molecule or compound that reduces the expression or biological activity of FOXM1 or CENPF protein.

"Subcellular localization of FOXM1 and CENPF" as used herein refers to the presence of FOXM1 and CENPF inside a cell. "Colocalization" means that both FOXM1 and CENPF are present in the same cell or if so designated, in the same subcellular compartment, for example colocalization in the nucleus or cytoplasm.

"Master regulator" as used herein refers to a protein that acts to drive any intermediary proteins in a key signaling pathway for a phenotype transition, such as a transition from indolent prostate cancer cell to an aggressive prostate cancer cell.

"Synergistic Master Regulator" as used herein refers to a multiple master regulators that together have a measured effect greater than a predicted sum of their individual measured effects.

"Cross-species computational analysis" as used herein refers to automatically searching molecular interaction networks ("interactomes") of two or more species, such as human and mouse models for human cells, using a computer system to discover interactions present ("conserved") in both species.

The term "probe" refers to any molecule which is capable of selectively binding to a specifically intended target molecule, for example, an oligonucleotide probe that specifically hybridizes to a prognostic biomarker mRNA such as CENPF or FOXM1, or an antibody that specifically binds CENPF or FOXM1. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to RNA, DNA, RNA/DNA chimeras, proteins, antibodies, and organic molecules.

Unless otherwise specified, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody moiety.

DETAILED DESCRIPTION

A method, composition of matter, article of manufacture and apparatus are described for discovery of synergistic master regulators and the diagnosis and treatment of aggressive prostate cancer. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

It has been discovered that the genes encoding FOXM1 and CENPF are prognostic biomarkers that are synergistic master regulators of aggressive prostate cancer in humans. Significantly elevated coexpression of both FOXM1 and CENPF genes in a prostate cancer sample at levels at least 35% above control levels is diagnostic of aggressive prostate cancer or of a high risk of developing aggressive prostate cancer, as is described in sample embodiments. Gene expression can be determined by mRNA or protein expression or combinations thereof. Regulatory drivers of prostate cancer malignancy were identified by assembling genome-wide regulatory networks (interactomes) for both human and mouse prostate cancer from expression profiling datasets of human tumors and genetically engineered mouse models, respectively. Cross-species computational analysis of these interactomes identified FOXM1 and CENPF as synergistic master regulators of prostate cancer malignancy that promote tumor growth by coordinated regulation of target gene expression and activation of key signaling pathways associated with prostate cancer malignancy. Thus, coexpression of FOXM1 and CENPF was identified for the first time as a robust prognostic indicator of aggressive prostate cancer with poor survival and metastasis.

Based on the data described herein, certain embodiments of the invention are directed to methods for diagnosing aggressive prostate cancer or a high risk of prostate cancer progressing to an aggressive form if the level of mRNA or protein expression for each of FOXM1 and CENPF in a prostate cancer sample from a subject is at least 35% higher than the corresponding level in a control prostate sample. In another embodiment aggressive prostate cancer is diagnosed if at least 50% of the cells in the prostate cancer sample from a subject express elevated levels of both FOXM1 protein and CENPF protein.

Other embodiments are directed to the treatment of aggressive prostate cancer in a subject by administering therapeutically effective amounts of either inhibitory oligonucleotides or other agent that reduces FOXM1 and CENPF expression in prostate cancer cells or both.

1. Overview

While both FOXM1 and CENPF have been implicated in various cancers, the current work has uncovered a novel synergistic interaction that had not been previously anticipated. FOXM1 encodes a Forkhead domain transcription factor that is frequently over-expressed in many different types of cancer, including prostate, see Alvarez-Fernandez and Medema, 2013; Halasi and Gartel, 2013a; Kalin et al., 2011; and Koo et al., 2012, for reviews. Many previous studies have established a role for FOXM1 expression and activity in the regulation of cellular proliferation, DNA damage, genomic stability, drug resistance, and metastasis, and have shown that FOXM1 interacts with other key regulators such as β-Catenin and MYB (Lefebvre et al., 2010; Zhang et al., 2011). In particular, the relevance of FOXM1 for prostate cancer has been shown by its gain- or loss-of-function in vivo, which elicit modest effects on tumor growth (Cai et al., 2013; Kalin et al., 2006).

CENPF (also known as mitosin or LEK1 in mouse), a known target of FOXM1, has also been implicated in various cancers, although not previously in prostate, and in some cases has been shown to undergo gene amplification and be associated with disease outcome (see Ma et al., 2006; Varis et al., 2006 for reviews). However, the actual functional role of CENPF has been more elusive and difficult to reconcile. In particular, while CENPF is named for its association with the centromere-kinetochore protein complex, such association is only transient. In fact, CENPF has been shown to have other functions, including regulation of mitosis and cellular proliferation (Bomont et al., 2005; Feng et al., 2006; Holt et al., 2005), which are mediated in part by protein interactions, including with members of the Retinoblastoma gene family as well as with the ATF transcription factor (see Ma et al., 2006; Varis et al., 2006 for reviews).

2. Cross Species Discovery of Regulatory Genes for Aggressive Prostate Cancer To assemble a human prostate cancer interactome, gene expression profile data reported in (Taylor et al., 2010) was analyzed, which is ideally suited because: (i) it is relatively large (n=185) and diverse, including gene expression profiles from primary prostate tumors, adjacent normal prostate tissue, metastases, and cell lines; (ii) its primary tumors encompass the full range of pathological Gleason scores and have well-annotated clinical outcome data; and (iii) it displays extensive genetic diversity and tumor heterogeneity, as shown by t-Distributed Stochastic Neighbor Embedding (t-SNE) analysis. Several characteristics of this dataset are described below with reference to FIG. 5. Notably, interactomes assembled from three alternative human prostate cancer datasets, also characterized in FIG. 5, were neither as complete nor as extensive. FIG. 1A is a block diagram and graph that illustrate example gene profiling data for multiple human subjects with various stages of prostate cancer, according to an embodiment. Details are set forth in Example 2.

Analysis of genetically engineered mouse models (GEMMs) can circumvent challenges associated with the inherent complexity of the more heterogeneous human cancer phenotypes. Investigations of mouse models of prostate cancer have contributed to characterization of disease-specific pathways, led to the identification of biomarkers of disease progression, and provided useful preclinical models for prevention and therapy (Irshad and Abate-Shen, 2013; Ittmann et al., 2013). Following the description of the first transgenic model of prostate cancer nearly 20 years ago, there are now numerous GEMMs that collectively model key molecular pathways de-regulated in human prostate cancer, and recapitulate the various stages of disease progression including pre-invasive lesions (prostate intraepithelial neoplasia, PIN), adenocarcinoma, castration-resistance, and metastasis (Irshad and Abate-Shen, 2013; Ittmann et al., 2013).

Inherent species differences often hinder direct comparative analyses of mouse models and human cancer. As described herein, a novel combination of computational approaches were applied to enable accurate cross-species integration of regulatory information from mouse to man in the context of prostate cancer. Recent advances in systems biology have led to the reverse engineering of regulatory networks (interactomes) that integrate large-scale datasets encompassing gene expression profiles, protein-protein interactions, genomic alterations, and epigenetic changes associated with cancer and other diseases (see Lefebvre et al., 2012 for a review). While individual analyses of human and murine interactomes led to relevant biological discoveries, cross-species interactome-based interrogation strategies have not been systematically implemented until now.

The results described here are based on an approach for accurate cross-species analysis of conserved cancer pathways based on reverse engineering and interrogation of genome-wide regulatory networks (i.e., interactomes) representing both human and mouse prostate cancer. To accomplish this, the first regulatory network obtained from in vivo perturbation of a repertoire of mouse cancer models was introduced, as well as its comparative analysis with a complementary regulatory network generated from human prostate cancer samples. Cross-species computational interrogation of these paired interactomes followed by experimental validation thus elucidated the synergistic interaction of FOXM1 and CENPF as a driver of aggressive prostate cancer malignancy.

Figure 1B:
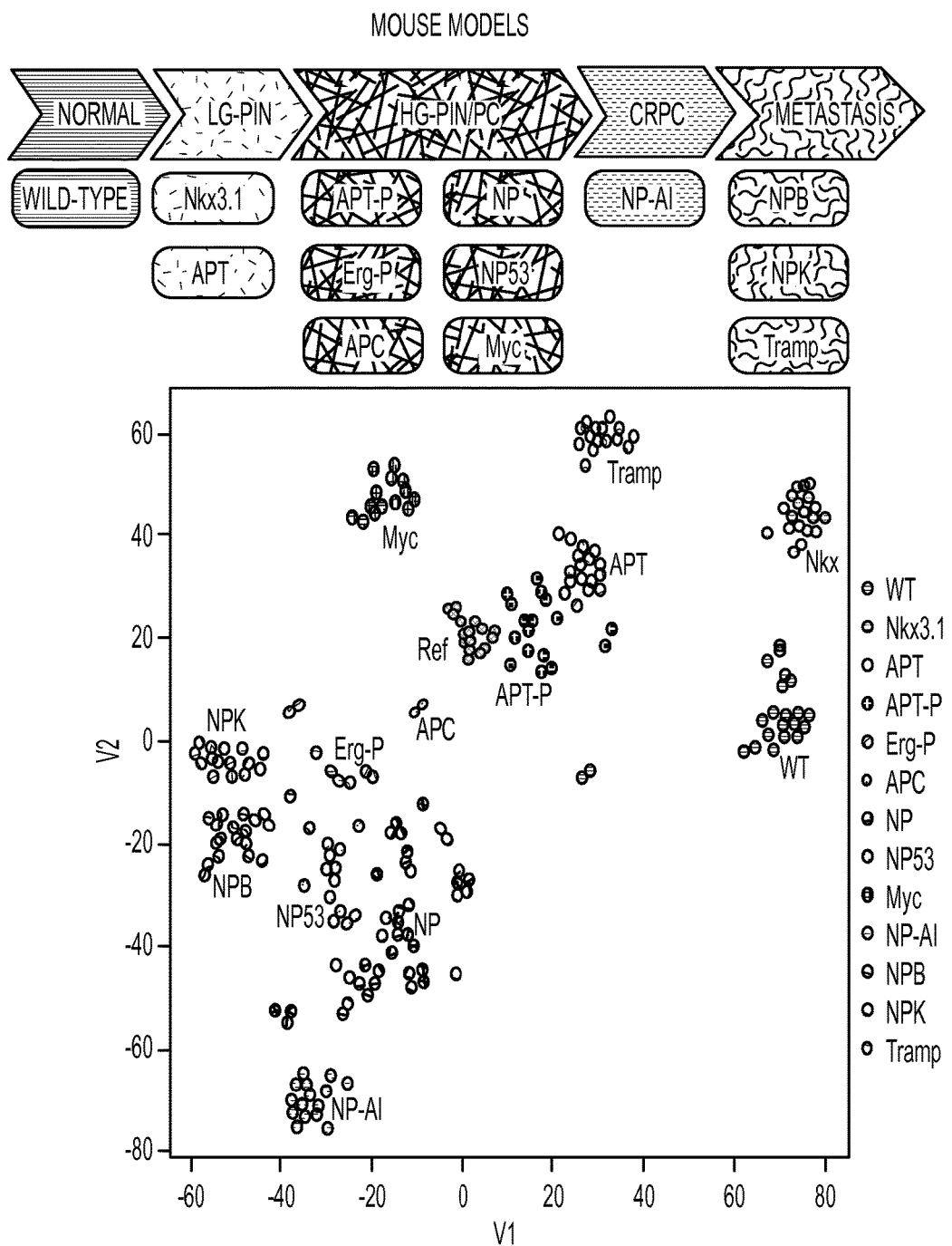
FIG. 1B is a block diagram and graph that illustrate example gene profiling data for multiple mouse models for prostate cancer, according to an embodiment.

To assemble a corresponding mouse prostate cancer interactome, it was first necessary to generate an appropriately sized gene expression profile dataset representing sufficient expression variability. To address this challenge, 13 distinct GEMMs were first selected, which together represent the full spectrum of prostate cancer phenotypes, including normal epithelium (wild-type), low-grade PIN (Nkx3.1 and APT), high-grade PIN and adenocarcinoma (APT-P, APC, Hi-Myc, NP, Erg-R, and NP53), castration-resistant prostate cancer (NP-AI), and metastatic prostate cancer (NPB, NPK, and TRAMP). FIG. 1B is a block diagram and graph that illustrate example gene profiling data for multiple mouse models for prostate cancer, according to an embodiment. The diagram groups the mouse models by phenotype listed above. The graph plots the t-SNE analysis showing relative distribution of the GEMMs. More detail is set forth in Example 2.

To generate a sufficient number of samples, while further increasing the variability of the corresponding expression profiles, a controlled set of exogenous perturbations was introduced by in vivo administration of 13 different small-molecule perturbagens to each GEMM. Perturbagens were selected for their clinical relevance and/or ability to modulate key prostate cancer pathways, including: hormone signaling (testosterone, calcitriol, or enzalutamide); PI3 kinase activity (MK2206, LY294002, and rapamycin); MAP kinase activity (PD035901); tyrosine kinase activity (imatinib, dasatinib, and sorafenib); NFB signaling (BAY 11-7082); JAK/STAT activity (WP1066); and chemotherapy (docetaxel). Following pilot studies to define the appropriate dose and schedule that produced the broadest range of gene expression changes, a universal schedule was adopted of 1 treatment per day for 5 days with dosage determined independently for each perturbagen, as described below in an experimental procedures section.

The resulting dataset contained 384 gene expression profiles, corresponding to the 13 GEMMs each treated with the 13 perturbagens or vehicles. The t-SNE analysis revealed that the resulting mouse dataset represented an extensive range of gene expression variability, as requisite for ARACNe. Specifically, while expression profiles from the same GEMMs and perturbagens clustered together, suggesting their effect was highly replicable, the diverse GEMMs and perturbagens provided independent and highly effective axes of expression heterogeneity. FIG. 1C is a block diagram and graph that illustrate example effects on gene profiling data for mouse models in response to various perturbagens, according to an embodiment. The schematic diagram depicts perturbagens used to treat the GEMMs. The graph plots the t-SNE analysis showing the relative distribution of perturbagens for a representative GEMM (i.e., the NP model).

Figure 2A:
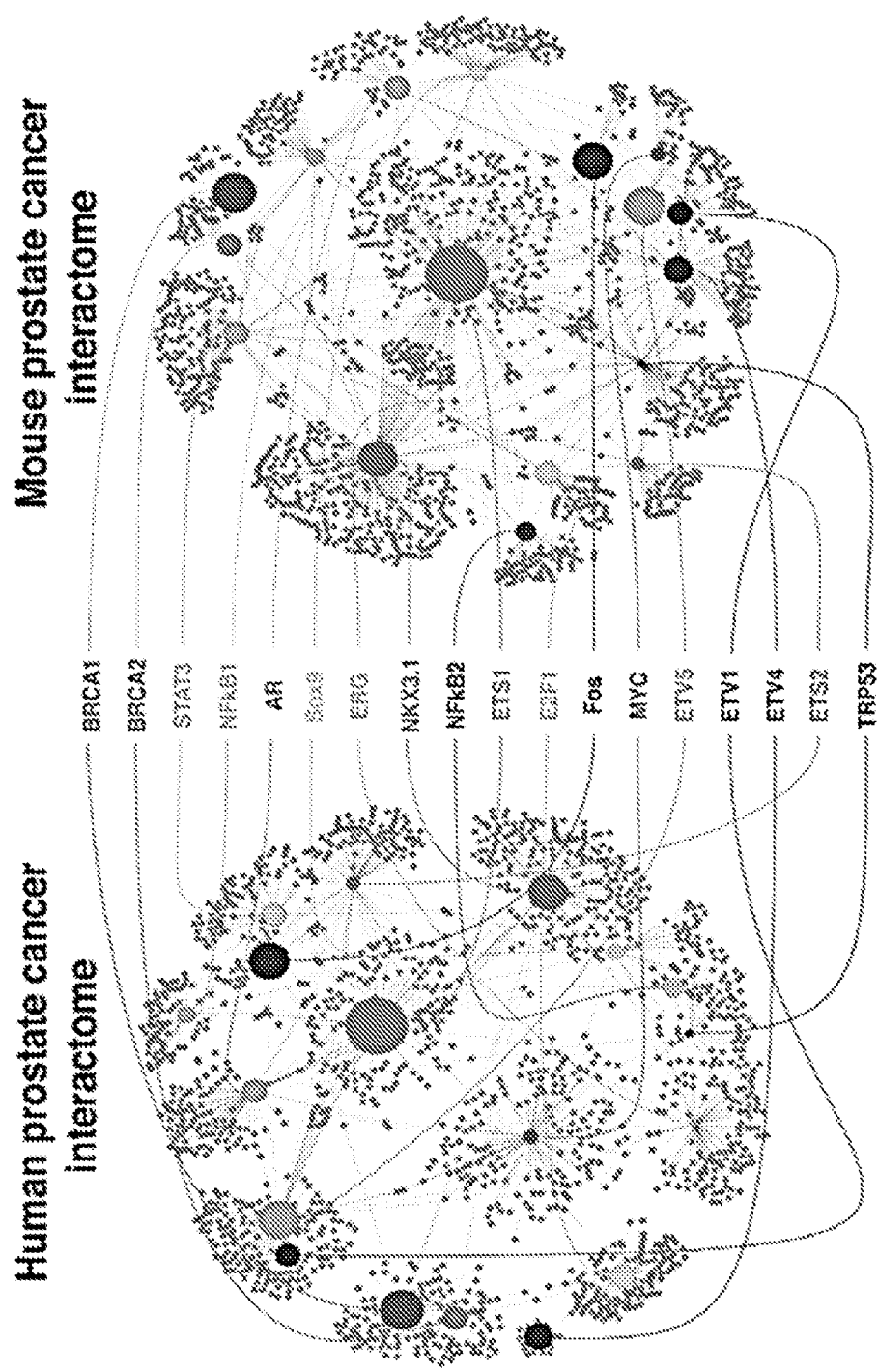
FIG. 2A is a block diagram and graph that illustrate example interactomes for human and mouse models with prostate cancer, according to an embodiment.

Regulatory networks (interactomes) for human and mouse prostate cancer were generated using the Algorithm for the Reconstruction of Accurate Cellular Networks. FIG. 2A is a block diagram and graph that illustrates example interactomes for human and mouse models with prostate cancer, according to an embodiment. The suitability of these mouse and human interactomes for cross-species interrogation was next evaluated by developing a novel computational approach to assess the global conservation of their transcriptional programs described in detail in Example 2. Notably, conserved transcriptional regulators included many genes known to play important roles in prostate cancer, such as AR, ETS1, ETV4, ETV5, STAT3, MYC, BRCA1, and NKX3.1. In particular, AR displayed extensive correlation of its transcriptional activity between the human and mouse interactomes, consistent with its known role as a key regulator of prostate development and prostate tumorigenesis The Master Regulator Inference algorithm (MARINa) (Carro et al., 2010; Lefebvre et al., 2010) was used to infer candidate master regulators (MRs) that act individually or synergistically to drive malignant prostate cancer in the conserved interactomes. MARINa estimates differential activity (DA) based on enrichment (differential expression, DE) of their activated and repressed targets in the malignancy signature. More specifically, MARINa identified candidate MRs based on the concerted differential expression of their ARACNe-inferred targets (i.e., their differential activity, DA). Specifically, "activated" MRs have positively-regulated and repressed targets significantly enriched among upregulated and downregulated genes, respectively, while "repressed" MRs have the converse. To interrogate the human prostate cancer interactome, a gene signature was used representing prostate cancer malignancy from the Taylor dataset, which compares aggressive prostate tumors (Gleason score ≥8 with rapid biochemical recurrence; sample size n=10) versus indolent ones (Gleason score 6 tumors with no biochemical recurrence; sample size n=39). The resulting independent lists of human and mouse MRs were then integrated to produce a ranked list of 20 conserved MRs, including 7 activated and 13 repressed (joint p-value: p≤0.0074 by Stouffer's method). Notably, these conserved MRs were more likely to be associated with disease outcome than the non-conserved ones, and were also more likely to be differentially expressed in aggressive prostate tumors (metastatic versus non-metastatic; 100% versus 60%). FIG. 3C is a table that illustrates example ranking of master regulators for their impact on prostate cancer by various available algorithms. Using the ARACNe method to analyze all possible pairs among the conserved activated MRs, the only pair that was found to be statistically significant was FOXM1 and CENPF. Both FOXM1 and CENPF were differentially co-expressed at significantly elevated levels in aggressive prostate tumors and were predicted to be significantly associated with disease outcome. Thus, subsequent analyses were focused on this pair of cross-species conserved, synergistic MRs.

3. Method of Diagnosis: FOXM1 and CENPF are Prognostic Biomarkers of Aggressive Prostate Cancer Analysis of high-density tissue microarrays (TMAs) revealed that the coexpression of FOXM1 and CENPF constituted a highly informative biomarker of poor disease outcome. FIG. 5 is a table that illustrates example clinical datasets used to determine whether synergistic master regulators FOXM1 and CENPF are prognostic biomarkers of prostate cancer outcomes, according to an embodiment. The datasets are listed along the top row, with their use in this study grouped by primary dataset (Taylor et al., 2010); secondary datasets; RNA gene expression datasets (Sboner et al., 2010; Glinsky et al., 2004); and protein immunohistochemistry tissue microarray (TMA) datasets (outcome TMA from MSKCC, and Metastasis TMA from Michigan). The categories of data in each dataset are given by the rows, as applicable. One row breaks down the number of samples for each cell type; one row gives the median age of the subjects. The next rows give the Pathology T stage; the clinical T stage; the Pathology N stage; the Pathology Gleason score; the biopsy Gleason score, the survival index (SVI); the extracapsular extension percentage; the biochemical recurrence (BCR) median time in months; the median overall survival in months; and, the median time to metastasis in months.

Analysis of protein expression of FOXM1 and CENPF was performed using high-density tissue primary tumor microarray (TMAs) (Donovan et al., 2008) and a metastasis TMA (Shah et al., 2004). Available clinico-pathological features of these cohorts as well as independent human datasets used for clinical validation are summarized in the Table of FIG. 5.

In particular, a high-density TMA containing primary tumors from a large cohort of subjects (sample size n=916) that had undergone prostatectomy at Memorial Sloan-Kettering Cancer Center from 1985 to 2003 (Donovan et al., 2008) was analyzed. These cases have extensive clinical follow-up data for up to 20 years, including time to biochemical recurrence, prostate-cancer specific survival, and time to metastasis. A second TMA was evaluated from the rapid autopsy program at the University of Michigan containing prostate cancer metastases (sample size n=60), including 6 lung, 11 liver, 22 lymph node, and 14 other sites (Shah et al., 2004). Immunostaining for FOXM1 or CENPF was performed on adjacent sections of each TMA slide and staining intensity was evaluated (see experimental procedures section, below).

Figure 6A:
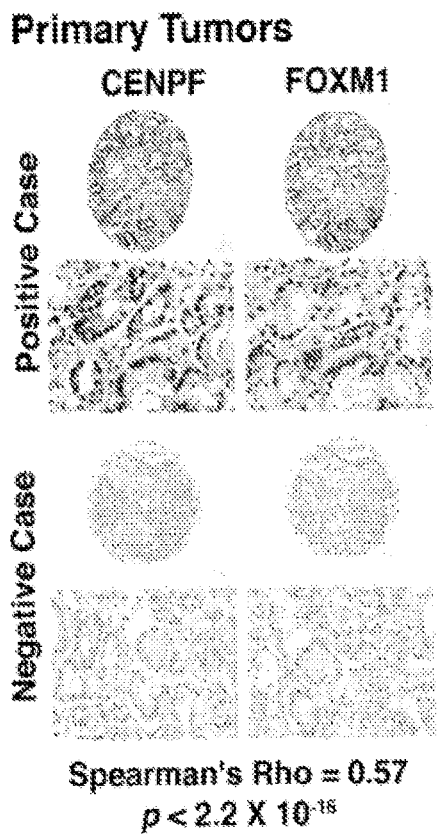
FIG. 6A is an image that illustrates example micrographs of FOXM1 and CENPF stained tissues showing enhanced concentrations of both in aggressive prostate cancer tumors compared to other prostate tumors, according to an embodiment.

FIG. 6A is an image that illustrates example micrographs of FOXM1 and CENPF stained tissues showing enhanced concentrations of both in aggressive prostate cancer tumors compared to other prostate tumors, according to an embodiment. These micrographs are based on the MSKCC prostatectomy TMA; and, analysis revealed that FOXM1 and CENPF were over-expressed in 33% and 37% of all cases, respectively, (sample size n=821 informative cases) with a trend toward increased expression in tumors with higher Gleason scores. Spearman rank correlation coefficient of FOXM1 and CENPF protein expression levels was 0.57 with p value $<2.2 \times 10^{-16}$, indicating the coexpression relationship is highly significant.

Figure 6B:
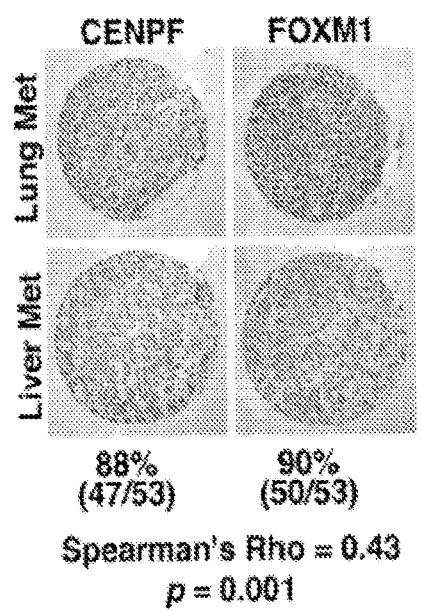
FIG. 6B is an image that illustrates example micrographs of FOXM1 and CENPF stained tissues showing enhanced concentrations of both in metastasized lung and liver tumors, according to an embodiment.

FIG. 6B is an image that illustrates example micrographs of FOXM1- and CENPF-stained tissues showing enhanced concentrations of both in prostate cancer that metastasized to lung and liver tumors. These micrographs are based on the Michigan metastasis TMA; and, analysis revealed that FOXM1 and CENPF were coexpressed in most of the prostate cancer metastases (88% and 90%, respectively, sample size n=53 informative cases) at significantly elevated levels. Spearman rank correlation coefficient of FOXM1 and CENPF protein expression levels was 0.43 with p value <0.001, indicating the coexpression is significant Thus, coexpression of FOXM1 and CENPF at above-threshold levels, particularly their nuclear colocalization, as described in more detail below, was well correlated in both the MSKCC prostatectomy TMA and the Michigan metastasis TMA. Additionally, both FOXM1 and CENPF were overexpressed at the mRNA level and their coexpression was well-correlated in advanced prostate cancer and metastases from independent cohorts of human prostate cancer.

Figure 6C:
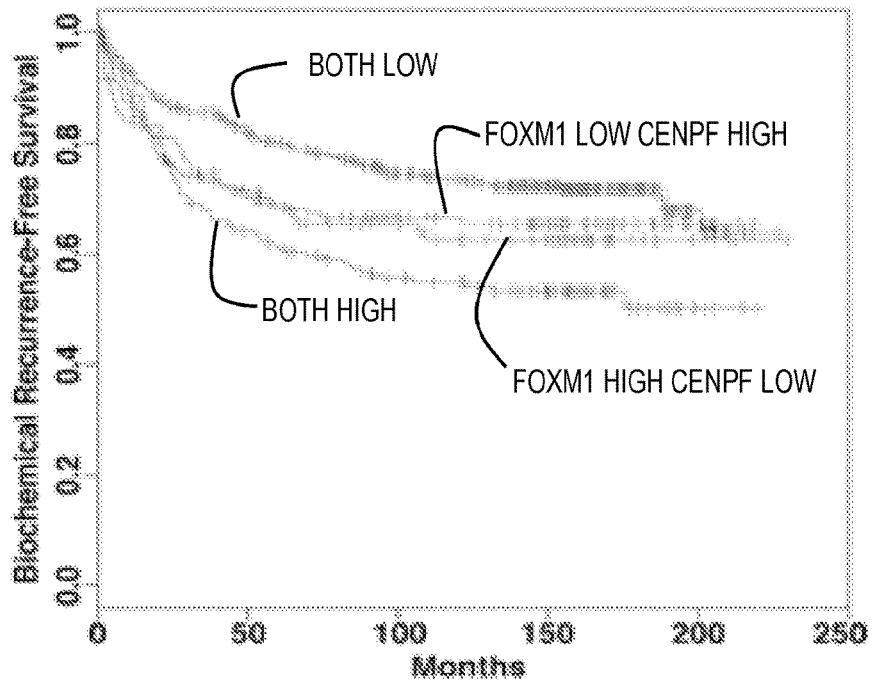
FIG. 6C through FIG. 6E are graphs that illustrate example Kaplan-Meier survival analysis based on protein expression levels of FOXM1 and CENPF with respect to time to biochemical recurrence, time to prostate cancer-specific death, or time to metastatic progression, respectively, according to an embodiment.
Figure 6D:
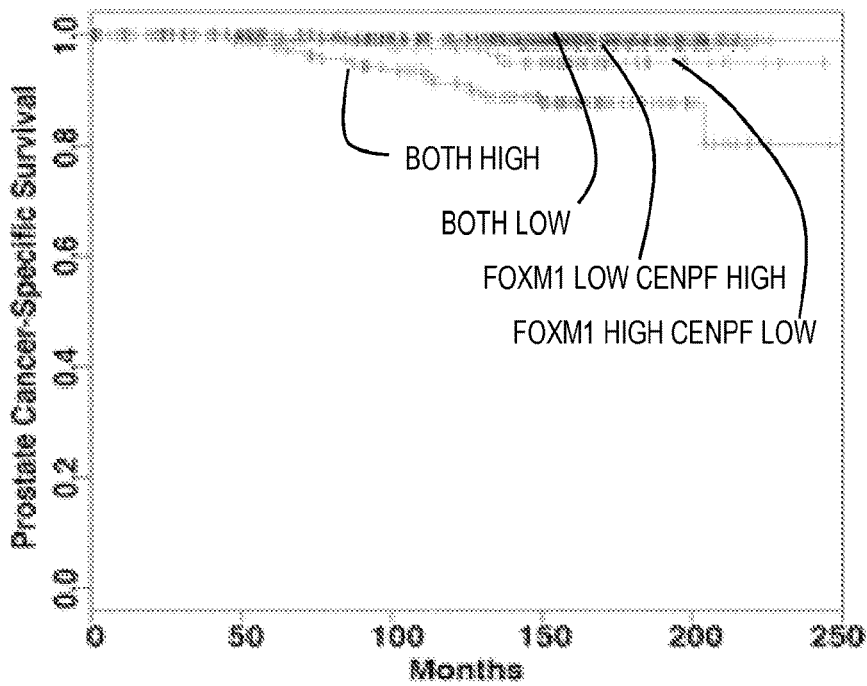
Figure 6E:
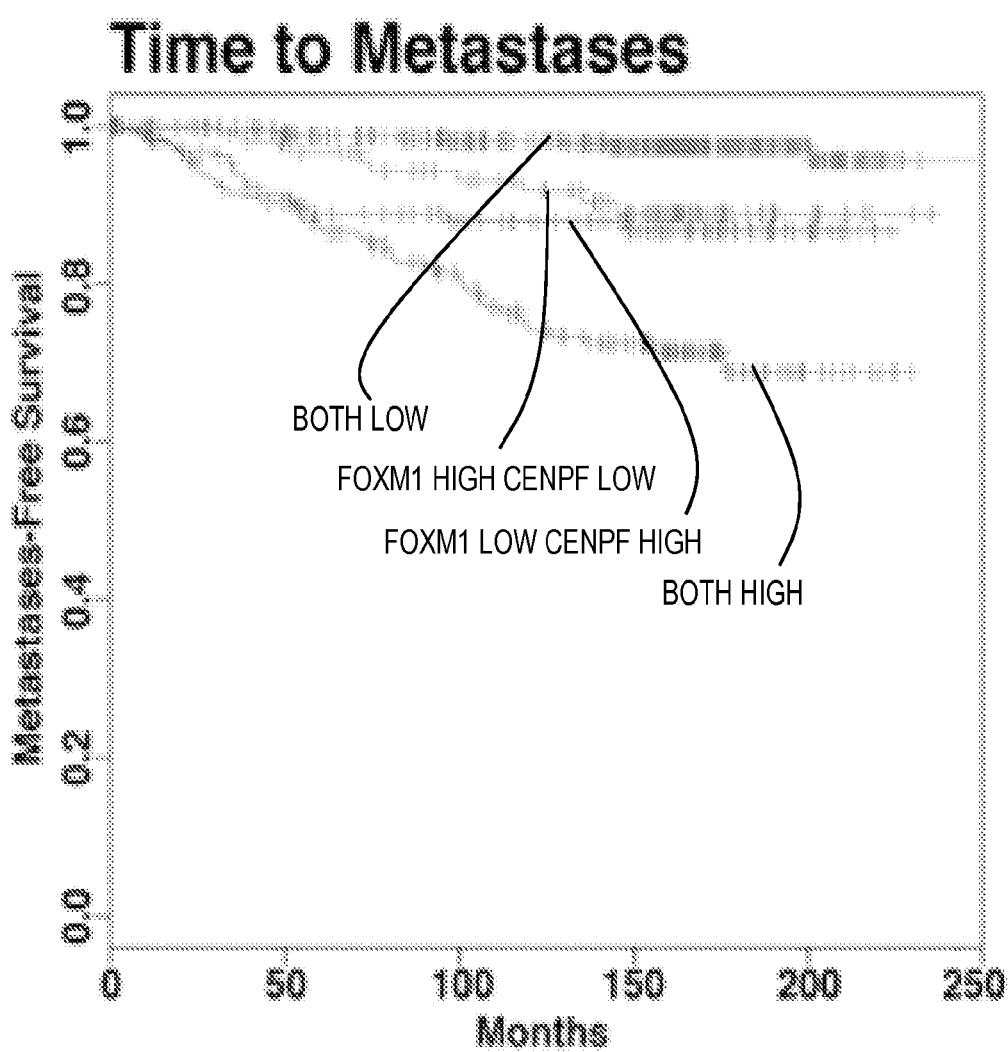

To determine whether expression of FOXM1 and/or CENPF is associated with disease outcome on the MSKCC TMA, 4 groups of subjects were defined based on their expression levels: (i) low/normal expression of both FOXM1 and CENPF (sample size n=418); (ii) high expression of FOXM1 and low/normal expression of CENPF (sample size n=97); (iii) high expression of CENPF and low/normal expression of FOXM1 (sample size n=133); and (iv) high expression of both FOXM1 and CENPF (sample size n=173). FIG. 6C through FIG. 6E are graphs that illustrate example Kaplan-Meier survival analysis based on protein expression levels of FOXM1 and CENPF with respect to time to biochemical recurrence, time to prostate cancer-specific death, or time to metastatic progression, respectively, according to an embodiment.

Kaplan-Meier survival analysis of these subject groups revealed that those having elevated expression of both FOXM1 and CENPF were associated with the worst outcome with high significance (low values of p) for three independent clinical endpoints, namely, time to biochemical-free recurrence ($p \leq 4.4 \times 10^{-6}$), death due to prostate cancer ($p \leq 5.9 \times 10^{-9}$), and time to metastasis ($p \leq 1.0 \times 10^{-16}$). The p-values correspond to a log-rank test and indicate the statistical significance of the association with outcome for each indicated branch compared to control (i.e., subjects with low protein expression of both FOXM1 and CENPF). Notably, co-subcellular localization of FOXM1 and CENPF in prostate tumors was also associated with the worst outcome for all three independent clinical endpoints, as described in more detail below. In contrast, elevated expression of only FOXM1 or CENPF was either not significant or marginally significant for biochemical recurrence and prostate-specific survival ($p \leq 0.053$ and $p \leq 0.011$ for FOXM1, respectively; $p \leq 0.078$ and $p \leq 0.402$ for CENPF, respectively), and was 10 to 13 orders of magnitude less significant, respectively, than coexpression for time to metastasis ($p \leq 0.001$ for FOXM1 and $p \leq 3.1 \times 10^{-6}$ for CENPF, respectively).

Figure 6F:
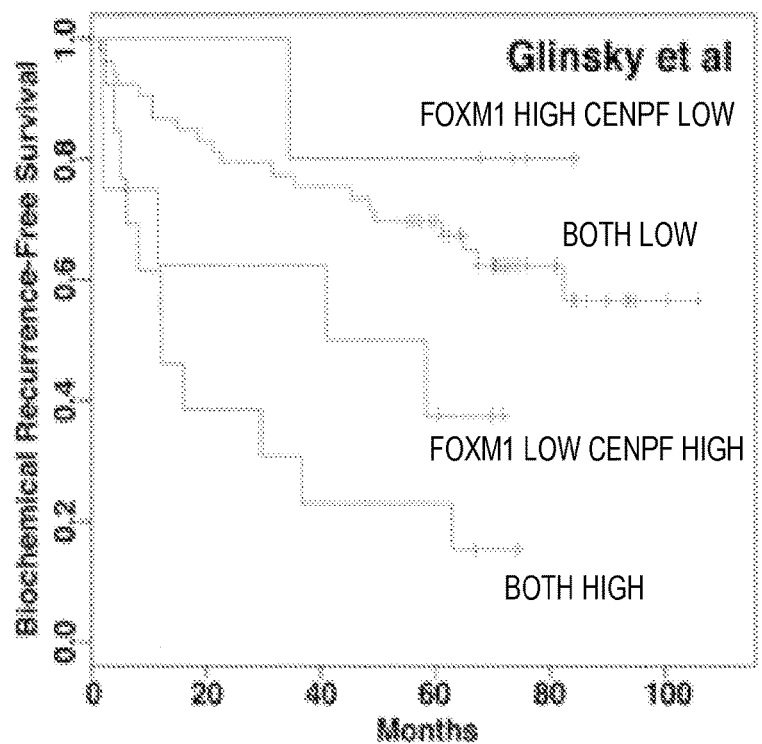
FIG. 6F and FIG. 6G are graphs that illustrate example Kaplan-Meier survival analysis based on the interactome-inferred activity levels of FOXM1 and CENPF with respect to time to biochemical recurrence, or time to prostate cancer-specific death, respectively, according to an embodiment.
Figure 6G:
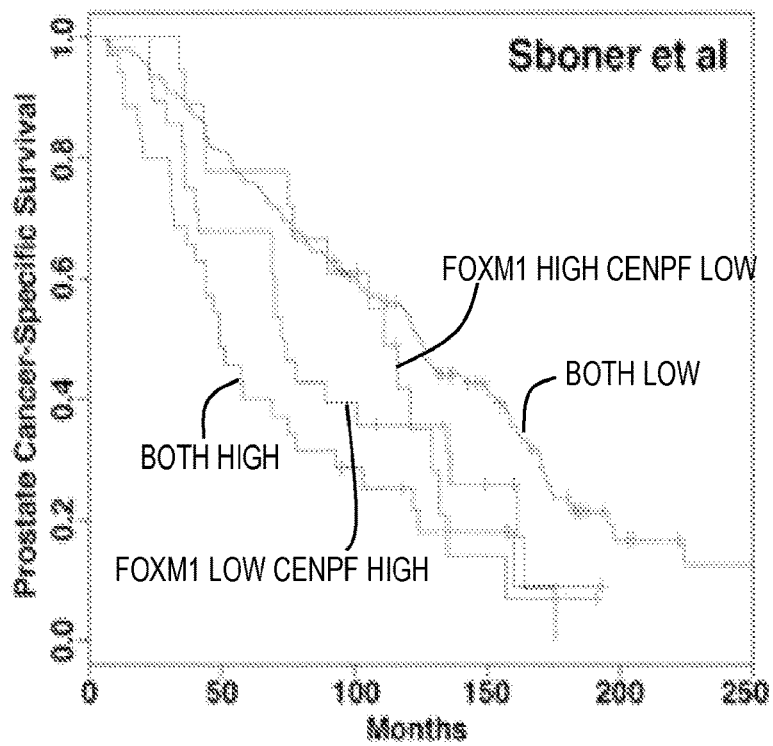

Association of FOXM1 and CENPF with disease outcome was independently corroborated in two independent human prostate cancer datasets that had not been used for training purposes elsewhere in this study; namely, the Glinsky dataset, in which biochemical recurrence is the clinical endpoint (Glinsky et al., 2004), and the Sboner dataset, in which the clinical endpoint is prostate cancer-specific overall survival (Sboner et al., 2010). Using these independent cohorts, the mRNA expression levels of FOXM1 and CENPF was evaluated as well as their MARINa-inferred activity. Kaplan-Meier survival analysis was then performed on 4 subject groups: (i) those with low inferred activity or expression for FOXM1 and CENPF; (ii) those with high inferred activity or expression only for FOXM1; (iii) those with high inferred activity or expression only for CENPF; and (iv) those with high inferred activity or expression for both FOXM1 and CENPF. FIG. 6F and FIG. 6G are graphs that illustrate example Kaplan-Meier survival analysis based on the interactome-inferred activity levels of FOXM1 and CENPF with respect to time to biochemical recurrence, or time to prostate cancer-specific death, respectively, according to an embodiment.

Similar to the analysis of protein expression on the TMA, subjects with high inferred activity or mRNA expression for both CENPF and FOXM1 were associated with the worst outcome in both cohorts, as measured by biochemical recurrence ($p \leq 6.5 \times 10^{-5}$) and prostate cancer-specific survival ($p \leq 4.0 \times 10^{-5}$). The ARACNe-inferred activities levels were assessed for each subject sample in both cohorts. The p-values correspond to a log-rank test and indicate the statistical significance of the association with outcome for each indicated branch compared to control (i.e., subjects with low activity levels of both FOXM1 and CENPF). Notably, these findings reveal that their ARACNe-inferred activities are well-correlated with the actual expression of FOXM1 and CENPF proteins on the TMA, and further demonstrate the striking association of their co-expression/co-activity with poor disease outcome.

FIG. 7 is a table that illustrates example prognostic power of coexpression of protein levels of FOXM1 and CENPF, with death due to prostate cancer and time to metastasis as evaluation endpoints, according to an embodiment. C-statistics give the proportion of pairs in which the predicted event probability (e.g., probability of survival from prostate cancer) is higher for the subject who experienced the event of interest (e.g., coexpression of FOXM1 and CENPF) than that of the subject who did not experience the event. Analysis of coexpression of FOXM1 and CENPF on the MSKCC prostatectomy TMA using C-statistics revealed their robust prognostic value for disease-specific survival (C=0.71; confidence interval=0.59-0.84, $p \leq 2.4 \times 10^{-4}$), as well as time to metastasis (C=0.77; confidence interval=0.71-0.83, $p \leq 3.0 \times 10^{-19}$). Notably, coexpression of FOXM1 and CENPF proteins as diagnostic markers of aggressive prostate cancer dramatically improved the prognostic value compared to Gleason score alone, for both disease-specific survival (C=0.86; confidence interval=0.80-0.93, $p \leq 1.0 \times 10^{-30}$; p value for improvement, $p \leq 2.0 \times 10^{-4}$) and time to metastasis (C=0.86; confidence interval=0.81-0.89, $p \leq 6.5 \times 10^{-58}$; p value for improvement, $p \leq 5.3 \times 10^{-13}$). In certain embodiments of the invention, diagnosis of aggressive prostate cancer further includes determining, in addition to elevated coexpression of both FOXM1 and CENPF, high Gleason scores of score $\geq 8$.

Taken together, these analyses of independent clinical cohorts using distinct statistical models demonstrate that elevated levels of coexpression of FOXM1 and CENPF is a good predictor of disease outcome. In an embodiment FOXM1 and CENPF are prognostic for aggressive prostate cancer or of prostate cancer progressing to an aggressive form when they are coexpressed at elevated levels of at least 35% compared to the levels expressed in control prostate tissue. Based on the results, certain embodiments are directed to a method for diagnosing aggressive prostate cancer or of identifying subjects with prostate cancer that is at high risk of progressing to an aggressive form by (a) obtaining a test prostate cancer sample from a subject having prostate cancer, and a control prostate tissue sample, (b) determining a level of expression of the prognostic genes (FOXM1) Forkhead box protein M1 and Centromere protein F (CENPF) in the test and control samples, (c) comparing the level of expression of prognostic genes FOXM1 and CENPF in the test sample to the corresponding level in the control sample, and (d) if the level of expression of both of the prognostic genes FOXM1 and CENPF in the test sample is at least 35% higher than the corresponding level in the control sample, then determining that the subject has an aggressive form of prostate cancer or is at high risk of developing an aggressive form of prostate cancer.

In certain embodiments the level of expression of FOXM1 and CENPF is determined by the level of mRNA encoding FOXM1 and CENPF, respectively; or by the level of FOXM1 protein and CENPF protein in the sample or combinations thereof. In another embodiment, a diagnosis of aggressive prostate cancer is reached by (a) obtaining a prostate cancer sample from a subject having prostate cancer, (b) determining a level of expression of FOXM1 protein and CENPF protein expression in the cancer cells in the sample by immunostaining with a first antibody that specifically binds to FOXM1 and a second antibody that specifically binds to CENPF, and (c) diagnosing aggressive prostate cancer if at least 50% of the cells in the test sample express both FOXM1 protein and CENPF protein at a composite score of at least 100 for each protein, wherein the composite score is calculated by multiplying the percent staining value by the staining intensity value. Any other method for determining that at least 50% of the cells in a prostate cancer sample coexpress both FOXM1 and CENPF proteins at levels of at least 35% above levels in control prostate tissue can be used, these include flow cytometry with differential florescent labeling of both proteins.

FIG. 8 is a flow chart that illustrates an example diagnostic method 800 for determining whether a subject has or is at high risk of undergoing a specific phenotypic transition based on coexpression of at least two synergistic master regulators, such as FOXM1 and CENPF for aggressive prostate cancer, according to an embodiment. Although steps are depicted in FIG. 8, and in subsequent flowchart FIG. 10, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 810, a subject is identified who has or is at high risk of producing the phenotype transition of interest, here development of aggressive prostate cancer from a prostate tumor or nodule detected in a subject. In step 803 a sample is taken from the identified subject, such as a biopsy of the prostate tumor or nodule. Biological samples for use in the present embodiments also include circulating prostate cancer cells or prostate tumor cells which can be detected using a variety of methods known in the art that select cells based on surface markers for example using antibodies against the surface markers, or expression of other prostate cancer markers. In some embodiments the prostate cancer cells can be selected by size. Biological samples for use in the present embodiments also include exosomes derived from prostate cancer cells, which are cell-derived vesicles that are present in many and perhaps all biological fluids, including blood. The reported diameter of exosomes is between 30 and 100 nm.

In step 805, the pattern of coexpression of synergistic master regulators, such as FOXM1 and CENPF, for the phenotype transition, such as to aggressive prostate cancer, is determined. For example, the pattern of certain genes' expression is determined by determining the relative level of coexpression of mRNA coding for the master regulators, or the intensity of immunostaining of polypeptides encoded by the master regulators, or the enhancement or deficiency of common targets of the master regulators, the latter by either mRNA levels or immunostaining intensities of polypeptides included. Step 805 is described in more detail below with reference to FIG. 10.

In step 807, it is determined whether the synergistic master regulators are coexpressed at significantly elevated (or reduced) levels above (below) some threshold level, or otherwise have different patterns than, determined in control prostate tissue. For diagnosis of aggressive prostate cancer or the risk of a tumor progressing to an aggressive form, it is determined whether FOXM1 and CENPF levels are both above corresponding threshold control levels, which are the levels seen in normal prostate tissue or indolent prostate cancer tumors. The threshold or pattern depends on the measurement type as described in more detail below with reference to FIG. 10.

If it is determined in step 807, that the synergistic master regulators are coexpressed at some elevated (or reduced) level or other different pattern, then control passes to step 811. Otherwise control passes to step 821.

In step 811, it is determined that the subject is at risk for developing the phenotype transition, or in fact is undergoing, or has undergone, the phenotype transition. In some embodiments the phenotype transition is to aggressive prostate cancer. In some embodiments, the risk is quantified based, at least in part, on the levels of coexpression of the synergistic master regulators. For example, the Gleason score is combined with the fact of elevated coexpression of FOXM1 and CENPF, to predict the risk of aggressive prostate cancer in the subject, as indicated by the table of FIG. 7. Control then passes to step 817 to treat the subject based on this risk or diagnosis.

In step 821, it is determined that the subject does not have or is at low risk or no risk for developing the phenotype transition, e.g., aggressive prostate cancer; and, the process ends, or is repeated with the same subject at a later time or with another subject.

Figure 9A:
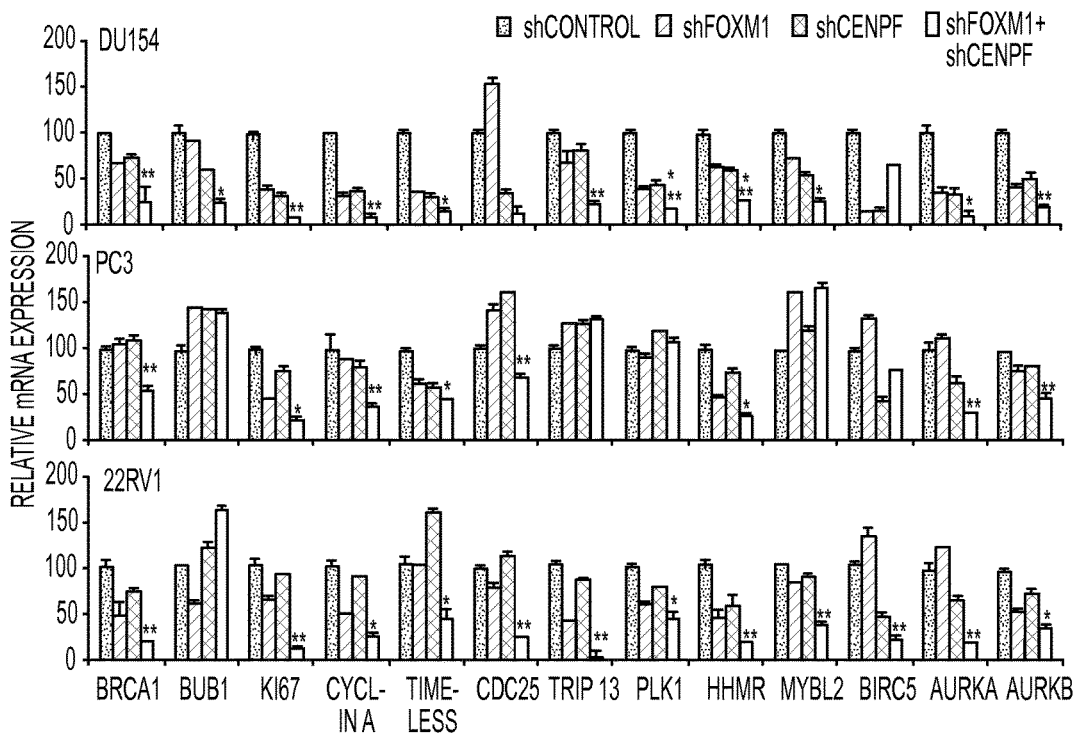
FIG. 9A is a graph that illustrates example resulting relative mRNA expression levels for the shared targets of FOXM1 and CENPF in the indicated cell lines following individual or co-silencing of FOXM1 and CENPF, according to an embodiment.

More information on the secondary effects of elevated coexpression of FOXM1 and CENPF was obtained by experiments that were performed to validate synergistic interactions of master regulators and elucidate underlying mechanisms, as well as to evaluate their relevance for clinical outcome. FIG. 9A is a graph shows relative mRNA expression levels for the indicated genes in the indicated cell lines following individual or co-silencing (i.e., silencing both) of FOXM1 and CENPF. The p-values (indicated by one or two *) show the significance of the predicted additive effect versus actual observed effect on gene expression (*=p<0.01; **=p<0.001). Silencing was performed using lentivirus vectors for shRNA for each or both of the two genes FOXM1 and CENPF, as described in more detail below. The ARACNe-inferred common target genes include BRCA1, BUB1, KI67, CYCLIN A, TIMELESS, CDC25, TRIP13, PLK1, HHMR, MYBL2, BIRC5, AURKA, AURKB.

Although target gene expression was somewhat reduced by their individual silencing, as shown in FIG. 9A, co-silencing of FOXM1 and CENPF produced a significantly greater reduction for the majority of targets, consistent with the synergistic regulation of target gene expression by FOXM1 and CENPF. Notably, these findings were observed in each cell line that express both FOXM1 and CENPF, but not in LNCaP cells which do not express CENPF.

Figure 9B:
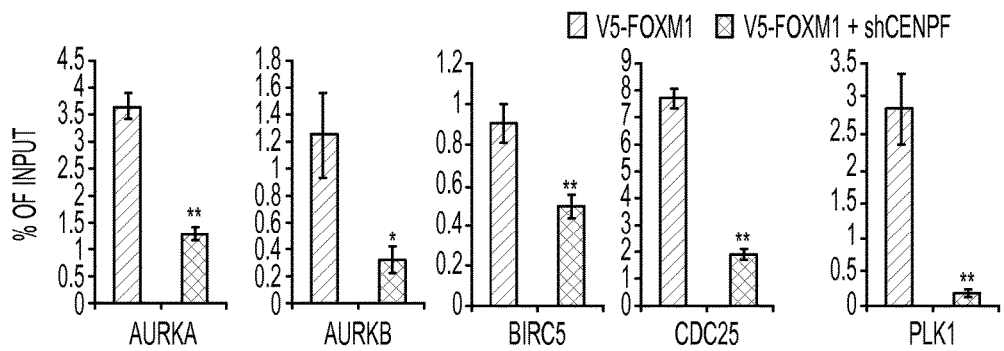
FIG. 9B is a graph that illustrates example enrichment of FOXM1 binding normalized to input with and without silencing of CENPF, according to an embodiment.

In addition, analyses of genomic binding of FOXM1 to its known target sites using chromatin immunoprecipitation (ChIP) was followed by quantitative PCR analyses. FIG. 9B is a graph that illustrates example enrichment of FOXM1 binding normalized to input with and without silencing of CENPF, according to an embodiment. Cells were infected with a lentivirus expressing a V5-tagged FOXM1 plus shRNA CENPF (or a control) and ChIP was done using an anti-V5 antibody. Data are expressed as fold of enrichment of FOXM1 binding normalized to input. This revealed that FOXM1 binding to its targets was abrogated by silencing CENPF, therefore suggesting that CENPF is required for appropriate genomic binding by FOXM1.

Figure 9C:
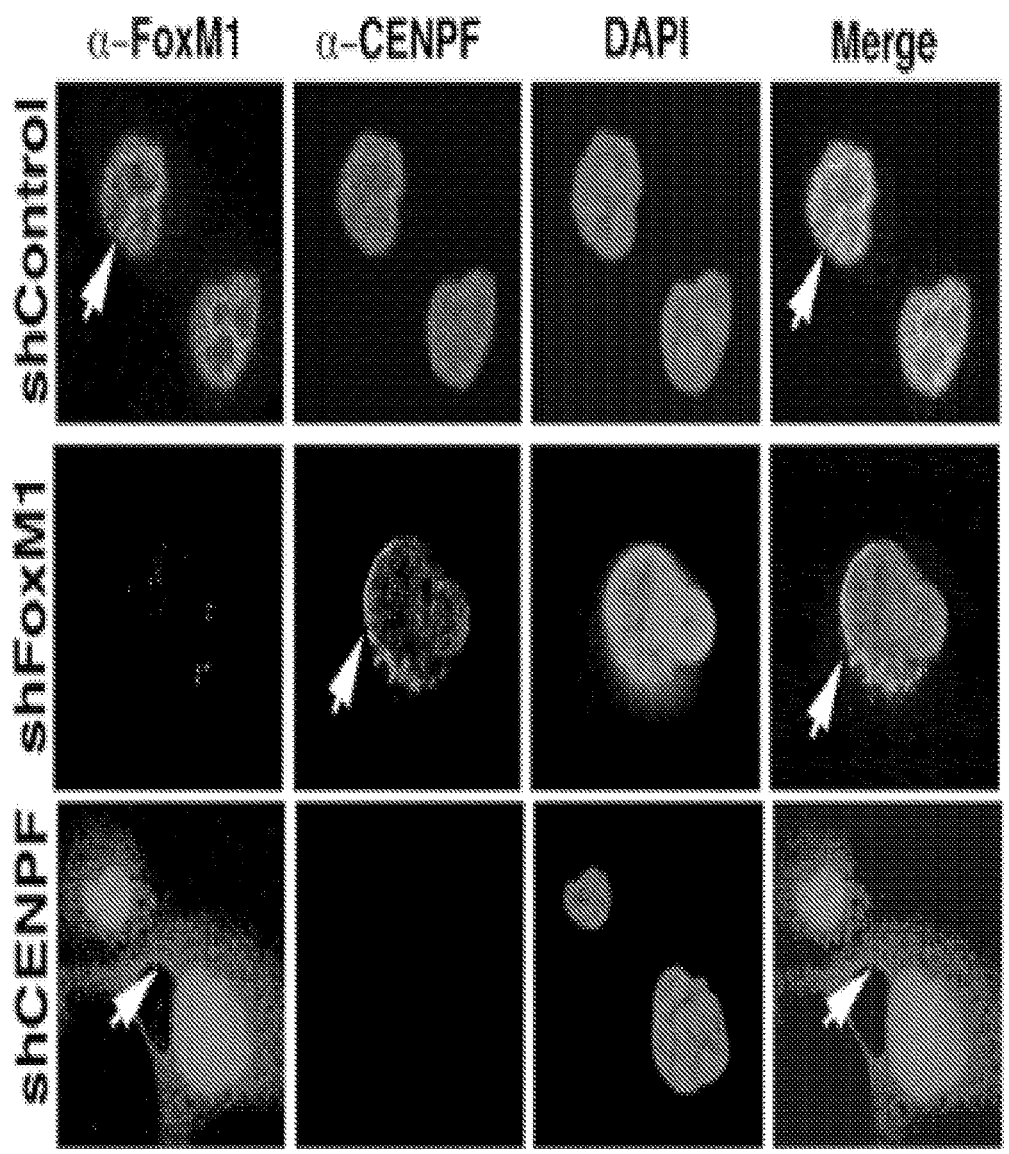
FIG. 9C is an image of micrographs that illustrate example changes in subcellular localization of FOXM1 and CENPF proteins in prostate cancer cells after silencing either, according to an embodiment.

Interestingly, although a direct protein-protein interaction of FOXM1 and CENPF in co-immunoprecipitation assays was not observed, it was observed that FOXM1 and CENPF were co-localized in the nucleus of prostate cancer cells and that their subcellular colocalization was mutually dependent. FIG. 9C is an image of micrographs that illustrate example changes in subcellular localization of FOXM1 and CENPF proteins in prostate cancer cells after silencing either, according to an embodiment. Shown are microphotographs of immunofluorescence staining for FOXM1 or CENPF in the control or silenced cells as indicated. Arrows indicate subcellular localization or the shift in localization following silencing.

In particular, silencing of CENPF resulted in the redistribution of FOXM1 to the cytoplasm as well the nucleus, and conversely silencing of FOXM1 resulted in the accumulation of CENPF at the nuclear periphery. Notably, subcellular co-localization of FOXM1 and CENPF was also observed in human prostate tumors and associated with disease outcome. Taken together, these findings show that FOXM1 and CENPF synergistically regulate expression of mutual target genes, which mediated in part through their subcellular colocalization in prostate cancer cells.

Determining Coexpression of the Synergistic Master Regulators FOXM1 and CENPF

Figure 10:
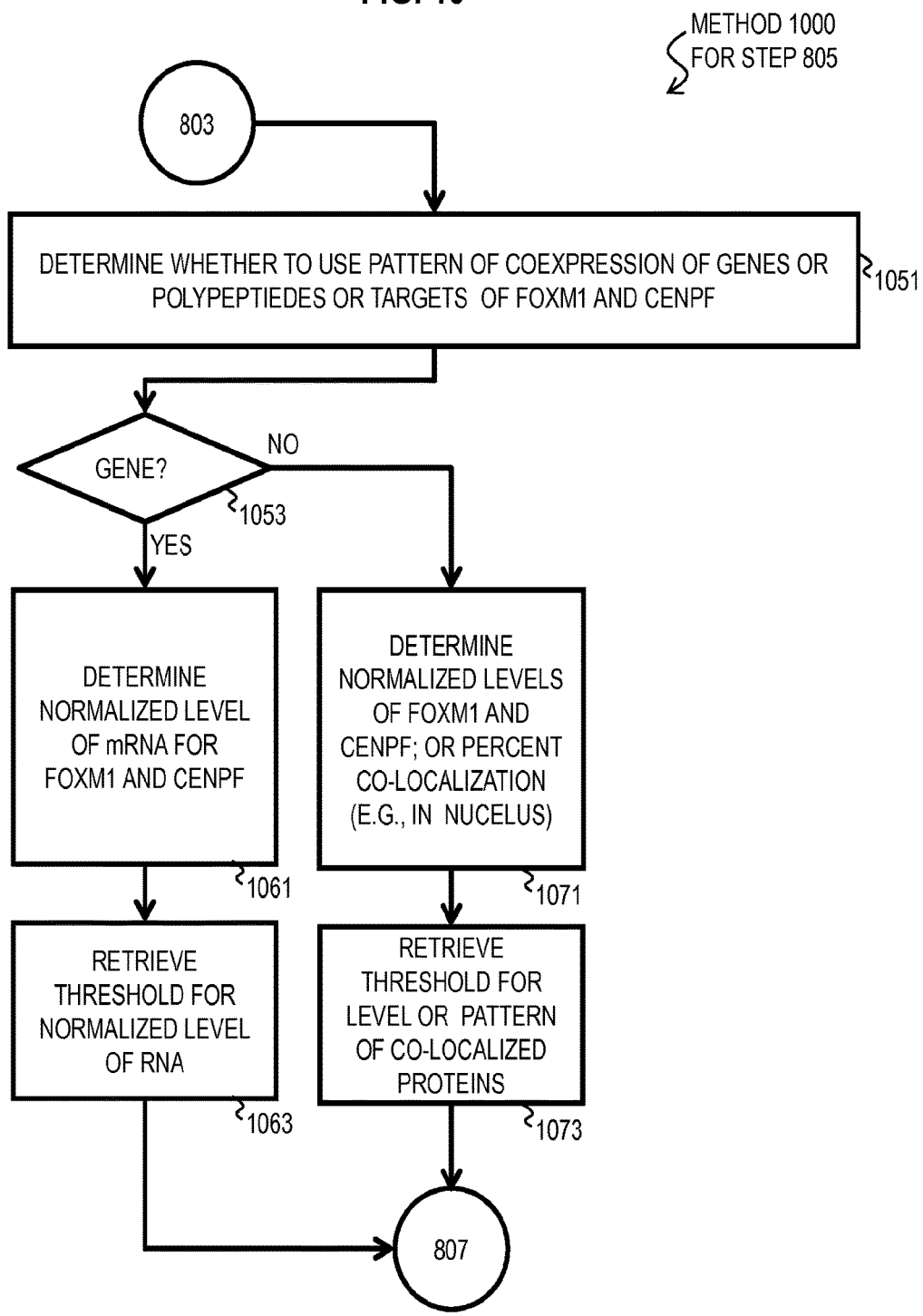
FIG. 10 is a flow chart that illustrates an example method for determining coexpression of the synergistic master regulators FOXM1 and CENPF, according to an embodiment.

FIG. 10 is a flow chart that illustrates an example method 1000 for determining coexpression of the synergistic master regulators such as FOXM1 and CENPF, according to an embodiment. Method 1000 is a particular embodiment of step 805, described above. In step 1051 it is determined whether to use expression of the genes for the synergistic master regulators, or expression of the master regulator proteins (e.g., polypeptides included), or expression of the genes or polypeptides of one or more the targets in the signaling pathways of the master regulators, or combinations thereof. In the illustrated embodiment, it is assumed that expression of one or more targets is not used in the method 1000.

In step 1053, it is determined whether the gene expression or polypeptide expression is to be evaluated. If the gene expression is to be determined, control passes to step 1061. Otherwise control passes to step 1071.

In step 1061, the normalized level of mRNA is determined for FOXM1 and CENPF in the prostate sample. Certain methods and primers for determining the relative or normalized levels of mRNA for FOXM1 and CENPF compared to other genes are also described in the experimental procedures section, below, with primer sequences listed in Table 1 in that later section. In an example, total RNA was isolated from a subject sample of prostate tissues/tumors using a MagMAX-96 total RNA isolation kit and biotin-labeled using the Illumina TotalPrep RNA Amplification Kit (Life Technologies). Slides were scanned using an iScan (Illumina) and the resulting files were uploaded and background-corrected in BeadStudio 3.1.3.0 (Illumina, Inc.). Expression profiling data were normalized using standard variance stabilizing transformation (VST) and robust spline normalization (RSN) with lumiT and lumiN functions from lumi library, in R-system v2.14.0 (The R Foundation for Statistical Computing, ISBN 3-900051-07-0.)

In step 1063, the threshold for significantly elevated coexpression is determined, e.g., retrieved from data storage. An mRNA level in the subject prostate cancer sample that is at least 35% higher than the level expressed in normal prostate tissue for each gene is considered elevated. In other embodiments other thresholds are used. In some embodiments, the threshold for each to be considered elevated is selected in a range from about 35% to about 100% or more. In some embodiments the threshold is at least 50%; and in other embodiments the threshold is at least 75%. Control then passes to step 807 of FIG. 8, described above, to determine if the measured level exceeds the threshold.

In step 1071, the level of immunostaining is determined for FOXM1 and CENPF proteins. Certain antibodies for immunostaining FOXM1 and CENPF are identified in the experimental procedures section below and listed in Table 2, and procedures for quantifying the intensity levels are also described. Any antibody that selectively binds to either FOXM1 or CENPF can be used. Protein levels were determined by percent of staining (e.g., from 0 to 100%) and intensity level of staining (e.g., 0, 1, 2, or 3) in each tumor sample. A composite protein level is determined by multiplying percent of staining and its intensity level for each tumor sample, for FOXM1 or CENPF. In some embodiments, step 1071 includes determining the relative amounts of FOXM1 and CENPF inside the membrane of the nucleus of the cells where the staining is observed in the top row of FIG. 9C when both FOXM1 and CENPF are expressed. In various embodiments, this determination of the relative amount within the nucleus is done in addition to, or instead of, determining the composite protein level.

In step 1073, the threshold for elevated coexpression is determined, e.g., retrieved from data storage. Composite protein level exceeding 100 for each protein was considered elevated. Thus, in some embodiments, FOXM1 and CENPF are considered to be co-expressed if the determined composite protein level in the subject prostate tumor sample for each is above about 100.

In some embodiments, the pattern of coexpression is determined by the relative amount of the total FOXM1 and CENPF that is inside the same cell, or in a particular subcellular compartment, such as inside of the nuclear membrane. For example, if at least 50% of the cells in the test sample express both FOXM1 protein and CENPF protein at a composite score of at least 100 for each protein, then determining that coexpression is elevated.

Control then passes to step 807 of FIG. 8, described above, to determine if the measured level exceeds the threshold.

Method for Detecting mRNA Expression

In some embodiments, the methods described herein comprise detecting the presence of FOXM1 or CENPF RNA expression (e.g. mRNA expression), including detecting of the absolute or relative quantity of the RNA, the half-life of the RNA, a splicing or processing of the RNA, the nuclear export of the RNA or the sub-cellular location of the RNA. Such detection can be by various techniques known in the art, including by sequencing all or part of the FOXM1 or CENPF RNA or by selective hybridization or selective amplification of all or part of the FOXM1 or CENPF RNA. As described herein, there exist many suitable methods for detecting the presence and level of a nucleic acid encoding a FOXM1 polypeptide or a CENPF polypeptide, including, but not limited to genotyping a sample, for example via gene sequencing, selective hybridization, amplification, gene expression analysis (e.g. microarray analysis), oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, 2000), or a combination thereof. Sequencing can be carried out using techniques well known in the art, using automatic sequencers. The sequencing can be performed on the complete gene or on specific domains thereof, such as those known or suspected to carry deleterious mutations or other alterations. Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immuno-enzymatic assays (IEMA). Some other approaches are based on specific hybridization between nucleic acids from the subject and a probe specific for wild type gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand-specific for the polypeptide, for example, the use of a specific antibody.

In certain embodiments, detection or quantification of a nucleic acid encoding a nucleic acid encoding a FOXM1 polypeptide or a CENPF polypeptide (or a fragment thereof) can be by hybridization based methods. In certain embodiments, hybridization-based detection methods can employ a step of forming specific hybrids between complementary nucleic acid sequences that serve to detect nucleic acid sequences. Microarrays are a suitable hybridization based detection technique that can be used in connection with the methods described herein. Microarrays employ nucleic acid probes specific for wild type gene or RNA and can be used to investigate the expression of a nucleic acid encoding a FOXM1 polypeptide or a CENPF polypeptide in samples from patients in a diagnostic context. In general, microarrays comprise a two dimensional arrangement of nucleic acid or polypeptide probes which comprises an intentionally created collection of nucleic acid or polypeptide probes of any length spotted onto a substrate/solid support. The array itself can have different formats, e.g. libraries of soluble probes or libraries of probes tethered to resin beads, silica chips, or other solid supports. The process of microarray fabrication is well-known to the person skilled in the art. The process can comprise preparing a glass (or other) slide (e.g. chemical treatment of the glass to enhance binding of the nucleic acid probes to the glass surface), obtaining DNA sequences representing genes of a genome of interest, and spotting sequences these sequences of interest onto glass slide. Sequences of interest can be obtained via creating a cDNA library from an mRNA source or by using publicly available databases, such as GeneBank, to annotate the sequence information of custom cDNA libraries or to identify cDNA clones from previously prepared libraries. Generally, it is recommendable to amplify obtained sequences by PCR in order to have sufficient amounts of DNA to print on the array. The liquid containing the amplified probes can be deposited on the array by using a set of microspotting pins. Ideally, the amount deposited should be uniform. The process can further include UV-crosslinking in order to enhance immobilization of the probes on the array. Microarray chips suitable for use with the methods described herein are well known to those of skill in the art (see, e.g., U.S. Pat. Nos. 6,308,170; 6,183,698; 6,306,643; 6,297,018; 6,287,850; 6,291,183, each incorporated herein by reference). These are exemplary patents that disclose nucleic acid microarrays and those of skill in the art are aware of numerous other methods and compositions for producing microarrays. A microarray composition of the present invention can be employed for the diagnosis and treatment of any condition or disease in which the expression of FOXM1 and/or CENPF is implicated. The microarray-based methods can be used for large scale genetic or gene expression analysis of a large number of target sequences, including nucleic acids encoding a FOXM1 polypeptide or nucleic acids encoding a CENPF polypeptide. The microarray can also be used in the diagnosis of diseases and in the monitoring of treatments. Further, microarrays can also be employed to investigate an individual's predisposition to a disease. Furthermore, the microarrays can be employed to investigate cellular responses to infection, drug treatment, and the like.

When microarrays are used in connection with the methods described herein, the formation of a plurality of detectable complexes between probes and target nucleic acid sequences can be assessed. The expression profiles can show unique expression patterns that are characteristic of the presence or absence of a disease or condition, such as a malignant prostate cancer. In certain embodiments where expression profiles are examined using microarray technology, complexes can be formed by hybridization of one or more probes having complementarity to a nucleic acid encoding a FOXM1 polypeptide or a nucleic acid encoding a CENPF polypeptide. Such a microarray can be employed in several applications including diagnostics, prognostics and treatment regimens, drug discovery and development, toxicological and carcinogenicity studies, forensics, pharmacogenomics, and the like. The probe can be in suspension or immobilized on a substrate or support (for example, as in nucleic acid array or chips technologies). For example, a sample from the subject can be contacted with a nucleic acid probe specific for a nucleic acid encoding a FOXM1 polypeptide or a nucleic acid encoding CENPF polypeptide.

In certain embodiments, the expression profile can be used to a nucleic acid encoding a FOXM1 polypeptide or a nucleic acid encoding CENPF polypeptide infer changes in the expression of target genes implicated in disease wherein the expression of such target genes is upregulated or down-regulated by FOXM1, CENPF, or by the concerted action of FOXM1 and CENPF. Example probes and primers useful for obtaining gene expression profiles in normal and malignant cells, and for comparing the gene expression in malignant and corresponding normal cells, are known in the art (Okabe et al., 2001; Kitahara et al., 2001; Lin et al., 2002; Hasegawa et al., 2002).

In certain embodiments, microarray-based detection and/or quantification of a nucleic acid encoding FOXM1 polypeptide and/or a nucleic acid encoding or a CENPF polypeptide can comprise steps of providing a biological sample from a person suspected of having a cancer (e.g. a malignant prostate cancer), and determining the level of expression of a nucleic acid encoding FOXM1 polypeptide and/or a nucleic acid encoding or a CENPF polypeptide in the cells of the biological sample. In particular, such embodiments of the methods described herein can comprises comprising the following steps: (a) contacting a cell sample nucleic acid with a microarray under conditions suitable for hybridization; (b) providing hybridization conditions suitable for hybrid formation between the cell sample nucleic acid and a polynucleotide of the microarray; (c) detecting the hybridization; and (d) diagnosing the disorder condition based on the results of detecting the hybridization.

For example, methods of purification of nucleic acids are described in Tijssen and van der Vliet, Laboratory Techniques in Biochemistry and Molecular Biology: Hybridization With Nucleic Acid Probes, Part I. Theory and Nucleic Acid Preparation, Elsevier, New York, 1993. In one case, total RNA is isolated using the TRIZOL reagent (Life Technologies, Gaithersburg Md.), and mRNA is isolated using oligo d (T) column chromatography or glass beads. Alternatively, when target polynucleotides are derived from an mRNA, the target polynucleotides can be a cDNA reverse transcribed from an mRNA, an RNA transcribed from that cDNA, a DNA amplified from that cDNA, an RNA transcribed from the amplified DNA, and the like. When the target polynucleotide is derived from DNA, the target polynucleotide can be DNA amplified from DNA or RNA reverse transcribed from DNA. In yet another alternative, the targets are target polynucleotides prepared by more than one method.

When target polynucleotides are amplified, it is desirable to amplify the nucleic acid sample and maintain the relative abundances of the original sample, including low abundance transcripts. Total mRNA can be amplified by reverse transcription using a reverse transcriptase and a primer consisting of oligo d(T) and a sequence encoding the phage T7 promoter to provide a single stranded DNA template. The second DNA strand is polymerized using a DNA polymerase and a RNAse which assists in breaking up the DNA/RNA hybrid. After synthesis of the double stranded DNA, T7 RNA polymerase can be added, and RNA transcribed from the second DNA strand template (Van Gelder et al., U.S. Pat. No. 5,545,522). RNA can be amplified in vitro, in situ or in vivo (see Eberwine, U.S. Pat. No. 5,514,545).

The sequence of the probes and primers suitable for use with hybridization or amplification based detection methods described herein can be derived from the sequences of a nucleic acid encoding a FOXM1 polypeptide or a CENPF polypeptide. According to the invention, a probe can be a polynucleotide sequence which is complementary to and specifically hybridizes with a, or a target portion of a nucleic acid encoding a FOXM1 polypeptide or a CENPF polypeptide, such as a DNA or RNA molecule encoding such polypeptides. Probes and primers suitable for use with the methods described herein include those that are complementary to a nucleic acid encoding a FOXM1 polypeptide or a CENPF polypeptide, can comprise single-stranded nucleic acids of between 8 to 1000 nucleotides in length, for instance between 10 and 800, between 15 and 700, or between 20 and 500. Exemplary probes and primers may be 8, 9, 10, 11, 12, 13, 14, 15, 16, 17, 18, 19, 20, 25, 30, 35, 40, 45, 50, 55, 60, 65, 70, 75, 80, 85, 90, 95, or more 100 nucleotides in length. In one embodiment, a useful probe or primers of the invention is a single stranded nucleic acid molecule of between 8 to 500 nucleotides in length, which can specifically hybridize to a region of a nucleic acid encoding a FOXM1 polypeptide or a CENPF polypeptide. Longer polynucleotides encoding 250, 500, or 1000 bases and longer are contemplated as well. Such oligonucleotides will find use, for example, as probes in Southern and Northern blots and as primers in amplification reactions.

Conditions can be selected for hybridization where an exactly complementary target and probes can hybridize, i.e., each base pair must interact with its complementary base pair. Alternatively, conditions can be selected where a target and probes have mismatches but are still able to hybridize. Suitable conditions can be selected, for example, by varying the concentrations of salt in the prehybridization, hybridization and wash solutions, by varying the hybridization and wash temperatures, or by varying the polarity of the prehybridization, hybridization or wash solutions.

Suitable hybridization conditions for the diagnostic methods are those conditions that allow the detection of gene expression from identifiable expression units such as genes. Exemplary stringent hybridization conditions include but are not limited to hybridization at 42° C. in a solution (i.e., a hybridization solution) comprising 50% formamide, 1% SDS, 1 M NaCl, 10% dextran sulfate, and washing twice for 30 minutes at 60° C. in a wash solution comprising 0.1×SSC and 1% SDS. Hybridization can be performed at low stringency with buffers, such as 6×SSPE with 0.005% Triton X-100 at 37° C., which permits hybridization between target and probes that contain some mismatches to form target polynucleotide/probe complexes. Subsequent washes are performed at higher stringency with buffers, such as 0.5× SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C. and washes are performed in 2×SSC/0.2% SDS and then in 0.1×SSC. Background signals can be reduced by the use of detergent, such as sodium dodecyl sulfate, Sarcosyl or Triton X-100, or a blocking agent, such as salmon sperm DNA. It is understood in the art that conditions of stringency can be achieved through variation of temperature and buffer, or salt concentration, as described in Ausubel, et al. eds., Protocols in Molecular Biology, John Wiley & Sons (1994), pp. 6.0.3 to 6.4.10. After hybridization, the microarray can be washed to remove nonhybridized nucleic acids, and complex formation between the hybridizable array elements and the target polynucleotides is detected. Modifications in hybridization conditions can be empirically determined or precisely calculated based on the length and the percentage of guanosine/cytosine (GC) base pairing of the probe. The hybridization conditions can be calculated as described in Sambrook, et al. eds., Molecular Cloning: A Laboratory Manual, Cold Spring Harbor Laboratory Press: Cold Spring Harbor, N.Y. (1989), pp. 9.47 to 9.51.

Detection of hybridization can be achieved by labelling probes or target polynucleotides (e.g. a nucleic acid encoding a FOXM1 polypeptide or a nucleic acid encoding a CENPF polypeptide with one or more labeling moieties. In one embodiment, the target polynucleotides are labeled with a fluorescent label, and measurement of levels and patterns of fluorescence indicative of complex formation is accomplished by fluorescence microscopy (e.g. confocal fluorescence microscopy). The labeling moieties can include compositions that can be detected by spectroscopic, photochemical, biochemical, bioelectronic, immunochemical, electrical, optical or chemical means. The labeling moieties include radioisotopes, such as 3H, 14C, 32P, 33P or 35S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Exemplary dyes include quinoline dyes, triarylmethane dyes, phthaleins, azo dyes, cyanine dyes, and the like. Fluorescent markers that emit light at wavelengths at least greater than 10 nm above the wavelength of the light absorbed can be used in some embodiments. Exemplary fluorescent markers include, but are not limited to, fluorescein, phycoerythrin, rhodamine, lissamine, and C3 and C5 available from Amersham Pharmacia Biotech (Piscataway N.J.). Labeling can also be carried out during an amplification reaction, such as polymerase chain reactions and in vitro transcription reactions, or by nick translation or 5' or 3'-end-labeling reactions. When the label may be incorporated after or without an amplification step, the label is incorporated by using terminal transferase or by phosphorylating the 5' end of the target polynucleotide using, e.g., a kinase and then incubating overnight with a labeled oligonucleotide in the presence of T4 RNA ligase. Alternatively, the labeling moiety can be incorporated after hybridization once a probe/target complex has formed. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

In embodiments where amplification used to detect the presence of a nucleic acid encoding a FOXM1 polypeptide or nucleic acid encoding a CENPF polypeptide, such methods can be based on the formation of specific hybrids between primers nucleic acid sequences having complete or partial complementarity to portions of a nucleic acid encoding a FOXM1 polypeptide or to portions of a nucleic acid encoding a CENPF polypeptide, wherein the primer sequences serve to initiate nucleic acid reproduction though, for example, PCR based methodologies. Numerous nucleic acid amplification techniques known in the art, including traditional polymerase chain reaction (PCR), quantitative PCR (qPCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR-SSCP. Nucleic acid primers useful for amplifying a nucleic acid encoding a FOXM1 polypeptide or nucleic acid encoding a CENPF polypeptide include, but are not limited to primers that specifically hybridize with a DNA encoding a FOXM1 polypeptide or nucleic acid encoding a CENPF polypeptide, or an RNA encoding a FOXM1 polypeptide or nucleic acid encoding a CENPF polypeptide.

In some embodiments, the detection is performed by sequencing all or part of a nucleic acid encoding a FOXM1 polypeptide or a CENPF polypeptide or by selective hybridization or amplification of all or part of a nucleic acid encoding a FOXM1 polypeptide or a CENPF polypeptide. In one embodiment, the sample can comprise prostate tissue sample from a subject.

Thus, in certain aspects, the diagnostic methods described herein comprise the use of a nucleic acid primer, wherein the primer can be complementary to and hybridize specifically to a portion of a coding sequence (e.g., gene or RNA) of a nucleic acid encoding FOXM1 or CENPF present in a sample form a subject having or at risk of developing a cancer, such as a prostate cancer, or a malignant prostate cancer. Primers suitable for use with the methods described herein include those that are specific for a nucleic acid encoding FOXM1 or CENPF. By using such primers, the detection of an amplification product indicates the presence of a nucleic acid encoding FOXM1 or CENPF or the absence of such. The use of such primers can also be employed to quantify the relative or absolute amount of a nucleic acid encoding FOXM1 or CENPF in a sample.

Primers suitable for use with the methods described herein, include, but are not limited to those having the sequence of SEQ ID NOs: 5, 6, 19 and 20. In certain embodiments, amplification of a FOXM1 nucleic acid sequence can be performed using a primer pair of SEQ ID NO: 5 and 19. In certain embodiments, amplification of a CENPF nucleic acid sequence can be performed using a primer pair of SEQ ID NO: 6 and 20. One of skill in the art will readily be able to design and synthesize primers suitable for amplifying FOXM1 or CENPF nucleic acid sequences.

Examples of primers of this invention can be single-stranded nucleic acid molecules of about 5 to 100 nucleotides in length, or about 8 to about 25 nucleotides in length. Exemplary primers may be 8, 9, 10, 11, 12, 13, 14, 15, 16, 17, 18, 19, 20, 25, 30, 35, 40, 45, 50, 55, 60, 65, 70, 75, 80, 85, 90, 95, 100 or more contiguous base pairs from the above sequences will be used, although others are contemplated. Primers suitable for use with the methods described herein can be labelled according to any method known in the art, including those described for use in labeling the probes and oligonucleotides suitable for use with the methods described herein. Labelling of primers can also be limited to labelling methods that do not interfere with the ability of the primer to be used for amplification purposes.

The sequence of a primer suitable for use with the methods described herein can be derived directly from a nucleic acid encoding FOXM1 or CENPF. Perfect complementarity is useful, to ensure high specificity. However, certain mismatch can be tolerated. For example, a nucleic acid primer or a pair of nucleic acid primers as described herein can be used in a method for detecting the presence of or a predisposition to prostate cancer in a subject.

Amplification methods include, e.g., polymerase chain reaction, PCR (see Innis ed., 1990; and Innis ed., 1995); ligase chain reaction (LCR) (see, e.g., Wu, 1989; Landegren, 1988; Barringer, 1990); transcription amplification (see, e.g., Kwoh, 1989); self-sustained sequence replication (see, e.g., Guatelli, 1990); Q Beta replicase amplification (see, e.g., Smith, 1997), automated Q-beta replicase amplification assay (see, e.g., Burg, 1996) and other RNA polymerase mediated techniques (e.g., NASBA, Cangene, Mississauga, Ontario); see also Berger, 1987; Sambrook; Ausubel; U.S. Pat. Nos. 4,683,195 and 4,683,202; Sooknanan, 1995. All the references stated above are incorporated by reference in their entireties.

Methods for Determining Protein Expression

According to the methods described herein, the coexpression of FOXM1 and CENPF protein is defined as being elevated to a diagnostic level if the amount of FOXM1 polypeptide and CENPF polypeptide expressed or present in a sample exceeds a defined composite score threshold. For example, in certain embodiments, a sample can be deemed to have elevated expression of FOXM1 and CENPF by investigating immunochemical staining (e.g. immunochemical staining using antibodies specific to FOXM1 or CENPF) of a sample from a subject, determining the percentage of the sample that is stained and assigning a percent staining value for the sample between 0% and 100%, determining an intensity for the staining and assigning a staining intensity value for the sample on a scale of 0, 1, 2, or 3, and calculating a score by multiplying the percent staining value by the staining intensity value, wherein a score exceeding 100% indicates that the FOXM1 polypeptide and CENPF polypeptide present or expressed in the sample is at an elevated level. Thus, in certain aspects, the invention described herein related to the finding that a composite score based on (a) the percentage of a sample that is stained with immunochemical (e.g. an antibody, or a composition comprising an antibody), and (b) the intensity of the stain, can be used to diagnose a subject as having an aggressive or malignant prostate cancer, having a risk of dying from a prostate cancer, and having a risk of a prostate cancer undergoing metastasis. One of skill in the art will readily appreciate that the scoring scales described herein need not be limited to integers and may include fractional values. One of skill in the art will also understand that many variants of the composite scoring scale can be envisioned. For example, staining intensity can be ranked on a scale of 0 to 7 while retaining the fidelity of the method. Similarly, staining intensity can be ranked on a scale of 0 to 10 while retaining the fidelity of the system.

Detection of a polypeptide in accordance with the methods described herein can comprise detecting the presence of FOXM1 or CENPF polypeptide sequences in samples. In certain embodiments, detection of a polypeptide can comprise assaying for the presence of an elevated quantity FOXM1 or CENPF polypeptide in a subject prostate cancer sample as compared to a control (noncancerous) sample. In certain embodiments, detection of a polypeptide can comprise detecting the subcellular localization of a quantity FOXM1 or CENPF polypeptide, and/or detection of colocalization of FOXM1 and CENPF polypeptide within a cell.

A variety of methods may be used to measure FOXM1 or CENPF protein levels including, but not limited to, immunologically based methods such as standard ELISA, immuno-polymerase chain reaction (immuno-PCR) (Sano, 1992), immunodetection amplified by T7 RNA polymerase (IDAT) (Zhang, 2001), radioimmunoassay, immunoblotting, etc. Other approaches include two-dimensional gel electrophoresis, mass spectrometry, and proximity ligation (Fredriksson, 2002).

In embodiments where detection of FOXM1 and CENPF is at the level of polypeptide expression, different types of ligands can be used, such as antibodies that specifically recognize FOXM1 or CENPF polypeptides. Thus, in certain embodiments where the methods described herein involve detection of a FOXM1 or a CENPF polypeptide, a test sample can be contacted with an antibody specific for a FOXM1 or a CENPF polypeptide and the formation of an immune complex can be subsequently determined to determine the presence or location of the polypeptide. Various methods for detecting an immune complex can be used, such as ELISA, radioimmunoassays (RIA) and immuno-enzymatic assays (IEMA).

Antibodies suitable for use with the methods described herein can be polyclonal antibodies, a monoclonal antibodies, as well as fragments or derivatives thereof having substantially the same antigen specificity. Fragments of antibodies that are suitable for use with the methods described herein include Fab, Fab'2, or CDR regions. Derivatives of antibodies that are suitable for use with the methods described herein include single-chain antibodies, humanized antibodies, or poly-functional antibodies. An antibody specific for a FOXM1 polypeptide or a CENPF polypeptide can be an antibody that selectively binds to FOXM1 or CENPF, namely, an antibody raised against FOXM1 or CENPF polypeptide or an epitope-containing fragment of either polypeptide. Although non-specific binding towards other antigens can occur, binding to the target polypeptide occurs with a higher affinity and can be reliably discriminated from non-specific binding. One of skill in the art will appreciate that many methods exist for labelling antibodies for microscopic detection in samples. Exemplary labelling methods include, but are not limited fluorescent labeling, radioactive labeling, and quantum dots.

The diagnostic methods described herein can be performed on any suitable sample which contains nucleic acids or polypeptides, including in vitro, ex vivo, or in vivo samples. Examples of samples suitable for use with the methods described herein include prostate tissue samples, especially samples of prostate tumor or cancerous prostate cells from tissue biopsies taken from a subject having prostate cancer or at risk of developing it. In one embodiment, the sample comprises a tumor tissue. In one embodiment, the sample comprises prostate tissue. In another embodiment, the sample is an isolated population of prostate stem cells. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), and centrifugation. Also, the nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of FOXM1 or CENPF polypeptides or nucleic acids. Contacting can be performed in any suitable device, such as a plate, tube, well, or glass. In specific embodiments, the contacting is performed on a substrate coated with the reagent, such as a nucleic acid array or a specific ligand array. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Diagnostic Kits

The invention also provides for diagnostic kits comprising products and reagents for detecting in a sample from a subject the presence of a FOXM1 or CENPF polypeptides or nucleic acids or FOXM1 or CENPF activity. The kits can be useful for determining whether a sample from a subject expresses significantly elevated levels of FOXM1 or CENF compared to the level expressed in normal prostate tissue. For example, the diagnostic kit according to the present invention comprises any primer, any pair of primers, any nucleic acid probe and/or any ligand, suitable for use with the methods described herein. The diagnostic kits according to the present invention can further comprise reagents and/or protocols for performing a hybridization, amplification or antigen-antibody immune reaction. In certain embodiments, the kits can comprise nucleic acid primers that specifically hybridize to and can prime a polymerase reaction from a nucleic acid encoding FOXM1 or a nucleic acid encoding CENPF. In some kits nucleic acids that specifically hybridize to a nucleic acid encoding FOXM1 or a nucleic acid encoding CENPF wherein in an embodiment the nucleic acid is affixed to a microarray support.

Some kits include anti-FOXM1 and/or anti-CENPF antibodies or fragments thereof, including monoclonal and polyclonal antibodies, and secondary antibodies that are labeled for easy detection for example with a fluorophore or horseradish peroxidase enzyme. The labeling moieties can include compositions that can be detected by spectroscopic, photochemical, biochemical, bioelectronic, immunochemical, electrical, optical or chemical means as described herein. For example, in certain embodiments, elevated nuclear colocalization of FOXM1 and CENPF can be microscopic immunofluorescent colocalization, wherein the extent of colocalization of FOXM1 and CENPF is determined using a Pearson colocalization co-efficient, a Spearman colocalization coefficient, or the like. In certain embodiments, an amount of nuclear colocalization yielding a Spearman colocalization coefficient P value of less than about $1.3 \times 10^{-11}$ indicates that the sample is from a subject having a prostate cancer that has undergone, or is at risk of undergoing metastasis. In certain embodiments, an amount of nuclear colocalization yielding a Spearman colocalization coefficient P value of less than about $6.2 \times 10^{-10}$ indicates that the sample is from a subject having a prostate cancer that has undergone, or is at risk of undergoing metastasis. In certain embodiments, an amount of nuclear colocalization yielding a Spearman colocalization coefficient P value of less than about $2.2 \times 10^{-6}$ indicates that the sample is from a subject at risk of dying from a prostate cancer. In certain embodiments, an amount of nuclear colocalization yielding a Spearman colocalization coefficient P value of less than about $3.5 \times 10^{-5}$ indicates that the sample is from a subject at risk of dying from a prostate cancer.

4. Method of Treatment of Aggressive Prostate Cancer

Co-Silencing of FOXM1 and CENPF Abrogated of Colony Formation in Each Cell Line that Expresses Both FOXM1 and CENPF It was discovered that silencing both FOXM1 and CENPF resulted in a dramatic reduction of prostate tumor weight and volume in vivo. To evaluate their functions and potential synergy in prostate cancer, FOXM1 and/or CENPF were silenced individually or together in four distinct human prostate cell lines, namely DU145, PC3, LNCaP and 22Rv1, which have differing tumorigenic properties and responses to androgen signaling (FIG. 5A). All of these cell lines express high levels of both FOXM1 and CENPF, with the exception of LNCaP cells that express FOXM1 but not CENPF (FIG. 5B), making LNCaP cells an excellent negative control for analysis of synergy. To silence FOXM1 and/or CENPF, doxycycline-inducible lentiviral vectors were engineered expressing shRNAs for FOXM1 or CENPF; alternatively a control shRNA was used. The co-silencing of FOXM1 and CENPF produced a significantly greater reduction for the majority of the targets of each gene than did silencing each gene individually, which is consistent with the synergistic regulation of target gene expression by FOXM1 and CENPF coexpression. These findings were observed in each cell line that express both FOXM1 and CENPF, but not in LNCaP cells which do not express CENPF.

Figure 11A:
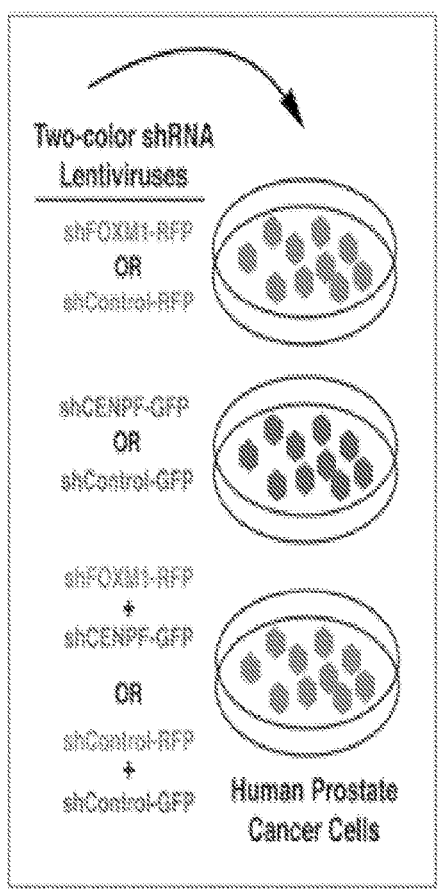
FIG. 11A is a block diagram that illustrates an example in vitro treatment using lentiviral silencing vectors expressing shRNA for FOXM1 or CENPF or both or a control, according to an embodiment.
Figure 11B:
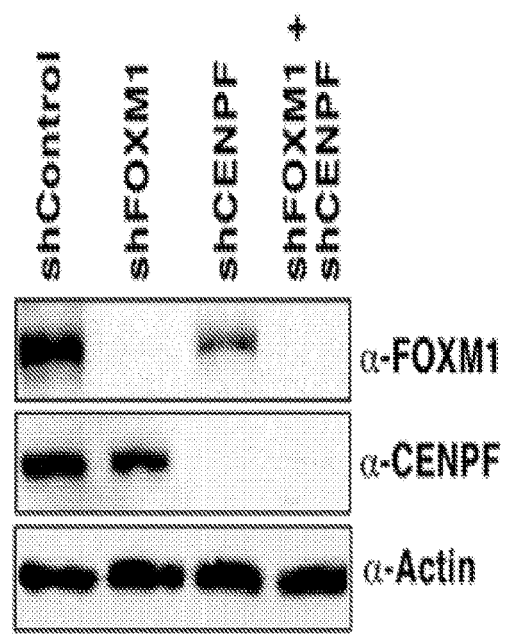
FIG. 11B is an image of Western blots that illustrate effectiveness of lentiviral silencing vectors, according to an embodiment.

FIG. 11A shows various protocols for silencing FOXM1 or CENPF expression using lentiviral silencing vectors expressing shRNA for FOXM1 or CENPF or both or a control vector lacking the FOXM1 or CENPF shRNA. Lentiviral silencing vectors expressing shRNA for FOXM1 and/or CENPF (or a control shRNA for no gene expressed with either an RFP (red) or GFP (green) reporter (i.e., a gene that codes for a red fluorescent protein, RFP, or green fluorescent protein, GFP), were introduced into human prostate cancer cells. Unless otherwise indicated, analyses were done using two independent shRNAs for each gene in each of four independent prostate cancer cell lines. FIG. 11B is an image of Western blots that illustrate effectiveness of lentiviral silencing vectors, according to an embodiment, by showing expression of FOXM1 or CENPF proteins in DU145 cells expressing the indicated shRNAs.

Figure 11C:
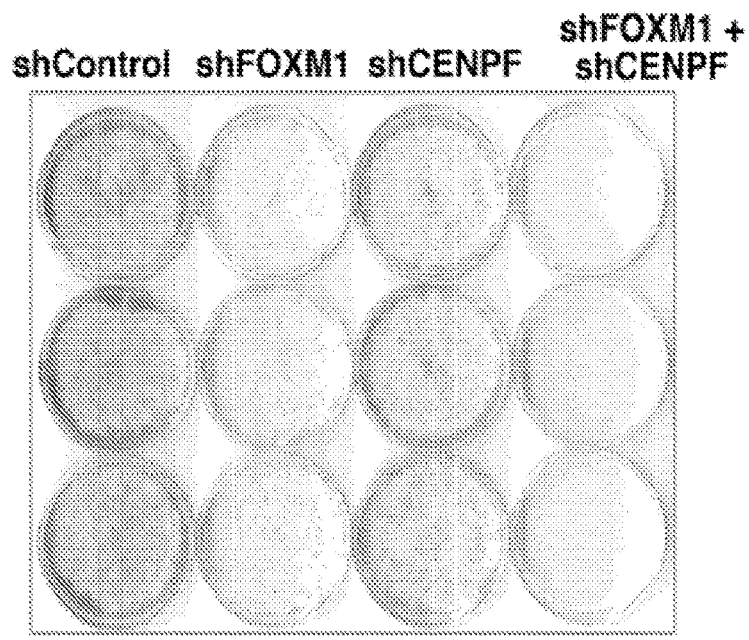
FIG. 11C is an image of photographs that illustrate DU145 cell colonies, visualized using crystal violet, are drastically reduced by silencing both FOXM1 and CENPF compared to other combinations, according to an embodiment.
Figure 11D:
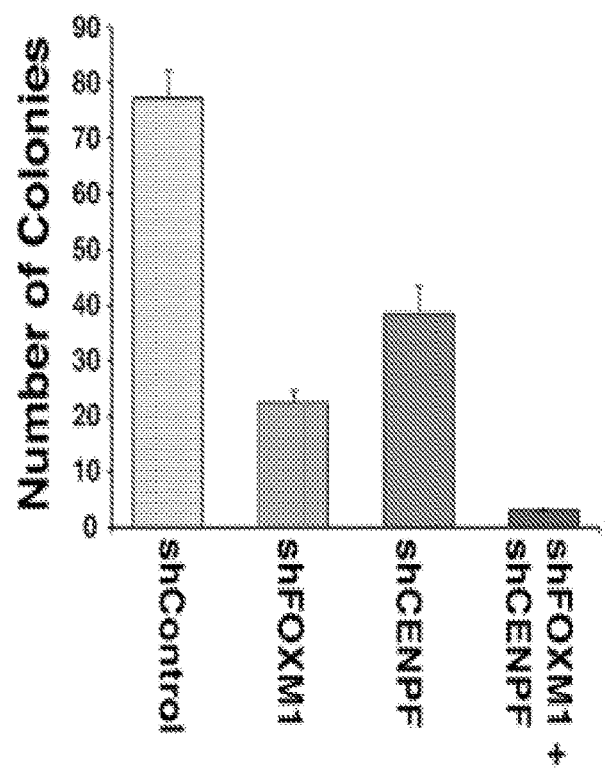
FIG. 11D is graph that illustrates the quantitative number of DU145 cell colonies are drastically reduced by silencing both FOXM1 and CENPF compared to other combinations, according to an embodiment.

FIG. 11C is an image that illustrates that DU145 cell colonies, visualized using crystal violet, are drastically reduced by silencing both FOXM1 and CENPF compared to other combinations. FIG. 11D is graph illustrating that the quantitative number of DU145 cell colonies are drastically reduced by silencing both FOXM1 and CENPF compared to other combinations. Quantification of colonies was performed using ImageJ.

In these various analyses, "synergistic" versus "additive" effects of FOXM1 and CENPF are distinguished by first extrapolating their "predicted additivity" based on their individual silencing and then comparing this predicted value to their "actual" observed effect following their co-silencing. See the experimental procedures discussion in a later section. For any given assay, if the "predicted additive" is statistically different from the "actual," it is concluded that FOXM1 and CENPF are synergistic rather than additive.

With respect to cellular proliferation depicted in FIG. 11C, individual silencing of FOXM1 and, to a lesser extent, CENPF resulted in reduced cell proliferation. However, the reduction following co-silencing was statistically greater ($p<0.01$; log linear model) than the "predicted additive" increase and therefore was synergistic for each cell line that expresses both FOXM1 and CENPF. Similarly, with respect to colony formation depicted in FIG. 11D, while individual silencing of FOXM1 or CENPF (Aytes et++al.) reduced the number of colonies, their co-silencing resulted in nearly complete abrogation of colony formation in each cell line that expresses both FOXM1 and CENPF ($p<0.001$; log linear model). Importantly, co-silencing of FOXM1 and CENPF was not associated with reduced viability, apoptosis, or further cell cycle arrest relative to their individual silencing, suggesting that their observed synergistic activities were not simply due to induction of cell death or secondary to cell cycle arrest.

Figure 11E:
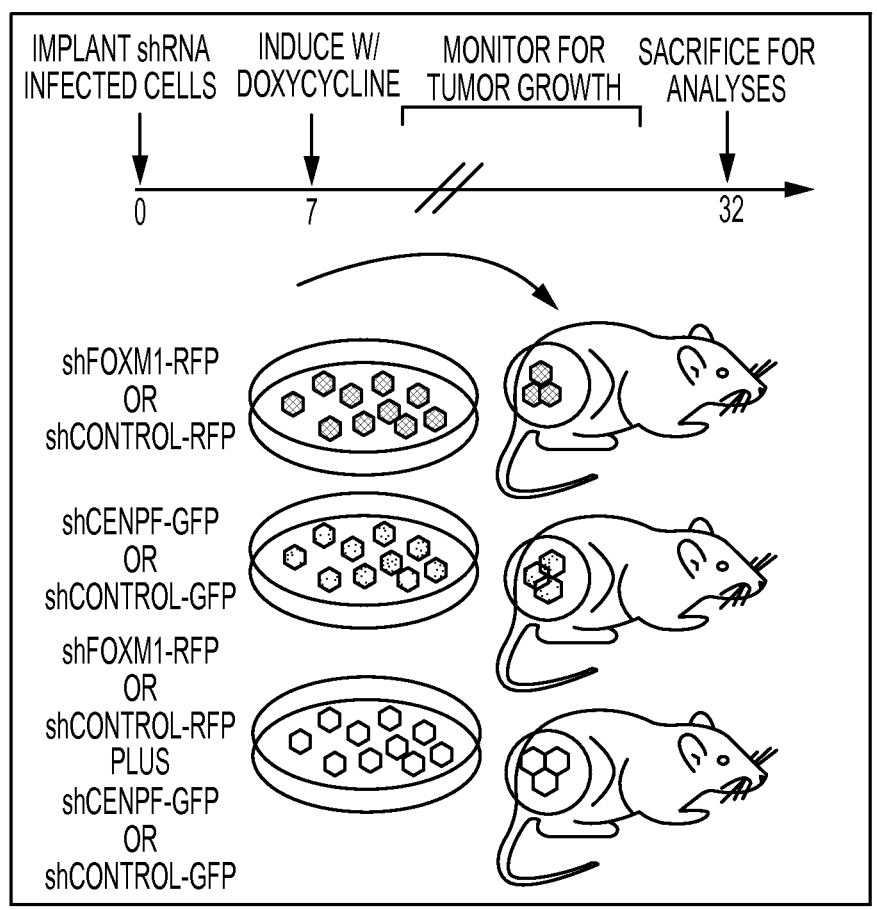
FIG. 11E is a block diagram that illustrates an example in vivo experiment based on tumor growth in the presence of silencing either FOXM1 or CENPF or both, according to an embodiment.
Figure 11F:
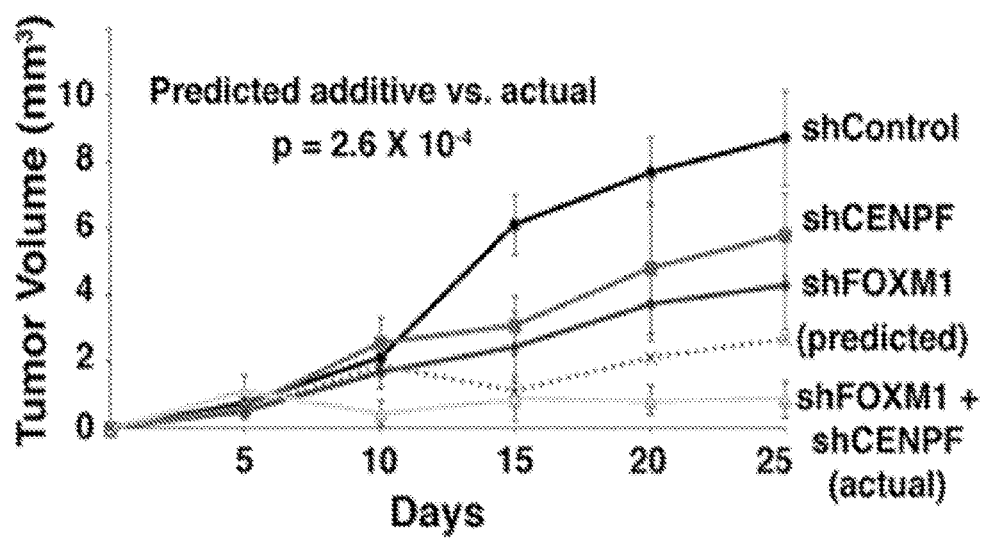
FIG. 11F is a graph that illustrates example in vivo tumor volume growth in the presence of silencing both is more than additive of the effects of silencing either FOXM1 or CENPF separately, according to an embodiment.
Figure 11G:
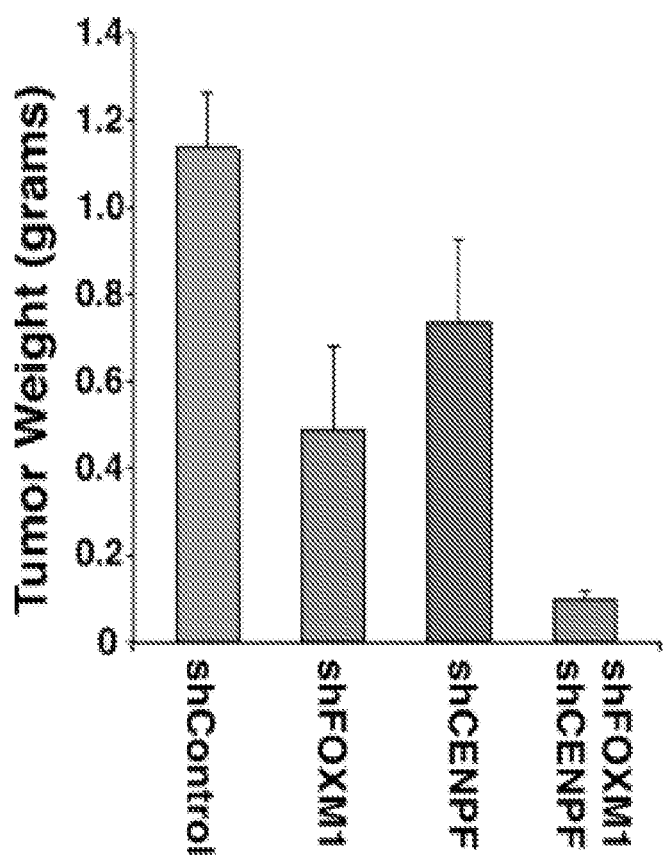
FIG. 11G is a graph that illustrates example in vivo tumor weight at time of sacrifice in the presence of silencing either or both FOXM1 or CENPF, according to an embodiment.
Figure 11H:
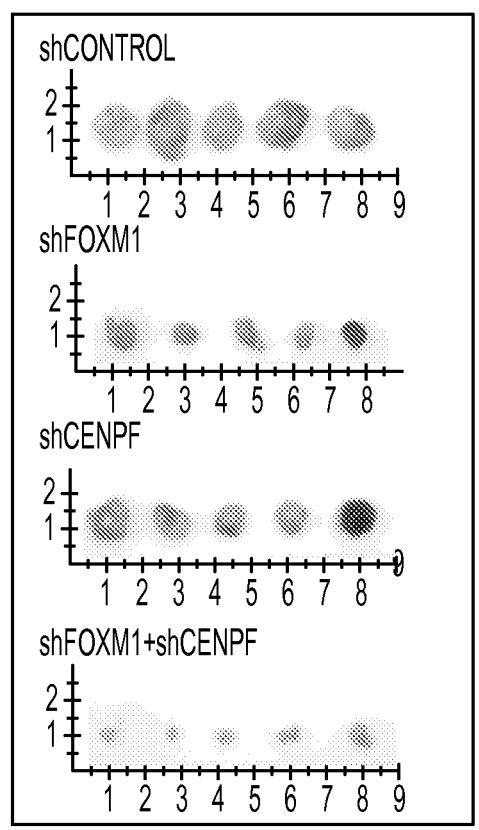
FIG. 11H is an image that illustrates example micrographs of tumors form several mice on identical distance scales in the presence of silencing either or both FOXM1 or CENPF, according to an embodiment.

Co-Silencing FOXM1 and CENPF Completely Abrogated Tumor Growth and Caused a Profound Reduction in Tumor Weight To investigate their consequences of silencing FOXM1 and CENPF on prostate tumor growth in vivo, DU145 cells expressing silencing vectors for FOXM1 and/or CENPF (or controls) were engrafted into immunodeficient mice and prostate tumor growth was monitored in vivo. FIG. 11E is a block diagram illustrating an example in vivo experiment based on prostate tumor growth with silencing of either FOXM1 or CENPF or both. Beginning on day 7, mice were administered doxycycline to induce shRNA expression and tumor growth was monitored for one month. FIG. 11F shows that in vivo prostate tumor volume growth was dramatically reduced when both FOXM1 and CENPF were silenced, and this effect was more than additive of the effects of silencing either FOXM1 or CENPF separately. The dashed line shows the predicted additive effect of co-silencing FOXM1 and/or CENPF estimated using a log linear model; the p-value indicates the significance between the predicted additive versus and the actual observed consequences of co-silencing FOXM1 and CENPF. FIG. 11G shows that in vivo tumor weight at time of sacrifice was also dramatically reduced when both FOXM1 and CENPF were silenced compared to silencing either FOXM1 or CENPF separately. Associated p values indicate the difference between the predicted additive and the actual observed consequences of co-silencing FOXM1 and CENPF was significant and therefore that the results are synergistic. FIG. 11H shows micrographs of prostate tumors from several mice on identical distance scales in co-silenced FOXM1 and CENPF compared to silencing only one.

Consistent with the cell culture studies, individual silencing of FOXM1 or CENPF resulted in a modest but statistically significant reduction in tumor growth (2.0 fold, $p \leq 2 \times 10^{-3}$ and 1.5 fold, $p \leq 2 \times 10^{-3}$, respectively), as well as tumor weight (2.3 fold, $p \leq 7 \times 10-3$, and 1.6 fold, $p \leq 1 \times 10^{-2}$, respectively). However, co-silencing of FOXM1 and CENPF resulted in a complete abrogation of tumor growth (10.2 fold reduced, $p \leq 1.3 \times 10^{-5}$) and profound reduction in tumor weight (12.9 fold, $p \leq 1.1 \times 10^{-5}$). Notably, the actual observed inhibition of tumor growth following co-silencing FOXM1 and CENPF were significantly greater than their "predicted additive" reduction based on their individual silencing (3.3 fold difference, $p < 2.6 \times 10^{-4}$; log-linear model) (see FIG. 11F), supporting the conclusion that FOXM1 and CENPF synergistically regulate tumor growth in vivo.

Figure 11I:
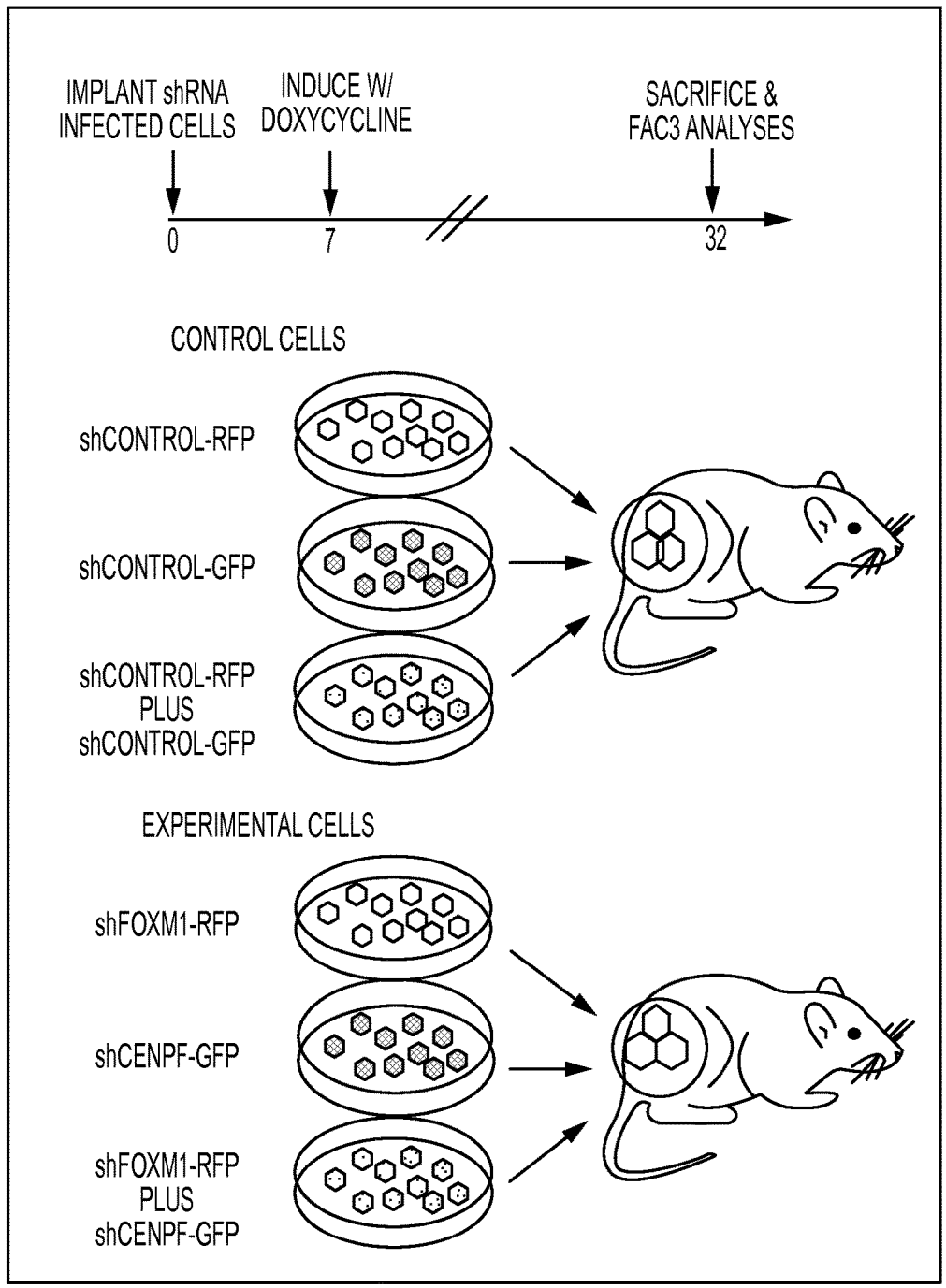
FIG. 11I is a block diagram that illustrates an example in vivo competition assay in which equal numbers of DU145 cells expressing the control shRNA (control cells), or the experimental shRNA for FOXM1 or CENPF or both (experimental cells) as well as red or green reporters (RFP or GFP, respectively) were implanted into mouse hosts, according to an embodiment.

To further evaluate the synergistic activity of FOXM1 and CENPF for prostate tumor growth, an in vivo competition assay was developed. FIG. 11I shows an example in vivo competition assay in which equal numbers of DU145 cells expressing the control shRNA (control cells), or the experimental shRNA for FOXM1 or CENPF or both (experimental cells) as well as red or green reporters (RFP or GFP, respectively) were implanted into mouse hosts. Specifically, DU145 cells were infected with silencing vectors expressing an FOXM1 shRNA and an RFP reporter (R) or a CENPF shRNA and a GFP reporter (G), or both lentiviruses (resulting in cells stained in yellow, Y). As negative controls, DU145 cells were infected with control vectors lacking the FOXM1 or CENPF shRNA but expressing the fluorescent reporters. Equal numbers of viable red, green, or yellow cells from the experimental or control groups were then implanted into immunodeficient mice. Tumor growth in vivo was monitored for one month. Following the one month growth in vivo, tumors were collected and sorted by fluorescence-activated cell sorting (FACS) to quantify the total number of red, green, or yellow cells in individual tumors for control and experimental groups.

Figures 11J, 11K:
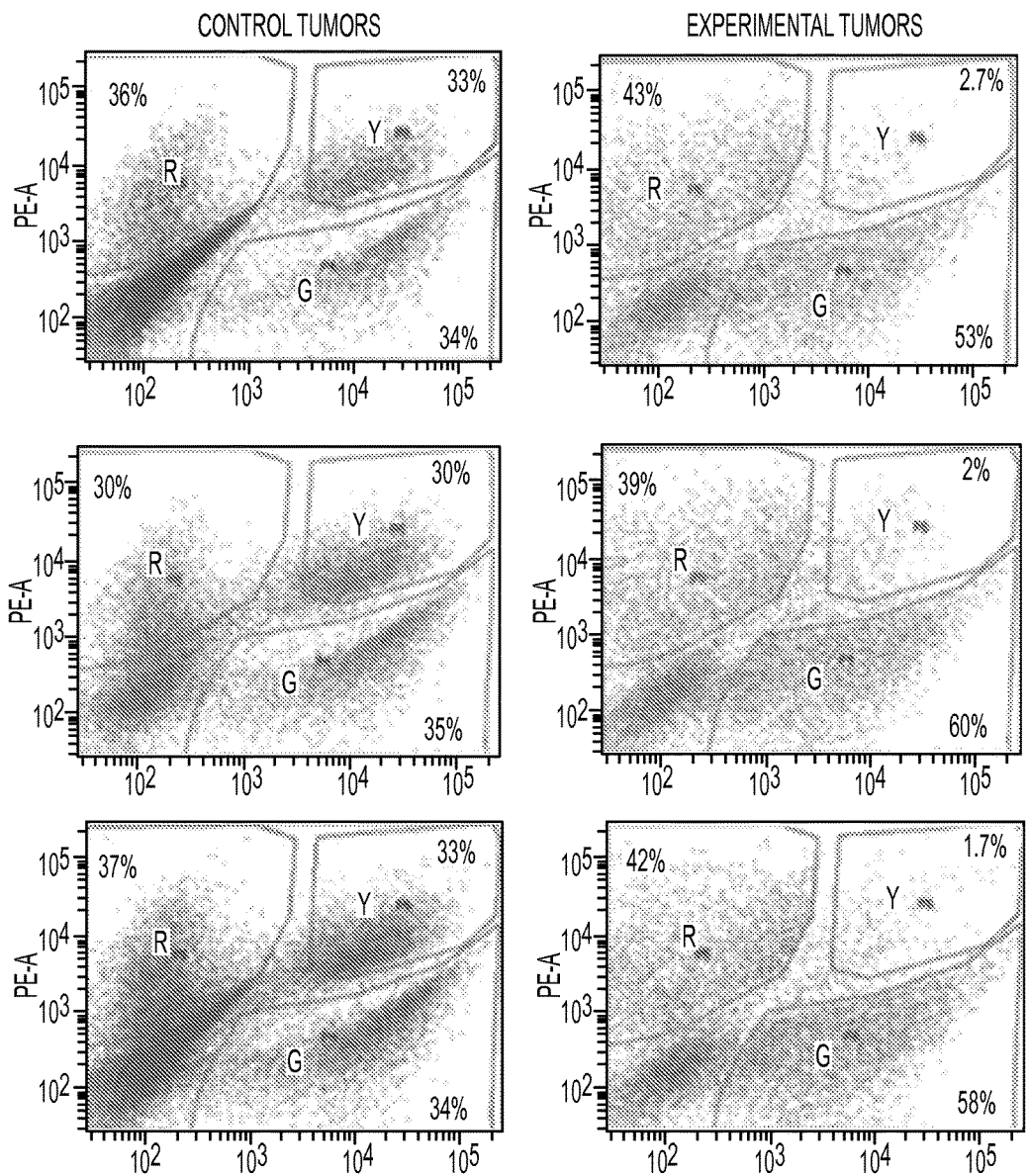
FIG. 11J and FIG. 11K are graphs that illustrate example fluorescence-activated cell sorting (FACS) plots showing the percentage of red cells (R, FOXM1 silenced), green cells (G, CENPF silenced) or yellow cells (Y, both silenced) relative to the total number of fluorescent cells for control tumors and experimental tumors, respectively, according to an embodiment.

FIG. 11J and FIG. 11K provide example fluorescence-activated cell sorting (FACS) plots showing the percentage of red cells (R, FOXM1 silenced), green cells (G, CENPF silenced) or yellow cells (Y, both silenced) relative to the total number of fluorescent cells for control tumors and experimental tumors, respectively, according to an embodiment. FIG. 11L and FIG. 11M are graphs that illustrate example percentages of red, green or yellow cells relative to the total number of fluorescent cells for control tumors and experimental tumors, respectively, indicating profound selection against cells co-silenced for FOXM1 and CENPF.

Tumors derived from control cells (sample size n=4) were comprised of equivalent numbers of red (34%±0.6%), green (34%±2.7%) and yellow (33%±1.2%) cells, indicating that the respective lentiviral vectors offer no selective growth advantage ($p \leq 0.614$; Hotelling's one-sample T-squared test) (FIG. 11K through FIG. 11M). In striking contrast, tumors derived from the experimental cells (sample size n=7) were comprised primarily of green CENPF-silenced cells (57%±3.5%) and red FOXM1-silenced cells (41%±2.6%), while there were virtually no yellow, co-silenced cells (2.0%±0.3%). This profound selection against cells co-silenced for FOXM1 and CENPF was highly significant ($p \leq 1 \times 10^{-4}$; Hotelling's one-sample T-squared test) showing that tumor cells in which both genes are co-silenced do not survive. This further supports the conclusion that FOXM1 and CENPF synergistically regulate tumor growth in vivo.

To elucidate molecular pathways that underlie their synergistic interaction for prostate tumor growth, gene expression profiles from prostate cancer cells in which FOXM1 and/or CENPF were individually silenced or co-silenced were analyzed. Among the genes that were differentially expressed (relative to control cells) following individual silencing of FOXM1 or CENPF were a majority of their ARACNe-inferred targets ($p \leq 0.0028$ for enrichment of FOXM1 targets; $p \leq 0.001$ for enrichment of CENPF targets), further confirming the accuracy of the ARACNe analysis. Inspection of these target genes as well as gene set enrichment analysis (GSEA) of enriched biological pathways confirmed the known individual functions of FOXM1 and CENPF as regulators of cellular proliferation, reduction of stress response and/or regulation of mitosis.

Co-silencing of FOXM1 and CENPF also revealed a new repertoire of significantly differentially expressed genes and enriched biological pathways that had not been evident by their individual silencing. In particular, co-silencing of FOXM1 and CENPF revealed the enrichment of key biological pathways associated with tumorigenesis, including: "Cell cycle" (normalized enrichment score (NES) 1.32; $p \leq 0.001$), "stress pathway" (NES 1.58; $p \leq 0.01$), "regulation of insulin-like growth factor" (NES 1.89; $p \leq 0.001$), "signaling by NGF" (NES 1.25; $p \leq 0.001$), "Metabolism of amino acids" (NES 1.25; $p \leq 0.01$), "PI3-Akt signaling" (NES 1.89; $p \leq 0.001$), "MAP kinase pathway" (NES 1.34; $p \leq 0.008$), "Telomere maintenance" (NES 1.35; $p \leq 0.01$) and "Cell adhesion molecules" (NES 1.32; $p \leq 0.001$). Of particular interest was the enrichment of PI3-kinase and MAP kinase signaling pathways, which were enriched following co-silencing of FOXM1 and CENPF, as these constitute established hallmarks of aggressive prostate cancer (Aytes et al., 2013; Taylor et al., 2010).

FIG. 11N is an image of Western blots that illustrate example changes in expression of the indicated representative markers of the PI3-kinase and MAP kinase signaling pathways associated with tumor growth in DU145 and PC3 prostate cancer cells after silencing either FOXM1 or CENPF or both, according to an embodiment. As evident by this Western blot analysis, both pathways are completely abrogated following co-silencing of FOXM1 and CENPF showing that therapeutic targeting FOXM1 and CENPF in prostate cancer cells may be effective for inactivation of key signaling pathways such as PI3-kinase and MAP kinase.

Although the individual functions of FOXM1 and CENPF in cancer have been well-studied, the findings described here have uncovered their novel synergistic interaction in aggressive prostate cancer, which could not have been anticipated from their previous analyses. Cumulatively, the new findings show that coexpression of FOXM1 and CENPF in aggressive prostate cancer leads to co-regulation of transcriptional programs, which ultimately result in activation of the key signaling pathways associated with cancer malignancy, including activation of PI3K and MAPK signaling pathways.

Based on the described results, certain embodiments are directed to methods of slowing the progression of non-aggressive prostate cancer to an aggressive form, and for treating aggressive prostate cancer by administering therapeutically effective amounts of active agents to significantly reduce the expression of FOXM1 and CENPF; typically these are different agents. In various embodiments the therapeutic agents are inhibitory oligonucleotides including inter alia antisense, siRNA and shRNA, which reduce expression of the gene or mRNA encoding FOXM1 and CENPF, which agents are described in more detail below. FOXM1 and CENPF can also be targeted pharmacologically using for example non-oligonucleotides. Such agents that reduce CENPF expression include Rapamycin, mTOR inhibitors, PI3K inhibitors, MEK inhibitors, tyrosine kinase inhibitors, and AKT kinase inhibitors (Halasi and Gartel, 2013b; Pan and Yeung, 2005; Radhakrishnan et al., 2006).

mTOR inhibitors include Rapamycin, but deforolimus (AP23573, MK-8669), everolimus (RAD001), and temsirolimus (CCI-779) are the newly developed rapamycin analogs. Rapamycin analogs are small molecule inhibitors that have been evaluated as anticancer agents. The analogs are reported to have a more favorable pharmacokinetic profile compared to rapamycin, the parent drug, despite the same binding sites for mTOR and FKBP12. Rapamycin analog temsirolimus (CCI-779)] is also a noncytotoxic agent which delays tumor proliferation. The second generation of mTOR inhibitors, some of which are in clinical trials, are known as ATP-competitive mTOR kinase inhibitors. mTORC1/mTORC2 dual inhibitors are designed to compete with ATP in the catalytic site of mTOR. They inhibit all of the kinase-dependent functions of mTORC1 and mTORC2 and therefore, block the feedback activation of PI3K/AKT signaling, unlike analogs that only target mTORC1. They also decrease protein translation, attenuate cell cycle progression, and inhibit angiogenesis in many cancer cell lines and also in human cancer.

The close interaction of mTOR with the PI3K pathway has also led to the development of mTOR/PI3K dual inhibitors including NVP-BEZ235, BGT226, SF1126, PKI-587 and many more. Compared with drugs that inhibit either mTORC1 or PI3K, these drugs have the benefit of inhibiting mTORC1, mTORC2, and all the catalytic isoforms of PI3K. Targeting both kinases at the same time reduces the upregulation of PI3K, which is typically produced with an inhibition on mTORC1. mTORC1/mTORC2 dual inhibitors (TORCdIs) include INK128, AZD8055, and AZD2014.

MEK inhibitors are chemicals or drugs that inhibit the mitogen-activated protein kinase kinase enzymes MEK1 and/or MEK2 that affects the MAPK/ERK pathway, which is often overactive in some cancers. MEK inhibitors include Trametinib (GSK1120212), FDA-approved to treat BRAF-mutated melanoma; dabrafenib; Selumetinib, for use in treating non-small cell lung cancer (NSCLC); Binimetinib or MEK162, for treating biliary tract cancer and melanoma; PD-325901, for breast cancer, colon cancer, and melanoma; Cobimetinib or XL518, in combination with vemurafenib (Zelboraf(R)), for treatment of advanced melanoma; CI-1040; and PD035901.

Tyrosine kinase inhibitors include bosutinib (Bosulif); crizotinib (Xalkori); dasatinib Sprycel); erlotinib (Tarceva); imatinib (Gleevec); gefitinib; lapatinib (Tykerb); nilotinib (Tasigna0; sorafenib (Nexavar); and sunitinib (Sutent). Tyrosine kinases are enzymes responsible for the activation of many proteins by signal transduction cascades by adding a phosphate group to the protein (phosphorylation).

P13K inhibitors include many commercially available molecules: BEZ235 (NVP-BEZ235, Dactolisib), Pictilisib (GDC-0941), LY294002 (the first synthetic molecule known to inhibitPI3Kα/67/β), CAL-101 (Idelalisib, GS-1101) and many others available from Selleck/Pfeizer.

AKT Kinase inhibitors are also well known and include Perifosine (KRX-0401) is a novel Akt inhibitor, MK-2206 2HC1 is a highly selective inhibitor of Akt1/2/3, Miltefosine inhibits PI3K/Akt activity, MK-2206 2HCl is a highly selective inhibitor of Akt1/2/3, iltefosine inhibits PI3K/Akt activity, and SK690693 is a pan-Akt inhibitor targeting Akt1/2/3. These and others are available from Selleck/Pfeizer.

4.1. Administration and Pharmaceutical Formulations

The therapeutic agents that reduce expression or biological activity of FOXM1 and CENPF, as described above, can be administered in a single formulation or in separate formulations. They can be administered either locally, for example by injection into the prostate or prostate tumor, or systemically such as by oral or intramuscular or intravascular injection. Where the therapeutic agent is an inhibitory oligonucleotide, the preferred route is oral administration. In embodiments of the invention, inhibitory oligonucleotides, nonoligonucleotides and small molecular therapeutic/active agents that reduce FOXM1 and CENPF expression or biological activity are combined for treating aggressive prostate cancer, or to slow or prevent progression of non-aggressive prostate cancer to an aggressive form. Active agents can be combined in a single pharmaceutical formulation or administered in separate formulations, on the same day or on different days. Multiple administration is typically required over the course of days, weeks, months or years.

Small molecule inhibitors of FOXM1 and CENPF expression or biological activity for use in embodiments of the invention may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount.

Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. It is anticipated that some embodiment include the quaternization of any basic nitrogen-containing groups of the therapeutic agents disclosed herein. Water or oil-soluble or dispersible products may be obtained by such quaternization.

The therapeutic agents of some embodiments are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more hydrogens are replaced by deuterium or tritium, or the replacement of one or more carbons by $^{13}$C- or $^{14}$C-enriched carbon are within the scope of this invention.

The active agents and pharmaceutical compositions of the present invention may be administered in a number of ways depending upon whether local or systemic treatment is desired and upon the area to be treated. Administration may be oral or parenteral. Parenteral administration includes intravenous, intraarterial, subcutaneous, intraperitoneal or intramuscular injection or infusion; or intracranial, e.g., intrathecal or intraventricular, administration. Administration can also be pulmonary. Oligonucleotides with at least one 2'-O-methoxyethyl modification are believed to be particularly useful for oral administration.

In a preferred embodiment, the therapeutic agents of some embodiments are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the therapeutic agent with which it is formulated. Pharmaceutically acceptable carriers, adjuvants or vehicles that may be used in the compositions of some embodiments encompass any of the standard pharmaceutically accepted liquid carriers, such as a phosphate-buffered saline solution, water, as well as emulsions such as an oil/water emulsion or a triglyceride emulsion. Solid carriers may include excipients such as starch, milk, sugar, certain types of clay, stearic acid, talc, gums, glycols, or other known excipients. Carriers may also include flavor and color additives or other ingredients. The formulations of the combination of some embodiments may be prepared by methods well-known in the pharmaceutical arts and described herein. Exemplary acceptable pharmaceutical carriers have been discussed above. An additional carrier, Cremophor™, may be useful, as it is a common vehicle for Taxol.

The pharmaceutical compositions of some embodiments are prepared for oral administration, preferably as solid compositions. However, the pharmaceutical compositions may be administered by intravenous injection or by injection or infusion into the prostate gland or prostate tumor, parenterally, or via an implanted reservoir. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

The pharmaceutical compositions employed in some embodiments may be orally administered in any orally acceptable dosage form, including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

Solutions or suspensions used for parenteral, intradermal, or subcutaneous application can comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injection comprise sterile aqueous solutions (where water soluble) or dispersions and sterile powders for the extemporaneous preparation of sterile injectable solutions or dispersions. For intravenous administration, suitable carriers comprise physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as manitol, sorbitol, or sodium chloride. Prolonged absorption of an injectable composition can be achieved by including in the composition an agent that delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the methods of preparation comprise vacuum drying and freeze-drying which yields a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be comprised as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

4.2 Inhibitory Oligonucleotides for Clinical Use to Treat Aggressive Prostate Cancer In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. As used herein an inhibitory oligonucleotide includes without limitation antisense, siRNA, shRNA, ribozymes and MIRs that reduce the expression of a targeted FOXM1 or CENPF gene or protein.

In certain aspects, the invention relates to a pharmaceutical composition comprising one or more inhibitory nucleic acids (inhibitory oligonucleotides) capable of reducing expression or activity of a protein encoded by a FOXM1 or CENPF nucleic acid, and a pharmaceutically acceptable carrier. In another aspect, the methods described herein relate to treating a subject with prostate cancer, especially aggressive prostate cancer, by administering (or otherwise contacting a prostate cancer cell with) a therapeutically effective amount of an inhibitory nucleic acid capable of reducing expression or activity of a protein encoded by a FOXM1 or CENPF nucleic acid in a cancerous prostate cell, e.g., a cell of a subject. In the method the inhibitory nucleic acid is substantially complementary to the nucleotide sequence of the target (e.g. a nucleic acid encoding a FOXM1 or CENPF polypeptide). Such methods can be performed on a human or a non-human mammal by administering to a one of the inhibitory nucleic acid capable of reducing expression or activity of a protein encoded by a FOXM1 or CENPF nucleic acid or pharmaceutical compositions described herein.

The invention also relates to a method for treating a subject who has been diagnosed with any other cancer or a disorder characterized by overexpression of FOXM1 and CENPF and wherein the subject can be treated by administration of inhibitory nucleic acid capable of reducing expression or activity of a protein encoded by a FOXM1 or CENPF nucleic acid, thereby alleviating the symptoms associated with the overexpression of FOXM1 and CENPF.

A therapeutically effective amount a compound that reduces the expression or activity of FOXM1 and/or CENPF for the practice of the present invention can be further refined by one of ordinary skill in the art using known criteria including the age, weight and response of the individual patient, and interpreted within the context of the disease which is being treated or which is being prevented. In one embodiment, an effective amount is an amount of a compound that reduces the expression or activity of FOXM1 and/or CENPF, a pharmaceutical composition, or a medicine or medicament thereof that elicits the biological or medicinal response (such as inhibiting, preventing or treating) of a cancer in a tissue system, animal or human, that is being sought by a researcher, veterinarian, medical doctor, or other clinician.

In certain embodiments, the therapeutically effective amount of a compound that reduces the expression or activity of FOXM1 and/or CENPF can be delivered as a pharmaceutical composition. In certain embodiments, the pharmaceutical composition can be a product containing a compound that reduces the expression or activity of FOXM1 and/or CENPF, wherein the product comprises the specified ingredients in specified amounts, as well as any product that results, directly or indirectly, from such combinations of the specified ingredients in the specified amounts.

In other embodiments, the compositions described herein can be administered in a pharmaceutically acceptable form. In another embodiment, a pharmaceutically acceptable form can be a composition that is of sufficient purity or quality to be of use in the formulation of a pharmaceutical composition, medicine or medicament of the present invention. Since both human use and veterinary use are equally included within the scope of the present invention, a pharmaceutically acceptable formulation can include a pharmaceutical composition, medicine or medicament for either human or veterinary use.

In certain embodiments, the inhibitory nucleic acid that reduces the expression or activity of FOXM1 or CENPF (herein "a described inhibitory oligonucleotide") can comprise is an inhibitory nucleic acid which hybridizes to at least a portion of a FOXM1 or CENPF nucleic acid to modify expression of a protein encoded by the nucleic acid. The oligonucleotide may match the target region exactly or may contain several mismatches. A variety of nucleic acid species are capable of modifying gene expression or modifying the activity of a polypeptide encoded therefrom. These include antisense RNA, shRNA, siRNA, microRNA, RNA and DNA aptamers, and decoy RNAs. Each of these nucleic acid species can be used in connection with the methods described herein to reduce the expression or activity of FOXM1 or CENPF.

In certain embodiments, the described inhibitory nucleic acid can be an siRNA comprising a double stranded structure containing from about 15 to about 50 base pairs, for example from about 21 to about 25 base pairs, and having a nucleotide sequence identical or nearly identical to an expressed target gene or RNA within the cell. Antisense nucleotide sequences include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitory nucleic acid that reduces the expression or activity of FOXM1 or CENPF can contain ribonucleotides, deoxyribonucleotides, synthetic nucleotides, or any suitable combination such that the target RNA and/or gene is inhibited. In addition, these forms of nucleic acid can be single, double, triple, or quadruple stranded.

The described inhibitory nucleic acid can be produced chemically or biologically, or can be expressed from a recombinant plasmid or viral vector.

A described inhibitory nucleic acid can additionally be a short hairpin RNA (shRNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., 2002; McCaffrey et al., 2002; McManus et al., 2002; Yu et al., 2002. Such hairpin RNAs are engineered in cells or in an animal to ensure continuous and stable suppression of a desired gene. It is known in the art that siRNAs can be produced by processing a hairpin RNA in the cell.

In certain embodiments, shRNAs suitable for use with the methods described herein can be a shRNA having, consisting essentially of, or comprising the sequence of any of SEQ ID NOs 1-4. In certain embodiments, an shRNA having, consisting essentially of, or comprising the sequence of SEQ ID NO: 1 or 2 can be useful for reducing the expression of FOXM1 in connection with the methods described herein. In certain embodiments, an shRNA having, consisting essentially of, or comprising the sequence of SEQ ID NO: 3 or 4 can be useful for reducing the expression of CENPF in connection with the methods described herein.

Described inhibitory nucleic acids can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long) with a target RNA. Inhibitory nucleic acid capable of reducing expression or activity of a protein encoded by a FOXM1 or CENPF nucleic acid can be 18-100 nucleotides in length and, in certain embodiments can be designed by one of skill in the art to undergo processing to become mature. For example, mature miRNAs can have a length of 19-30 nucleotides, 21-25 nucleotides, particularly 21, 22, 23, 24, or 25 nucleotides, whereas miRNA precursors typically have a length of about 70-100 nucleotides and have a hairpin conformation.

The described inhibitory nucleic acid can be an oligomers or a polymer of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally occurring portions that function similarly.

A described inhibitory nucleic acid can include a nucleotide sequence sufficiently complementary to hybridize to an FOXM1 or CENPF target sequence. In certain embodiments, the sufficient complementarity can be of about 12 to 25 nucleotides, about 13 to 23 nucleotides, about 14 to 23 nucleotides or about 15 to 23 nucleotides. It is contemplated that a nucleic acid fragment of the present invention may be almost any length. A general size range for the Inhibitory nucleic acid capable of reducing expression or activity of a protein encoded by a FOXM1 or CENPF nucleic acid themselves will be 20 to 90-100 bases. It will be readily understood that intermediate lengths, such as 21, 22, 23, 24, 25, 26, 27, 28, 29, 30, 31, 32, 33, 34, 35, 36, 37 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99, are contemplated as well.

In certain non-limiting embodiments, a described inhibitory nucleic acid is considered to be targeted FOXM1 or CENPF if (1) the stability of the target gene transcript (e.g. FOXM1 or CENPF) is reduced in the presence of the inhibitory nucleic acid as compared with its absence; and/or (2) the inhibitory nucleic acid shows at least about 90%, more preferably at least about 91%, 92%, 93%, 94%, 95%, 96%, 97%, 98%, 99%, or 100% precise sequence complementarity with the target transcript (e.g. FOXM1 or CENPF) for a stretch of at least about 17, more preferably at least about 18 or 19 to about 21-23 nucleotides; and/or (3) the inhibitory nucleic acid hybridizes to the target transcript under stringent conditions.

The described inhibitory nucleic acid can also be produced biologically using an expression vector.

The described inhibitory nucleic acids can be synthesized in vivo by a cell-based system or in vitro by chemical synthesis. Inhibitory nucleic acids capable of reducing expression or activity of a protein encoded by FOXM1 or CENPF can be constructed using chemical synthesis and/or enzymatic ligation reactions using procedures known in the art.

A described inhibitory nucleic acid can include a region of sufficient complementarity to the target nucleic acid (e.g., target FOXM1 or CENPF), and is of sufficient length in terms of nucleotides, such that the miRNA inhibitory nucleic acid forms a duplex with the target nucleic acid. An inhibitory nucleic acid capable of reducing expression or activity of a protein encoded by a FOXM1 or CENPF nucleic acid is, or includes, a region that is at least partially, and in some embodiments fully, complementary to the target RNA (e.g., target FOXM1 or CENPF). It is not necessary that there be perfect complementarity between the Inhibitory nucleic acid capable of reducing expression or activity of a protein encoded by a FOXM1 or CENPF nucleic acid and the target, but the correspondence must be sufficient to enable the oligonucleotide agent, or a cleavage product thereof, to modulate (e.g., inhibit) target gene expression.

An inhibitory nucleic acid can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting.

The described inhibitory nucleic acid can be further stabilized against nucleolytic degradation such as by the incorporation of a modification, e.g., a nucleotide modification. The inhibitory nucleic acid capable of reducing expression or activity of a protein encoded by a FOXM1 or CENPF nucleic acid can include a phosphorothioate at least the first, second, or third internucleotide linkage at the 5' or 3' end of the nucleotide sequence. In certain embodiments, the inhibitory nucleic acid capable of reducing expression or activity of a protein encoded by a FOXM1 or CENPF nucleic acid can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a particular embodiment, the inhibitory nucleic acid capable of reducing expression or activity of a protein encoded by a FOXM1 or CENPF nucleic acid includes at least one 2'-O-methyl-modified nucleotide, and in some embodiments, all of the nucleotides of the inhibitory nucleic acid capable of reducing expression or activity of a protein encoded by a FOXM1 or CENPF nucleic acid include a 2'-O-methyl modification.

The described inhibitory nucleic acid can be further modified so as to be attached to a ligand that is selected to improve stability, distribution or cellular uptake of the agent, e.g., cholesterol. Such non-nucleotide moiety can be attached, e.g., to the 3' or 5' end of the oligonucleotide agent. In one embodiment, a cholesterol moiety is attached to the 3' end of the inhibitory nucleic acid. In certain embodiments, the inhibitory nucleic acid capable of reducing expression or activity of a protein encoded by a FOXM1 or CENPF nucleic acid includes a modification that improves targeting. Examples of modifications that target single-stranded oligonucleotide agents to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

In one embodiment, a described inhibitory nucleic acid, such as a single-stranded oligonucleotide agent, can have a nucleotide sequence that is substantially identical to a portion of a nucleic acid encoding FOXM1 or CENPF. Single-stranded oligonucleotide agents that are substantially identical to at least a portion of a nucleic acid encoding FOXM1 or CENPF, such as those described above, can be administered to a subject to treat a subject having, or at risk of having, a cancer.

A described inhibitory nucleic can be delivered into a cell in any of a variety of forms, including as naked plasmid or other DNA, formulated in liposomes, in an expression vector, which includes a viral vector (including RNA viruses and DNA viruses, including adenovirus, lentivirus, alphavirus, and adeno-associated virus). The amount of nucleic acid needed to sequester an Id protein in the cytoplasm can be readily determined by those of skill in the art, which also can vary with the delivery formulation and mode and whether the nucleic acid is DNA or RNA.

The described inhibitory nucleic acid can further be in isolated form or can be part of a pharmaceutical composition used for the methods described herein, particularly as a pharmaceutical composition formulated for parental administration. The pharmaceutical compositions can contain one or more inhibitory nucleic acid agents, and in some embodiments will contain two or more inhibitory nucleic acid agents, each one directed to a different target gene. For example, in certain embodiments, the pharmaceutical composition can comprise at least one inhibitory nucleic acid directed to FOXM1 and at least one inhibitory nucleic acid directed to CENPF.

In another aspect, the described inhibitory nucleic acids capable of reducing expression or activity of a protein encoded by a FOXM1 or CENPF nucleic acid can be expressed from transcription units inserted into DNA or RNA vectors. The recombinant vectors can be DNA plasmids or viral vectors. Viral vectors suitable for producing inhibitory nucleic acids capable of reducing expression or activity of a protein encoded by a FOXM1 or CENPF nucleic acid can be constructed based on, but not limited to, adeno-associated virus, retrovirus, adenovirus, or alphavirus. The recombinant vectors capable of expressing the inhibitory nucleic acids capable of reducing expression or activity of a protein encoded by a FOXM1 or CENPF nucleic acid can be delivered as described above, and can persist in target cells. Alternatively, viral vectors can be used that provide for transient expression of nucleic acid molecules. Such vectors can be repeatedly administered as necessary. Once expressed, the inhibitory nucleic acids capable of reducing expression or activity of a protein encoded by a FOXM1 or CENPF nucleic acid interacts with the target RNA and inhibits miRNA activity. A number of viruses can be used in connection with the methods described herein, including papovaviruses, e.g., SV40, adenovirus, vaccinia virus, adeno-associated virus, herpesviruses including HSV and EBV, and retroviruses of avian, murine, and human origin. In certain embodiments, lentiviral vectors can be used in connection with the methods described herein. In certain embodiments, the lentiviral vector can be a doxycycline-inducible lentiviral vector engineered to express one or more shRNAs against FOXM1, one or more an shRNAs against CENPF, or to express a plurality of shRNAs, wherein one or more is an shRNA against FOXM1 and one or more is an shRNA against CENPF.

Delivery of the inhibitory nucleic acid-expressing vectors can be systemic, such as by intravenous or intra-muscular administration, by administration to target cells ex-planted from a subject followed by reintroduction into the subject, or by any other means that would allow for introduction into the desired target cell (for a review see Couture et al., Trends in Genetics 12:510, 1996).

4.3 Pharmaceutical Formulation and Clinical Use of Inhibitory Oligonucleotides

Because nucleases that cleave the phosphodiester linkage in DNA are expressed in almost every cell, unmodified DNA molecules such as inhibitory oligonucleotides are generally modified to resist degradation. Additionally, most targets of antisense are located inside cells, and getting nucleic acids across cell membranes is taken into account. For clinical use, inhibitory oligos that have modified nucleotides that resist degradation are preferred. Additionally, other molecules may be conjugated to antisense molecules in order to improve their ability to target certain cells or to cross barriers like cell membranes or the blood brain barrier.

Chemical modifications of inhibitory oligonucleotides like antisense can significantly affect their bioavailability. Phosphorothioate modification of the antisense molecule promotes adhesion to cell surface proteins. Conjugation of a positively charged arginine-rich peptide to PMO-modified antisense oligonucleotides could be used to improve cellular delivery.

Intracellular delivery systems with potential in vivo applications include antisense oligonucleotide conjugation with cationic lipid carriers, carrier molecules that bind with cell-specific receptors, cyclodextrins, dendrimers, microparticles, and macromolecules. These delivery systems can enhance intracellular delivery either by protecting antisense oligonucleotide from nuclease degradation and/or by promoting absorptive endocytosis.

Included in the macromolecule class are cell-penetrating peptides (CPPs), short peptide sequences with a net positive charge that are conjugated to the antisense oligonucleotide via a disulphide bridge. Commonly used CPPs include penetratin, HIV TAT peptide 48-60, and transportan. Further, the addition of dioleylphosphatidylethanolamine to liposome delivery systems results in the destabilization of endosomal membranes and promotion of release of the antisense oligonucleotide after endocytosis.

The enhancement of bioavailability after oral administration can be enhanced by encapsulating in an inert, biodegradable albumin polymer matrix which has been shown to increase bioavailability from 9%, up to 70%. Moreover, the other pharmacokinetic parameters including half-life ($t_{1/2}$) and volume of distribution ($V_d$) increased for the microencapsulated form compared to the solution form of the drug (Uddin et al., 2013), A few nanoparticle-based siRNA delivery systems have been approved by the FDA and are in clinical trials for cancer therapy. All the nanoparticle-formulated siRNA delivery systems for cancer therapy that are currently in clinical trials are based on polymers or liposomes.

Nanoparticles conjugated to the targeting ligand for effective siRNA delivery increase the chance of binding the tumor surface receptor; however, the process also increases the overall size of the nanoparticle. The PEG coating of nanoparticles reduces uptake by RES, resulting in enhanced circulatory half-life, but reduces targeting specificity because PEG molecules sterically disrupt selective conjugation. Thus, the selection of appropriate cell-specific targeting moieties and careful design of stable and potent nanoparticle delivery systems is required for future development. Various nanoparticle-based delivery systems such as cationic lipids, polymers, dendrimers, and inorganic nanoparticles have been demonstrated to provide effective and efficient siRNA delivery in vitro and in vivo.

Antisense oligonucleotides can be delivered directly by systemic administration such as using oral formulations or stereotactic injection into prostate or prostate tumor, typically in saline with chemical modifications to enable uptake. Their phosphorothioate backbone binds to serum proteins, slowing excretion by the kidney. The aromatic nucleobases also interact with other hydrophobic molecules in serum and on cell surfaces. Many types of cells in vivo express surface receptors that actively take up oligonucleotides; these are often lost when cells are cultured, which explains why lipid seems more important for delivering ASOs in culture than in vivo.

Delivery is more challenging for duplex RNAs than single-stranded oligonucleotides. In an siRNA, all of the aromatic nucleobases are on the inside, leaving only heavily hydrated phosphates on the outside of the duplex. This hydrated surface interacts poorly with cell surfaces and is rapidly excreted in the urine. Thus researchers have invested heavily in the development of delivery vehicles for siRNAs. The predominant technologies for delivering siRNAs involve complexing the RNA with cationic and neutral lipids, although encouraging results have also been obtained using peptide transduction domains and cationic polymers. Including PEGylated lipids in the formulation prolongs the circulating half-life of the particles. Conjugation of cholesterol to one strand of the siRNA gave effective knockdown in the liver of mice, but the quantities of material required (50 mg/kg) were several orders of magnitude higher than current lipid-based formulations (as low as 0.01 mg/kg).

One type of optimization of single-stranded DNA or RNA oligonucleotides is the use of chemical modifications to increase the nuclease resistance such as the introduction of phosphorothioate (PS) linkages in place of the phosphodiester bond. This modification greatly improved stability towards digestion by nucleases. PS linkages also improved binding to serum proteins in vivo, increasing half-life and permitting greater delivery of active compound to tissues. ASOs that only contain PS modifications were capable of producing antisense effects inside cells, but potencies were not always high nor were reliable results routine.

Chemical modifications can also improve potency and selectivity by increasing binding affinity of oligonucleotides for their complementary sequences. Widely used modifications include 2'-O-methyl (2'-O-Me), 2'-fluoro (2'-F), and 2'-O-methoxyethyl (2'-MOE) RNA. Even more affinity can be gained using oligonucleotides modified with locked nucleic acid (LNA), which contains a methylene bridge between the 2' and 4' position of the ribose. This bridge "locks" the ribose ring in a conformation that is ideal for binding, leading to high affinity for complementary sequences. Related bridged nucleic acid (BNA) compounds have been developed and share these favorable properties. Their high affinity has permitted the development of far shorter oligonucleotides than previously thought possible which nonetheless retain high potency. The chemistry for introducing 2'-O-Me, 2'-MOE, 2'-F, or LNA into oligonucleotides is compatible with DNA or RNA synthesis, allowing chimeras with DNA or RNA bases to be easily obtained. This compatibility allows the properties of chemically modified oligonucleotides to be fine-tuned for specific applications—a major advantage for development that makes LNAs and other BNAs convenient tools for many applications.

Over the past decade, double-stranded short interfering RNAs (siRNAs) have become widely used tools for silencing gene expression. When a duplex RNA enters cells it binds the protein machinery of the RNA induced silencing complex (RISC). Synthetic RNAs used for gene silencing are usually 19-22 bp duplexes. This length is sufficient to form a stable duplex and be recognized by RISC, but short enough to avoid most of the strong interferon response provoked by duplexes greater than 30 bp in length.

Since publication of the first report of gene silencing in mammalian cells in 2001, siRNAs have been the subject of thousands of experimental studies aimed at examining function. While antisense oligonucleotides continue to be used for gene silencing, the robust nature of siRNAs and the relative ease of identifying active siRNAs have made them a favored silencing tool for many laboratories.

Unmodified duplex RNA is surprisingly stable and chemical modification of siRNAs is usually not essential for silencing gene expression in cultured cells. In vivo, however, unmodified siRNAs are not highly active and chemical modification can significantly improve their properties. Chemically modified siRNAs can feature improved nuclease stability and an associated increase in duration of action. Unmodified RNA is also rapidly cleared and chemical modification, complexation with carrier agent, and local delivery to a disease target can help achieve improved in vivo results.

In vivo, the choice of ASO versus siRNA is unsettled and will continue to evolve over the next decade. For example, in animal models of Huntington's disease, antisense oligonucleotides or siRNAs have been infused directly into the central nervous system. In the case of single-stranded oligonucleotides, researchers observed wide distribution throughout the mouse CNS including deep-brain penetration. In contrast, others found that siRNA infused into the monkey brain penetrated into brain tissue only up to about 12 mm from the site of infusion.

ASOs and siRNAs share important similarities as drug candidates. Both platforms are intended to modulate gene expression. Both are nucleic acids and contain an antisense strand intended to recognize a target mRNA. They also have important differences. ASOs have one strand while siRNAs have two, a basic fact that may lower cost and simplify delivery. On the other hand, siRNAs have proven to be a more robust technology in cell culture in the hands of most users. It is not clear whether this will be true in vivo, but the possibility that siRNAs might have superior potency for at least some applications is a major driving force for their continued development.

An example of the new wave of promising antisense oligonucleotides is Mipomersen, an ASO from ISIS Pharmaceuticals designed to inhibit expression of Apo-B. Mipomersen is a gapmer containing phosphorothioate-modified DNA and 2'-O-MOE-RNA. Data from animal models show a robust and prolonged repression of target apo-B expression. In patients, the desired physiologic response upon systemic administration was demonstrated in four separate Phase III clinical trials. Some toxic effects have been noted, and while these have been relatively mild they may (at least initially) limit the patient population to patients who are at the most severe risk for atherosclerosis.

As of 2013, eleven other traditional antisense oligonucleotides were in advanced clinical trials. Targets relevant to cancer are the most highly represented, but there are also ASOs in trials against asthma, corneal neovascularization and ulcerative colitis. Many of these ASOs contain optimized chemistry and are taking advantage of the lessons learned over the past two decades in terms of delivery.

Three splice-switching ASOs are in Phase II or III clinical trials, all of them for treatment of Duchenne muscular dystrophy. Prosenza has developed 2'-OMe phosphorothioate oligonucleotides while AVI BioPharma has favored development of morpholino oligomers. Both drugs show promise in clinical development.

A decade after the first siRNA experiments, at least dozen siRNA drugs are in clinical development. The four most advanced are in Phase II trials. As with ASOs, some of the earliest drugs to enter trials were very simple "first generation" siRNAs containing no chemical modifications.

The oligonucleotides used in accordance with various embodiments may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

Therapeutic administration of inhibitory nucleic acids capable of reducing expression or activity of a protein encoded by a FOXM1 or CENPF nucleic acid to cells for use with the methods described herein include any method by which a nucleic acid (e.g., DNA), as known to one of ordinary skill in the art. For treatment of aggressive prostate cancer, delivery is preferably by oral administration or injection into the prostate gland or tumor or both. Nucleic acid molecules can be administered to cells by a variety of methods known to those of skill in the art, including, but not restricted to, encapsulation in liposomes, by ionophoresis, or by incorporation into other vehicles, such as hydrogels, cyclodextrins, biodegradable nanocapsules, and bioadhesive microspheres, or by proteinaceous vectors.

In certain embodiments, the inhibitory nucleic acids capable of reducing expression or activity of a protein encoded by a FOXM1 or CENPF nucleic acid can be delivered to an organelle, a cell, a tissue, a tumor or an organism via one or more injections (i.e., a needle injection), such as, for example, subcutaneously, intradermally, intramuscularly, intravenously, intraperitoneally, etc.

A described inhibitory nucleic acid or other active agent can be incorporated into pharmaceutical compositions suitable for administration. For example, pharmaceutical compositions can comprise one or more the inhibitory nucleic acids capable of reducing expression or activity of a protein encoded by a FOXM1 or CENPF nucleic acid and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A described inhibitory nucleic acid may be provided in sustained release compositions. The use of immediate or sustained release compositions depends on the nature of the condition being treated. If the condition consists of an acute or over-acute disorder, treatment with an immediate release form can be conducted over a prolonged release composition. Alternatively, for certain preventative or long-term treatments, a sustained release composition may be appropriate.

A described inhibitory nucleic acid can be administered in a single dose or in multiple doses. Where the administration of the active agent is by infusion, the infusion can be a single sustained dose or can be delivered by multiple infusions. Injection of the agent can be directly into the tissue at or near the site of aberrant or unwanted target gene expression. Multiple injections of an inhibitory nucleic acid capable of reducing expression or activity of a protein encoded by a FOXM1 or CENPF nucleic acid can be made into the tissue—for example, into the prostate gland, into the prostate tumor, or near the tumor.

In addition to treating pre-existing aggressive or non-aggressive prostate cancers, active agents capable of reducing expression or activity of a protein encoded by a FOXM1 or CENPF nucleic acid can be administered prophylactically in order to prevent or slow the conversion of a non-aggressive prostate cancer to an aggressive form. The described inhibitory nucleic acids can be employed in combination therapies, meaning that the present compositions can be administered concurrently with, prior to, or subsequent to, one or more other desired therapeutic agents or medical procedures. The combination of therapies (therapeutic agents or procedures) to employ in a combination regimen will take into account compatibility of the desired therapeutic agents and/or procedures and the desired therapeutic effect to be achieved. It will also be appreciated that the therapies employed can achieve a desired effect for the same disorder (for example, a compound described herein can be administered concurrently with another therapeutic agent used to treat the same disorder), or they can achieve different effects (e.g., control of any adverse effects).

Known agents useful for treating cancers can be combined with the described inhibitory nucleic acids to treat a cancer wherein both FOXM1 and CENPF are elevated, such as a prostate cancer. For example, a described inhibitory nucleic acid can be administered with another therapeutic agent simultaneously or sequentially in separate unit dosage forms or together in a single unit dosage form.

The described inhibitory nucleic acids and methods of the present invention are useful for individuals who have received prior medication for a cancer, as well as individuals who have received no prior medication for a cancer. Individuals of any age can be treated by the methods compositions of the invention.

It is understood that the appropriate dose of an active agent depends upon a number of factors within the knowledge of the ordinarily skilled physician, veterinarian, or researcher. The dose(s) vary, for example, depending upon the identity, size, and condition of the subject or sample being treated, further depending upon the route by which the active agents and pharmaceutical compositions are to be administered, and the effect which the practitioner desires the an active agent to have. It is furthermore understood that appropriate doses of an active agent depend upon the potency with respect to the expression or activity to be modulated. Such appropriate doses may be determined using the assays described herein. When one or more of these active agents are to be administered to an animal (e.g., a human) in order to reduce expression or activity of FOXM1 and CENPF protein, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

5. Examples 5.1 Example 1. Experimental Procedures

Pilate perturbagen studies were performed to evaluate optimal dosage and scheduling. As an example, rapamycin treatment of NP mice involved treating mice for 1, 2, or 5 days and concentrations varied from 10, 25 and 50 mg/kg. Following treatment, expression profiling was done on prostate tumors to evaluate the dose and schedule that produced the optimal range of gene expression changes. The number of differentially expressed genes at different p-value thresholds (0.01 or 0.05) with or without a 1.5-fold change (FC) cut-off was determined. The perturbagen studies were used for assembly of the mouse prostate cancer interactome.

The primary gene expression profile dataset used for ARACNe-based reverse engineering was Taylor et al (GSE21034), which consists of primary human prostatectomy samples, adjacent normal tissue, and metastases arrayed on a Affymetrix human Exon 1.0 ST microarray platform (Taylor et al., 2010). Additional expression profile datasets used were: (i) Yu et al (GSE6919): primary human prostatectomy samples and adjacent normal tissue arrayed on a Affymetrix U95a, U95b and U95c microarray platforms (ii) Wang et al (a) (GSE17951): primary human prostatectomy samples, prostate biopsies, and normal prostate arrayed on a Affymetrix U133Plus2.0 platform; (iii) Wang et al (b) (GSE8218): primary human prostatectomy samples and normal prostate on a Affymetrix U133A platform; and (iv) Balk (GSE32269): biopsies of primary tumors from subjects with hormone-naïve prostate cancer and of bone marrow with confirmed tumor content from subjects with metastatic castration resistant prostate cancer (CRPC) on Affymetrix U133A platform. Available clinico-pathological information is provided in the table of FIG. 5.

For expression profiling analyses, prostate tumors were macrodissected, and the content of tumor/cellular atypia was verified by H&E analyses. Total RNA was isolated from prostate tissues/tumors using a MagMAX-96 total RNA isolation kit and biotin-labeled using the Illumina TotalPrep RNA Amplification Kit (Life Technologies). The resulting cRNA was hybridized on mouseWG-6 v2 BeadArrays (Illumina). Slides were scanned using an iScan (Illumina) and the resulting files were uploaded and background-corrected in BeadStudio 3.1.3.0 (Illumina, Inc.). Expression profiling data were normalized using standard variance stabilizing transformation (VST) and robust spline normalization (RSN) with lumiT and lumiN functions from lumi library, in R-system v2.14.0 (The R Foundation for Statistical Computing, ISBN 3-900051-07-0). The raw and normalized data files are deposited in Gene Expression Omnibus (GEO), accession number GSE53202.

Immunostaining was performed as described in Irshad et al., 2013. Immunostaining for FOXM1 or CENPF was performed on adjacent sections of each TMA slide. For immunofluorescent staining on cells in culture, $1\times10^5$ cells infected with the experimental or control shRNA were seeded in triplicate and grown in culture slides (BD Biosciences) for three days in the presence of 0.5 µg/ml of doxycycline. Cells were washed with PBS, fixed in ice cold acetone and permeabilized in 0.25% Triton X-100 in PBS and stained with antibodies for FOXM1 and CENPF (see Table 2, below). Images of the cellular localization of FOXM1 and CENPF were obtained using a Leica TCS SP5 spectral confocal microscope. Protein levels were determined by percent of staining (i.e. from 0 to 100%) and intensity level of staining (i.e., 0, 1, 2, or 3) in each tumor sample. We defined a composite protein level by multiplying percent of staining and its intensity level for each tumor sample, for FOXM1 or CENPF. Composite protein level exceeding 100 were considered elevated.

Statistical analysis was performed with survcomp package using R v2.14.0. Cox proportional hazard model was estimated with the surv and coxph functions. Kaplan-Meier survival analysis was performed using surv, survfit, and survdiff functions. Concordance indexes (c-index) were estimated and compared using coxp and concordance.index (counting ties) and cindex.comp functions.

Predicting additive effects by extrapolating individual effects of silencing FOXM1 or CENPF was evaluated as follows. To quantitatively evaluate synergy versus additivity of the tumor growth rate, an estimate of an "additive" effect was projected using a log-linear regression model, which assumes that the silencing of either master regulator individually induces a fractional reduction in tumor growth from that of control mice. The difference between the projected "additive" model versus the actual observed consequence of co-silencing was calculated using a one-sample t-test.

MARINa was used to estimate the activity levels of FOXM1 and CENPF, based on their ARACNe-inferred transcriptional targets, for each sample (i.e., each subject) in the Sboner and Glinsky human prostate cancer datasets (FIG. 5) (Glinsky et al., 2004; Sboner et al., 2010). The activity was defined as elevated if activated targets were positively enriched in the sample signature (i.e., positive NES) and at the same time repressed targets were negatively enriched in the sample signature (i.e., negative NES) and these enrichment scores fell into the upper/lower 35% percentile of NES distribution. Subjects were then divided into four groups: (i) those with non-elevated inferred activity for FOXM1 and CENPF; (ii) those with elevated inferred activity only for FOXM1; (iii) those with elevated inferred activity only for CENPF; and (iv) those with elevated inferred activity for both FOXM1 and CENPF. For these and all subsequent analyses, association with disease outcome was evaluated using Kaplan-Meier survival analysis calculated along with the log-rank p value using Surv, survfit, and survdiff functions from survcomp package in R v 2.14.0.)

Gene silencing of FOXM1 and CENPF as well as forced expression of FOXM1 were done using lentiviral shRNAs or expression vectors (Open Biosystems and CCSB Human ORFeome Library, respectively). Functional studies were done in four independent human cancer cell lines, which were obtained from ATCC. All experiments using animals were performed according to protocols approved by the Institutional Animal Care and Use Committee (IACUC) at Columbia University Medical Center.

Silencing was performed using the pTRIPZ lentiviral vector (Open Biosystems), which express an shRNAmir (microRNA-adapted shRNA, hereafter referred to as shRNA) and, for functional analysis, a tRFP fluorescent reporter under the control of a tetracycline responsive element (TRE) promoter such that expression of the shRNA can be induced by addition of doxycycline (0.5 µg/ml). For two-color fluorescence analyses, which were used for selection of cells expressing two different shRNA, the pTRIPZ vector was engineered to express eGFP using the AgeI and ClaI sites to replace the tRFP cassette. Following induction with doxycycline, cells infected with the pTRIPZ-RFP virus are detected by RFP expression (red), those infected with the pTRIPZ-GFP virus by GFP expression (green), and those infected with both pTRIPZ-RFP/pTRIPZ-GFP virus by expression of both tRFP and the eGFP (yellow). The shRNAs used to silence FOXM1 and CENPF were purchased from Open Biosystems; sequences are provided in Table 1. Unless otherwise indicated, analyses were done using two alternative shRNA and co-silencing was done using each combination of the experimental or control shRNA lentivirus.

TABLE 1

Sequences of shRNA and Primers for this study

| Purpose and name shRNA | Clone ID | SEQ ID NO | Mature antisense |
|---|---|---|---|
| FOXM1 shRNA#1 | V3THS_283849 | 1 | ATAATTAGAGGATAATTTG |
| FOXM1 shRNA#2 | V3THS_396941 | 2 | TGATGGTCATGTTCCGGCG |
| CENPFshRNA#1 | V2THS_115502 | 3 | ATCTGATTCACTCAGTCTG |
| CENPF shRNA#2 | V2THS_115504 | 4 | TTTCTTCCAACAGTAACTG |
| Scramble shRNA | RH54743 |  | N/A |

| Real Time qPCR | SEQ ID NO | Forward | SEQ ID NO | Reverse |
|---|---|---|---|---|
| FOXM1 | 5 | CGTCGGCCACTGATTCTCAAA | 19 | GGCAGGGGATCTCTTAGGTTC |
| CENPF | 6 | CTCTCCCGTCAACAGCGTTC | 20 | GTTGTGCATATTCTTGGCTTGC |
| BRCA1 | 7 | GCTCGTGGAAGATTTCGGTGT | 21 | TCATCAATCACGGACGTATCATC |
| BUB1 | 8 | AAATGACCCTCTGGATGTTTGG | 22 | GCATAAACGCCCTAATTTAAGCC |
| KI67 | 9 | GGGCCAATCCTGTCGCTTAAT | 23 | GTTATGCGCTTGCGAACCT |
| CYCLIN A2 | 10 | CGCTGGCGGTACTGAAGTC | 24 | GAGGAACGGTGACATGCTCAT |
| TIMELESS | 11 | TCTGATCCGCTATTTGAGGCA | 25 | GGCAGAAGGTCGCTCTGTAG |
| CDC25 | 12 | ACGCACCTATCCCTGTCTC | 26 | CTGGAAGCGTCTGATGGCAA |
| TRIP13 | 13 | ACTGTTGCACTTCACATTTTCC | 27 | TCGAGGAGATGGGATTTGACT |
| PLK1 | 14 | AAAGAGATCCCGGAGGTCCTA | 28 | GGCTGCGGTGAATGGATATTTC |
| HMMR | 15 | ATGATGGCTAAGCAAGAAGGC | 29 | TTTCCCTTGAGACTCTTCGAGA |
| MYBL2 | 16 | CCGGAGCAGAGGGATAGCA | 30 | CAGTGCGGTTAGGGAAGTGG |
| ACTIN | 17 | GTCTGCCTTGGTAGTGGATAATG | 31 | TCGAGGACGCCCTATCATGG |
| GAPDH | 18 | TGTGGGCATCAATGGATTTGG | 32 | ACACCATGTATTCCGGGTCAAT |
| ChiP |  |  |  |  |
| FOXM | 33 | CCGGAGCTTTCAGTTTGTTC | 41 | CGGAATGCCGAGACAAGG |
| CENPF | 34 | CACCTCCAGTAGAGGGGCTTG | 42 | TACCTCCACGCCTATTGGTC |
| AURKA | 35 | AGGACAAGGGCCTTCTTAGG | 43 | TAGTGGGTGGGAGACAGAC |
| AURKB | 36 | GGGGTCCAAGGCACTGCTAC | 44 | GGGGCGGGAGATTTGAAAAG |
| BIRC5 | 37 | CCATTAACCGCCAGATTTGA | 45 | TGTAGAGATGCGGTGGTCCT |
| CDC25 | 38 | AAGAGCCCATCAGTTCCGCTTG | 46 | CCCATTTTACAGACCTGGACGC |
| PLK1 | 39 | CCAGAGGGAGAAGATGTCCA | 47 | GTCGTTGTCCTCGAAAAAGC |
| CYCLIN B2 | 40 | TCCTTTGCCGAAAGCTAGAG | 48 | GCAACTGCCAATCTGAAAAAG |

Lentiviral particles were made using the 2nd generation packaging vectors, psPAX2 and pMD2.G (Addgene) in HEK-293T cells (ATCC), and concentrated using the Lenti-X Concentrator reagent (Clonetech). Human prostate cancer cells used in this study were DU145, PC3, LNCaP, and 22Rv1 (ATCC). Following infection with the lentiviruses, cells were selected using 4 µg/ml of puromycin for three days, following which shRNA expression was induced by addition of 0.5 µg/ml of doxycycline. The optimal time-point for silencing was determined to be 72 h following induction and used for all analyses, unless otherwise indicated. For enrichment of shRNA-expression, single-cell suspensions of the induced cells were FACS sorted on a BD-FACSAria cell sorter (BD biosciences) using the FITC (emission wavelength 525 nm, GFP positive) and/or PE-A (627-702 nm emission wavelength, RFP positive) channels and cells having the 20% highest-level expression were collected and used for analyses. Silencing of FOXM1 and CENPF RNA and protein were confirmed by qPCR and western blot analyses, respectively. Sequences of primers used for real time PCR are provided above in Table 1; antibodies are described in Table 2, with antibodies for immunohistochemistry indicated by the initials IHC.

TABLE 2

Antibodies used in this study

| Description | Source | Type | Dilution | Use |
|---|---|---|---|---|
| FOXM1 (human) | Abcam, Ab550066 | Mouse monoclonal | 1:1000 | Western blot, IF |
| FOXM1 (human) | Abcam, Ab550066 | Mouse monoclonal | 1:400 | IHC |
| CENPF (human) | Abcam, Ab5 | Rabbit polyclonal | 1:200 | Western blot, IF |
| CENPF (human) | Abcam, Ab90 | Mouse monoclonal | 1:400 | IHC |
| pAKT | Cell Signaling #9271 | Rabbit polyclonal | 1:1000 | Western blot |
| pERK | Cell Signaling #9101 | Rabbit polyclonal | 1:500 | Western blot |
| pS6 | Cell Signaling #2211 | Rabbit polyclonal | 1:1000 | Western blot |
| Actin | Cell Signaling 4970 | Rabbit polyclonal | 1:2000 | Western blot |
| PARP | Cell Signaling #9542 | Rabbit polyclonal | 1:1000 | Western blot |
| V5 | Invitrogen #R96025 | Mouse monoclonal | 1:5000 | Western blot, ChIP |
| V5 | Sigma #A7345 | Mouse monoclonal | 0.2 µg | IP |

Determining mRNA expression of FOXM1 or CENPF or both, total RNA was isolated from lentiviral-infected cells using TRIZOL and hybridized on Illumina Human HT-12 v4 Expression BeadChip Arrays. Hybridization and expression data processing were done as described above. Differential gene expression analysis was estimated with student t-test using p<0.05 as significant.

5.2 Example 2. Method of Discovery

Gene Profiling

The t-Distributed Stochastic Neighbor Embedding (t-SNE) is a machine learning algorithm for dimensionality reduction. It is a nonlinear dimensionality reduction technique that is particularly well suited for embedding high-dimensional data into a space of two or three dimensions, which can then be visualized in a scatter plot. Specifically, it models each high-dimensional object by a two- or three-dimensional point in such a way that similar objects are modeled by nearby points and dissimilar objects are modeled by distant points. In the illustrated embodiment, the gene expression data is reduced to the two dimensions V1 and V2. The gene expression data was divided into 6 classes associated with normal cells adjacent to a tumor (AdjN), four Gleason scores (G6, G7, G8, and G9 or more), and metastasized (met). This analysis was done to evaluate the relative heterogeneity of human and mouse datasets used to assemble the prostate cancer interactomes. FIG. 1A depicts t-SNE analysis of the Taylor dataset relative to Gleason score. Each point is the two dimensional representation of the relative expression of many genes. The 26,445 genes are considered in the t-SNE analysis. Each point is the two dimensional representation of the similarity and divergence between the data sample (i.e., gene expression profile) and all other data samples.

Interactomes

Regulatory networks (interactomes) for human and mouse prostate cancer were generated using the Algorithm for the Reconstruction of Accurate Cellular Networks (ARACNe) (Basso et al., 2005; Margolin et al., 2006b). ARACNe is an unbiased algorithm that infers transcriptional interactions by computing the mutual information between each transcriptional regulator (transcription factors and co-factors) and its potential targets, and then by removing indirect interactions using the Data Processing Inequality (DPI). For optimal analysis, ARACNe requires large data-sets of gene expression profiles ($\geq 100$) having significant endogenous (i.e., genetic) and/or exogenous (i.e., perturbation-induced) heterogeneity. Thus ARACNe analysis was performed on the Taylor data set.

ARACNe was run independently on the human and mouse datasets using a conservative mutual information threshold ($p \leq 1.0 \times 10^{-9}$, e.g., $p \leq 0.05$, Bonferroni corrected for all candidate interactions). This resulted in highly robust regulatory networks in which the human interactome represented 249,896 interactions between 2,681 transcriptional regulators and their inferred target genes, while the mouse interactome represented 222,787 interactions for 2,072 transcriptional regulators.

FIG. 2A is a block diagram and graph that illustrates example interactomes for human and mouse models with prostate cancer, according to an embodiment. ARACNE sub-networks from the human and the mouse prostate cancer interactomes highlight selected conserved transcriptional regulators. The scaled size of the transcriptional regulator nodes (filled circles) indicates the level of conservation while the relative distance between them approximates the strength of their association.

The suitability of these mouse and human interactomes for cross-species interrogation was next evaluated by developing a novel computational approach to assess the global conservation of their transcriptional programs.

A quantitative metric was developed to compare conservation of the human and mouse interactomes. In particular, a modification of the MARINa algorithm was developed that allows for single-sample analysis to infer the differential activity of 2028 transcriptional regulators represented in both interactomes on a sample-by-sample basis, from the expression of their interactome-specific targets. The analysis was performed on 1009 expression profiles representing 4 human datasets listed in the Table of FIG. 5, as well as across the mouse datasets, to determine whether the activity of each regulator, inferred either from the expression of its human interactome targets or its murine interactome targets, was significantly correlated ($p \leq 0.05$), indicating that the murine and human regulatory programs were therefore conserved. The accuracy of this metric was demonstrated by comparing two equivalent same-species interactomes from the human and mouse datasets (i.e., positive control), in which virtually all transcriptional regulators were conserved (>90%), contrasting with randomized interactomes (i.e., negative control) that had virtually no conservation. Histogram (density plots) showed the distribution of the correlation coefficients of activity profiles of transcriptional regulators for randomized interactomes (negative control) and the positive control interactomes for human and mouse. The degree of correlations was measured by the Z-score, and the Spearman correlation coefficient. The Z-score, also called the standard score, is the (signed) number of standard deviations an observation or datum is above the mean; and, is useful in comparing different populations. The Spearman's rank correlation coefficient, also called Spearman's rho, is a non-parametric measure of statistical dependence between two variables. It assesses how well the relationship between two variables can be described using a monotonic function. If there are no repeated data values, a perfect Spearman correlation of +1 or −1 occurs when each of the variables is a perfect monotone function of the other.

Figure 2B:
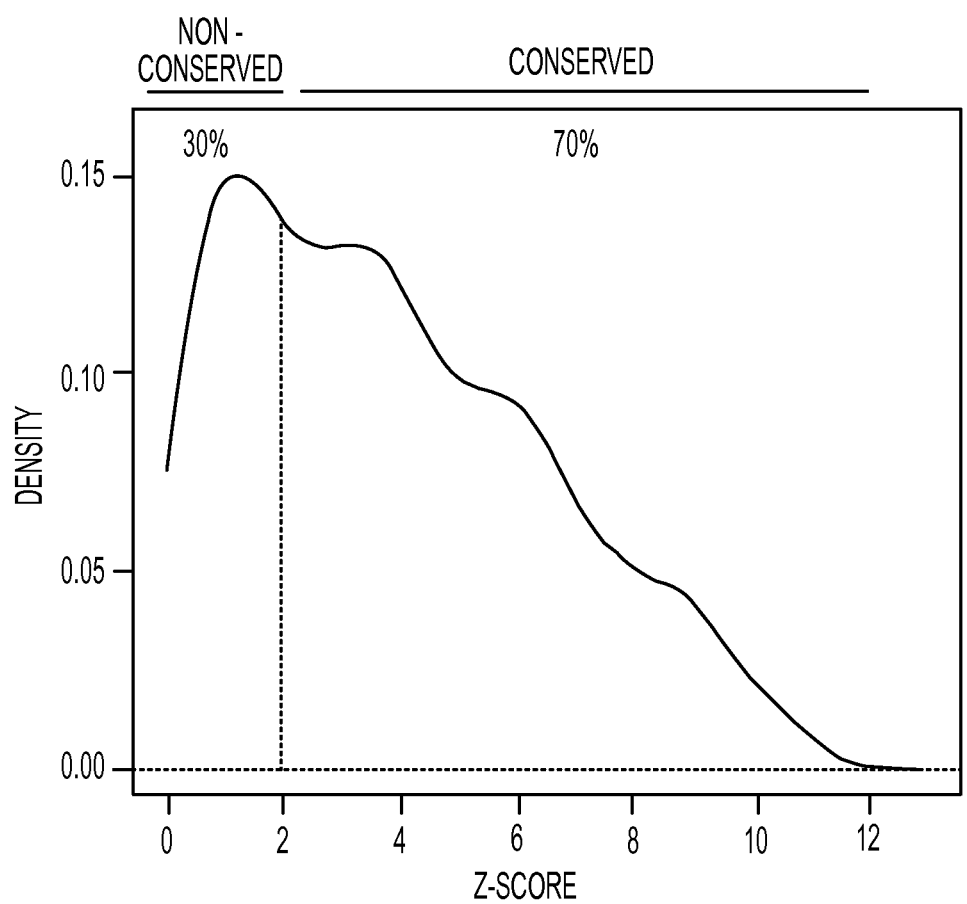
FIG. 2B is a graph that illustrates example percentage of the interactomes that are conserved between human and mouse models with prostate cancer, according to an embodiment.

Using these metrics, it was found that 70% of the transcriptional regulators in the human and mouse prostate cancer interactomes regulate statistically conserved programs ($p \leq 0.05$). FIG. 2B is a graph that illustrates example percentage of the interactomes that are conserved between human and mouse models with prostate cancer, according to an embodiment. This histogram shows the distribution of the Z-scores for conservation of activity profiles between the human and mouse interactomes at $p \leq 0.05$. Comparison of the androgen receptor (AR) activity levels in each sample from Taylor et al. and the mouse dataset was performed using the Spearman correlation coefficient.

Notably, conserved transcriptional regulators included many genes known to play important roles in prostate cancer, such as AR, ETS1, ETV4, ETV5, STAT3, MYC, BRCA1, and NKX3.1. In particular, AR displayed extensive correlation of its transcriptional activity between the human and mouse interactomes, consistent with its known role as a key regulator of prostate development and prostate tumorigenesis.

Master Regulators

The Master Regulator Inference algorithm (MARINa) (Carro et al., 2010; Lefebvre et al., 2010) was then used to infer candidate master regulators (MRs) that act individually or synergistically to drive malignant prostate cancer in the conserved interactomes. MARINa estimates differential activity (DA) based on enrichment (differential expression, DE) of their activated and repressed targets in the malignancy signature. More specifically, MARINa identified candidate MRs based on the concerted differential expression of their ARACNe-inferred targets (i.e., their differential activity, DA). Specifically, "activated" MRs have positively-regulated and repressed targets significantly enriched among upregulated and downregulated genes, respectively, while "repressed" MRs have the converse.

To interrogate the human prostate cancer interactome, a gene signature was used representing prostate cancer malignancy from the Taylor dataset, which compares aggressive prostate tumors (Gleason score $\geq 8$ with rapid biochemical recurrence; sample size n=10) versus indolent ones (Gleason score 6 tumors with no biochemical recurrence; sample size n=39). These analyses identified 175 candidate MRs, including 49 activated and 126 repressed ($p \leq 0.05$).

To investigate the robustness of these MRs, MARINa was performed using a second, independent malignancy signature from the Balk dataset (see the table of FIG. 5), which compares lethal CRPC (sample size n=29) with indolent, hormone-naïve prostate cancer (sample size n=22). These independent MR analyses significantly overlapped with those identified from the Taylor malignancy signature (36 MRs in common; Fisher exact test p<0.0001). The Fisher exact test was used to compare two populations with the same number of members and determine the probability p that deviations from the null hypothesis, here that the two distributions are the same could be explained by random events. Furthermore, MARINa analyses of 15 independent interactomes using the Taylor human prostate cancer malignancy signature showed that the inferred MRs were highly overlapping with those inferred from two additional independent prostate cancer interactomes ($p<7\times10^{-9}$ and $p<8\times10^{-20}$, Fisher exact test) but not with MRs inferred from non-prostate cancer specific interactomes (13 orders of magnitude different in significance). Thus, inference of master regulators of human prostate cancer malignancy required a prostate cancer-specific interactome but was independent of the specific dataset used for its interrogation.

To identify a corresponding mouse malignancy signature, MARINa was performed on four independent GEMM signatures, which are associated with prostate cancer malignancy and represent the diverse range of prostate cancer phenotypes represented among the GEMMs, including the NPK, NPB, NP, NP-AI, Myc, and NP53 mouse models. Meta-analyses of independent MR lists from these four independent GEMM signatures led to the identification of 229 candidate mouse MRs, including 110 activated and 119 repressed MRs ($p \leq 0.001$).

Figure 3A:
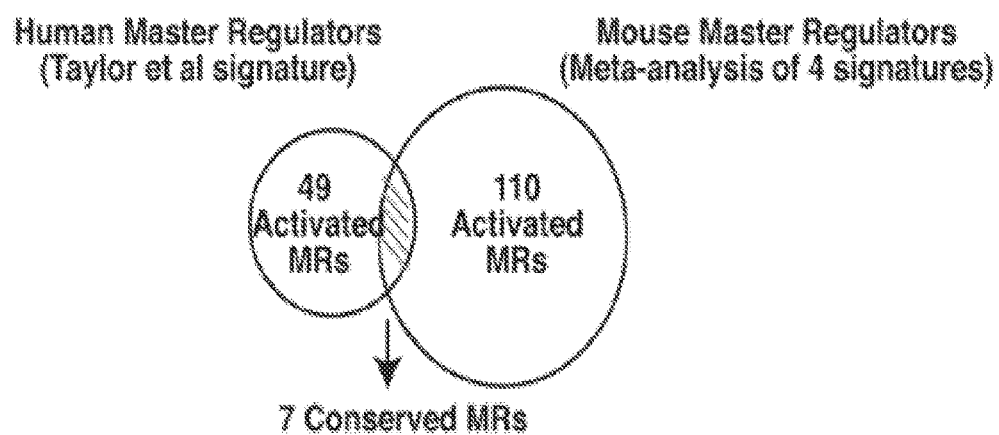
FIG. 3A is a Venn diagram and table that illustrate example selection of a subset of master regulators from a full set determined by available automated computer processes, according to an embodiment.

Conserved MRs were More Likely to be Associated with Disease Outcome than the Non-Conserved Ones The resulting independent lists of human and mouse MRs were then integrated to produce a ranked list of 20 conserved MRs, including 7 activated and 13 repressed (joint p-value: $p \leq 0.0074$ by Stouffer's method). FIG. 3A is a Venn diagram and table that illustrates example selection of a subset of master regulators from a full set determined by available automated computer processes, according to an embodiment. Notably, these conserved MRs were more likely to be associated with disease outcome than the non-conserved ones, as assessed by a univariate COX proportional hazard regression model (43% versus 21%; $p \leq 0.05$), and were also more likely to be differentially expressed in aggressive prostate tumors (metastatic versus non-metastatic; 100% versus 60%).

Figure 3B:
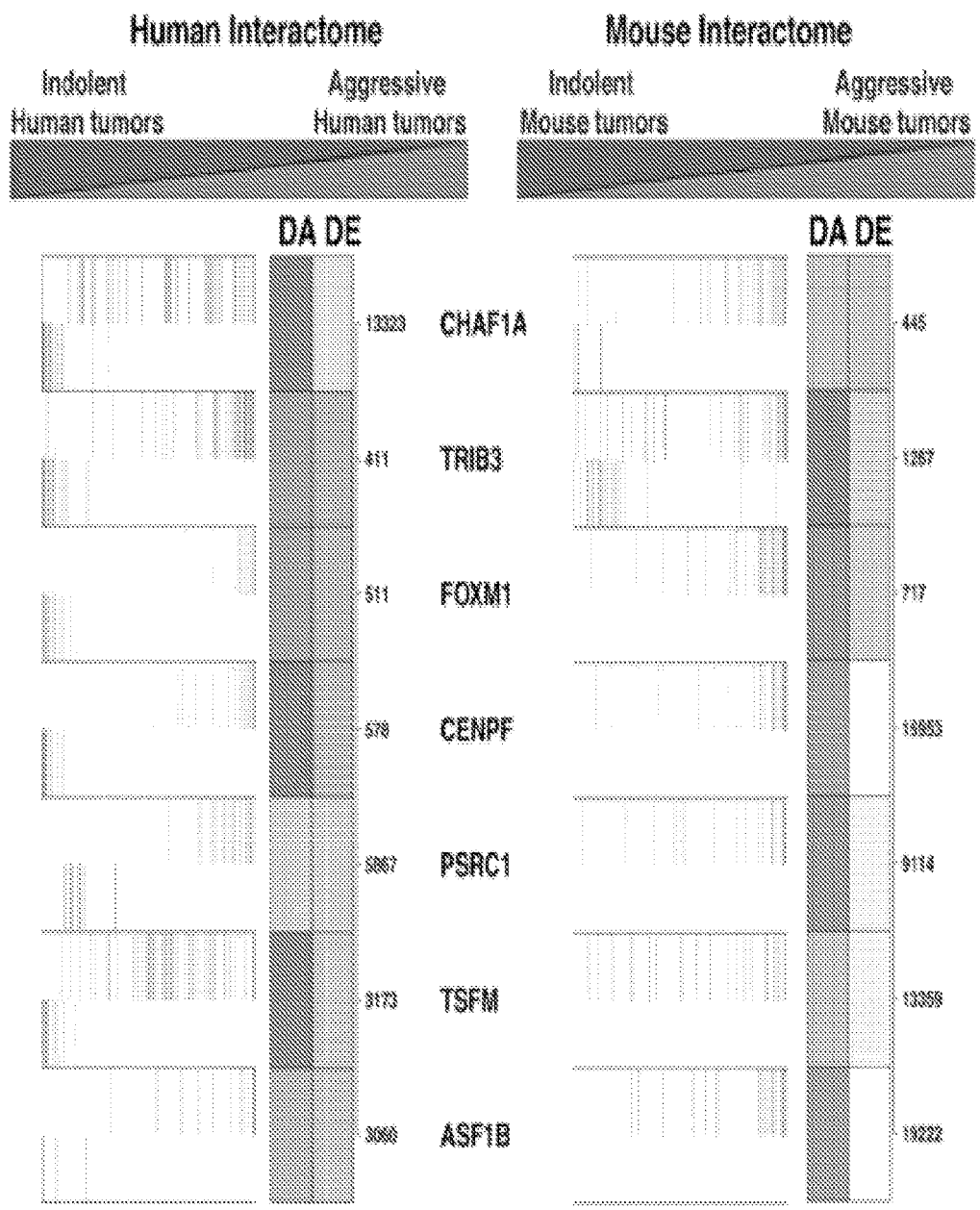
FIG. 3B is a diagram that illustrates example ranking of master regulators for their impacts on prostate cancer, according to an embodiment.

Subsequent analysis focused on the subset of activated conserved MRs, each of which has been associated with cancer-related biological processes: CHAF1A (chromatin activity); TRIB3 (regulation of cell signaling in transcriptional control); FOXM1 (cell cycle progression); CENPF (mitosis); PSRC1 (growth control); TSFM (translational elongation); and ASF1B (regulation of nucleosome assembly). FIG. 3B is a diagram that illustrates example ranking of activated master regulators for their impacts on prostate cancer, according to an embodiment. Conserved activated MRs are shown for the human (left) and mouse (right) malignancy signatures, depicting the different positive (activated; upper bars) and negative (repressed; lower bars) targets. The ranks of differential activity (DA) and differential expression (DE) are shown by the shaded boxes; the numbers indicate the rank of the DE in the signature. Differential expression is defined by comparing expression levels of a gene between two groups of samples (here, aggressive and indolent prostate cancer samples) using the t-test. Genes ranked (i.e., sorted from the most over-expressed to the most under-expressed) by their differential expression define a signature. For example, 411 represents a higher position in the signature and thus a stronger differential expression, compared to 13323.

FIG. 3C is a table that illustrates example ranking of master regulators for their impact on prostate cancer by various available algorithms, according to an embodiment. In this summary of conserved MRs are shown: joint p-value from human and mouse MARINa analysis, calculated using Stouffer's method; p-value for COX proportional hazard regression model applied to mRNA expression levels and predicted MR activity; and average p-values for differential expression of MRs in metastatic versus non-metastatic primary tumors. Smaller p values means that the deviations from the null hypothesis, that the regulator is not important, are less likely due to chance and thus the corresponding regulator is more significant contributors. FOXM1 and CENPF are significant ($p<0.05$) for all measures.

Synergistic Master Regulators FOXM1 and CENPF are Differentially Expressed in Aggressive Prostate Tumors These MRs were further prioritized by computationally evaluating their potential synergistic interactions. By these criteria, any pair of MRs was considered "synergistic" if their co-regulated ARACNe-inferred targets were significantly more enriched in the malignancy signature than their individual targets ($p\leq0.001$) (Carro et al., 2010; Lefebvre et al., 2010). Using this computational approach to analyze all 21 possible pairs among the conserved activated MRs, the only pair that was found to be statistically significant was FOXM1 and CENPF.

FIG. 3D is a table that illustrates example predicted synergy of FOXM1 And CENPF among other pairs in the subset of master regulators using available algorithms, according to an embodiment. Shown are synergy p-values (i.e., enrichment of shared versus non-shared targets in the malignancy signature) for conserved MRs, inferred by MARINa. Clearly, the synergy of FOXM1 and CENPF is least likely to be random ($p<0.001$), and thus most significant.

Figure 4B:
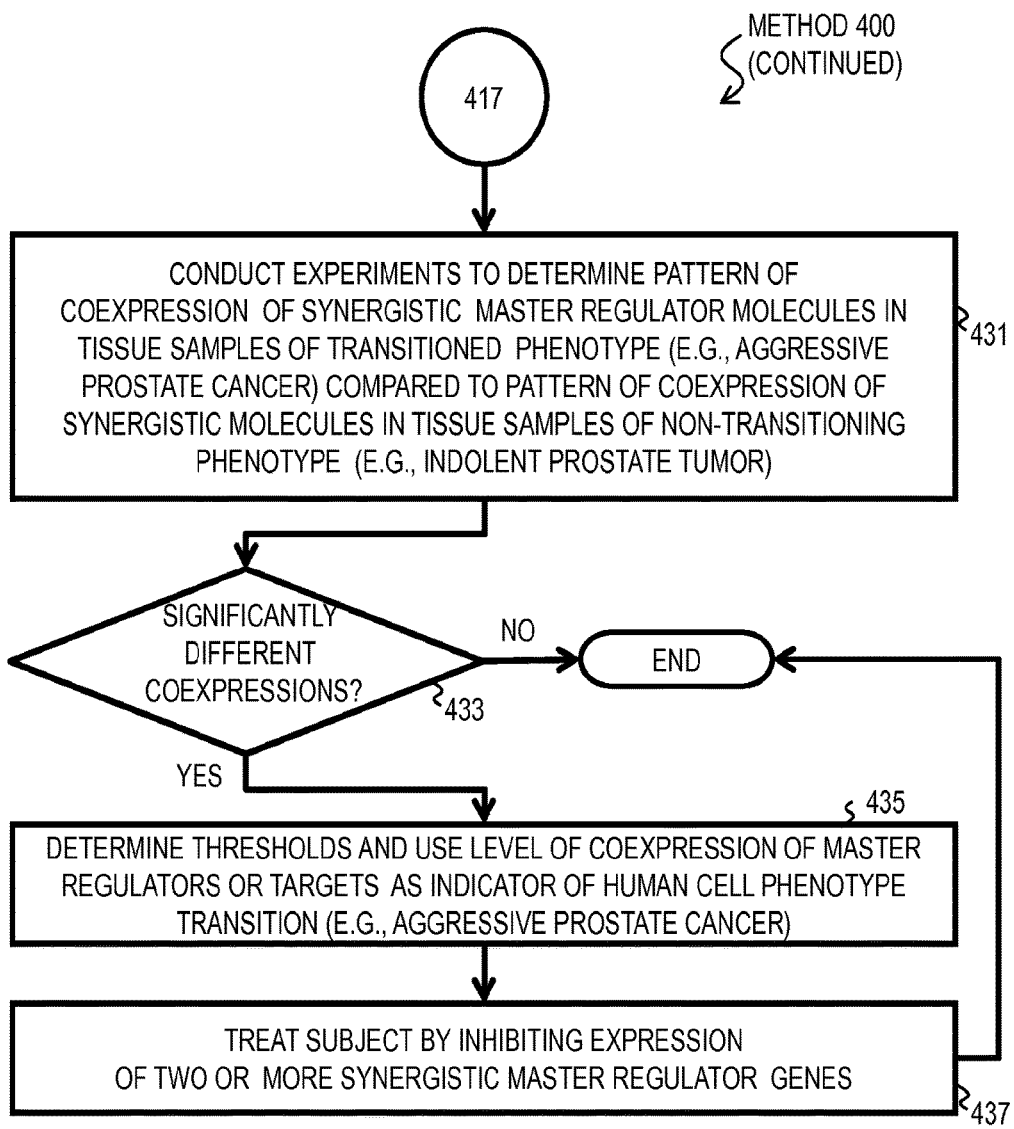

5.3 Example 3. Method to Discover Synergistic Master Regulators of Phenotype Transitions As demonstrated above, genome-wide cross-species interrogation of regulatory networks represents a valuable new strategy to identify causal mechanisms of human cancer. It is here proposed that analysis of genome-wide, cross-species regulatory networks provides an effective new paradigm for elucidating causal mechanisms of other complex diseases and phenotype transitions in general. FIG. 4 is a flow chart that illustrates an example method for determining various synergistic master regulators for other phenotype transitions, according to an embodiment. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401, a gene expression profile dataset of one or more gene expression profiles is determined for human tissue in a context of interest (e.g., a prostate cancer). In step 403, based on said expression profile dataset, an interactome of human tissue in the context of interest is determined automatically on a processor (e.g., using ARACNe, or Context Likelihood of Relatedness (CLR), or Bayesian-networks algorithms as described in Akavia et al., 2010; Faith et al., 2007). In step 405, a gene expression profile dataset of one or more gene expression profiles is determined for animal tissue in a context of interest (e.g., murine prostate cancer) from multiple in vivo perturbations of one or more genetically distinct animals (e.g., mouse transgenic models of prostate cancer). Hereinafter for convenience, these gene expression profiles are termed an animal model gene expression dataset. The perturbations are performed to extend the dynamic range of cellular interactions beyond what is known or can be tried in human subjects. In step 407, based on animal tissue in the same context expression profiles, an interactome of animal cell context is determined automatically on a processor (e.g., using ARACNe, CLR, and Bayesian Networks).

In step 409, a cellular signature is generated. The cellular signature represents a cell phenotype transition of interest from a first phenotype to a second phenotype (e.g., normal cell→cancer cell or, as in the embodiment illustrated above, indolent prostate cancer→aggressive prostate cancer). At least one gene expression profile in the dataset is associated with the first phenotype, and at least one other gene expression profile in the dataset is associated with the second phenotype. The signature is a ranked list of genes sorted from the most under- to the most over-expressed in the second cellular phenotype (e.g. aggressive prostate cancer) compared to the first cellular phenotypes (e.g. indolent prostate cancer), as computed by a differential expression analysis algorithm (e.g., t-test, u-test, etc.), as well as the statistical significance of their differential expression (i.e., p-value, z-score, or others).

In step 413, one or more master regulator molecules (genes or corresponding proteins) are determined automatically on a processor (e.g., using MARINa). The MARINa algorithm uses the interactome to address the following question: which are the proteins in the interactome that are most likely to have produced the cellular signature and hence the phenotype transition. This analysis is performed independently for a signature representing an animal model cell state transition and an animal model interactome and for a signature representing a human cell state transition and a human interactome. That is, the interactome and the signature are from the same species. This is accomplished as follows for the human datasets. An analogous process is followed for the animal mode gene expression datasets and signatures.

Each protein in the human interactome is associated with its targets, i.e., the protein "regulon." For each protein regulon the enrichment of the regulon genes is determined in genes that are differentially expressed in the human signature. The master regulators are based on the enrichment scores.

Enrichment is determined in various embodiments, using one or more of the following approaches, labeled A, B and C. Approach A is to determine whether the overlap between the statistically significant differentially expressed genes in the human signature (i.e., those with significant p-values, e.g. $p\leq0/05$) and the protein regulon gene is statistically significant, using the Fisher's exact test, at a predefined significance threshold (e.g., $p\leq0.05$). The master regulators are determined as those proteins with a statistically significant Fisher's exact test.

Approach B is to determine whether the normalized enrichment score (NES) representing the enrichment of the protein targets in differentially expressed human signature genes is statistically significant. The NES is the sum of (i) the normalized enrichment score (NES+) of the positive targets of the protein (e.g., those with Spearman correlation with the protein's associated gene expression above a pre-defined threshold, such as $SC\geq0$) enrichment in over- or under-expressed human signature genes, determined by Gene Set Enrichment analysis algorithm or other equivalent algorithms and (ii) the normalized enrichment score (NES−) of the negative targets of the protein (e.g., those with Spearman correlation with the protein's associated gene expression below a predefined threshold, such as SC<0) enrichment in under- or over-expressed human signature genes, using the Gene Set Enrichment analysis algorithm or other equivalent algorithms. The positive master regulator (MR) proteins are determined as those proteins with a positive and statistically significant NES; and negative MR proteins are determined as those proteins with a negative and statistically significant NES.

Approach C is to determine whether a modified normalized enrichment score (NES) representing the enrichment of the protein targets in differentially expressed human signature genes is statistically significant. In approach C, the modified NES is the sum of (i) the NES+ of positive targets as determined by probabilistic analysis of their Spearman correlation (ii) the NES− of negative targets as determined by probabilistic analysis of their Spearman correlation and (iii) the NES= of targets that cannot be assigned to either the positive or negative target set of the protein in differentially expressed genes, regardless of their over or under expression. The positive master regulator (MR) proteins are determined as those proteins with a positive and statistically significant modified NES; and negative MR proteins are determined as those proteins with a negative and statistically significant modified NES.

Step 415 includes determining, manually or automatically on a processor, MRs common to interactomes of both human and animal models. For example, a novel modification of the MARINa algorithm is used, which allows for single-sample analysis to infer the differential activity of all transcriptional regulators represented in both interactomes (e.g., 2028 transcriptional regulators in the prostate interactomes) on a sample-by-sample basis, from the expression of their interactome-specific targets. In this novel process a protein P is selected. Then, the human regulon of P is identified from the human interactome and designated $R_H$; and, the animal model regulon of P from the animal model interactome and designated $R_M$. From a set of samples (1 . . . N) in a large dataset of both human and animal model gene expression profiles, a vector is determined that represents the corresponding human interactome specific differential activity of P, designated $A_H$, using the $R_H$ regulon genes, and a second vector is determined that represents the corresponding animal model specific differential activity of P, designated $A_M$ using the $R_M$ regulon genes. The vector $A_H$ is determined by computing the normalized enrichment score (NES or modified NES, described above) of the $R_H$ genes in genes that are differentially expressed in the human signature on each gene expression profile in the dataset. The vector $A_M$ is determined by computing the normalized enrichment score (NES or modified NES, described above) of the $R_H$ genes in genes that are differentially expressed in the animal model signature on each gene expression profile in the dataset. The Fisher exact test was used to compare the observed and expected MR overlap and determined the probability p that deviations from the null hypothesis, here that the observed and the expected overlap are the same, could be explained by random events.

Then, it is determined, automatically on a processor, whether the activity vectors of each regulator, inferred either from its human interactome targets $A_H$ or from its animal model targets $A_M$, are significantly correlated (e.g., p≤0.05 by Pearson or Spearman correlation). If so, the protein program is conserved across species, and the animal model experiments involving the study of P in the animal model are applicable to human subjects.

In step 417 it is determined, automatically on a processor, those that are synergistic, e.g., using MARINa. This step assesses whether the NES of the targets regulated by both proteins (i.e., the intersection of their regulons) is statistically significantly greater than the NES of either protein regulon.

In step 431, experiments are conducted to determine pattern of coexpression of synergistic master regulator molecules in tissue samples of transitioned phenotype (e.g., aggressive prostate cancer) compared to a pattern of coexpression of synergistic molecules in tissue samples of non-transitioning phenotype (e.g., persistently benign prostate tumors, called "indolent tumors" herein). In step 433, it is determined, manually or automatically using a processor, whether there are significantly different levels of coexpression in the two groups (transitioning and non-transitioning). If not, the process ends; or, control returns to step 409 to try a different set of synergistic master regulators common to all interactomes. Otherwise control passes to step 435.

In step 435, thresholds are determined and pattern of coexpression of master regulators or targets are used as indicators of human cell phenotype transition (e.g., aggressive prostate cancer). It is also determined whether suppression of two or more synergistic MRs leads to major abrogation of phenotype transition. If so, then, in step 437, a subject is treated by inhibiting expression of two or more synergistic master regulator molecules. Then the process ends, or is repeated.

Following the independent analyses of human and mouse master regulators, conserved master regulators were defined as those that were statistically significant (p≤0.05) in both the human and mouse analysis and thus had an integrated p-value (by Stouffer's method) p≤0.0074.

This general approach for evaluating conservation of regulatory networks can be used for comparative, cross-species analyses of regulatory networks for other cancers or other diseases and can be easily adapted to cross-species analyses of networks reverse-engineered with alternative algorithms, such as those based on the Context Likelihood of Relatedness (CLR) and Bayesian-networks algorithms (Akavia et al., 2010; Faith et al., 2007). Indeed, it is envisioned that the ability to quantitatively evaluate conservation of cross-species regulatory programs will be broadly applicable for other physiological and pathological comparisons, and particularly beneficial for accurate integration of pre-clinical findings from genetically engineered mice to human clinical trials.

Computational Hardware Overview

Figure 12:
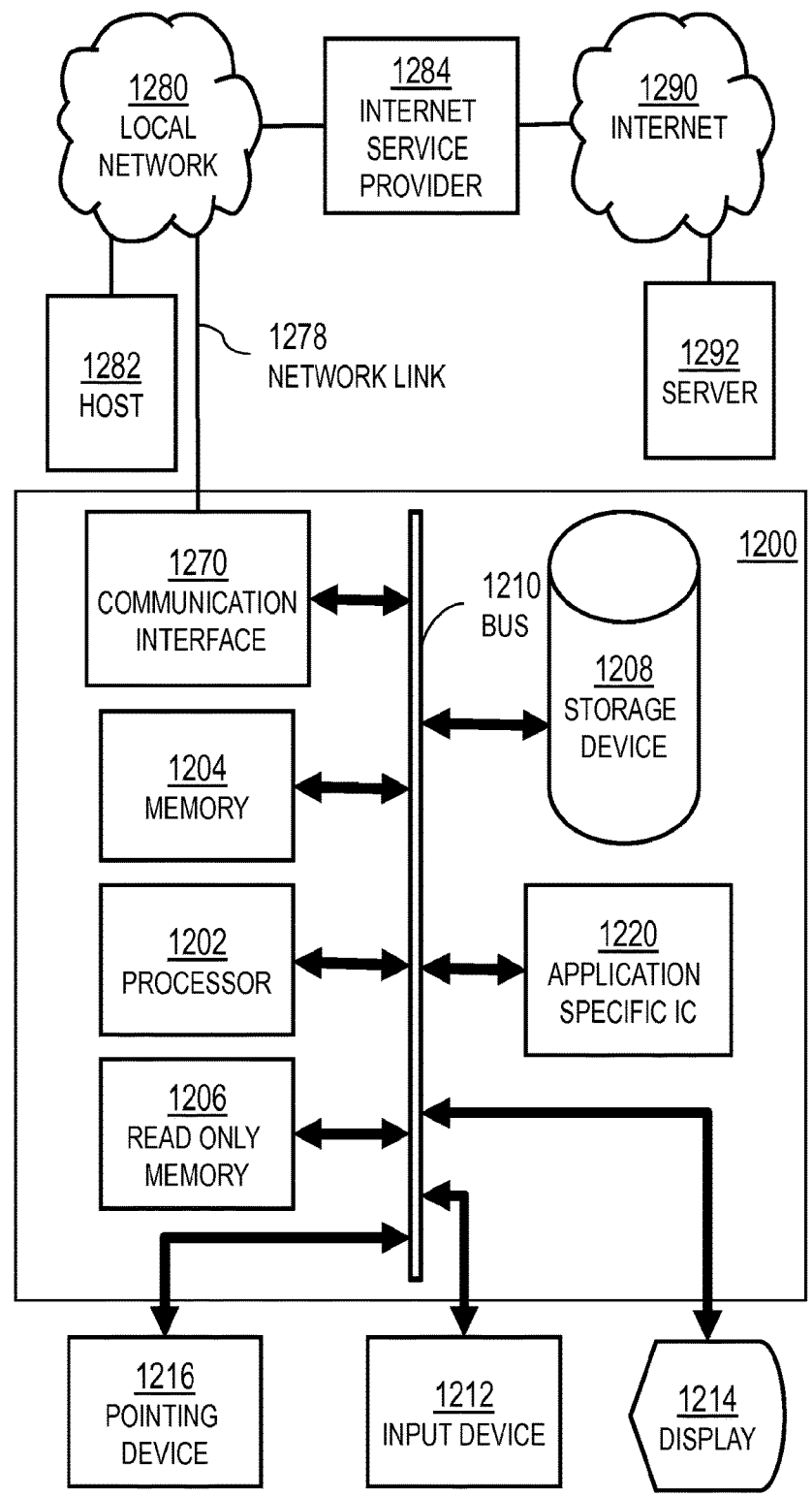
FIG. 12 is a block diagram that illustrates a computer system upon which an embodiment of the invention may be implemented.

FIG. 12 is a block diagram that illustrates a computer system 1200 upon which an embodiment of the invention may be implemented. Computer system 1200 includes a communication mechanism such as a bus 1210 for passing information between other internal and external components of the computer system 1200. Information is represented as physical signals of a measurable phenomenon, typically electric voltages, but including, in other embodiments, such phenomena as magnetic, electromagnetic, pressure, chemical, molecular, atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing one or more steps of one or more methods described herein.

A sequence of binary digits constitutes digital data that is used to represent a number or code for a character. A bus 1210 includes many parallel conductors of information so that information is transferred quickly among devices coupled to the bus 1210. One or more processors 1202 for processing information are coupled with the bus 1210. A processor 1202 performs a set of operations on information. The set of operations include bringing information in from the bus 1210 and placing information on the bus 1210. The set of operations also typically include comparing two or more units of information, shifting positions of units of information, and combining two or more units of information, such as by addition or multiplication. A sequence of operations to be executed by the processor 1202 constitutes computer instructions.

Computer system 1200 also includes a memory 1204 coupled to bus 1210. The memory 1204, such as a random access memory (RAM) or other dynamic storage device, stores information including computer instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of computer instructions. The computer system 1200 also includes a read only memory (ROM) 1206 or other static storage device coupled to the bus 1210 for storing static information, including instructions, that is not changed by the computer system 1200. Also coupled to bus 1210 is a non-volatile (persistent) storage device 1208, such as a magnetic disk or optical disk, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into signals compatible with the signals used to represent information in computer system 1200. Other external devices coupled to bus 1210, used primarily for interacting with humans, include a display device 1214, such as a cathode ray tube (CRT) or a liquid crystal display (LCD), for presenting images, and a pointing device 1216, such as a mouse or a trackball or cursor direction keys, for controlling a position of a small cursor image presented on the display 1214 and issuing commands associated with graphical elements presented on the display 1214.

In the illustrated embodiment, special purpose hardware, such as an application specific integrated circuit (IC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1270 sends and receives electrical, acoustic or electromagnetic signals, including infrared and optical signals, which carry information streams, such as digital data.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1202, except for carrier waves and other signals.

Logic encoded in one or more tangible media includes one or both of processor instructions on a computer-readable storage media and special purpose hardware, such as ASIC 1220.

Network link 1278 typically provides information communication through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290. A computer called a server 1292 connected to the Internet provides a service in response to information received over the Internet. For example, server 1292 provides information representing video data for presentation at display 1214.

The invention is related to the use of computer system 1200 for implementing the techniques described herein. According to one embodiment of the invention, those techniques are performed by computer system 1200 in response to processor 1202 executing one or more sequences of one or more instructions contained in memory 1204. Such instructions, also called software and program code, may be read into memory 1204 from another computer-readable medium such as storage device 1208. Execution of the sequences of instructions contained in memory 1204 causes processor 1202 to perform the method steps described herein. In alternative embodiments, hardware, such as application specific integrated circuit 1220, may be used in place of or in combination with software to implement the invention. Thus, embodiments of the invention are not limited to any specific combination of hardware and software.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server 1292 transmits program code for a particular application, requested by a message sent from computer 1200, through Internet 1290, ISP equipment 1284, local network 1280 and communications interface 1270. The received code may be executed by processor 1202 as it is received, or may be stored in storage device 1208 or other non-volatile storage for later execution, or both. In this manner, computer system 1200 may obtain application program code in the form of a signal on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red a carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

6. Alternatives and Extensions

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

7. References

Reference to the following publications can be found herein.

Akavia, U. D., Litvin, O., Kim, J., Sanchez-Garcia, F., Kotliar, D., Causton, H. C., Pochanard, P., Mozes, E., Garraway, L. A., and Pe'er, D. (2010). An integrated approach to uncover drivers of cancer. Cell 143, 1005-1017.

Alvarez-Fernandez, M., and Medema, R. H. (2013). Novel functions of FoxM1: from molecular mechanisms to cancer therapy. Frontiers in oncology 3, 30.

Aytes, A., Mitrofanova, A., Kinkade, C. W., Lefebvre, C., Lei, M., Phelan, V., LeKaye, H. C., Koutcher, J. A., Cardiff, R. D., Califano, A., et al. (2013). ETV4 promotes metastasis in response to activation of PI3-kinase and Ras signaling in a mouse model of advanced prostate cancer. Proc Natl Acad Sci USA 110, E3506-3515.

Baca, S. C., Prandi, D., Lawrence, M. S., Mosquera, J. M., Romanel, A., Drier, Y., Park, K., Kitabayashi, N., MacDonald, T. Y., Ghandi, M., et al. (2013). Punctuated evolution of prostate cancer genomes. Cell 153, 666-677.

Barringer, K., Orgel, L., Wahl, G., Gingeras, T. R. (1990). Blunt-end and single-strand ligations by *Escherichia coli* ligase: influence on an in vitro amplication scheme. Gene 89:117-122.

Basso, K., Margolin, A. A., Stolovitzky, G., Klein, U., Dalla-Favera, R., and Califano, A. (2005). Reverse engineering of regulatory networks in human B cells. Nat Genet 37, 382-390.

Berger, S., Kimmel, A., Abelson, J., Simon, M. (1987). Methods in Enzymology 152:307-316.

Bomont, P., Maddox, P., Shah, J. V., Desai, A. B., and Cleveland, D. W. (2005). Unstable microtubule capture at kinetochores depleted of the centromere-associated protein CENP-F. EMBO J 24, 3927-3939.

Burg, L. J., Juffras, A. M., Wu, Y., Blomquist, C. L., Du, Y. (1996). Single molecule detection of RNA reporter probes by amplification with Qβ replicase. Mol. Cell. Probes 10:257-271.

Cai, Y., Balli, D., Ustiyan, V., Fulford, L. A., Hiller, A., Misetic, V., Zhang, Y., Paluch, A. M., Waltz, S. E., Kasper, S., and Kalin, T. V. (2013). Foxm1 Expression in Prostate Epithelial Cells is Essential for Prostate Carcinogenesis. J Biol Chem 288, 22527-22541.

Carro, M. S., Lim, W. K., Alvarez, M. J., Bollo, R. J., Zhao, X., Snyder, E. Y., Sulman, E. P., Anne, S. L., Doetsch, F., Colman, H., et al. (2010). The transcriptional network for mesenchymal transformation of brain tumours. Nature 463, 318-325.

Donovan, M. J., Hamann, S., Clayton, M., Khan, F. M., Sapir, M., Bayer-Zubek, V., Fernandez, G., Mesa-Tejada, R., Teverovskiy, M., Reuter, V. E., et al. (2008). Systems pathology approach for the prediction of prostate cancer progression after radical prostatectomy. J Clin Oncol 26, 3923-3929.

Faith, J. J., Hayete, B., Thaden, J. T., Mogno, I., Wierzbowski, J., Cottarel, G., Kasif, S., Collins, J. J., and Gardner, T. S. (2007). Large-scale mapping and validation of Escherichia coli transcriptional regulation from a compendium of expression profiles. PLoS Biol 5, e8.

Feng, J., Huang, H., and Yen, T. J. (2006). CENP-F is a novel microtubule-binding protein that is essential for kinetochore attachments and affects the duration of the mitotic checkpoint delay. Chromosoma 115, 320-329.

Fredriksson, S., Gullberg, M., Jarvius, J., Olsson, C., Pietras, K., Gustafsdottir, S. M., Ostman, A., Landegren, U. (2002). Protein detection using proximity-dependent DNA ligation assays. Nat. Biotechnol. 20, 473-477.

Glinsky, G. V., Glinskii, A. B., Stephenson, A. J., Hoffman, R. M., and Gerald, W. L. (2004). Gene expression profiling predicts clinical outcome of prostate cancer. J Clin Invest 113, 913-923.

Guatelli, J. C., Whitfield, K. M., Kwoh, D. Y., Barringer, K. J., Richman, D. D., Gingeras, T. R. (1990). Isothermal, in vitro amplification of nucleic acids by a multienzyme reaction modeled after retroviral replication. Proc. Natl. Acad. Sci. USA 87:1874-78.

Halasi, M., and Gartel, A. L. (2013a). FOX(M1) news—it is cancer. Mol Cancer Ther 12, 245-254.

Halasi, M., and Gartel, A. L. (2013b). Targeting FOXM1 in cancer. Biochemical pharmacology 85, 644-652.

Hanahan, D., and Weinberg, R. A. (2011). Hallmarks of cancer: the next generation. Cell 144, 646-67

Hasegawa, S., Furukawa, Y., Li, M., Satoh, S., Kato, T., Watanabe, T., Katagiri, T., Tsunoda, T., Yamaoka, Y., Nakamura, Y. (2002). Genome-Wide Analysis of Gene Expression in Intestinal-Type Gastric Cancers Using a Complementary DNA Microarray Representing 23,040 Genes. Cancer Res 62:7012-7.

Holt, S. V., Vergnolle, M. A., Hussein, D., Wozniak, M. J., Allan, V. J., and Taylor, S. S. (2005). Silencing Cenp-F weakens centromeric cohesion, prevents chromosome alignment and activates the spindle checkpoint. J Cell Sci 118, 4889-4900.

Innis, M. ed. (1990). PCR Protocols: A Guide to Methods and Applications. Academic Press, N.Y.

Innis, M. ed. (1995). PCR Strategies. Academic Press, N.Y.

Irshad, S., and Abate-Shen, C. (2013). Modeling prostate cancer in mice: something old, something new, something premalignant, something metastatic. Cancer metastasis reviews 32, 109-122.

Ittmann, M., Huang, J., Radaelli, E., Martin, P., Signoretti, S., Sullivan, R., Simons, B. W., Ward, J. M., Robinson, B. D., Chu, G. C., et al. (2013). Animal models of human prostate cancer: the consensus report of the New York meeting of the Mouse Models of Human Cancers Consortium Prostate Pathology Committee. Cancer Res 73, 2718-2736.

Jones, A. C., Sampson, J. R., Hoogendoorn, B., Cohen, D., Cheadle, J. P. (2000). Application and evaluation of denaturing HPLC for molecular genetic analysis in tuberous sclerosis. Hum Genet. 106(6):663-8.

Kalin, T. V., Ustiyan, V., and Kalinichenko, V. V. (2011). Multiple faces of FoxM1 transcription factor: lessons from transgenic mouse models. Cell Cycle 10, 396-405.

Kalin, T. V., Wang, I. C., Ackerson, T. J., Major, M. L., Detrisac, C. J., Kalinichenko, V. V., Lyubimov, A., and Costa, R. H. (2006). Increased levels of the FoxM1 transcription factor accelerate development and progression of prostate carcinomas in both TRAMP and LADY transgenic mice. Cancer Res 66, 1712-1720.

Kitahara, O., Furukawa, Y., Tanaka, T., Kihara, C., Ono, K., Yanagawa, R., Nita, M., Takagi, T., Nakamura, Y., Tsunoda, T. (2001). Alterations of Gene Expression during Colorectal Carcinogenesis Revealed by cDNA Microarrays after Laser-Capture Microdissection of Tumor Tissues and Normal Epithelia. Cancer Res 61: 3544-9.

Koo, C. Y., Muir, K. W., and Lam, E. W. (2012). FOXM1: From cancer initiation to progression and treatment. Biochim Biophys Acta 1819, 28-37.

Kwoh, D. Y., Davis, G. R., Whitfield, K. M., Chappelle, H. L., DiMichele, L. J., Gingeras, T. R. (1989). Proc. Natl. Acad. Sci. USA 86:1173-77.

Landegren, U., Kaiser, R., Sanders, J., Hood, L. (1988). A ligase-mediated gene detection technique. Science 241: 1077-80.

Lefebvre, C., Rajbhandari, P., Alvarez, M. J., Bandaru, P., Lim, W. K., Sato, M., Wang, K., Sumazin, P., Kustagi, M., Bisikirska, B. C., et al. (2010). A human B-cell interactome identifies MYB and FOXM1 as master regulators of proliferation in germinal centers. Mol Syst Biol 6, 377.

Lefebvre, C., Rieckhof, G., and Califano, A. (2012). Reverse-engineering human regulatory networks. Wiley interdisciplinary reviews Systems biology and medicine 4, 311-325.

Lin, Y-M., Furukawa, Y., Tsunoda, T., Yue, C.-T., Yang, K.-C., Nakamura, Y. (2002). Molecular diagnosis of colorectal tumors by expression profiles of 50 genes expressed differentially in adenomas and carcinomas. Oncogene 21:4120-8.

Ma, L., Zhao, X., and Zhu, X. (2006). Mitosin/CENP-F in mitosis, transcriptional control, and differentiation. Journal of biomedical science 13, 205-213.

Margolin, A. A., Nemenman, I., Basso, K., Wiggins, C., Stolovitzky, G., Dalla Favera, R., and Califano, A. (2006a). ARACNE: an algorithm for the reconstruction of gene regulatory networks in a mammalian cellular context. BMC Bioinformatics 7 Suppl 1, S7.

Margolin, A. A., Wang, K., Lim, W. K., Kustagi, M., Nemenman, I., and Califano, A. (2006b). Reverse engineering cellular networks. Nat Protoc 1, 662-671.

McCaffrey, A. P., Meuse, L., Pham, T. T., Conklin, D. S., Hannon, G. J., Kay M. A. (2002). RNA interference in adult mice. Nature, 418:38-9.

McManus, M. T., Petersen, C. P., Haines, B. B., Chen, J., Sharp P. A. (2002). Gene silencing using micro-RNA designed hairpins. RNA, 8:842-50.

Okabe, H., Satoh, S., Kato, T., Kitahara, O., Yanagawa, R., Yamaoka, Y., Tsunoda, T., Furukawa, Y., Nakamura, Y. (2001). Genome-wide Analysis of Gene Expression in Human Hepatocellular Carcinomas Using cDNA Microarray: Identification of Genes Involved in Viral Carcinogenesis and Tumor Progression. Cancer Res 61:2129-37.

Paddison, P. J., Caudy, A. A., Bernstein, E., Hannon, G. J., Conklin, D. S. (2002). Short hairpin RNAs (shRNAs) induce sequence-specific silencing in mammalian cells. Genes Dev, 16:948-58

Pan, J., and Yeung, S. C. (2005). Recent advances in understanding the antineoplastic mechanisms of farnesyltransferase inhibitors. Cancer Res 65, 9109-9112.

Radhakrishnan, S. K., Bhat, U. G., Hughes, D. E., Wang, I. C., Costa, R. H., and Gartel, A. L. (2006). Identification of a chemical inhibitor of the oncogenic transcription factor forkhead box M1. Cancer Res 66, 9731-9735.

Ryan, C. J., and Tindall, D. J. (2011). Androgen receptor rediscovered: the new biology and targeting the androgen receptor therapeutically. J Clin Oncol 29, 3651-3658.

Sano, T., Smith, C. L., Cantor, C. R. (1992). Immuno-PCR: Very sensitive antigen detection by means of specific antibody-DNA conjugates. Science 258, 120-122.

Sboner, A., Demichelis, F., Calza, S., Pawitan, Y., Setlur, S. R., Hoshida, Y., Perner, S., Adami, H. O., Fall, K., Mucci, L. A., et al. (2010). Molecular sampling of prostate cancer: a dilemma for predicting disease progression. BMC Med Genomics 3, 8.

Scher, H. I., and Sawyers, C. L. (2005). Biology of progressive, castration-resistant prostate cancer: directed therapies targeting the androgen-receptor signaling axis. J Clin Oncol 23, 8253-8261.

Schoenborn, J. R., Nelson, P., and Fang, M. (2013). Genomic profiling defines subtypes of prostate cancer with the potential for therapeutic stratification. Clin Cancer Res 19, 4058-4066.

Shah, R. B., Mehra, R., Chinnaiyan, A. M., Shen, R., Ghosh, D., Zhou, M., Macvicar, G. R., Varambally, S., Harwood, J., Bismar, T. A., et al. (2004). Androgen-independent prostate cancer is a heterogeneous group of diseases: lessons from a rapid autopsy program. Cancer Res 64, 9209-9216.

Shen, M. M., and Abate-Shen, C. (2010). Molecular genetics of prostate cancer: new prospects for old challenges. Genes Dev 24, 1967-2000.

Smith, J. H., Radcliffe, D., Rigmy, S., Mahan, D., Lane, D. J., Klinger, J. D. (1997). Performance of an automated Q-beta replicase amplification assay for *Mycobacterium tuberculosis* in a clinical trial. Clin. Microbiol. 35:1477-1491.

Sooknanan, R., Malek, L. T. (1995). A detection and amplification system uniquely suited for RNA. Nature Biotechnology 13:563-564.

Taylor, B. S., Schultz, N., Hieronymus, H., Gopalan, A., Xiao, Y., Carver, B. S., Arora, V. K., Kaushik, P., Cerami, E., Reva, B. (2010). Integrative genomic profiling of human prostate cancer. Cancer Cell 18, 11-22.

Uddin, M. N., Patel N. J., Bhowmik T., D'Souza B., Akalkotkar A., Etzlar F., Oettinger C. W., D'Souza, M. (2013). Enhanced bioavailability of orally administered antisense oligonucleotide to nuclear factor kappa B mRNA after microencapsulation with albumin. J Drug Target 21(5), 450-457 (doi:10.3109/1061186X.2013.765440).

Varis, A., Salmela, A. L., and Kallio, M. J. (2006). Cenp-F (mitosin) is more than a mitotic marker. Chromosoma 115, 288-295.

Wu, D. Y., Wallace, R. B. (1989). The ligation amplification reaction (LAR)—amplification of specific DNA sequences using sequential rounds of template-dependent ligation. Genomics 4:560-569.

Yu, J.-Y., DeRuiter, S. L., Turner, D. L. (2002). RNA interference by expression of short-interfering RNAs and hairpin RNAs in mammalian cells. Proc Natl Acad Sci USA, 99:6047-52.

Zhang, H. T., Kacharmina, J. E., Miyashiro, K., Greene, M. I., Eberwine, J. (2001). Protein quantification from complex protein mixtures using a proteomics methodology with single-cell resolution. J. Proc. Natl. Acad. Sci. USA 98, 5497-5502.

Zhang, N., Wei, P., Gong, A., Chiu, W. T., Lee, H. T., Colman, H., Huang, H., Xue, J., Liu, M., Wang, Y., et al. (2011). FoxM1 promotes beta-catenin nuclear localization and controls Wnt target-gene expression and glioma tumorigenesis. Cancer Cell 20, 427-442.

Zhang, Q. C., Petrey, D., Deng, L., Qiang, L., Shi, Y., Thu, C. A., Bisikirska, B., Lefebvre, C., Accili, D., Hunter, T., et al. (2012). Structure-based prediction of protein-protein interactions on a genome-wide scale. Nature 490, 556-560.

What is claimed is:

1. A method for treating prostate cancer or preventing the progression of a nonaggressive form of prostate cancer to an aggressive form, in a mammal, the method comprising: administering to the mammal a therapeutically effective amount of one or more active agents that reduce the expression or biological activity of both Forkhead box protein M1 (FOXM1) and Centromere protein F (CENPF) or biologically active fragments thereof, wherein the active agent is selected from the group consisting of an isolated short hairpin RNA (shRNA), short interfering RNA (siRNA), antisense RNA, antisense DNA, Chimeric Antisense DNA/RNA, microRNA, and ribozymes that are sufficiently complementary to either a gene or an mRNA encoding FOXM1 or CENPF.

2. The method of claim 1, wherein the prostate cancer is aggressive prostate cancer.

3. The method of claim 1, wherein the active agent is administered orally.

4. The method of claim 1, wherein the active agent is administered locally to a prostate gland or prostate tumor.

5. The method of claim 1, wherein the active agent is a nucleic acid comprising a sequence selected from the group consisting of SEQ ID NO: 1, SEQ ID NO: 2; SEQ ID NO: 3; and SEQ ID NO: 4.

* * * * *